US010385085B2

(12) United States Patent
Klopp et al.

(10) Patent No.: US 10,385,085 B2
(45) Date of Patent: Aug. 20, 2019

(54) CRYSTAL FORMS OF SIALIC ACID OR SALT OR SOLVATE THEREOF

(71) Applicant: Ultragenyx Pharmaceutical Inc., Novato, CA (US)

(72) Inventors: John Klopp, San Francisco, CA (US); Hayley Reece, Midlothian (GB); Jean-Baptiste Arlin, Almere (NL); Corinna Marie Reisinger-Becker, Hanau (DE); Fabrice Dufour, Hanau-Mittelbuchen (DE)

(73) Assignee: Ultragenyx Pharmaceutical Inc., Novato, CA (US)

( * ) Notice: Subject to any disclaimer, the term of this patent is extended or adjusted under 35 U.S.C. 154(b) by 233 days.

(21) Appl. No.: 15/265,215

(22) Filed: Sep. 14, 2016

(65) Prior Publication Data

US 2017/0073366 A1    Mar. 16, 2017

Related U.S. Application Data

(60) Provisional application No. 62/218,446, filed on Sep. 14, 2015.

(51) Int. Cl.
*C07H 15/12* (2006.01)
*C07H 13/04* (2006.01)

(52) U.S. Cl.
CPC ............. *C07H 15/12* (2013.01); *C07H 13/04* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 4,698,332 A | 10/1987 | Ogasawara et al. |
| 5,624,677 A | 4/1997 | El-Rashidy et al. |
| 5,747,475 A | 5/1998 | Nordquist et al. |
| 6,156,544 A | 12/2000 | Dawson et al. |
| 6,444,649 B1 | 9/2002 | Inamori et al. |
| 8,524,772 B2 | 9/2013 | Arad et al. |
| 8,840,926 B2 | 9/2014 | Kakkis et al. |
| 9,221,858 B2 | 12/2015 | Kakkis et al. |
| 9,241,896 B2 | 1/2016 | Kakkis |
| 9,511,015 B2 | 12/2016 | Kakkis |
| 9,554,987 B2 | 1/2017 | Kakkis |
| 10,065,981 B2 | 9/2018 | Kakkis et al. |
| 2004/0192642 A1 | 9/2004 | Yang et al. |
| 2008/0085306 A1 | 4/2008 | Nangia et al. |
| 2008/0260824 A1 | 10/2008 | Nangia et al. |
| 2010/0159001 A1 | 6/2010 | Cardinal et al. |
| 2010/0160363 A1 | 6/2010 | Cardinal et al. |
| 2010/0226855 A1 | 9/2010 | Nangia et al. |
| 2012/0264928 A1 | 10/2012 | Noguchi et al. |
| 2013/0225513 A1 | 8/2013 | Kakkis |
| 2013/0273160 A1 | 10/2013 | Kakkis |
| 2016/0297846 A1 | 10/2016 | Kakkis et al. |
| 2017/0136051 A1 | 5/2017 | Kakkis |
| 2017/0157160 A1 | 6/2017 | Kakkis |

FOREIGN PATENT DOCUMENTS

| | | |
|---|---|---|
| EP | 2332552 | 6/2011 |
| EP | 2593109 | 5/2013 |
| JP | S63-139193 | 6/1988 |
| JP | 2010-529021 | 8/2010 |
| KR | 10-2001-0042603 | 5/2001 |
| WO | WO 1999/052931 | 10/1999 |
| WO | WO 2004/000366 | 12/2003 |
| WO | WO 2006/096161 | 9/2006 |
| WO | WO 2008/150477 | 12/2008 |
| WO | WO 2009/032605 | 3/2009 |
| WO | WO 2010/080580 A2 | 7/2010 |
| WO | WO 2010/131712 | 11/2010 |
| WO | WO 2012/009474 | 1/2012 |
| WO | WO 2013/063149 | 5/2013 |
| WO | WO 2013/109906 | 7/2013 |
| WO | WO 2016/121810 | 8/2016 |
| WO | WO 2017/048817 | 3/2017 |

OTHER PUBLICATIONS

Supplementary European Search Report for European Application No. 12843460.2, dated Aug. 12, 2015, 13 pages.
Supplementary Partial European Search Report for European Application No. 12843460.2, dated Feb. 25, 2015, 6 pages.
International Preliminary Report on Patentability for International Application No. PCT/US2012/061737, dated Apr. 29, 2014, 9 pages.
International Search Report and Written Opinion for International Application No. PCT/US2012/061737, dated Mar. 15, 2013, 13 pages.
Supplementary European Search Report for European Application No. 11807478.0, dated Dec. 5, 2013, 5 pages.
International Preliminary Report on Patentability for International Application No. PCT/US2011/043910, dated Jan. 15, 2013, 8 pages.
International Search Report and Written Opinion for International Application No. PCT/US2011/043910, dated Oct. 18, 2011, 10 pages.
Supplementary European Search Report for European Application No. 13739040.7, dated Aug. 4, 2015, 8 pages.
International Preliminary Report on Patentability for International Application No. PCT/US2013/022167, dated Jul. 22, 2014, 4 pages.
Aich, U. et al, "Development of Delivery Methods for Carbohydrate-based Drugs: Controlled Release of Biologically-Active Short Chain Fatty Acid-Hexosamine Analogs," Glycoconjugate Journal, 27(4):445-459 (2010).
Allevi, P. et al., "Chemoselective synthesis of sialic acid 1,7-lactones," J. Org. Chem., 75(16):5542-5548 (2010).
Argov, Z. et al., "Hereditary inclusion body myopathy. The Middle Eastern genetic cluster," Neurology, 60(9):1519-1523 (2003).

(Continued)

*Primary Examiner* — Shaojia A Jiang
*Assistant Examiner* — Bahar Craigo
(74) *Attorney, Agent, or Firm* — Cooley LLP

(57) ABSTRACT

The present invention includes crystalline forms of N-acetylneuraminic acid (NeuAc) and crystalline forms of salts and/or solvates of N-acetylneuraminic acid (NeuAc). Furthermore, the present invention provides compositions comprising these crystalline forms and therapeutic use of the crystalline forms.

16 Claims, 92 Drawing Sheets

(56) References Cited

OTHER PUBLICATIONS

Askanas, V. et al., "Sporadic inclusion-body myositis and hereditary inclusion-body myopathies: current concepts of diagnosis and pathogenesis," Curr. Opin. Rheumatol., 10:530-542 (1998).
Broccolini, A. et al., "Novel GNE mutations in Italian families with autosomal recessive hereditary inclusion-body myopathy," Human Mutation, 23(6):632 (2004).
Colombo, R. et al., "The first synthesis of N-acetylneuraminic acid 1,7-lactone," Chem. Commun., 43:5517-5519 (2008).
Dufner, G. et al., "Base- and Sugar-Modified Cytidine Monophosphate N-Acetylneuraminic Acid (CMP-Neu5Ac) Analogues—Synthesis and Studies with α(2-6)-Sialyltransferase from Rat Liver," European Journal of Organic Chemistry, 2000(8):1467-1482 (Apr. 2000).
Eisenberg, I. et al., "The UDP-N-acetylglucosamine 2-epimerase/N-acetylmannosamine kinase gene is mutated in recessive hereditary inclusion body myopathy," Nat. Genet., 29(1):83-87 (2001).
Fuchidori Kuuhou wo tomonau enigata myopathy no konponteki no konponteki chiryouhou kaihatu [Development of fundamental therapy of distal therapy of distal type myopathy involving rimmed vacuole rimmed vacuole], Heiesei-19 generalization allotment study report, Apr. 2008, pp. 1-7 (with English translation of relevant portion), 9 pages.
Frost, R. A. et al., "Regulation of insulin-like growth factor-I in skeletal muscle and muscle cells," Minerva Endocrinol., 28(1):53-73 (2003).
Galeano, B. et al., "Mutation in the key enzyme of sialic acid biosynthesis causes severe glomerular proteinuria and is rescued by N-acetylmannosamine," The Journal of Clinical Investigation, 117(6):1585-1594 (2007).
Gavezzotti, A., "Are Crystal Structures Predictable?", Accounts of Chemical Research, 27:309-314 (1994).
Horn, E. J. et al., "Investigation into an efficient synthesis of 2,3-dehydro-N-acetyl neuraminic acid leads to three decarboxylated sialic acid dimers," Carbohydrate Research, 343(5):936-940 (2008).
Jay, C. M. et al., "Hereditary Inclusion Body Myopathy (HIBM2)," Gene Regulation and Systems Biology, 3:181-190 (2009).
Liu, J. L-C et al., "Overproduction of CMP-Sialic Acid Synthetase for Organic Synthesis," J. Am. Chem. Soc., 114(10):3901-3910 (1992).
Malicdan, M. C. V. et al., "Prophylactic treatment with sialic acid metabolites precludes the development of the myopathic phenotype in the DMRV-hIBM mouse model," Nature Medicine, 15(6):690-695 (2009).
Martin, R. et al., "The synthesis and enzymatic incorporation of sialic acid derivatives for use as tools to study the structure, activity, and inhibition of glycoproteins and other glycoconjugates," Bioorganic & Medicinal Chemistry, 6(8):1283-1292 (1998).
Nishino, I. et al., "Distal myopathy with rimmed vacuoles is allelic to hereditary inclusion body myopathy," Neurology, 59:1689-1693 (2002).
Nishino, I. et al., "Muscular dystrophies," Current Opinion in Neurology, 15:539-544 (2002).
Nishino, I., "Development of a Fundamental Therapy for Distal Myopathy with Rimmed Vacuoles," Research Report Summary, Heisei 19 Soukatsu / Bunten Kenkyu Houkokusho, pp. 1-7 (2008) (with English Abstract).
Noguchi, S. et al., "Reduction of UDP-N-acetylglucosamine 2-Epimerase/N-Acetylmannosamine Kinase Activity and Sialylation in Distal Myopathy with Rimmed Vacuoles," The Journal of Biological Chemistry, 279(12):11402-11407 (2004).
Oetke, C. et al., "Evidence for efficient uptake and incorporation of sialic acid by eukaryotic cells," European Journal of Biochemistry, 268(16):4553-4561 (2001).
Oetke, C. et al., "Versatile Biosynthetic Engineering of Sialic Acid in Living Cells Using Synthetic Sialic Acid Analogues," The Journal of Biological Chemistry, 277:6688-6695 (2002).
Penner, J. et al., "Influence of UDP-GlcNAc 2-Epimerase/ManNAc Kinase Mutant Proteins on Hereditary Inclusion Body Myopathy," Biochemistry, 45:2968-2977 (2006).
Pubchem Compound Database, CID 440962, "N-acetylneuraminate 9-phosphate," Created on Jun. 24, 2005, 5 pages.
Rezende, M. C. et al., "A facile route to 9-phosphorylated neuraminic acid derivatives," Synthetic Communications, 28(23):4393-4400 (1998).
Ricci, E. et al., "NCAM is hyposialylated in hereditary inclusion body myopathy due to GNE mutations," Neurology, 66:755-758 (2006).
Rota, P. et al., "General and chemoselective N-transacylation of secondary amides by means of perfluorinated anhydrides," Angewandte Chemie International Edition, 49(10):1850-1853 (2010).
Sato, S. et al., "Studies on sialic acids. XIV. Lactone derivatives of N-Acetylneuraminic acid," Chemical & Pharmaceutical Bulletin, 36(12):4678-4688 (1988).
Seppala, R. et al., "Mutations in the Human UDP-N-Acetylglucosamine 2-Epimerase Gene Define the Disease Sialuria and the Allosteric Site of the Enzyme," Am. J. Hum. Genet., 64:1563-1569 (1999).
Sparks, S. E. et al., "Use of a cell-free system to determine UDP-N-acetylglucosamine 2-epimerase and N-acetylmannosamine kinase activities in human hereditary inclusion body myopathy," Glycobiology, 15(11):1102-1110 (2005).
Vippagunta, S. R. et al., "Crystalline Solids," Advanced Drug Delivery Reviews, 48:3-26 (2001).
Wajnrajch, M. P., "Physiological and Pathological Growth Hormone Secretion," Journal of Pediatric Endocrinology & Metabolism, 18(4):325-338 (2005).
Yao, R. (ed.), Polymers for Pharmaceuticals, Second Edition, Chemistry Industry Press, Mar. 2008, pp. 76-87 (with English translation of relevant portion).
ClinicalTrials.gov, "A Phase 1 Study to Evaluate the Safety and Pharmacokinetics of Single and Repeat Doses of Sialic Acid Extended Release (SA-ER) Tables in Patients With Hereditary Inclusion Body Myopathy (HIBM)", NCT01359319, ClinicalTrials.gov [Online], First Received: May 20, 2011. Retrieved from the Internet: <URL: https://clinicaltrials.gov/ct2/show/NCT01359319>, 6 pages.
ClinicalTrials.gov, "Pharmacokinetic Study on N-acetylneuraminic Acid in Patients With Distal Myopathy With Rimmed Vacuoles (DMRV)—Hereditary Inclusion Body Myopathy (hIBM)", NCT01236898, ClinicalTrials.gov [Online], First Received: Nov. 8, 2010. Retrieved from the Internet: <URL: https://clinicaltrials.gov/ct2/show/NCT01236898>, 4 pages.
International Search Report and Written Opinion for International Application No. PCT/US2016/051694, dated Dec. 30, 2016, 9 pages.
Cornforth, J. W. et al., "The synthesis of N-Acetylneuraminic acid," Biochemical Journal, 68(1):57-61 (Jan. 1958).
Scheinthal, B. M. et al., "Multiple forms of sialic acids," Carbohydrate Research, 6:257-265 (1968).
CAS Registry No. 1053644-78-2; STN Entry Date Sep. 28, 2008.

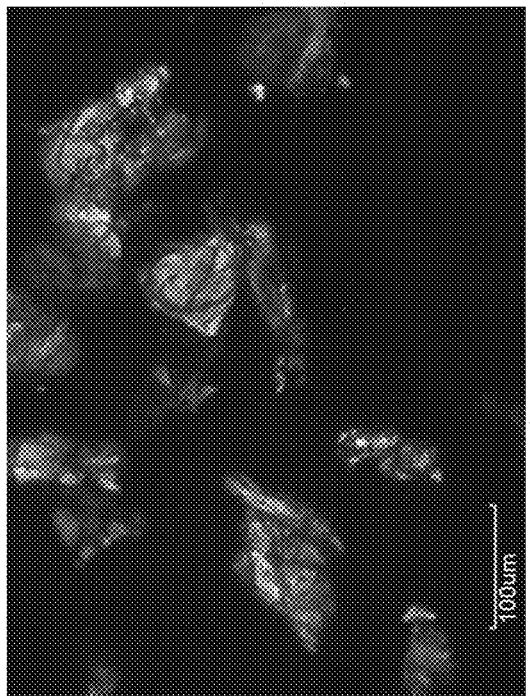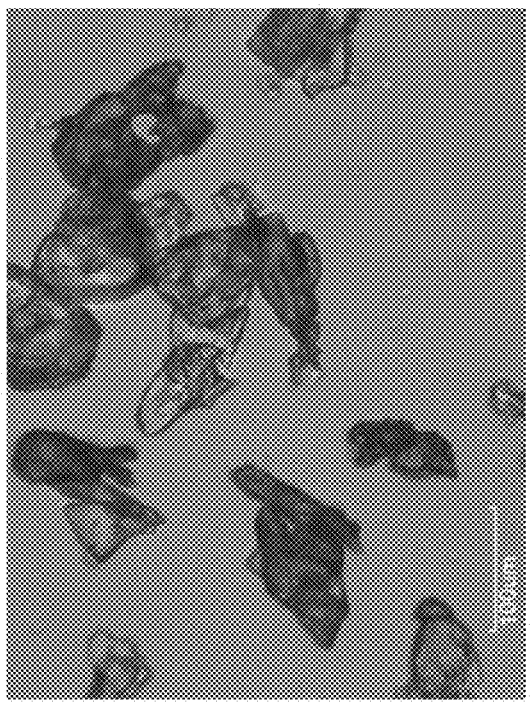
Figure 20

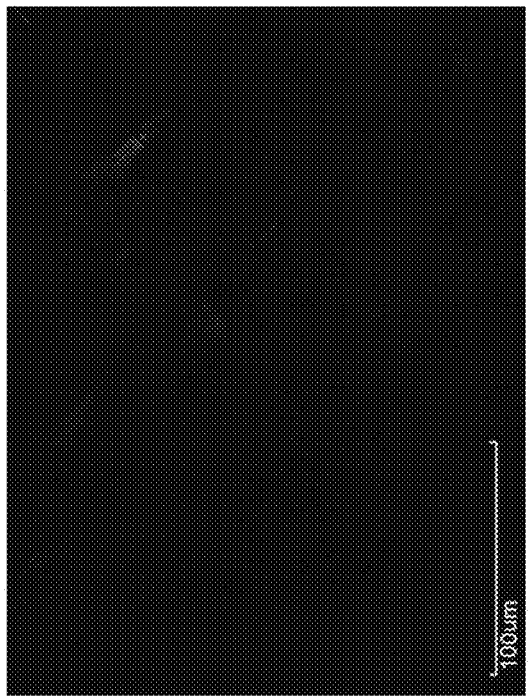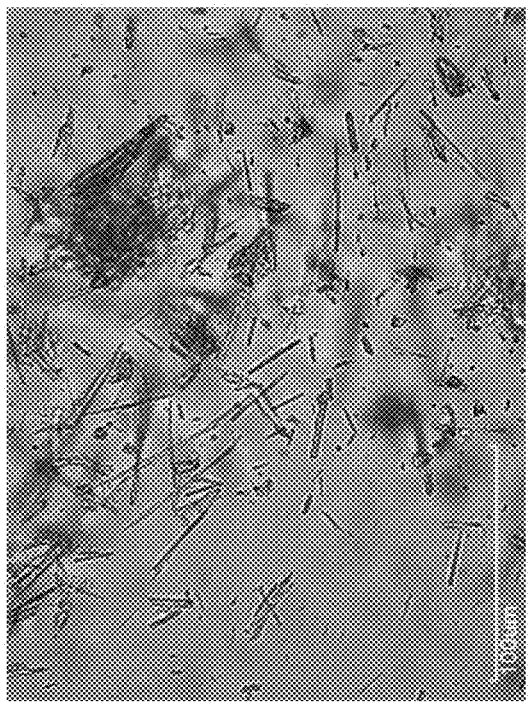
Figure 28

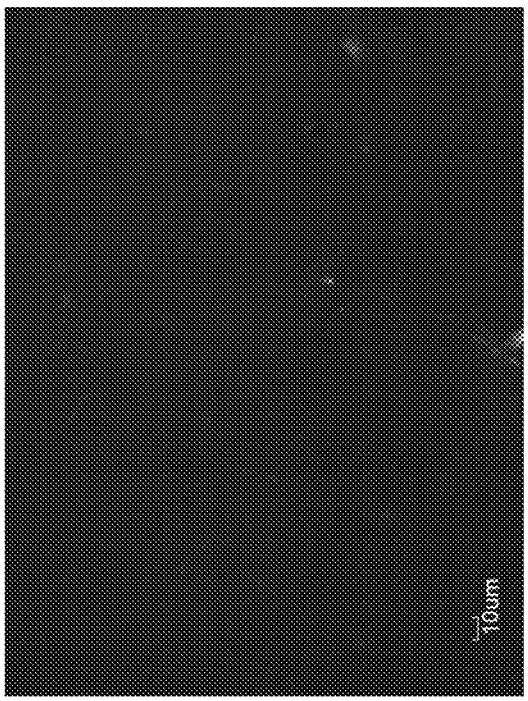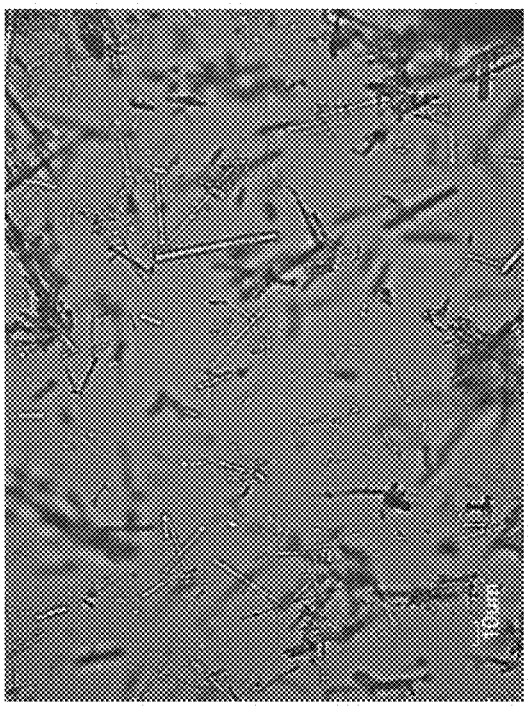
Figure 36

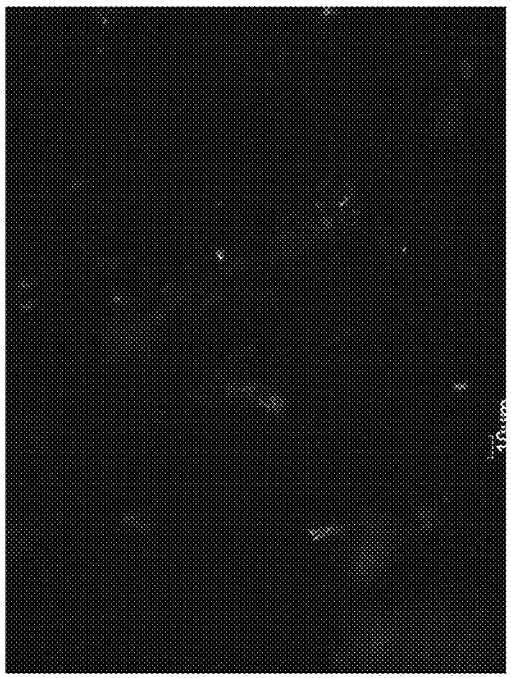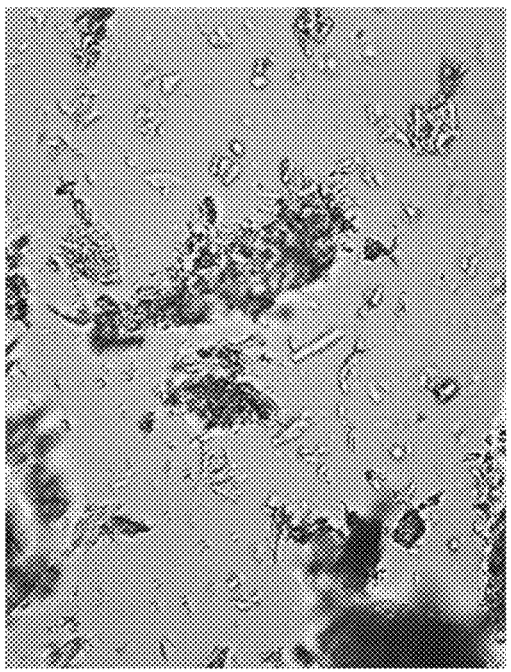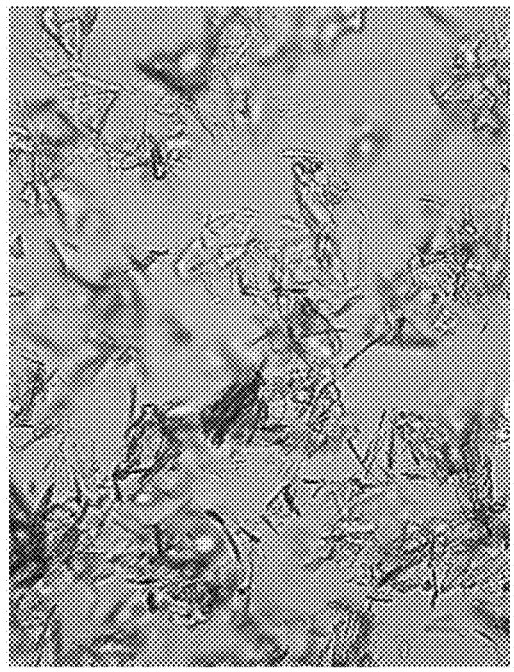
Figure 49

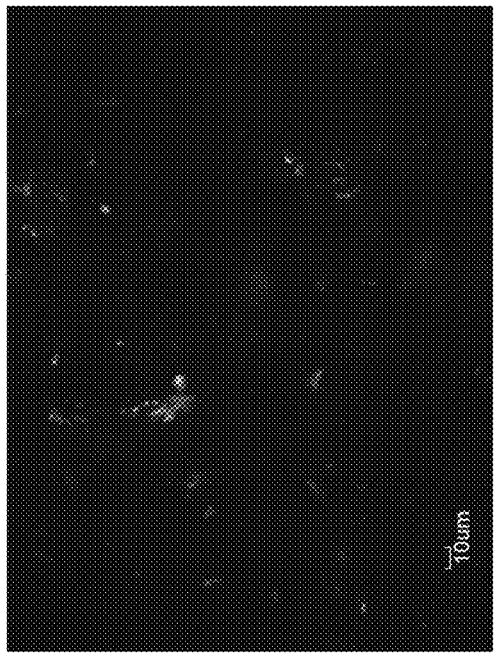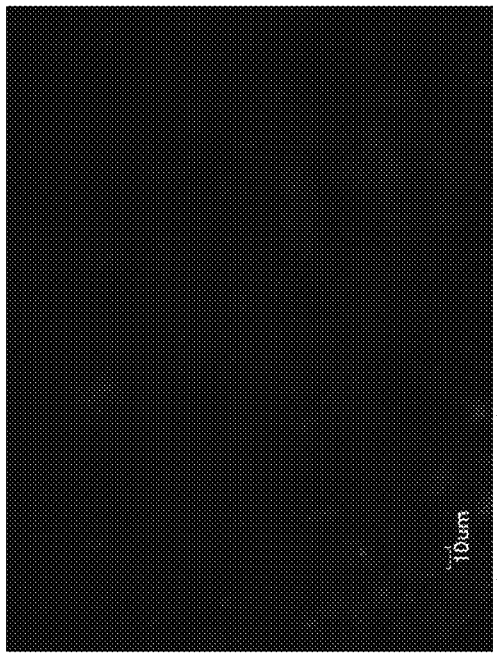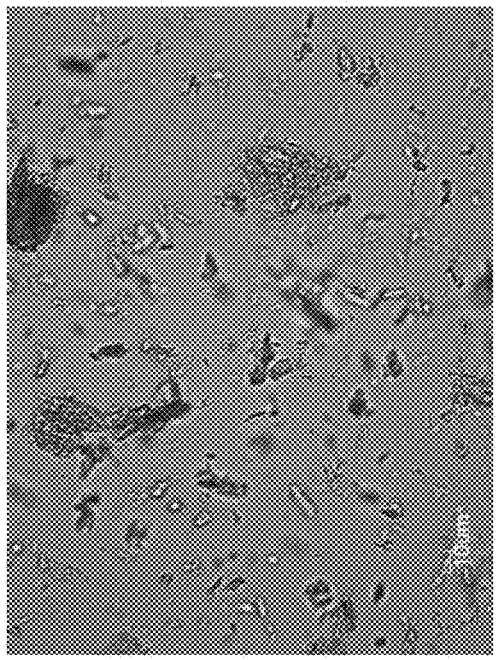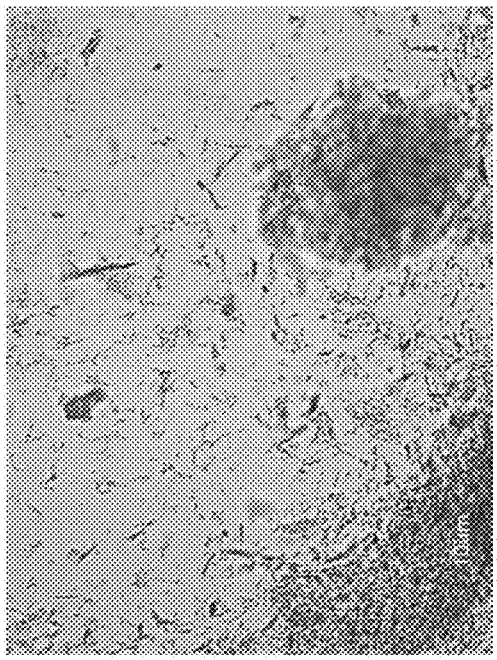
Figure 54

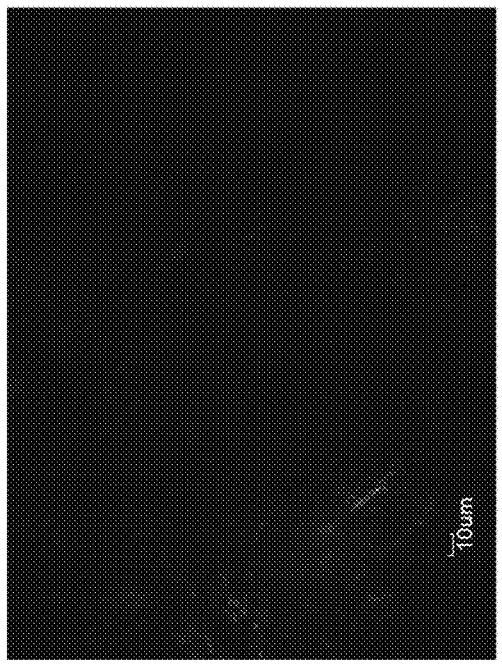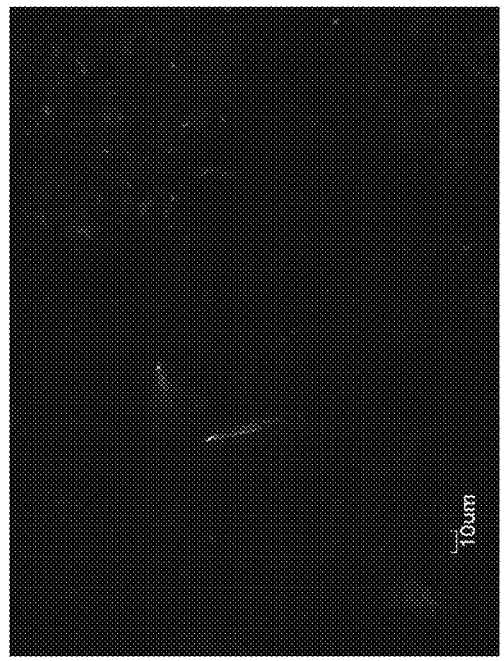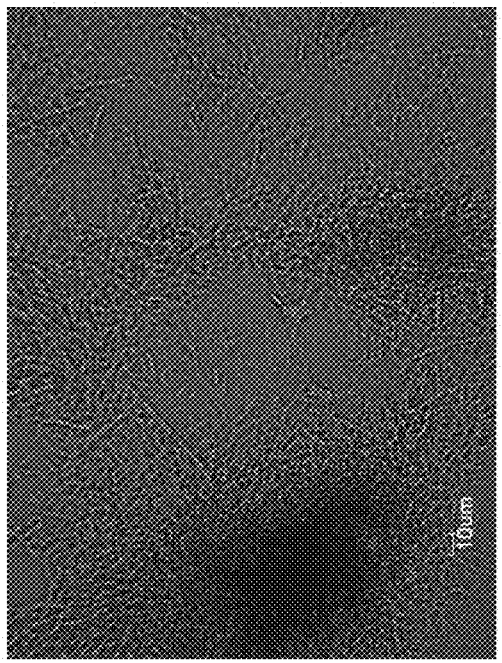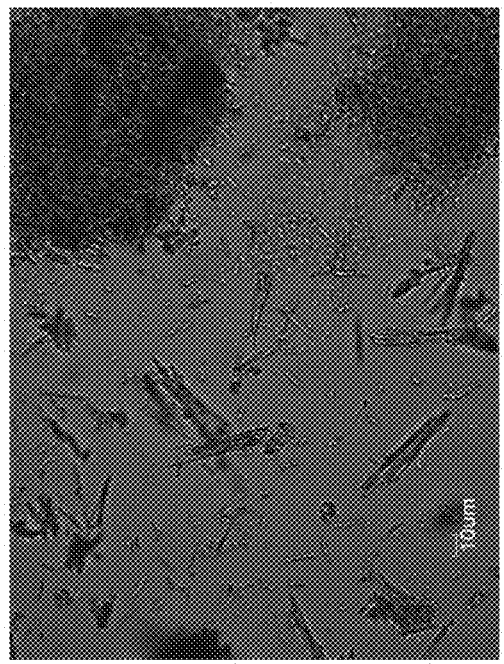
Figure 64B

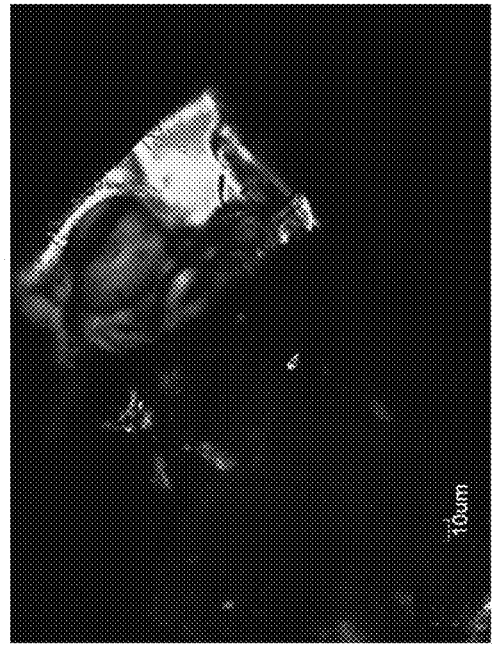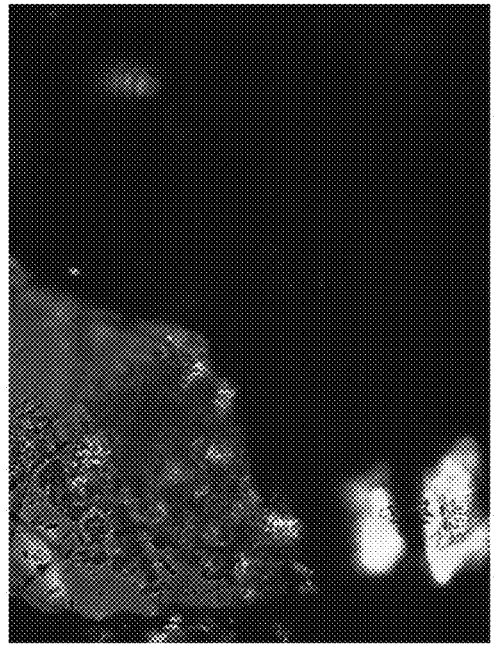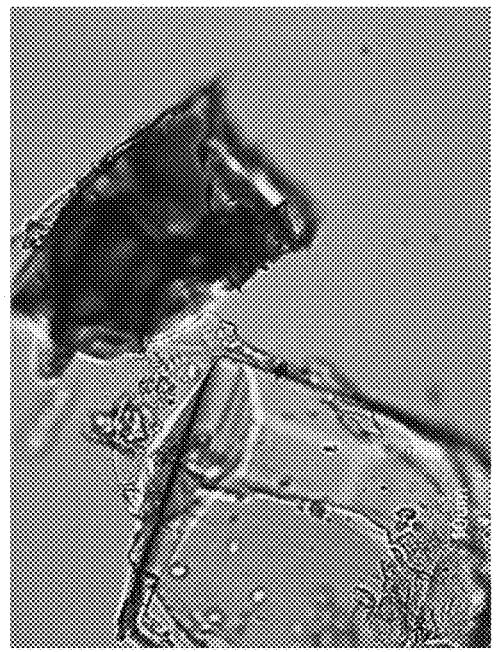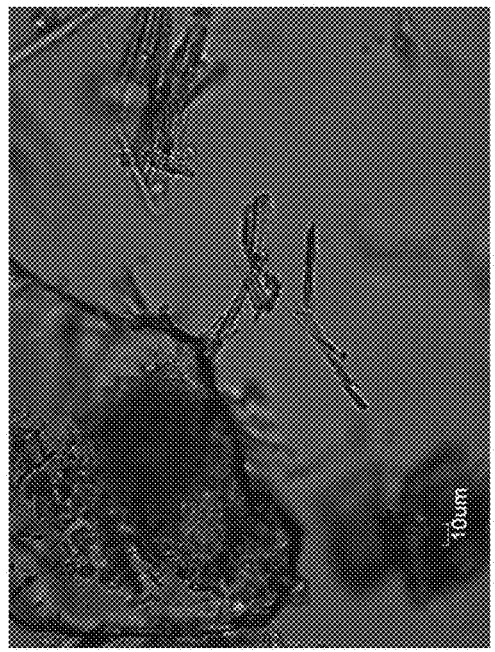
Figure 64F

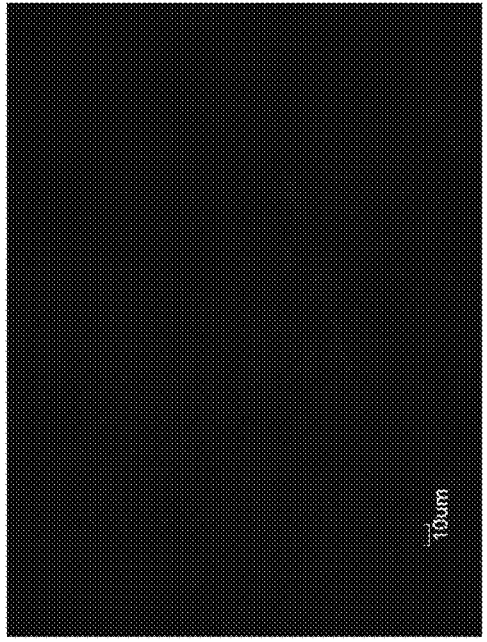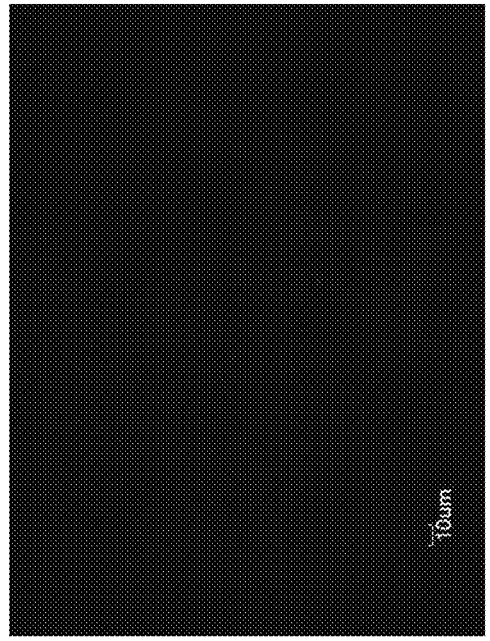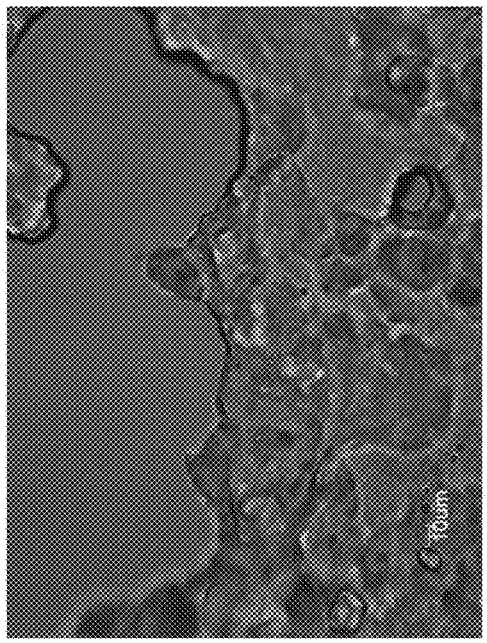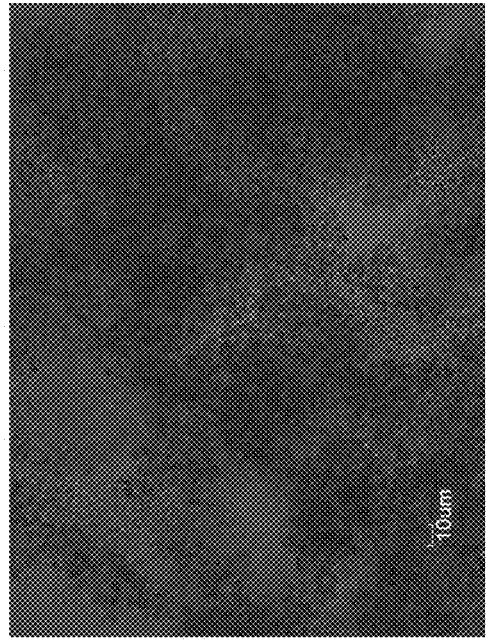
Figure 66C

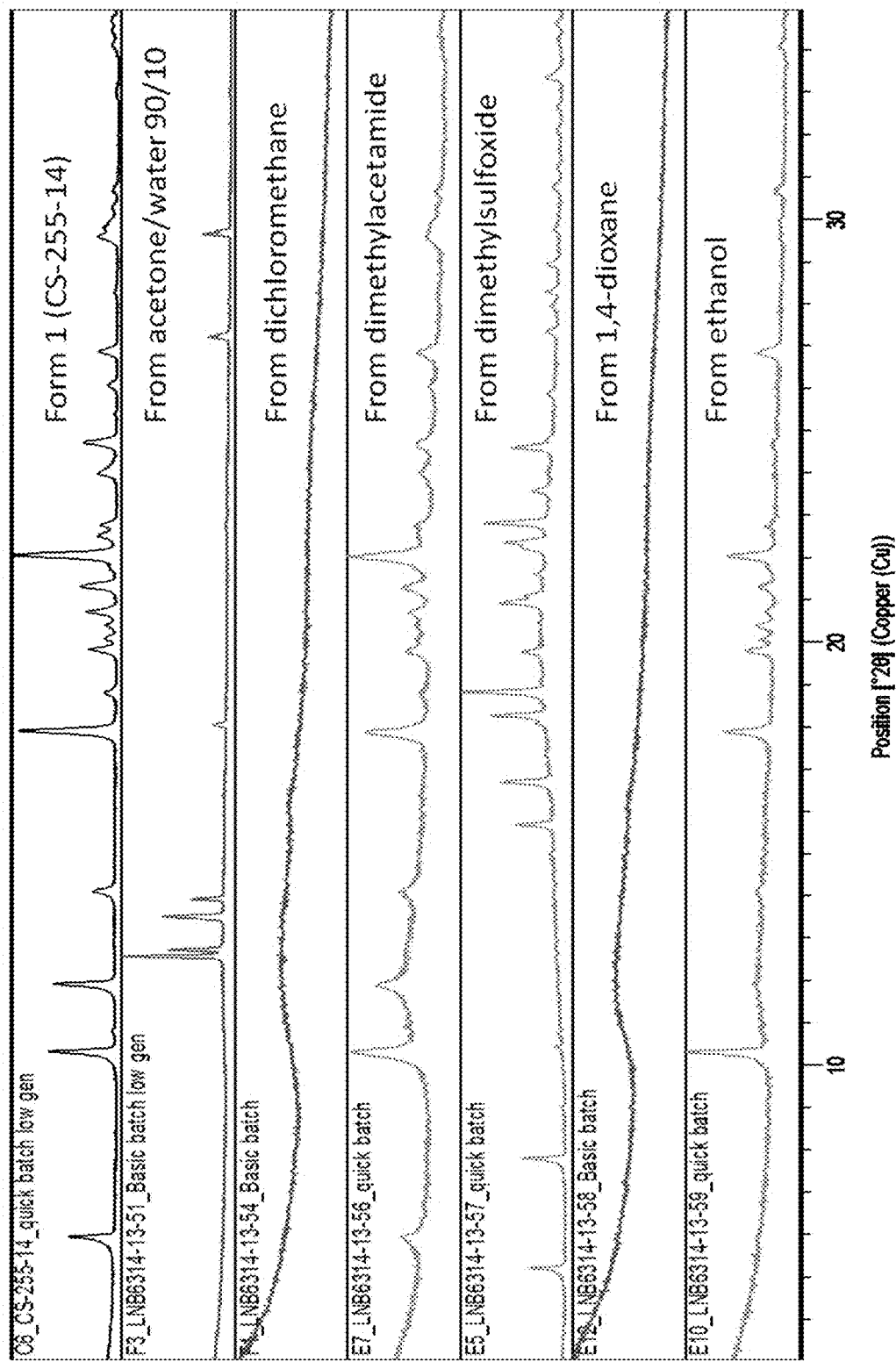

|  | Form 1 | Not enough solid (poor diffraction) | No solid |
|---|---|---|---|
|  |  | - |  |

| solvent | cooling 5°C | Cooling -20°C | anti-solvent |
|---|---|---|---|
| Acetic acid |  |  |  |
| Acetone |  |  |  |
| Acetone/H₂O 9/1 |  |  | - |
| Ethanol/acetone 5/5 |  |  |  |
| Acetonitrile |  |  |  |
| Dichloromethane |  |  |  |
| Diisopropyl ether |  |  |  |
| 1,4-Dioxane |  | , |  |
| Ethanol |  |  |  |
| Ethanol/H₂O 9/1 |  |  |  |
| Ethynol | , |  |  |
| Ethyl acetate | , | , |  |
| Methanol |  |  |  |
| Methylethyl ketone | , | , | , |
| Methylisobutyl ketone |  | , |  |
| 2-Methyl THF | , | , |  |
| 2-propanol | , | , |  |
| Tetrahydrofuran | , | , | , |
| Toluene | , |  | , |

Figure 68

CRYSTAL FORMS OF SIALIC ACID OR SALT OR SOLVATE THEREOF

CROSS REFERENCE TO RELATED APPLICATIONS

This application claims the benefit of U.S. Provisional Application No. 62/218,446, filed on Sep. 14, 2015, the entire contents of which are hereby incorporated by reference in their entirety for all purposes.

FIELD OF THE INVENTION

The present invention relates to crystalline forms of sialic acid, such as aceneuramic acid, and crystalline forms of the salts and/or solvates of sialic acid, processes of preparing thereof and the use thereof in a pharmaceutical composition containing thereof.

BACKGROUND OF THE INVENTION

Sialic acid (SA) is a sugar with a net negative charge; it is often present on terminating branches of N-glycans, O-glycans, and glucosphingolipids (gangliosides), and occasionally capping side chains of GPI anchors. Sialic acid modification of cell surface molecules plays a role in many biological phenomena such as protein structure stability, regulation of cell adhesion, and signal transduction. Sialic acid deficiency disorders such as GNE Myopathy, which is also known as Hereditary Inclusion Body Myopathy (HIBM), Distal Myopathy with Rimmed Vacuoles (DMRV) or Nonaka Myopathy are clinical diseases resulting from a reduction in sialic acid production.

Because the production of sialic acid is the key reason the mutation causes the disease, replacing a metabolite after the genetic block in the pathway could, in theory, alleviate symptoms of a sialic acid deficiency. Jay et al., Gene Reg. and Sys. Biology 3: 181-190 (2009). In practice, however, administering one or more compounds in the sialic acid biosynthetic pathway in vivo is a significant challenge. These compounds have extraordinarily rapid clearance rates and are excreted in the urine before they can be metabolized. Thus, release formulations of sialic acid, or a pharmaceutically acceptable salt, solvate, or ester thereof, has been developed and described in WO 2012/009474 and WO 2013/109906, the contents of which are hereby incorporated by reference.

Another aspect which is important in drug development is that active substances should have stable possible crystalline morphology for pharmaceutical quality medicinal formulations. Those skilled in the pharmaceutical arts understand that crystallization of an active pharmaceutical ingredient offers the best method for controlling important physiochemical qualities, such as stability, solubility, bioavailability, particle size, bulk density, flow properties, polymorphic content, and other properties. Thus, there is a need for crystalline forms of sialic acid and processes to produce such forms. These crystalline forms should be suitable for pharmaceutical use.

SUMMARY OF THE INVENTION

The present invention provides, among other things, sialic acid and a pharmaceutical acceptable salt and/or solvate thereof in various crystalline forms for treating a sialic acid deficiency.

In one aspect, the present invention provides a crystalline form of N-acetylneuraminic acid (NeuAc).

In one embodiment, a crystalline form of sialic acid is polymorphic Form 1. In another embodiment, the present invention provides a polymorphic Form 2. In another embodiment, the present invention provides a polymorphic Form 3. In another embodiment, the present invention provides polymorphic Form 4. In another embodiment, the present invention provides polymorphic Form 5. In one embodiment, polymorphic Forms 1-5 refer to a crystalline form of NeuAc.

In one embodiment, a crystalline form of NeuAc is a polymorphic Form 1. In some embodiment, Form 1 exhibits X-ray powder diffraction pattern comprising peaks at about 10.34±0.3; 17.91±0.3; and 22.06±0.3 degrees two-theta. In other embodiments, Form 1 exhibits an X-ray powder diffraction pattern further comprising peaks at about 5.95±0.3 and 11.93±0.3. In some embodiments, Form 1 exhibits an X-ray powder diffraction pattern comprising peaks at about 5.95±0.3; 10.34±0.3; 11.93±0.3; 14.12±0.3; and 17.91±0.3 degrees two-theta. In one embodiment, Form 1 further exhibits an X-ray powder diffraction pattern peaks at about 19.84±0.3; 20.72±0.3; 21.31±0.3; 22.06±0.3; 24.73±0.3; and/or 29.60±0.3 degrees two-theta. In another embodiment, Form 1 exhibits an X-ray powder diffraction pattern comprising three or more peaks at degree two-theta selected from the group consisting of: 5.95±0.3; 10.34±0.3; 11.93±0.3; 14.12±0.3; 17.91±0.3; 19.84±0.3; 20.72±0.3; 21.31±0.3; 22.06±0.3; 24.73±0.3; and 29.60±0.3. In one embodiment, Form 1 exhibits an X-ray powder diffraction pattern comprising five or more peaks at degree two-theta selected from the group consisting of: 5.95±0.3; 10.34±0.3; 11.93±0.3; 14.12±0.3; 17.91±0.3; 19.84±0.3; 20.72±0.3; 21.31±0.3; 22.06±0.3; 24.73±0.3; and 29.60±0.3. In some embodiments, Form 1 exhibits an X-ray powder diffraction pattern comprising five or more peaks at degree two-theta selected from Table 1.

In one embodiment, Form 1 exhibits a Differential Scanning calorimetry (DSC) thermogram having an endotherm with an onset of about 188.6° C.

In one embodiment, Form 1 is anhydrous.

In some embodiments, Form 1 has a chemical purity of about 98.5%; 98.6%; 98.7%; 98.8%; 98.9%; 99.0%; 99.1%; 99.2%; 99.3%; or higher.

In one embodiment, Form 1 has a polymorphic purity of about 50%, 60%, 70%, 80%, 90%, or 95% or higher. In another embodiment, Form 1 has a polymorphic purity of 95% or higher.

In some embodiments, Form 1 contains ethanol in an amount of about 1.0%; 0.9%; 0.8%; 0.7%; 0.6%; 0.5%; 0.4%; 0.3%; or less. In another embodiment, Form 1 contains acetic acid in an amount of about 1.0%; 0.9%; 0.8%; 0.7%; 0.6%; 0.5%; 0.4%; 0.3%; or less. In some embodiments, Form 1 contains N-acetyl-D-glucosamine in an amount of about 0.5%; 0.4%; 0.3%; 0.2%, or less.

In one embodiment, Form 1 is substantially pure from other polymorphic forms of NeuAc. In one embodiment, Form 1 contains polymorphic Form 2 of NeuAc in an amount of about 0.5%; 0.4%; 0.3%; 0.2%, or less. In other embodiments, Form 1 contains polymorphic Form 3 of NeuAc in an amount of about 0.5%; 0.4%; 0.3%; 0.2%, or less. In some embodiments, Form 1 contains polymorphic Form 4 of NeuAc in an amount of about 0.5%; 0.4%; 0.3%; 0.2%, or less.

In one embodiment, a crystalline form of NeuAc is a polymorphic Form 2. In some embodiments, Form 2 exhibits an X-ray powder diffraction pattern comprising peaks at about 5.79±0.3; 10.28±0.3; and 16.95±0.3 degrees two-theta. In one embodiment, Form 2 exhibits an X-ray powder diffraction pattern further comprising peaks at about 11.59±0.3; 20.37±0.3; and 20.68±0.3 degrees two-theta. In other embodiments, Form 2 exhibits an X-ray powder diffraction pattern comprising peaks at about 5.79±0.3; 10.28±0.3; 11.59±0.3; 16.95±0.3; and 18.87±0.3 degrees two-theta. In some embodiments, Form 2 further exhibits X-ray powder diffraction pattern peaks at about 20.68±0.3; and/or 24.24±0.3 degrees two-theta. In one embodiment, Form 2 exhibits an X-ray powder diffraction pattern comprising three or more peaks at degree two-theta selected from the group consisting of: 5.79±0.3; 10.28±0.3; 11.59±0.3; 16.95±0.3; 18.87±0.3; 20.37±0.3; 20.68±0.3; and 24.24±0.3. In another embodiment, Form 2 exhibits an X-ray powder diffraction pattern comprising five or more peaks at degree two-theta selected from the group consisting of: 5.79±0.3; 10.28±0.3; 11.59±0.3; 16.95±0.3; 18.87±0.3; 20.37±0.3; 20.68±0.3; and 24.24±0.3. In one embodiment, form 2 exhibits an X-ray powder diffraction pattern comprising five or more peaks at degree two-theta selected from Table 2.

In one embodiment, Form 2 exhibits a Differential Scanning calorimetry (DSC) thermogram an endotherm with an onset of about 181.0° C.

In one embodiment, Form 2 is anhydrous.

In one embodiment, Form 2 has a chemical purity of about 98.7%; 98.8%; 98.9%; 99.0%; 99.1%; 99.2%; 99.3%; 99.4%; 99.5%; or higher.

In another embodiment, Form 2 has a polymorphic purity of about 50%, 60%, 70%, 80%, 90%, or 95% or higher. In some embodiment, Form 2 has a polymorphic purity of 95% or higher.

In one embodiment, Form 2 is substantially pure from other polymorphic forms of NeuAc. In another embodiment, Form 2 contains polymorphic Form 3 of NeuAc in an amount of about 0.5%; 0.4%; 0.3%; 0.2%, or less.

In one embodiment, a crystalline form of NeuAc is a polymorphic Form 3. In some embodiment, Form 3 exhibits an X-ray powder diffraction pattern comprising peaks at about 10.42±0.3; 17.28±0.3; and 21.85±0.3 degrees two-theta. In one embodiment, Form 3 exhibits an X-ray powder diffraction pattern further comprising peaks at about 4.97±0.3; 20.05±0.3; and 19.58±0.3 degrees two-theta. In some embodiments, Form 3 exhibits an X-ray powder diffraction pattern comprising peaks at about 4.97±0.3; 9.95±0.3; 10.42±0.3; 14.94±0.3; and 17.28±0.3 degrees two-theta. In one embodiment, Form 3 further exhibits an X-ray powder diffraction peaks at about 19.58±0.3; 20.05±0.3; 21.85±0.3; 24.12±0.3; and/or 26.76±0.3 degrees two-theta. In one embodiment, Form 3 exhibits an X-ray powder diffraction pattern comprising three or more peaks at degree two-theta selected from the group consisting of: 4.97±0.3; 9.95±0.3; 10.42±0.3; 14.94±0.3; 17.28±0.3; 19.58±0.3; 20.05±0.3; 21.85±0.3; 24.12±0.3; and 26.76±0.3. In some embodiments, Form 3 exhibits an X-ray powder diffraction pattern comprising five or more peaks at degree two-theta selected from the group consisting of: 4.97±0.3; 9.95±0.3; 10.42±0.3; 14.94±0.3; 17.28±0.3; 19.58±0.3; 20.05±0.3; 21.85±0.3; 24.12±0.3; and 26.76±0.3. In a certain embodiment, Form 3 exhibits an X-ray powder diffraction pattern comprising five or more peaks at degree two-theta selected from Table 3.

In one embodiment, Form 3 exhibit a Differential Scanning calorimetry (DSC) thermogram two endotherms with onsets of about 107.0° C. and/or about 180.9° C.

In one embodiment, Form 3 is an acetic acid solvate of NeuAc. In another embodiment, Form 3 is a mono acetic acid solvate of NeuAc.

In one embodiment, Form 3 has a chemical purity of about 98.7%; 98.8%; 98.9%; 99.0%; 99.1%; 99.2%; 99.3%; 99.4%; 99.5%; or higher.

In another embodiment, Form 3 has a polymorphic purity of about 50%, 60%, 70%, 80%, 90%, or 95% or higher. In one embodiment, Form 3 has a polymorphic purity of 95% or higher.

In one embodiment, a crystalline form of NeuAc is a polymorphic Form 4. In some embodiment, Form 4 exhibits an X-ray powder diffraction pattern comprising peaks at about 16.73±0.3; 18.86±0.3; 22.42±0.3; and 22.86±0.3 degrees two-theta. In one embodiment, Form 4 exhibits an X-ray powder diffraction pattern further comprising peaks at about 5.20±0.3; 7.81±0.3; 18.30±0.3; and 20.94±0.3 degrees two-theta. In some embodiments, Form 4 exhibits an X-ray powder diffraction pattern comprising peaks at about 5.20±0.3; 7.81±0.3; 15.63±0.3; 16.73±0.3; 18.30±0.3, and 18.86±0.3 degrees two-theta. In another embodiment, Form 4 further exhibits X-ray powder diffraction pattern peaks at about 20.94±0.3; 22.42±0.3; and/or 24.61±0.3 degrees two-theta. In one embodiment, Form 4 exhibits an X-ray powder diffraction pattern comprising three or more peaks at degree two-theta selected from the group consisting of: 5.20±0.3; 7.81±0.3; 15.63±0.3; 16.73±0.3; 18.30±0.3; 18.86±0.3; 20.94±0.3; 22.42±0.3; and 24.61±0.3. In another embodiment, Form 4 exhibits an X-ray powder diffraction pattern comprising five or more peaks at degree two-theta selected from the group consisting of: 5.20±0.3; 7.81±0.3; 15.63±0.3; 16.73±0.3; 18.30±0.3; 18.86±0.3; 20.94±0.3; 22.42±0.3; and 24.61±0.3. In one embodiment, Form 4 exhibits an X-ray powder diffraction pattern comprising five or more peaks at degree two-theta selected from Table 4.

In one embodiment, Form 4 is a DMSO solvate of NeuAc. In another embodiment, Form 4 is a DMSO bis-solvate of NeuAc.

In one embodiment, Form 4 has a chemical purity of about 98.7%; 98.8%; 98.9%; 99.0%; 99.1%; 99.2%; 99.3%; 99.4%; 99.5%; or higher.

In one embodiment, Form 4 has a polymorphic purity of about 50%, 60%, 70%, 80%, 90%, or 95% or higher. In another embodiment, Form 4 has a polymorphic purity of 95% or higher.

In one embodiment, a crystalline form of NeuAc is a polymorphic Form 5. In some embodiment, Form 5 exhibits an X-ray powder diffraction pattern comprising peaks at about 12.90±0.3; 18.99±0.3; and 22.73±0.3 degrees two-theta. In one embodiment, Form 5 exhibits an X-ray powder diffraction pattern further comprising peaks at about 13.94±0.3; 24.67±0.3; and 24.75±0.3 degrees two-theta. In another embodiment, Form 5 exhibits an X-ray powder diffraction pattern comprising peaks at about 11.51±0.3; 12.90±0.3; 13.94±0.3; 18.13±0.3; and 18.99±0.3 degrees two-theta. In another embodiment, Form 5 further exhibits X-ray powder diffraction pattern peaks at about 19.25±0.3; 22.73±0.3; 23.86±0.3; 24.35±0.3; 24.75±0.3; and/or 25.90±0.3 degrees two-theta. In one embodiment, Form 5 exhibits an X-ray powder diffraction pattern comprising three or more peaks at degree two-theta selected from the group consisting of: 11.51±0.3; 12.90±0.3; 13.94±0.3; 18.13±0.3; 18.99±0.3; 19.25±0.3, 22.73±0.3, 23.86±0.3, 24.35±0.3, 24.67±0.3, 24.75±0.3, and 25.90±0.3. In some embodiments, Form 5 exhibits an X-ray powder diffraction pattern comprising five or more peaks at degree two-theta selected from the group consisting of: 11.51±0.3; 12.90±0.3;

13.94±0.3; 18.13±0.3; 18.99±0.3; 19.25±0.3, 22.73±0.3, 23.86±0.3, 24.35±0.3, 24.67±0.3; 24.75±0.3, and 25.90±0.3. In other embodiments, Form 5 exhibits an X-ray powder diffraction pattern comprising five or more peaks at degree two-theta selected from Table 5.

In one embodiment, Form 5 exhibit a Differential Scanning calorimetry (DSC) thermogram two endotherms with onsets of about 90.5° C. and about 192.0° C.

In one embodiment, Form 5 is a hydrate of NeuAc. In another embodiment, Form 5 is a dihydrate of NeuAc.

In one embodiment, Form 5 has a chemical purity of about 98.7%; 98.8%; 98.9%; 99.0%; 99.1%; 99.2%; 99.3%; 99.4%; 99.5%; or higher.

In another embodiment, Form 5 has a polymorphic purity of about 50%, 60%, 70%, 80%, 90%, or 95% or higher. In one embodiment, Form 5 has a polymorphic purity of 95% or higher.

In one embodiment, a crystalline form of NeuAc is present as a mixture of Form 1 and Form 5. In one embodiment, a crystalline form of NeuAc comprise polymorphic Form 1 and Form 5 in ratio of about 5:95 to about 95:5.

In one aspect, the present invention provides a composition comprising one or more crystalline forms of the present invention. In one embodiment, a dosage form is provided comprising one or more crystalline forms of the present disclosure. In one embodiment, the dosage form comprising a crystalline form of sialic acid is selected from capsules, tables, powders, suppositories, sachets, troches or lozenges. In one embodiment, the dosage form comprising a crystalline form of sialic acid is an oral unit dosage form.

In one embodiment, an oral dosage form, one or more crystalline forms of the present disclosure is present in an amount equivalent to about 100 mg to about 1000 mg of NeuAc. In another embodiment dosage form contains the one or more crystalline forms in an amount equivalent to about 325 mg or 500 mg of NeuAc.

In one embodiment of the present disclosure, a pharmaceutical composition comprising one or more crystalline forms of sialic acid and a pharmaceutically acceptable carrier is provided.

In one aspect, the present invention provides a method for treating a sialic acid deficiency comprising administering to a patient in need of such treatment a composition comprising one or more crystalline forms of the present invention. In one embodiment, the method of the present disclosure provides administering to a patient in need of such treatment a therapeutically effective amount of any one or more crystalline forms as disclosed herein.

In some embodiments, the sialic acid deficiency is a myopathy associated with sialic acid deficiency. In some embodiments, the myopathy associated with sialic acid deficiency is Hereditary Inclusion Body Myopathy (HIBM), Nonaka myopathy, and/or Distal Myopathy with Rimmed Vacuoles (DMRV).

In another embodiment of the present disclosure, process of preparing one or more crystalline forms of sialic acid is provided. In one embodiment, preparation of polymorphic Form 1 comprises first crystallization and a second crystallization. In one embodiment of the preparation of Form 1, the second crystallization uses acetone or water slurry. In another embodiment of the preparation of Form 1, the second crystallization does not use ethanol. In one embodiment of the preparation of Form 1, the second crystallization uses acetone/water slurry.

In one embodiment of the preparation of Form 1, polymorphic Form 2 is converted into Form 1. In another embodiment of the preparation of Form 2, Form 3 is converted into Form 1. In another embodiment of the preparation of Form 2, Form 4 is converted into Form 1.

BRIEF DESCRIPTION OF THE DRAWINGS

FIG. 20 are PLM images: non-polarised (left) and polarized (right) of polymorphic Form 5.

FIG. 28 is a PLM image of polymorphic Form 3 under a non-polarized lens (left) and a polarized lens (right).

FIG. 36 is a PLM image of polymorphic Form 2 under a non-polarized lens (left) and a polarized lens (right).

FIG. 49 includes PLM images under a non-polarized lens (left) and under a polarized lens (right) from temperature cycling experiments conducted in different solvent systems: acetic acid (top) and acetone (bottom).

FIG. 54 includes PLM images under a non-polarized lens (left) and under a polarized lens (right) from temperature cycling experiments conducted in different solvent systems: ethanol (top); ethanol/water 90/10 v/v (bottom).

FIG. 61E includes PLM images under a non-polarized lens (left) and a polarized lens (right) from evaporation experiments conducted in different solvent systems: methanol (top); 2-methyl THF (bottom).

FIG. 66C are PLM images under a non-polarized lens (left) and a polarized lens (right) from anti-solvent additions experiments conducted in different solvent systems: N-methyl-2-pyrrolidone with acetonitrile as anti-solvent (top); dimethylacetamide with acetonitrile as anti-solvent (bottom).

FIGS. 67A and 67B are XRPD diffractograms from anti-solvent addition experiments. When polymorphic Form 1 is identified the pattern is in orange, when polymorphic Form 4 is identified the pattern is in green, when polymorphic Form 5 is identified the pattern is in red and when no form is identified the pattern is in fuchsia.

FIG. 68 shows extra results from solvent having 10% NMP. Only one physical form was identified: polymorphic Form 1 was observed from adding acetonitrile as anti-solvent to the acetone/water/NMP mixture.

DETAILED DESCRIPTIONS OF THE INVENTION

Figure 1:
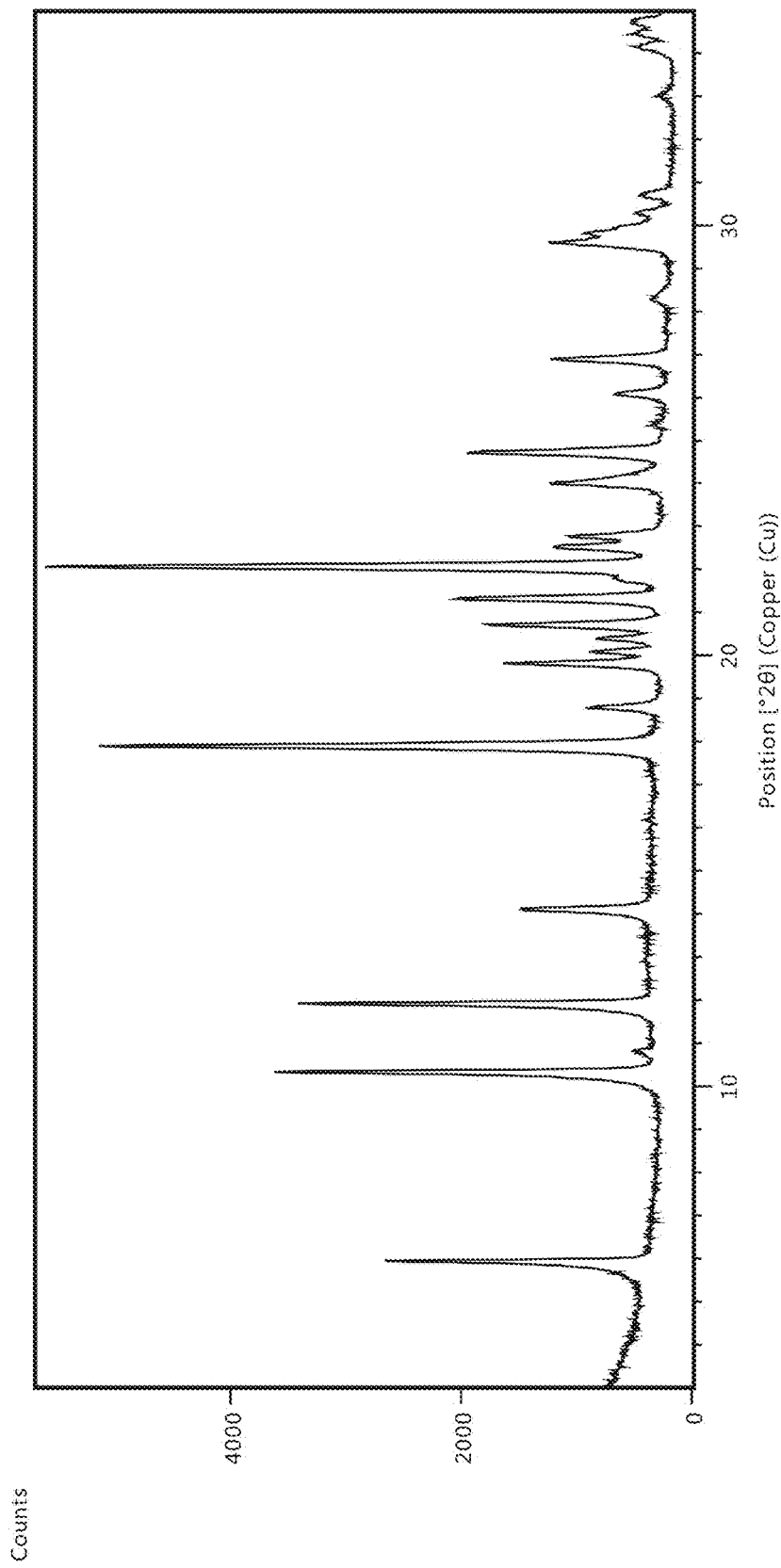
FIG. 1 shows a X-ray Powder Diffraction (XRPD) pattern of polymorphic Form 1.

The present invention relates to crystalline forms of sialic acid as well as crystalline forms of salts and/or solvates of sialic acid. These crystalline materials can be formulated into pharmaceutical compositions and used for substrate replacement and treatment to alleviate symptoms of a sialic acid deficiency in patients.

Definitions

It is to be understood that the terminology used herein is for the purpose of describing particular embodiments only and is not intended to be limiting.

Unless defined otherwise, all technical and scientific terms used herein have the same meaning as commonly understood to one of ordinary skill in the art to which the present application belongs. Although any methods and materials similar or equivalent to those described herein can be used in the practice or testing of the present application, representative methods and materials are herein described.

Following long-standing patent law convention, the terms "a", "an", and "the" refer to "one or more" when used in this application, including the claims. Thus, for example, reference to "a carrier" includes mixtures of one or more carriers, two or more carriers, and the like.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the present application. Generally the term "about", as used herein when referring to a measurable value such as an amount of weight, time, dose, etc. is meant to encompass in one example variations of ±15% or ±10%, in another example ±5%, in another example ±1%, and in yet another example ±0.1% from the specified amount, as such variations are appropriate to perform the disclosed method.

Polymorphism can be characterized as the ability of a compound to crystallize into different crystal forms, while maintaining the same chemical formula. A crystalline polymorph of a given drug substance is chemically identical to any other crystalline polymorph of that drug substance in containing the same atoms bonded to one another in the same way, but differs in its crystal forms, which can affect one or more physical properties, such as stability, solubility, melting point, bulk density, flow properties, bioavailability, etc.

The term "composition" denotes one or more substance in a physical form, such as solid, liquid, gas, or a mixture thereof. One example of composition is a pharmaceutical composition, i.e., a composition related to, prepared for, or used in medical treatment.

As used herein, "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

"Sialic acid", as used herein, is a generic term for the N- or O-substituted derivatives of neuraminic acid. In one particular embodiment, a type of sialic acid is N-acetylneuraminic acid (NeuAc), also known as aceneuramic acid.

"Salts" include derivatives of an active agent, wherein the active agent is modified by making acid or base addition salts thereof. Preferably, the salts are pharmaceutically acceptable salts. Such salts include, but are not limited to, pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Base addition salts include but are not limited to, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e. g., lysine and arginine dicyclohexylamine and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. Standard methods for the preparation of pharmaceutically acceptable salts and their formulations are well known in the art, and are disclosed in various references, including for example, "Remington: The Science and Practice of Pharmacy", A. Gennaro, ed., 20th edition, Lippincott, Williams & Wilkins, Philadelphia, Pa.

As used herein, "solvate" means a complex formed by solvation (the combination of solvent molecules with molecules or ions of the active agent of the present invention), or an aggregate that consists of a solute ion or molecule (the active agent of the present invention) with one or more solvent molecules. In the present invention, the preferred solvate is hydrate. Examples of hydrate include, but are not limited to, hemihydrate, monohydrate, dihydrate, trihydrate, hexahydrate, etc. It should be understood by one of ordinary skill in the art that the pharmaceutically acceptable salt of the present compound may also exist in a solvate form. The solvate is typically formed via hydration which is either part of the preparation of the present compound or through natural absorption of moisture by the anhydrous compound of the present invention. Solvates including hydrates may be consisting in stoichiometric ratios, for example, with two, three, four salt molecules per solvate or per hydrate molecule. Another possibility, for example, that two salt molecules are stoichiometric related to three, five, seven solvent or hydrate molecules. Solvents used for crystallization, such as alcohols, especially methanol and ethanol; aldehydes; ketones, especially acetone; esters, e.g. ethyl acetate; may be embedded in the crystal grating. Preferred are pharmaceutically acceptable solvents.

The term "substantially similar" as used herein means an analytical spectrum, such as XRD pattern, Raman spectroscopy, and etc., which resembles the reference spectrum to a great degree in both the peak locations and their intensity.

The terms "excipient", "carrier", and "vehicle" are used interchangeably throughout this application and denote a substance with which a compound of the present invention is administered.

"Therapeutically effective amount" means the amount of a crystalline form that, when administered to a patient for treating a disease or other undesirable medical condition, is sufficient to have a beneficial effect with respect to that disease or condition. The therapeutically effective amount will vary depending on the crystalline form, the disease or condition and its severity, and the age, weight, etc. of the patient to be treated. Determining the therapeutically effective amount of a given crystalline form is within the ordinary skill of the art and requires no more than routine experimentation.

Crystalline Materials

Provided herein are crystalline forms of sialic acid and crystalline forms of the salts and/or solvates of sialic acid. In some embodiments, the chemical purity of the crystalline forms is about 96.0%; 96.1%; 96.2%; 96.3%; 96.4%; 97.5, 96.6%, 96.7%; 96.8%; 96.9%; 97.0%; 97.1%; 97.2%; 97.3%; 97.4%; 97.5, 97.6%, 97.7%; 97.8%; 97.9%; 98.0%; 98.1%; 98.2%; 98.3%; 98.4%; 98.5, 98.6%, 98.7%; 98.8%; 98.9%; 99.0%; 99.1%; 99.2%; 99.3%; 99.4%; 99.5%; or higher. In some embodiments, the chemical purity of the crystalline forms of sialic acid and crystalline forms of the salts and/or solvates of sialic acid is about 98.5, 98.6%, 98.7%; 98.8%; 98.9%; 99.0%; 99.1%; 99.2%; 99.3%; 99.4%; 99.5%; or higher.

In some embodiments, the chemical purity of the crystalline forms of NeuAc is about 96.0%; 96.1%; 96.2%; 96.3%; 96.4%; 97.5, 96.6%, 96.7%; 96.8%; 96.9%; 97.0%; 97.1%; 97.2%; 97.3%; 97.4%; 97.5, 97.6%, 97.7%; 97.8%; 97.9%; 98.0%; 98.1%; 98.2%; 98.3%; 98.4%; 98.5, 98.6%, 98.7%; 98.8%; 98.9%; 99.0%; 99.1%; 99.2%; 99.3%; 99.4%; 99.5%; or higher. In some embodiment, the chemical purity of the crystalline form of NeuAc is about 98.5, 98.6%, 98.7%; 98.8%; 98.9%; 99.0%; 99.1%; 99.2%; 99.3%; 99.4%; 99.5%; or higher.

In one embodiment, a crystalline form of N-acetylneuraminic acid (NeuAc) comprises 0.20% or less, 0.15% or less, 0.10% or less, or 0.05% or less of 5-(1-acetamido-2, 3,4,5-tetrahydroxypentyl)-2-oxo-2,5-dihydrofuran-3-yl-6-acetamido-4,7-dihydroxy-3-(hydroxymethyl)-2,9-dioxabicyclo[3.3.1]nonane-1-carboxylate. In one embodiment, a crystalline form of N-acetylneuraminic acid (NeuAc) comprises 0.10% or less of 5-(1-acetamido-2,3,4,5-tetrahydroxypentyl)-2-oxo-2,5-dihydrofuran-3-yl-6-acetamido-4, 7-dihydroxy-3-(hydroxymethyoxabicyclo[3.3.1]nonane-1-carboxylate.

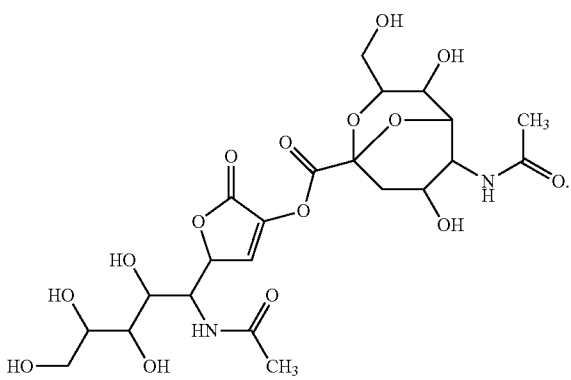 [SMILES: CC(=O)NC(C1C=C(OC(=O)C23CC(O)C(NC(C)=O)C(O2)C(O)C(CO)O3)C(=O)O1)C(O)C(O)C(O)CO]

In one embodiment, a crystalline form of N-acetylneuraminic acid (NeuAc) comprises 0.20% or less, 0.15% or less, 0.10% or less, or 0.05% or less of N-(1-{4-[2-(1-acetamido-2,3,4,5-tetrahydroxypentyl)-4-hydroxy-5-oxo-2,5-dihydrofuran-3-yl]-5-oxo-2,5-dihydrofuran-2-yl}-2,3,4,5-tetrahydroxypentyl)acetamide. In one embodiment, a crystalline form of N-acetylneuraminic acid (NeuAc) comprises 0.10% or less of N-(1-{4-[2-(1-acetamido-2,3,4,5-tetrahydroxypentyl)-4-hydroxy-5-oxo-2,5-dihydrofuran-3-yl]-5-oxo-2,5-dihydrofuran-2-yl}-2,3,4,5-tetrahydroxypentyl)acetamide.

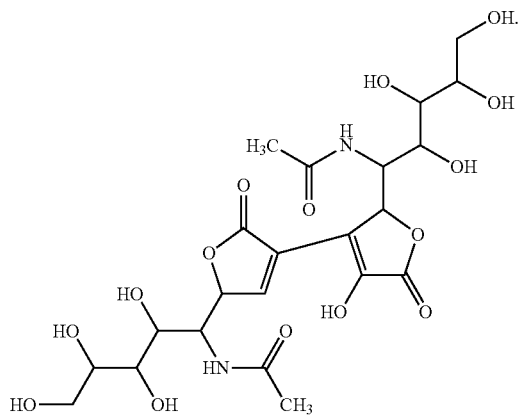 [SMILES: CC(=O)NC(C1C=C(C2=C(O)C(=O)OC2C(NC(C)=O)C(O)C(O)C(O)CO)C(=O)O1)C(O)C(O)C(O)CO]

In one embodiment, a crystalline form of N-acetylneuraminic acid (NeuAc) comprises 0.40% or less, 0.30% or less, 0.20% or less, 0.15% or less, 0.10% or less, or 0.05% or less of 5-acetamido-2,4,6,7-tetrahydroxy-8-(hydroxymethyl)oxocane-2-carboxylic acid. In one embodiment, a crystalline form of N-acetylneuraminic acid (NeuAc) comprises 0.20% or less of 5-acetamido-2,4,6,7-tetrahydroxy-8-(hydroxymethyl)oxocane-2-carboxylic acid.

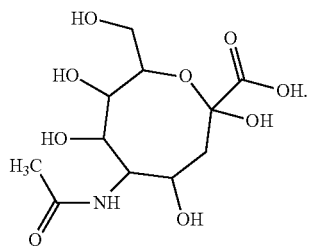 [SMILES: CC(=O)NC1C(O)CC(O)(C(=O)O)OC(CO)C(O)C1O]

In one embodiment, a crystalline form of N-acetylneuraminic acid (NeuAc) comprises 0.20% or less, 0.15% or less, 0.10% or less, or 0.05% or less of N-acetyl mannosamine. In one embodiment, a crystalline form of N-acetylneuraminic acid (NeuAc) comprises 0.10% or less of N-acetyl mannosamine.

In one embodiment, a crystalline form of N-acetylneuraminic acid (NeuAc) comprises 0.20% or less, 0.15% or less, 0.10% or less, or 0.05% or less of N-acetyl glucosamine. In one embodiment, a crystalline form of N-acetylneuraminic acid (NeuAc) comprises 0.10% or less of N-acetyl glucosamine.

In one embodiment, a crystalline form of N-acetylneuraminic acid (NeuAc) comprises 0.40% or less, 0.30% or less, 0.20% or less, 0.15% or less, 0.10% or less, or 0.05% or less of a combination of N-acetyl mannosamine and N-acetyl glucosamine. In one embodiment, a crystalline form of N-acetylneuraminic acid (NeuAc) comprises 0.20% or less of a combination of N-acetyl mannosamine and N-acetyl glucosamine.

In one embodiment, a crystalline form of N-acetylneuraminic acid (NeuAc) comprises 0.20% or less, 0.15% or less, 0.10% or less, or 0.05% or less of pyruvic acid. In one embodiment, a crystalline form of N-acetylneuraminic acid (NeuAc) comprises 0.10% or less of pyruvic acid.

In one embodiment, a crystalline form of N-acetylneuraminic acid (NeuAc) comprises 0.60% or less, 0.50% or less, 0.40% or less, 0.30% or less, 0.20% or less, 0.15% or less, 0.10% or less, or 0.05% or less of 2-[3-(6-carboxy-3-acetamido-4,6-dihydroxyoxan-2-yl)-2,3-dihydroxypropoxy]-5-acetamido-4-hydroxy-6-(1,2,3-trihydroxypropyl)oxane-2-carboxylic acid. In one embodiment, a crystalline form of N-acetylneuraminic acid (NeuAc) comprises 0.30% or less of 2-[3-(6-carboxy-3-acetamido-4,6-dihydroxyoxan-2-yl)-2,3-dihydroxypropoxy]-5-acetamido-4-hydroxy-6-(1,2,3-trihydroxypropyl)oxane-2-carboxylic acid.

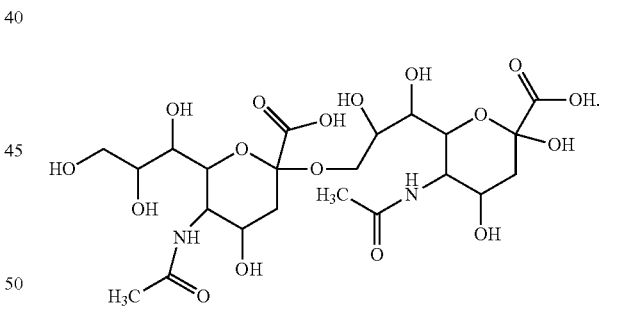

In one embodiment, a crystalline form of N-acetylneuraminic acid (NeuAc) comprises 0.40% or less, 0.30% or less, 0.20% or less, 0.15% or less, 0.10% or less, or 0.05% or less of a combination of N-[(1R)-4-(1,2-dihydroxyethyl)-1,7-dihydroxy-2-oxo-3,9-dioxabicyclo[3.3.1]nonan-6-yl]acetamide and N-[2,3,4,5-tetrahydroxy-1-(4-hydroxy-5-oxo-2,5-dihydrofuran-2-yl)pentyl]acetamide. In one embodiment, a crystalline form of N-acetylneuraminic acid (NeuAc) comprises 0.20% or less of a combination of N-[(1R)-4-(1,2-dihydroxyethyl)-1,7-dihydroxy-2-oxo-3,9-dioxabicyclo[3.3.1]nonan-6-yl]acetamide (Impurity Peak 3a) and N-[2,3,4,5-tetrahydroxy-1-(4-hydroxy-5-oxo-2,5-dihydrofuran-2-yl)pentyl]acetamide.

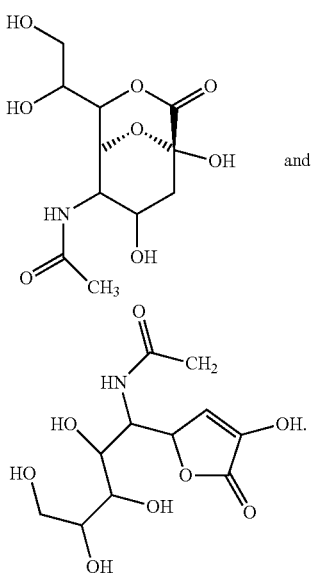

In one embodiment, a crystalline form of NeuAc comprises 0.50% or less, 0.40% or less, 0.30% or less, 0.20% or less, 0.15% or less, 0.10% or less, or 0.05% or less of total organic impurities. In some embodiments, organic impurities do not include heavy metals, solvents, or microbials. In one embodiment, a crystalline form of NeuAc comprises 0.15% or less of total organic impurities.

In one embodiment, a crystalline form of NeuAc comprises 2.0 ppm or less, 1.5 ppm or less, 1.0 ppm or less, 0.5 ppm or less, 0.25 ppm or less, or 0.10 ppm or less of a heavy metal element selected from As, Hg, Pb, or Cd.

In one embodiment, a crystalline form of NeuAc comprises 10,000 ppm or less, 8,000 ppm or less, 6,000 ppm or less, 5,000 ppm or less, 4,000 ppm or less, 3,000 ppm or less, or 2,000 ppm or less of one type of solvent. Solvent may be ethanol, acetone, ethyl acetate, or acetic acid.

In one embodiment, a crystalline form of NeuAc comprises 10% or less, 9% or less, 8% or less, 7% or less, 6% or less, 5% or less, 4% or less, 3% or less, 2% or less, or 1% or less water. In one embodiment, a crystalline form of NeuAc comprises 2% or less water. In one embodiment, the water content in a crystalline form of NeuAc is determined by Karl Fischer titration.

In one embodiment, a crystalline form of N-acetylneuraminic acid (NeuAc) is polymorphic Form 1. In another embodiment, the present invention provides a polymorphic Form 2 of N-acetylneuraminic acid (NeuAc). In another embodiment, the present invention provides a polymorphic Form 3 of N-acetylneuraminic acid (NeuAc). In another embodiment, the present invention provides polymorphic Form 4 of N-acetylneuraminic acid (NeuAc). In another embodiment, the present invention provides polymorphic Form 5 of N-acetylneuraminic acid (NeuAc).

In one embodiment, the crystalline forms of NeuAc may have different morphpologies, e.g., shapes of the crystalline form. In another embodiment, one type of polymorphic form of NeuAc may be observed to have different morphologies, for example, as shown under a polarized light microscopy. That is, a particular crystalline morphology of NeuAc does not necessarily imply the presence of a particular polymorphic form, e.g., Form 1, Form 2, Form 3, Form 4, and/or Form 5. Further, the morphology of a particular crystalline form of NeuAc may not imply a specific purity level of Form 1, Form 2, Form 3, Form 4, and/or Form 5.

In one embodiment, the crystalline form of NeuAc may comprise of a mixture of one or more polymorphic forms. In one embodiment, the crystalline form of NeuAc may comprise a substantially pure form of one polymophic type. In one embodiment, the crystalline form of NeuAc may comprise over about 99.9%, about 99.8%, about 99.7%, about 99.6%, about 99.5%, about 99.4%, about 99.3%, about 99.2%, about 99.1%, or about 99.0% of one polymorph type. In another embodiment, the crystalline form of NeuAc may comprise over about 99%, 98%, 97%, 96%, 95%, 94%, 93%, 92%, 91%, or 90% of one polymorph type. In some embodiments, the crystalline form of NeuAc may comprise over about 90%, 85%, 80%, 75%, 70%, 65%, 60%, 55%, 50%, 45%, or 40% of one polymorph of Compound. As used herein "polymorphic purity" refers to purity of a crystalline form with respect to one specified polymorphic form. For example, 98% polymorphic purity of Form 1 indicates that there are less than 2% of combination of all other forms, such as Form 2, Form 3, Form 4, and Form 5.

In other embodiments, polymorphic Form 1 of NeuAc has a polymorphic purity of at least about 99.9%, about 99.8%, about 99.7%, about 99.6%, about 99.5%, about 99.4%, about 99.3%, about 99.2%, about 99.1%, about 99.0%, about 98%, about 97%, about 96%, about 95%, about 94%, about 93%, about 92%, about 91%, about 90%, about 85%, about 80%, about 75%, about 70%, about 65%, about 60%, about 55% or about 50%.

In one embodiment, polymorphic Form 1 of NeuAc may comprise about 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 25%, 30%, 35%, 40%, 45% or 50% of each of Form 2, Form 3, Form 4, or Form 5 of a crystalline form of NeuAc.

In other embodiments, polymorphic Form 2 of NeuAc has a polymorphic purity of at least about 99.9%, about 99.8%, about 99.7%, about 99.6%, about 99.5%, about 99.4%, about 99.3%, about 99.2%, about 99.1%, about 99.0%, about 98%, about 97%, about 96%, about 95%, about 94%, about 93%, about 92%, about 91%, about 90%, about 85%, about 80%, about 75%, about 70%, about 65%, about 60%, about 55% or about 50%.

In one embodiment, polymorphic Form 2 of NeuAc may comprise about 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 25%, 30%, 35%, 40%, 45% or 50% of each of Form 1, Form 3, Form 4, or Form 5 of a crystalline form of NeuAc.

In other embodiments, polymorphic Form 3 of NeuAc has a polymorphic purity of at least about 99.9%, about 99.8%, about 99.7%, about 99.6%, about 99.5%, about 99.4%, about 99.3%, about 99.2%, about 99.1%, about 99.0%, about 98%, about 97%, about 96%, about 95%, about 94%, about 93%, about 92%, about 91%, about 90%, about 85%, about 80%, about 75%, about 70%, about 65%, about 60%, about 55% or about 50%.

In one embodiment, polymorphic Form 3 of NeuAc may comprise about 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 25%, 30%, 35%, 40%, 45% or 50% of each of Form 1, Form 2, Form 4, or Form 5 of a crystalline form of NeuAc.

In other embodiments, polymorphic Form 4 of NeuAc has a polymorphic purity of at least about 99.9%, about 99.8%, about 99.7%, about 99.6%, about 99.5%, about 99.4%, about 99.3%, about 99.2%, about 99.1%, about 99.0%, about 98%, about 97%, about 96%, about 95%, about 94%, about 93%, about 92%, about 91%, about 90%, about 85%, about 80%, about 75%, about 70%, about 65%, about 60%, about 55% or about 50%.

In one embodiment, polymorphic Form 4 of NeuAc may comprise about 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 25%, 30%, 35%, 40%, 45% or 50% of each of Form 1, Form 2, Form 3, or Form 5 of a crystalline form of NeuAc.

In other embodiments, polymorphic Form 5 of NeuAc has a polymorphic purity of at least about 99.9%, about 99.8%, about 99.7%, about 99.6%, about 99.5%, about 99.4%, about 99.3%, about 99.2%, about 99.1%, about 99.0%, about 98%, about 97%, about 96%, about 95%, about 94%, about 93%, about 92%, about 91%, about 90%, about 85%, about 80%, about 75%, about 70%, about 65%, about 60%, about 55% or about 50%.

In one embodiment, polymorphic Form 5 of NeuAc may comprise about 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 25%, 30%, 35%, 40%, 45% or 50% of each of Form 2, Form 3, or Form 4 of a crystalline form of NeuAc.

In one embodiment, the crystalline forms are characterized by the interlattice plane intervals determined by an X-ray powder diffraction pattern (XRPD). The spectrum of XRPD is typically represented by a diagram plotting the intensity of the peaks versus the location of the peaks, i.e., diffraction angle 2θ (two-theta) in degrees. The intensities are often given in parenthesis with the following abbreviations: very strong=vst; strong=st; medium=m; weak=w; and very weak=vw. The characteristic peaks of a given XRPD can be selected according to the peak locations and their relative intensity to conveniently distinguish this crystalline structure from others.

Those skilled in the art recognize that the measurements of the XRPD peak locations and/or intensity for a given crystalline form of the same compound will vary within a margin of error. The values of degree 2θ allow appropriate error margins. Typically, the error margins are represented by "±". For example, the degree 2θ of about "8.716±0.3" denotes a range from about 8.716+0.3, i.e., to 9.016, to about 8.716−0.3, i.e., about 8.416. Depending on the sample preparation techniques, the calibration techniques applied to the instruments, human operational variation, and etc, those skilled in the art recognize that the appropriate error of margins for a XRPD can be ±0.5; ±0.4; ±0.3; ±0.2; ±0.1; ±0.05; or less.

Additional details of the methods and equipment used for the XRPD analysis are described in the Examples section.

Figure 75:
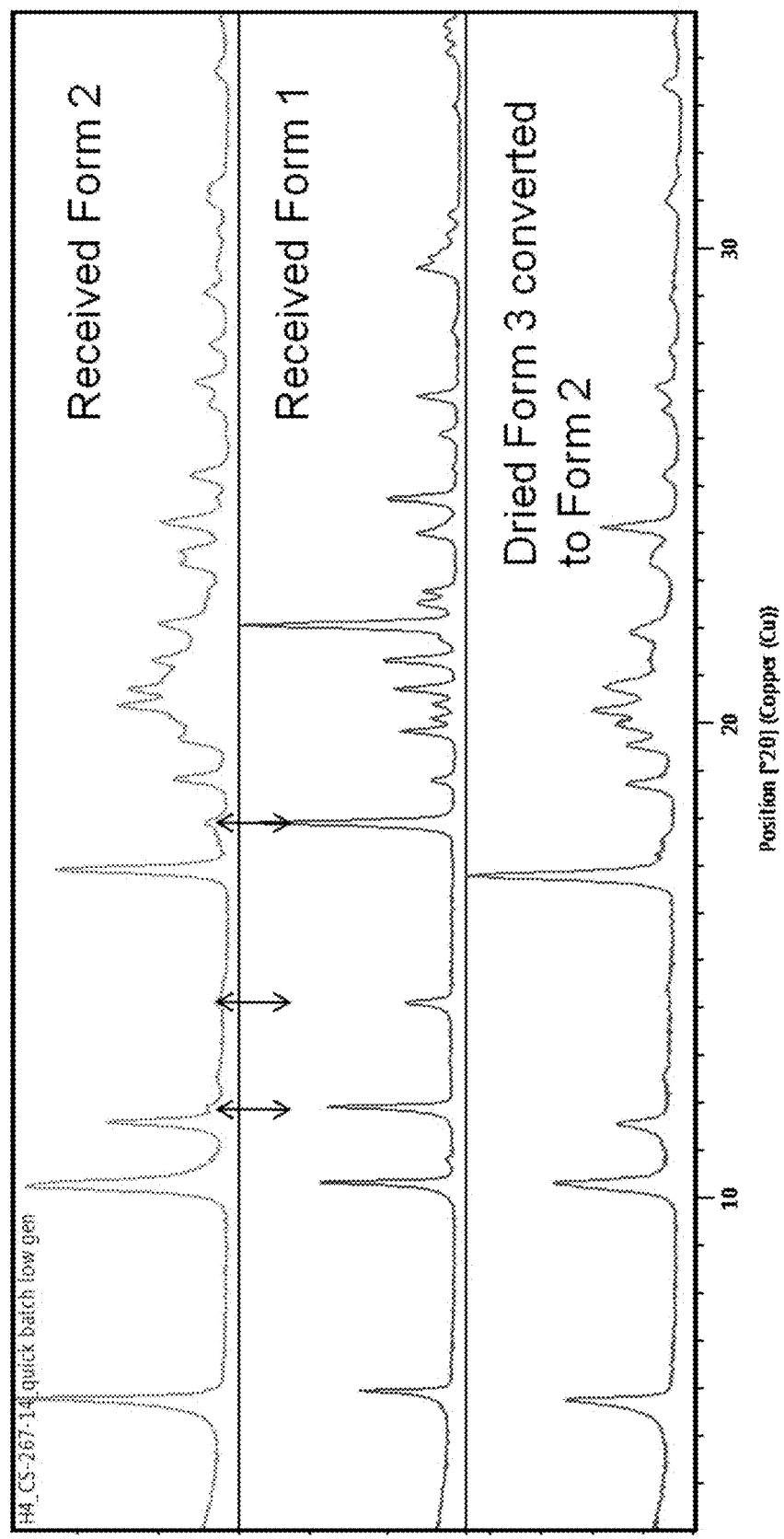
FIG. 75 are stacked diffractograms of an embodiment of Form 2 (green), Form 1 (blue) and Form 2 (prepared from dried Form 3). Arrows show traces of Form 1 in Form 2. An embodiment of Form 2 corresponded predominantly with the prepared Form 2, however traces of Form 1 are also present in the embodiment of Form 2.

In some embodiments XRPD may be useful in identifying whether a crystalline form of NeuAc comprises more than one polymorphic form. For example, FIG. 75 shows traces of Form 1 in Form 2 as indicated by the arrow.

Figure 80:
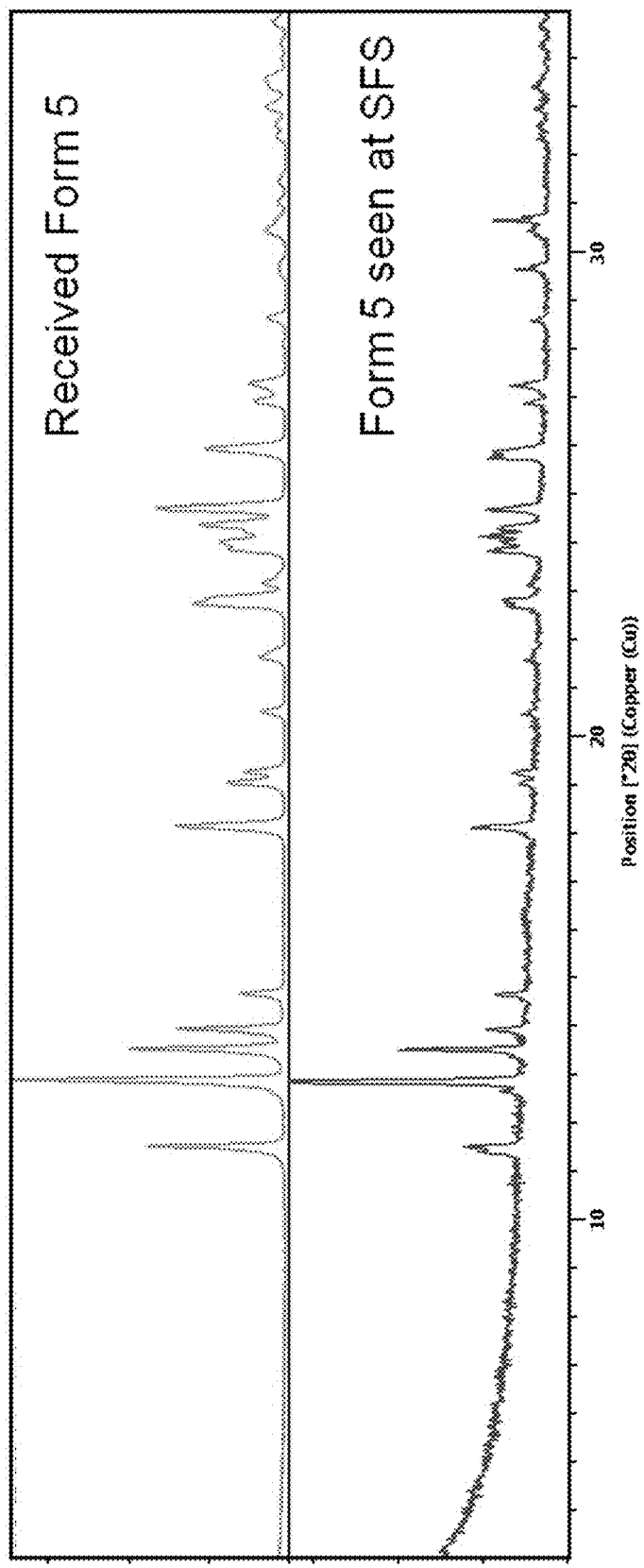
FIG. 80 is XRPD of an embodiment of Form 5 (green) and produced Form 5 (blue). An embodiment of Form 5 is consistent with produced Form 5.

In another embodiment, XRPD may be useful in identifying that two different lots of a crystalline form comprise the same or different polymorphic forms (FIG. 80).

In one embodiment, the crystalline forms are characterized by Raman spectroscopy. The Raman spectrum is typically represented by a diagram plotting the Raman intensity of the peaks versus the Raman shift of the peaks. The "peaks" of Raman spectroscopy are also known as "absorption bands". The intensities are often given in parenthesis with the following abbreviations: strong=st; medium=m; and weak=w. The characteristic peaks of a given Raman spectrum can be selected according to the peak locations and their relative intensity to conveniently distinguish this crystalline structure from others.

Those skilled in the art recognize that the measurements of the Raman peak shifts and/or intensity for a given crystalline form of the same compound will vary within a margin of error. The values of peak shift, expressed in reciprocal wave numbers ($cm^{-1}$), allow appropriate error margins. Typically, the error margins are represented by "±". For example, the Raman shift of about "1310±10" denotes a range from about 1310+10, i.e., about 1320, to about 1310−10, i.e., about 1300. Depending on the sample preparation techniques, the calibration techniques applied to the instruments, human operational variations, and etc, those skilled in the art recognize that the appropriate error of margins for a Raman shift can be ±12; ±10; ±8; ±5; ±3; ±1; or less.

In one embodiment, the crystalline forms are characterized by Differential Scanning calorimetry (DSC). The DSC thermogram is typically expressed by a diagram plotting the normalized heat flow in units of Watts/gram ("W/g") versus the measured sample temperature in degree C. The DSC thermogram is usually evaluated for extrapolated onset and end (outset) temperatures, peak temperature, and heat of fusion. The single maximum value of a DSV thermogram is often used as the characteristic peak to distinguish this crystalline structure from others.

Those skilled in the art recognize that the measurements of the DSC thermogram for a given crystalline form of the same compound will vary within a margin of error. The values of a single maximum value, expressed in degree C., allow appropriate error margins. Typically, the error margins are represented by "±". For example, the single maximum value of about "53.09±2.0" denotes a range from about 53.09+2, i.e., about 55.09, to about 53.09-2, i.e., about 51.09. Depending on the sample preparation techniques, the calibration techniques applied to the instruments, human operational variations, and etc, those skilled in the art recognize that the appropriate error of margins for a single maximum value can be ±2.5; ±2; ±1.5; ±1; ±0.5; or less.

Additional details of the methods and equipment used for the DSC thermogram analysis are described in the Examples section.

Additional methods of characterizing the present crystalline forms are described in the Example section of this application.

Form 1

In one embodiment, a crystalline form of N-acetylneuraminic acid (NeuAc) is polymorphic Form 1.

In one embodiment, the polymorphic Form 1 exhibits an XRPD comprising peaks at about 5.95; 10.34; 11.93; 14.12; and 17.91 degrees two-theta with the margin of error of about ±0.5; about ±0.4; about ±0.3; about ±0.2; about ±0.1; about ±0.05; or less. In another embodiment, the XRPD of the polymorphic Form 1 further comprises peaks at about 19.84; 20.72; 21.31; 22.06; 24.73; and 29.60 degrees two-theta with the margin of error of about ±0.5; about ±0.4; about ±0.3; about ±0.2; about ±0.1; about ±0.05; or less. In some embodiments, the XRPD of the polymorphic Form 1 comprises three or more peaks at degree two-theta selected from the group consisting of: 5.95; 10.34; 11.93; 14.12; 17.91; 19.84; 20.72; 21.31; 22.06; 24.73; and 29.60 with the margin of error of about ±0.5; about ±0.4; about ±0.3; about ±0.2; about ±0.1; about ±0.05; or less. In some embodiments, the XRPD of the polymorphic Form 1 comprises five or more peaks at degree two-theta selected from the group consisting of: 5.95; 10.34; 11.93; 14.12; 17.91; 19.84; 20.72; 21.31; 22.06; 24.73; and 29.60 with the margin of error of about ±0.5; about ±0.4; about ±0.3; about ±0.2; about ±0.1; about ±0.05; or less. In yet another embodiment, the polymorphic Form 1 exhibits an XRPD comprising peaks shown in the table below:

TABLE 1

XRPD Table of the polymorphic Form 1.

| Pos. [° 2θ] | Height [cts] | d-spacing [Å] | Rel. Int. [%] |
|---|---|---|---|
| 5.9540 | 2260.47 | 14.84418 | 41.61 |
| 10.3408 | 3338.11 | 8.55475 | 61.44 |
| 10.8205 | 188.64 | 8.17656 | 3.47 |
| 11.9312 | 3180.65 | 7.41772 | 58.54 |
| 14.1210 | 1158.04 | 6.27201 | 21.31 |
| 17.9099 | 4929.74 | 4.95278 | 90.74 |
| 18.8235 | 556.81 | 4.71440 | 10.25 |
| 19.8361 | 1260.58 | 4.47596 | 23.20 |
| 20.0772 | 517.40 | 4.42276 | 9.52 |
| 20.4096 | 515.78 | 4.35147 | 9.49 |
| 20.7199 | 1526.69 | 4.28699 | 28.10 |
| 21.3090 | 1751.35 | 4.16979 | 32.24 |
| 21.7546 | 366.09 | 4.08537 | 6.74 |
| 22.0629 | 5433.05 | 4.02898 | 100.00 |
| 22.4948 | 891.49 | 3.95260 | 16.41 |
| 22.7717 | 824.10 | 3.90515 | 15.17 |
| 23.9813 | 950.25 | 3.71085 | 17.49 |
| 24.7322 | 1677.71 | 3.59987 | 30.88 |
| 25.3699 | 113.39 | 3.51080 | 2.09 |
| 26.0672 | 456.05 | 3.41845 | 8.39 |
| 26.8970 | 980.33 | 3.31484 | 18.04 |
| 28.2534 | 146.71 | 3.15872 | 2.70 |
| 29.5985 | 1071.14 | 3.01816 | 19.72 |
| 29.8150 | 735.17 | 2.99674 | 13.53 |
| 30.2980 | 298.52 | 2.95005 | 5.49 |
| 30.6802 | 263.82 | 2.91417 | 4.86 |
| 33.0277 | 116.14 | 2.71221 | 2.14 |
| 34.1157 | 310.37 | 2.62816 | 5.71 |
| 34.4243 | 318.44 | 2.60530 | 5.86 |
| 34.7741 | 336.67 | 2.57989 | 6.20 |

In one specific embodiment, the polymorphic Form 1 exhibits an XRPD that is substantially similar to FIG. 1.

Figure 9:
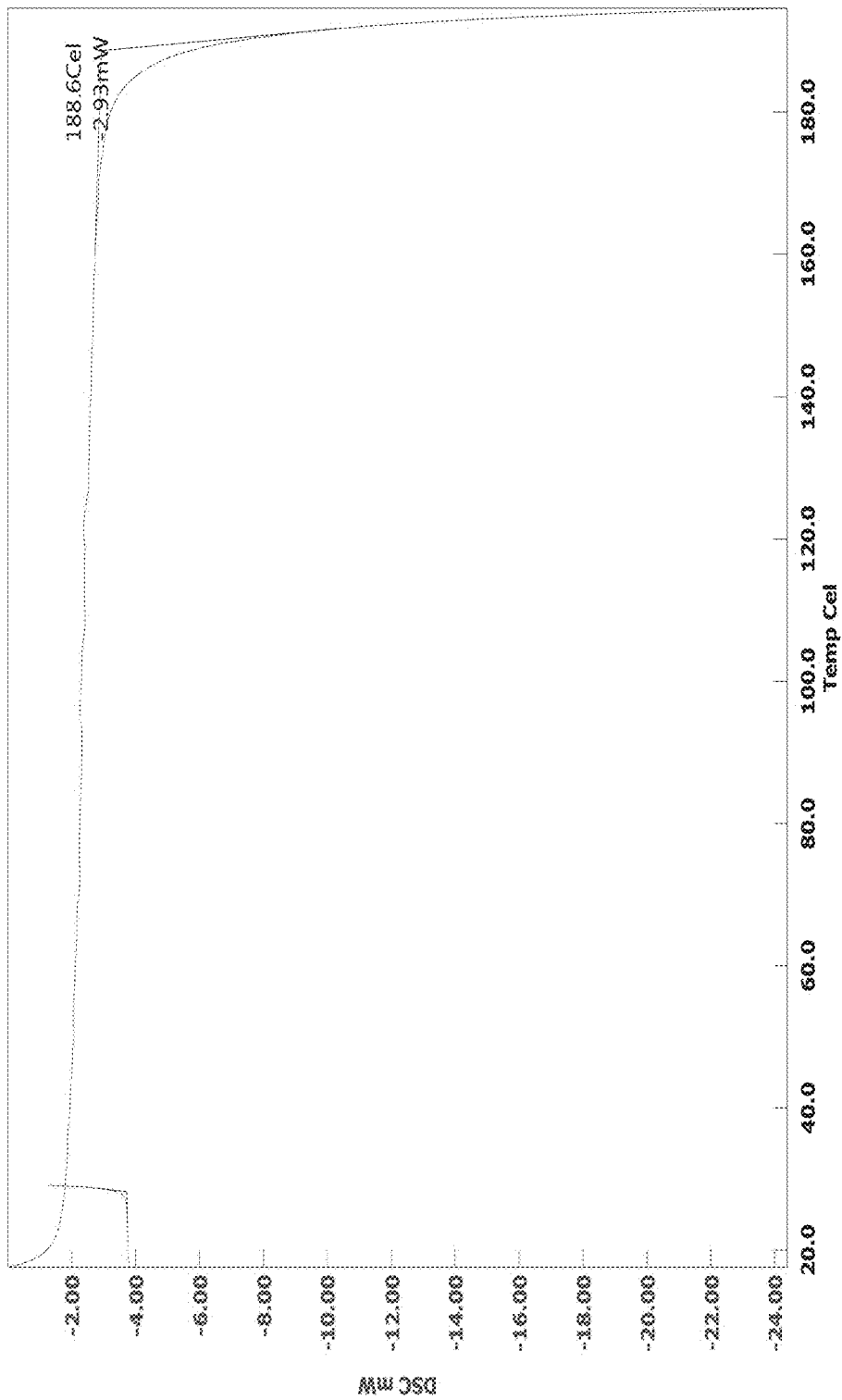
FIG. 9 is a Differential Scanning calorimetry (DSC) thermogram of polymorphic Form 1.
Figure 10:
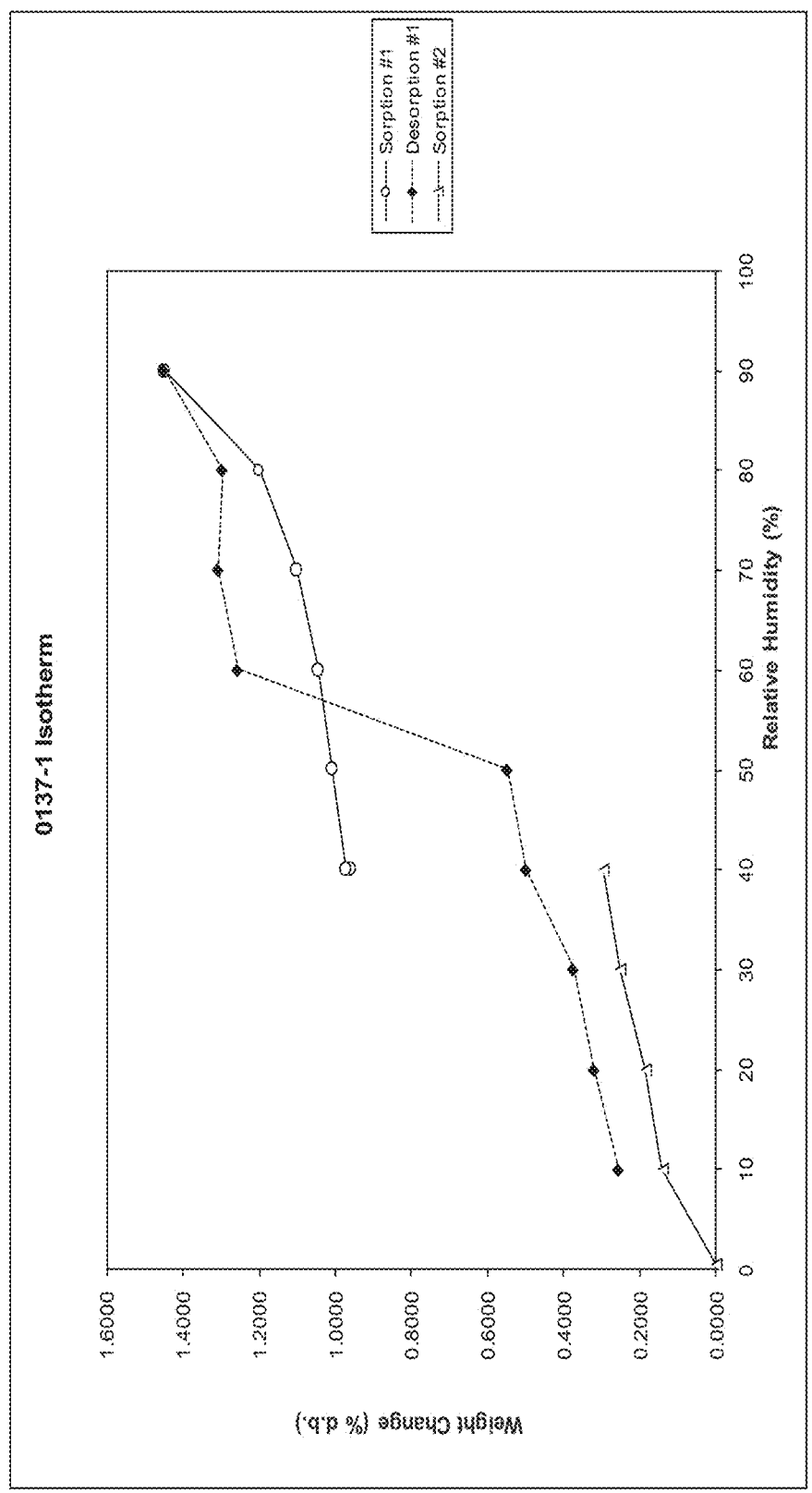
FIG. 10 is an isothermal plot for Gravimetric Vapour Sorption (GVS) experiment on polymorphic Form 1.
Figure 11:
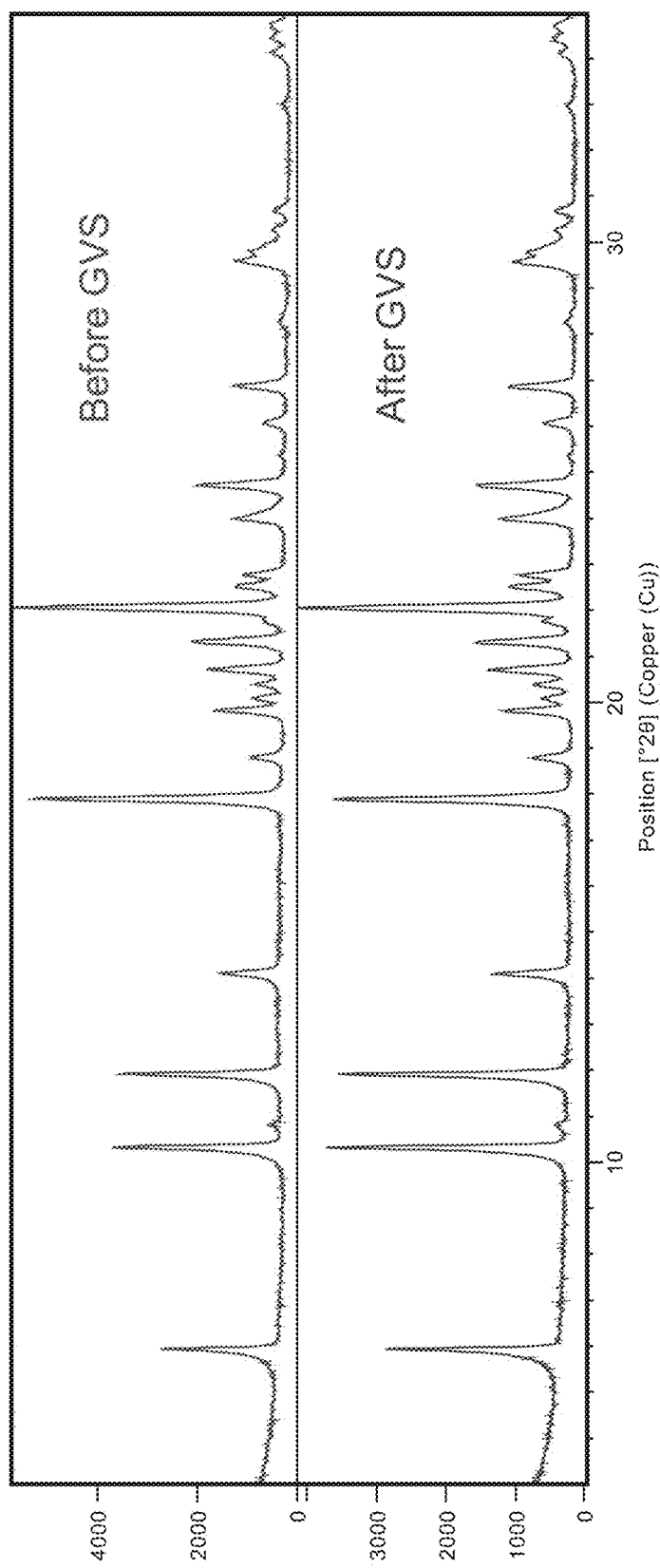
FIG. 11 is a stacked powder pattern of polymorphic Form 1 (top) and the reclaimed material after GVS experiment (bottom).
Figure 12:
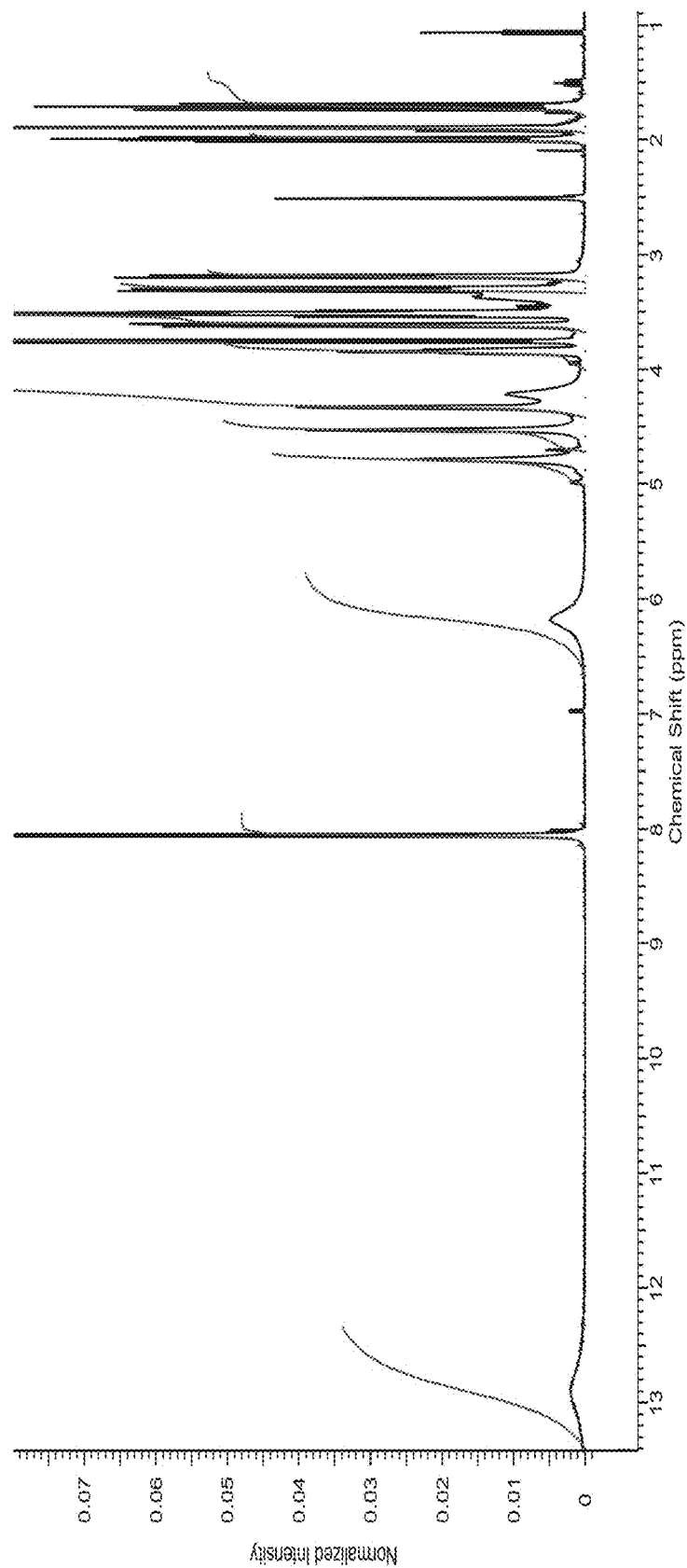
FIG. 12 is a $^1$H Nuclear Magnetic Resonance ($^1$H-NMR) spectrum of polymorphic Form 1 in DMSO.
Figure 13:
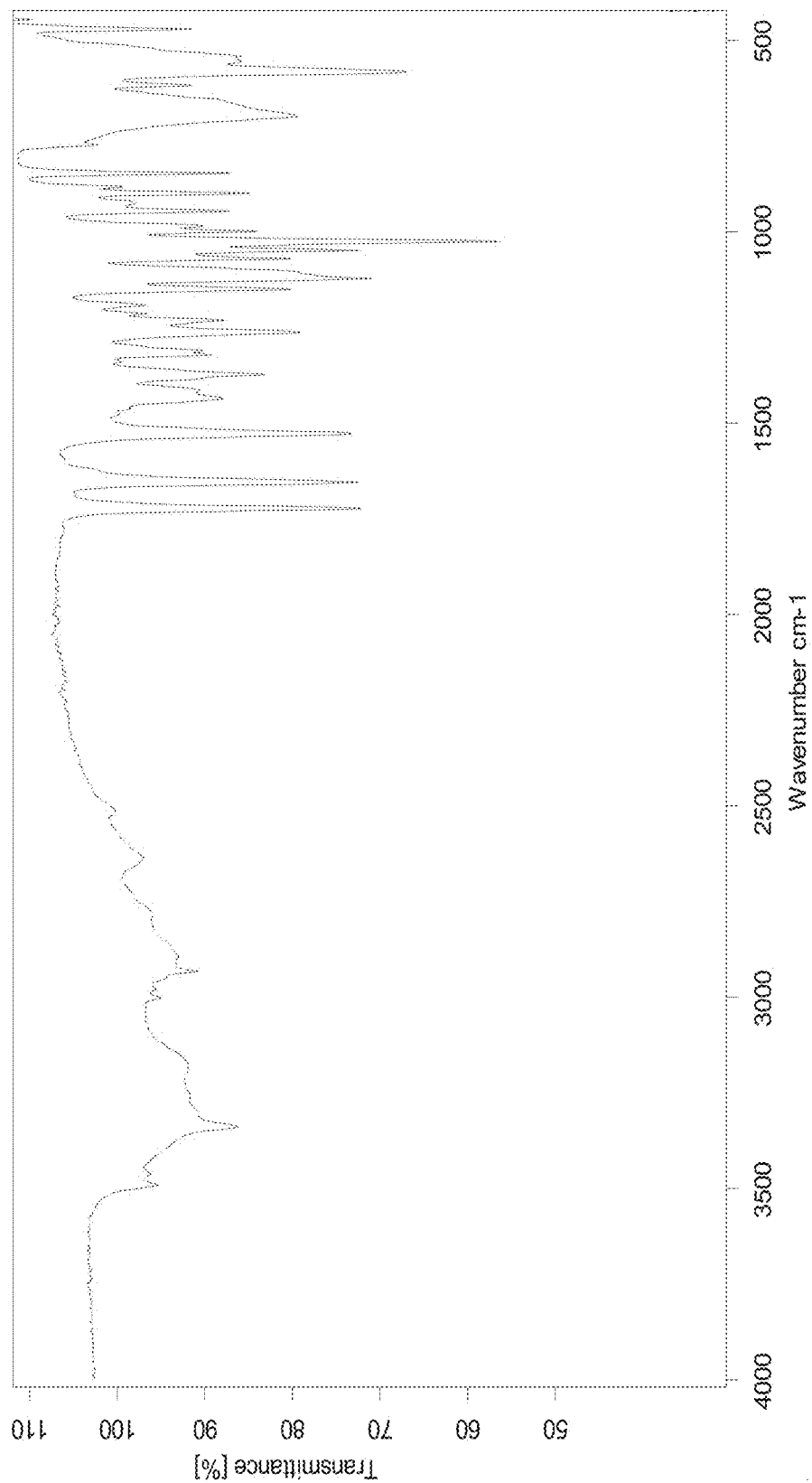
FIG. 13 is an infrared (IR) spectrum of polymorphic Form 1.
Figure 14:
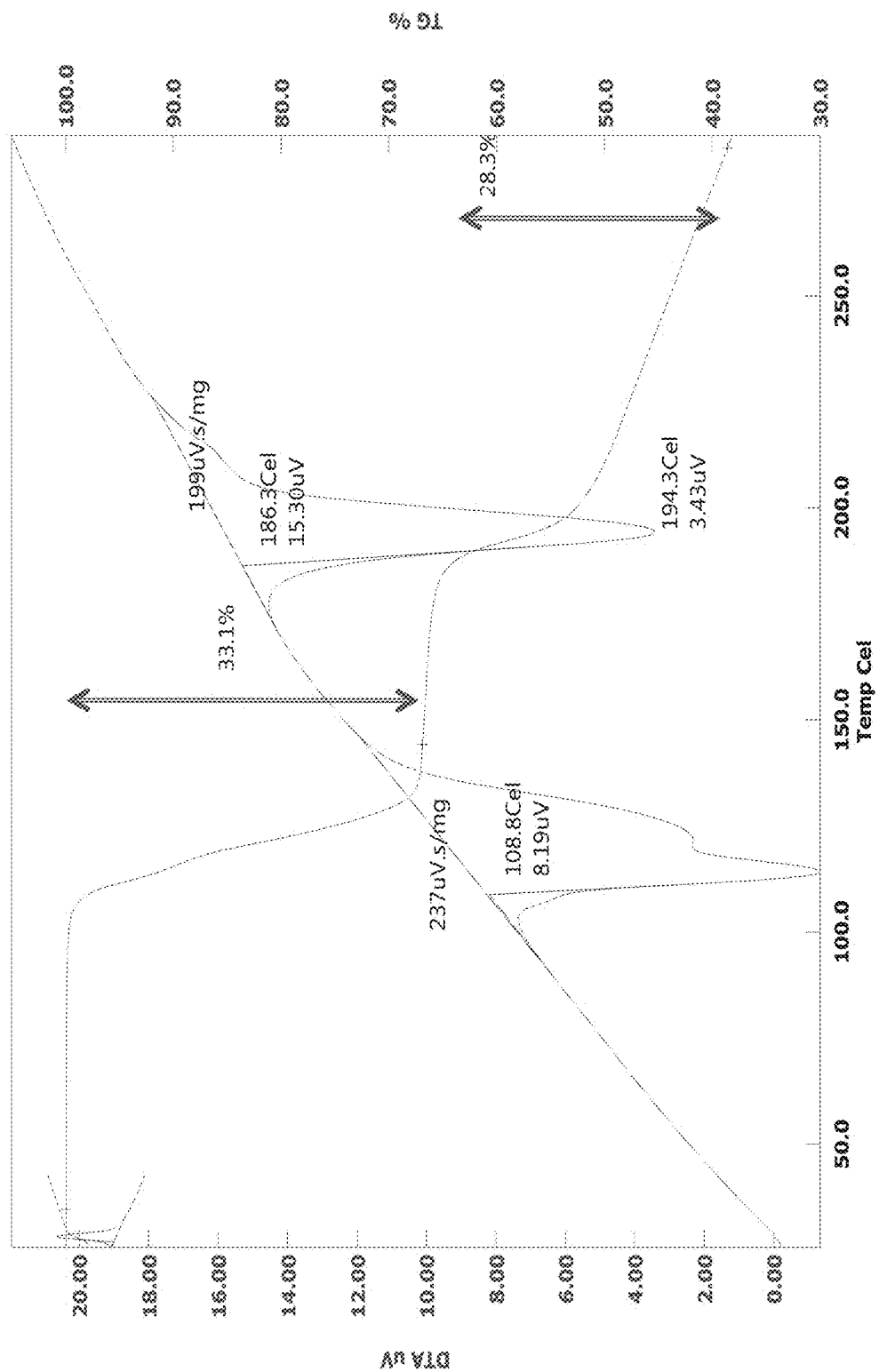
FIG. 14 is an overlay of TG and DTA thermograms of polymorphic Form 4.
Figure 15:
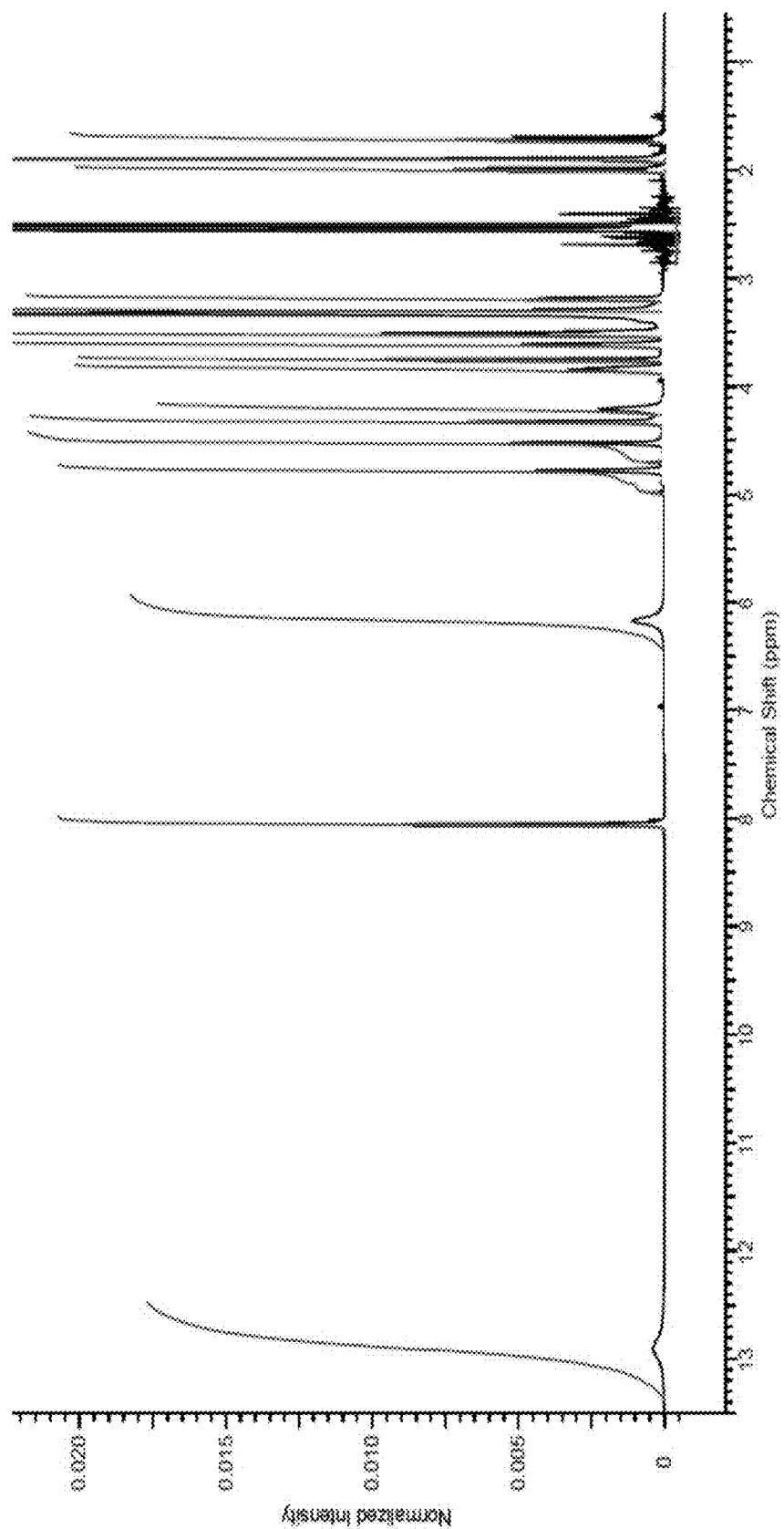
FIG. 15 is a $^1$H-NMR spectrum of polymorphic Form 4.
Figure 16:
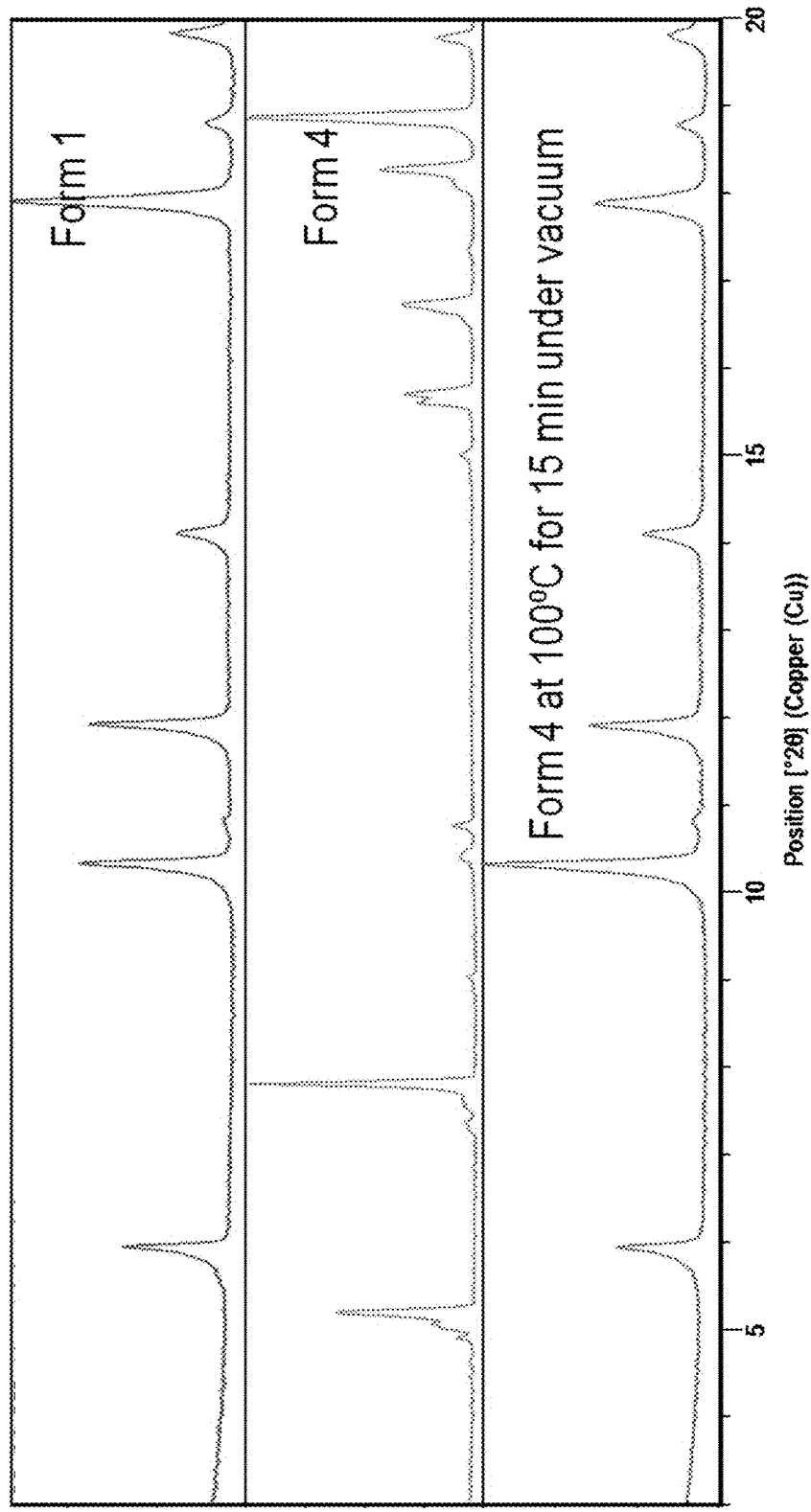
FIG. 16 is diffractogram of polymorphic Form 4 desolvation showing conversion to Form 1.
Figure 17:
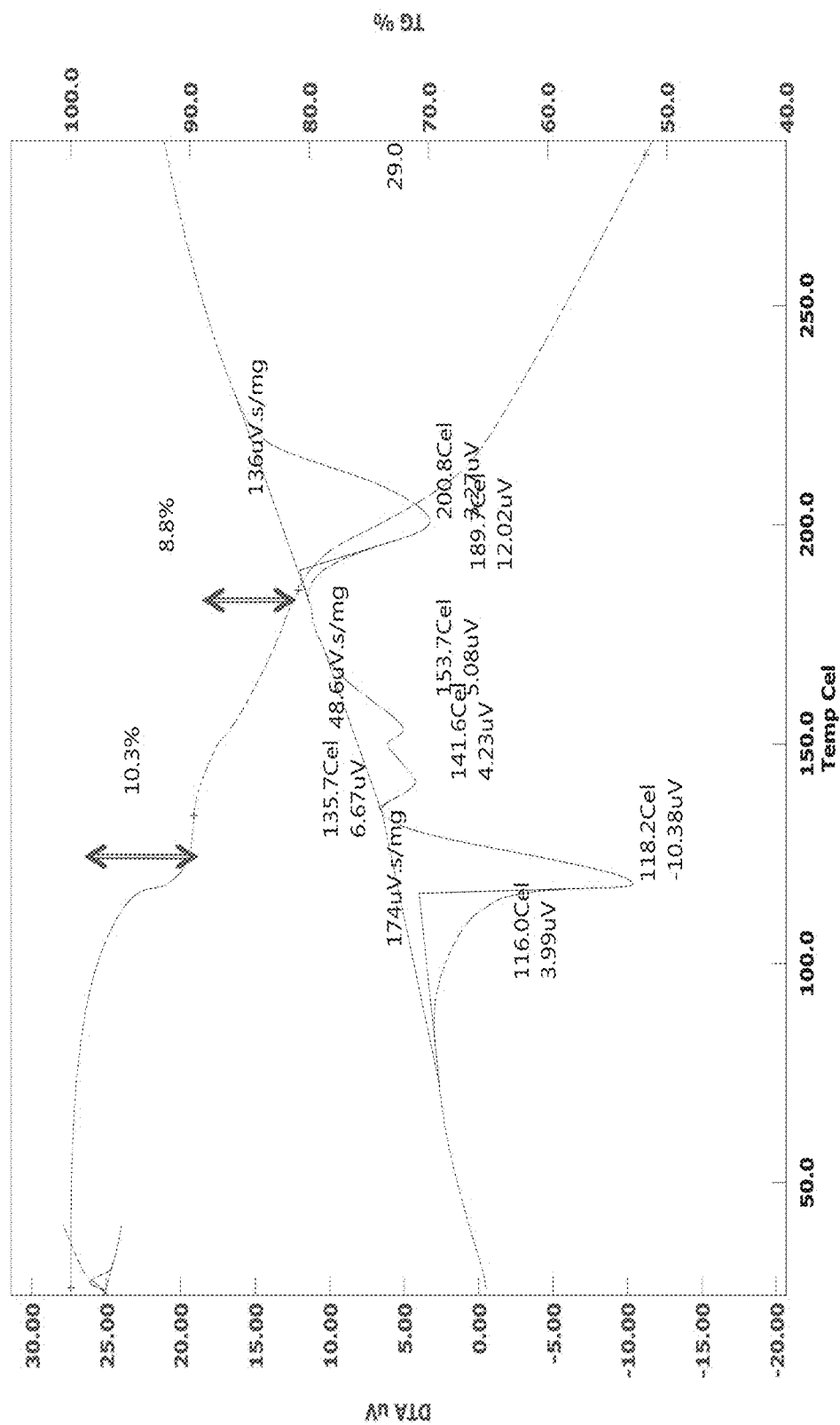
FIG. 17 is an overlay of TG and DTA thermograms of polymorphic Form 5.
Figure 18:
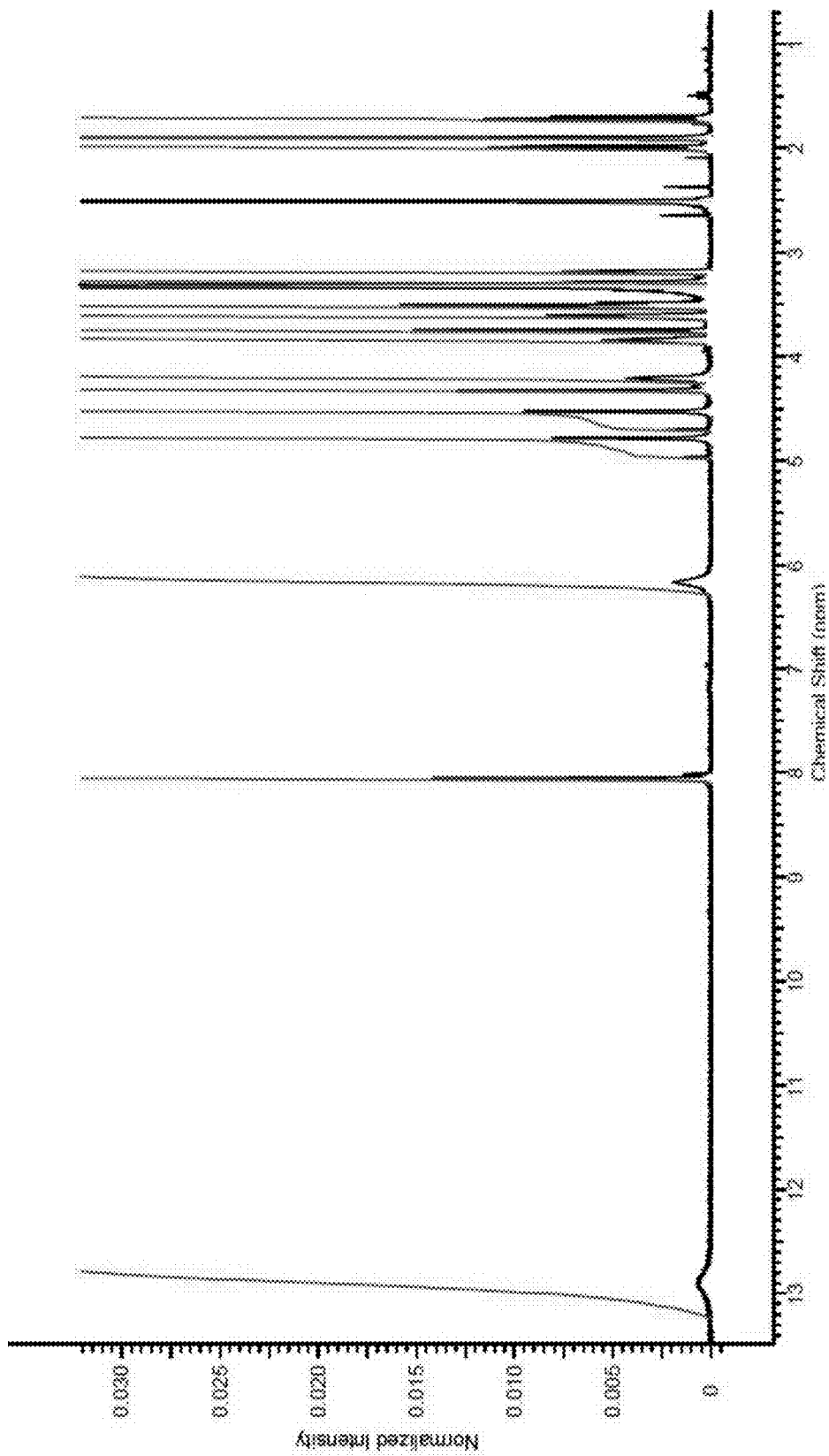
FIG. 18 is a $^1$H-NMR spectrum of polymorphic Form 5.
Figure 19:
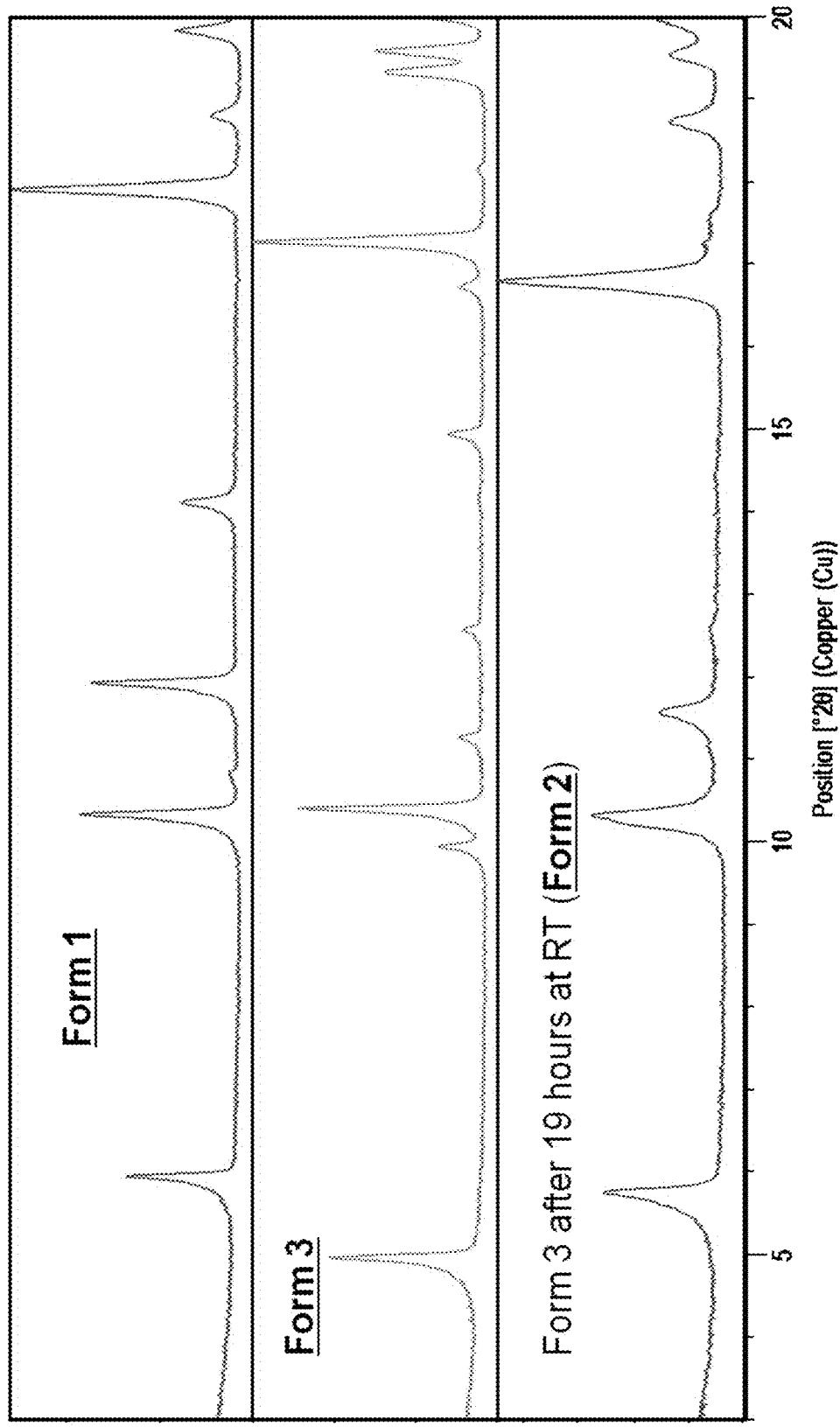
FIG. 19 is diffractogram showing formation of polymorphic Form 3 (middle) and then polymorphic Form 2 (bottom) obtained by drying polymorphic Form 3.
Figure 21:
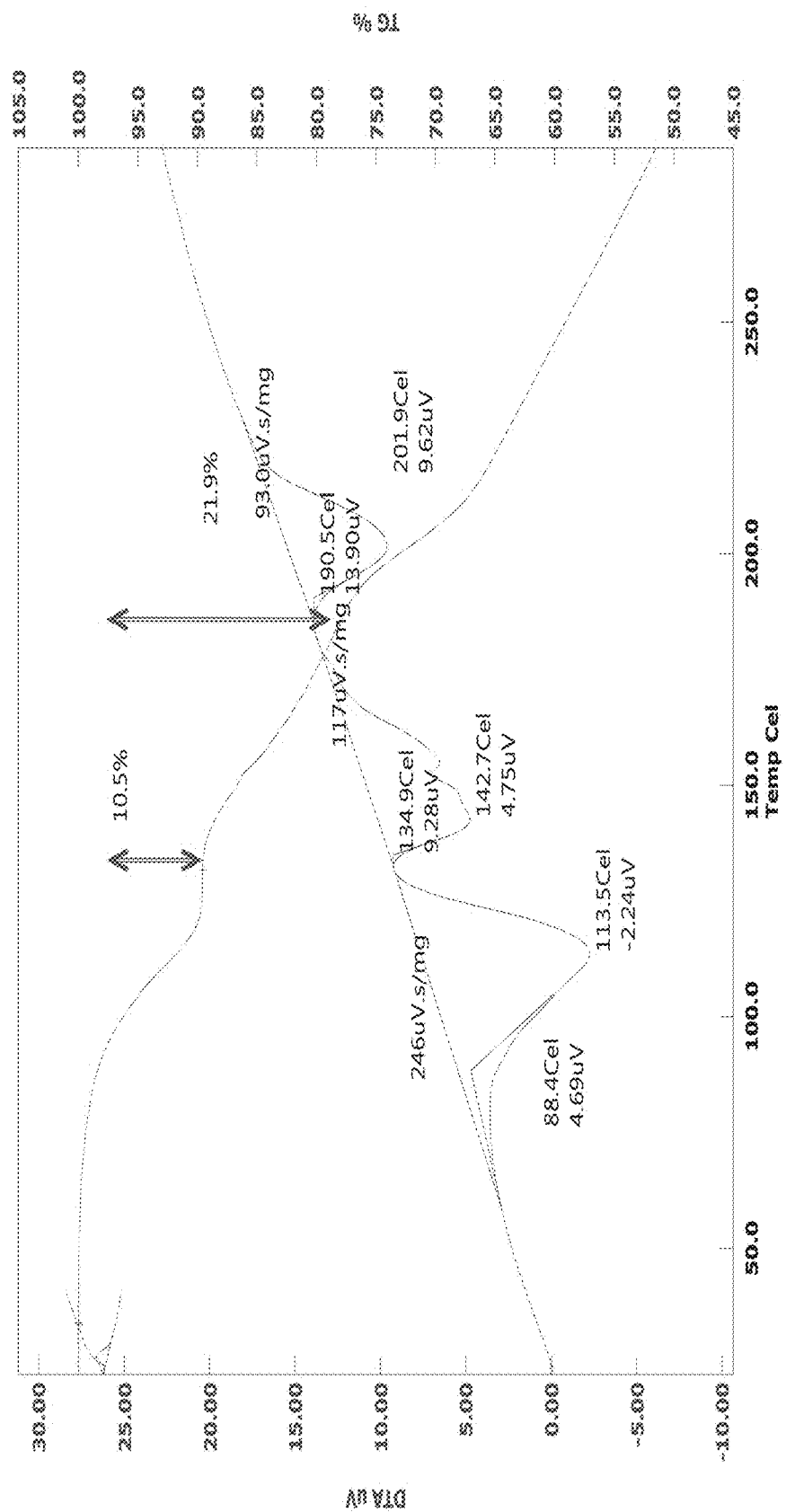
FIG. 21 is an overlay of TG and DTA thermograms of polymorphic Form 5.

In one embodiment, the polymorphic Form 1 exhibits a DSC thermogram comprising a single maximum value at about 188.6° C. with the error of margin of about ±2.5; about ±2; about ±1.5; about ±1; about ±0.5; or less. In one specific embodiment, the polymorphic Form 1 exhibits a DSC thermogram that is substantially similar to FIG. 9.

The present invention also provides processes of preparing various crystalline forms of sialic acid and crystalline forms of the salts and/or solvates of sialic acid. In some embodiments, a process of preparing polymorphic Form 1 comprises a first crystallization and a second crystallization. The second crystallization can use acetone slurry, water slurry or acetone/water slurry. Alternatively or additionally, the second crystallization does not use ethanol.

In some embodiments, a process of preparing polymorphic Form 1 comprises conversion of polymorphic Form 2, polymorphic Form 3, or polymorphic Form 4 to polymorphic Form 1.

Form 2

In one embodiment, a crystalline form of N-acetylneuraminic acid (NeuAc) is polymorphic Form 2.

In one embodiment, the polymorphic Form 2 exhibits an XRPD comprising peaks at about 5.79; 10.28; 11.59; 16.95; and 18.87 degrees two-theta with the margin of error of about ±0.5; about ±0.4; about ±0.3; about ±0.2; about ±0.1; about ±0.05; or less. In another embodiment, the XRPD of the polymorphic Form 2 further comprises peaks at about 20.68; and 24.24 degrees two-theta with the margin of error of about ±0.5; about ±0.4; about ±0.3; about ±0.2; about ±0.1; about ±0.05; or less. In some embodiments, the XRPD of the polymorphic Form 2 comprises three or more peaks at degree two-theta selected from the group consisting of: 5.79; 10.28; 11.59; 16.95; 18.87; 20.37; 20.68; and 24.24 with the margin of error of about ±0.5; about ±0.4; about ±0.3; about ±0.2; about ±0.1; about ±0.05; or less. In some embodiments, the XRPD of the polymorphic Form 2 comprises five or more peaks at degree two-theta selected from the group consisting of: 5.79; 10.28; 11.59; 16.95; 18.87; 20.37; 20.68; and 24.24 with the margin of error of about ±0.5; about ±0.4; about ±0.3; about ±0.2; about ±0.1; about ±0.05; or less. In yet another embodiment, the polymorphic Form 2 exhibits an XRPD comprising peaks shown in the table below:

TABLE 2

XRPD Table of the polymorphic Form 2.

| Pos. [° 2θ] | Height [cts] | d-spacing [Å] | Rel. Int. [%] |
|---|---|---|---|
| 5.7937 | 1611.29 | 15.25456 | 100.00 |
| 10.2755 | 1317.74 | 8.60181 | 81.78 |
| 11.5936 | 751.94 | 7.62666 | 46.67 |
| 12.5627 | 176.07 | 7.04624 | 10.93 |
| 14.4247 | 67.40 | 6.14061 | 4.18 |
| 16.9527 | 998.86 | 5.23021 | 61.99 |
| 18.8682 | 332.06 | 4.70333 | 20.61 |
| 19.6134 | 399.37 | 4.52628 | 24.79 |
| 20.0815 | 546.27 | 4.42181 | 33.90 |
| 20.3740 | 756.76 | 4.35899 | 46.97 |
| 20.6814 | 785.06 | 4.29489 | 48.72 |
| 20.9010 | 531.25 | 4.24673 | 32.97 |
| 21.3221 | 512.79 | 4.16726 | 31.83 |
| 21.9573 | 484.32 | 4.04812 | 30.06 |
| 23.3676 | 485.03 | 3.80690 | 30.10 |
| 23.6450 | 404.72 | 3.76286 | 25.12 |
| 24.2422 | 600.21 | 3.67151 | 37.25 |
| 25.2355 | 346.13 | 3.52920 | 21.48 |
| 26.6423 | 157.54 | 3.34595 | 9.78 |
| 27.1338 | 275.27 | 3.28645 | 17.08 |
| 27.9248 | 137.58 | 3.19513 | 8.54 |
| 29.0100 | 161.04 | 3.07803 | 9.99 |
| 30.9258 | 225.78 | 2.89158 | 14.01 |
| 33.8040 | 82.54 | 2.65168 | 5.12 |

Figure 2:
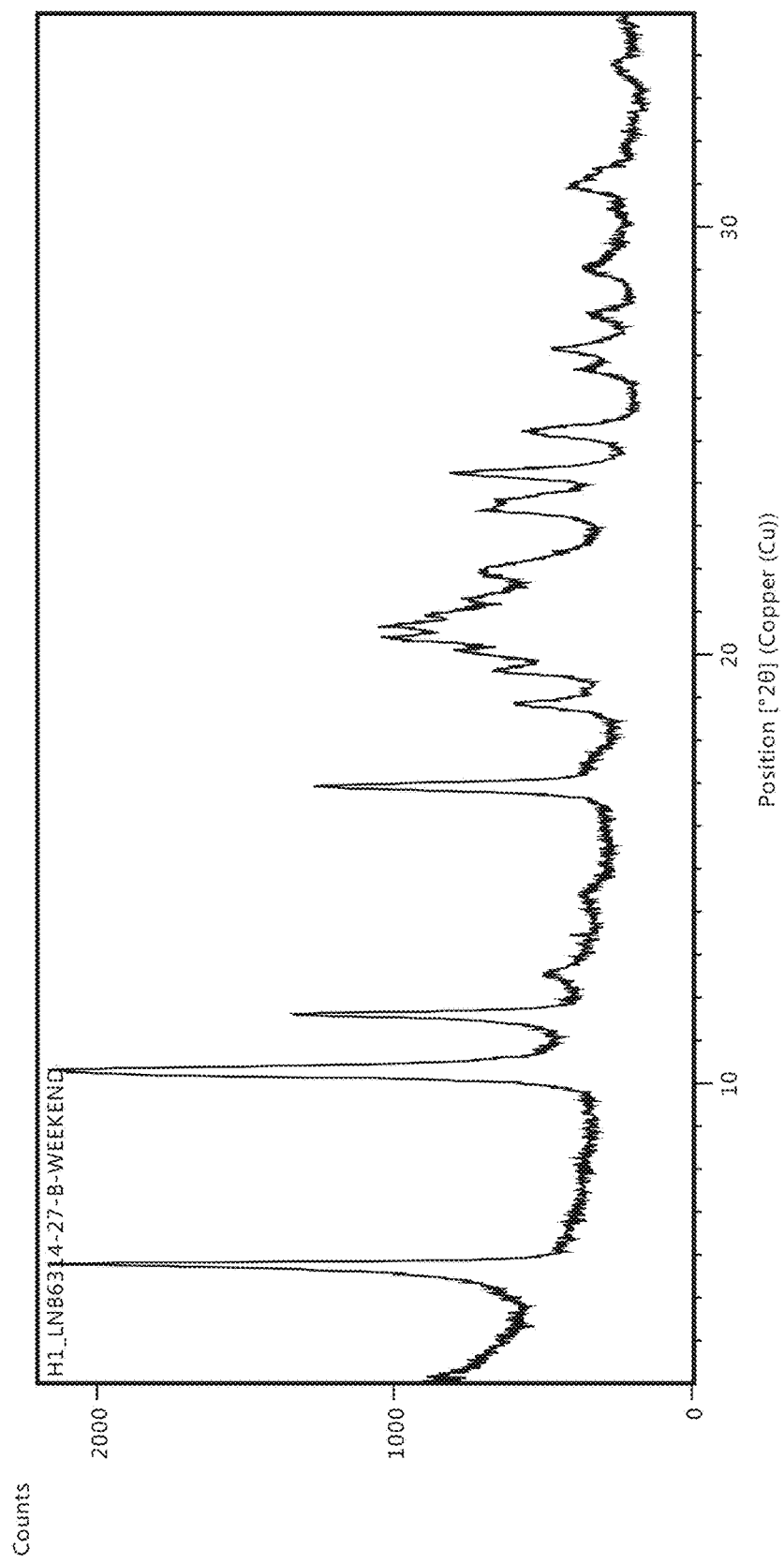
FIG. 2 shows are graphs of a XRPD pattern of polymorphic Form 2.

In one specific embodiment, the polymorphic Form 2 exhibits an XRPD that is substantially similar to FIG. 2.

Figure 38:
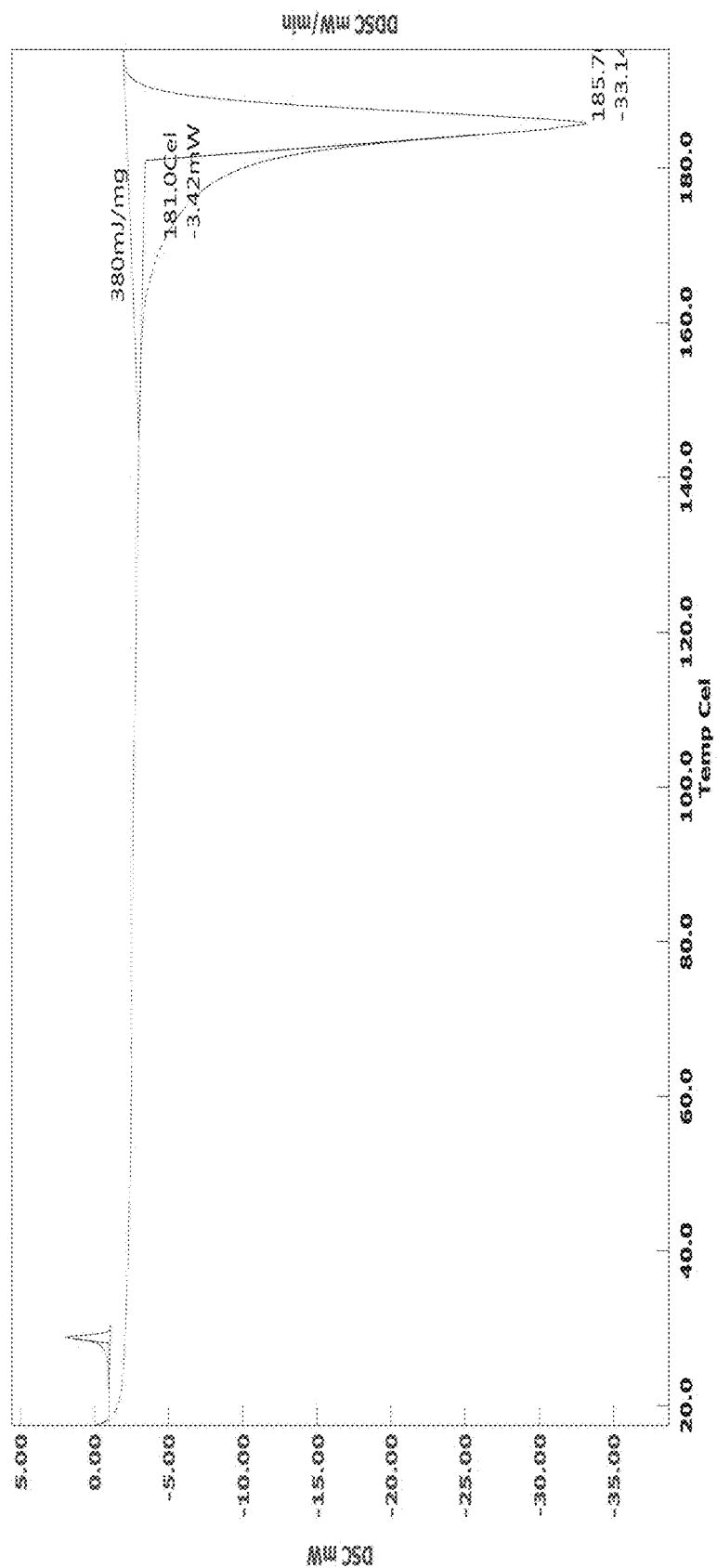
FIG. 38 is a DSC thermogram of polymorphic Form 2.
Figure 39:
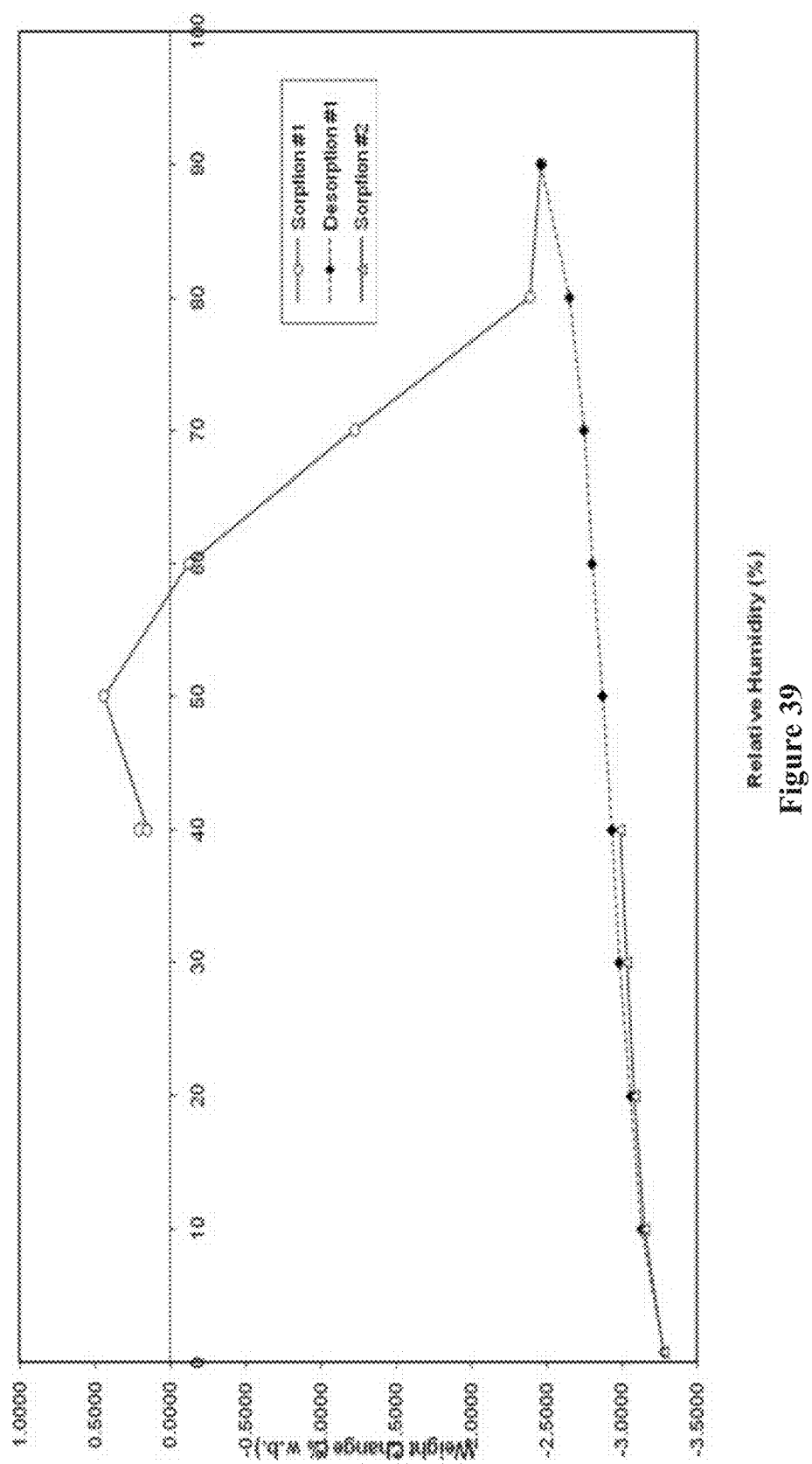
FIG. 39 is an isothermal plot for GVS experiment on polymorphic Form 2.
Figure 40:
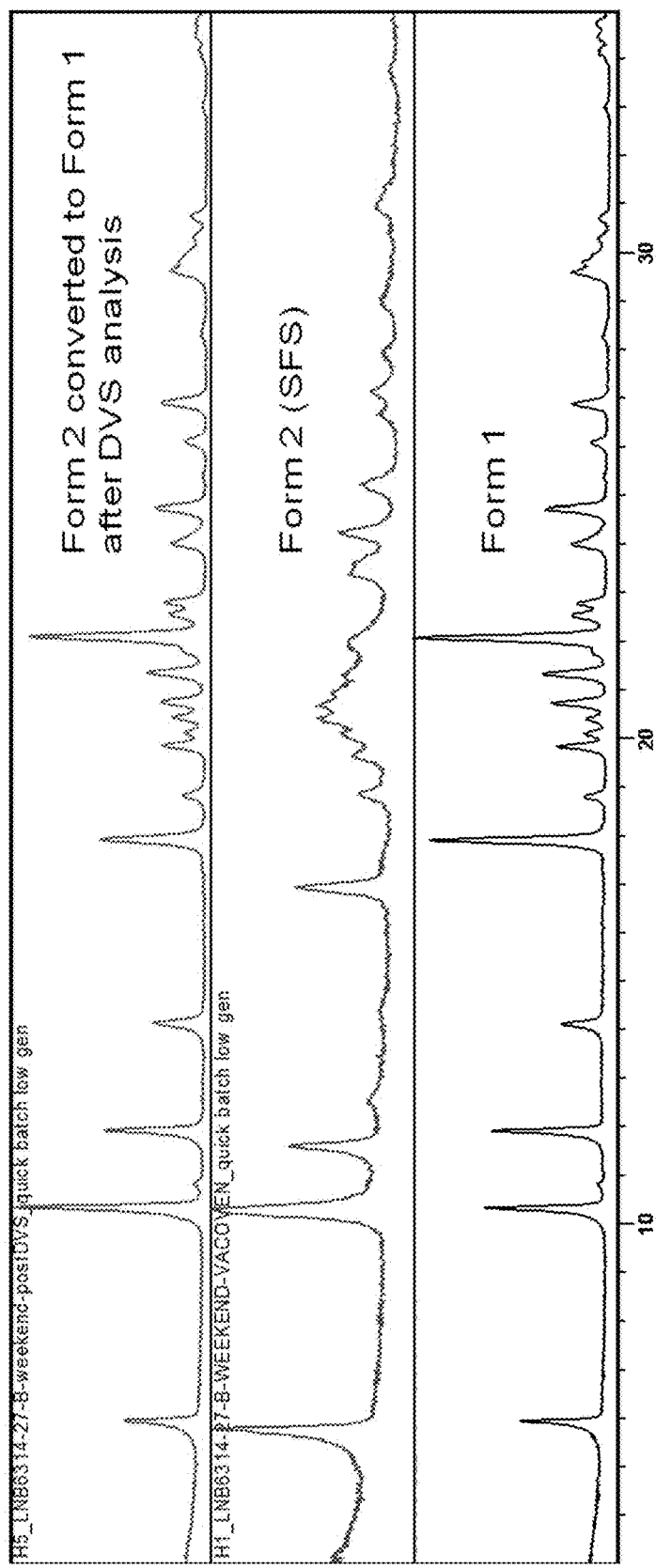
FIG. 40 are stacked powder patterns of polymorphic Form 1 (bottom), polymorphic Form 2 (middle) and the reclaimed material after DVS experiment (top)
Figure 41:
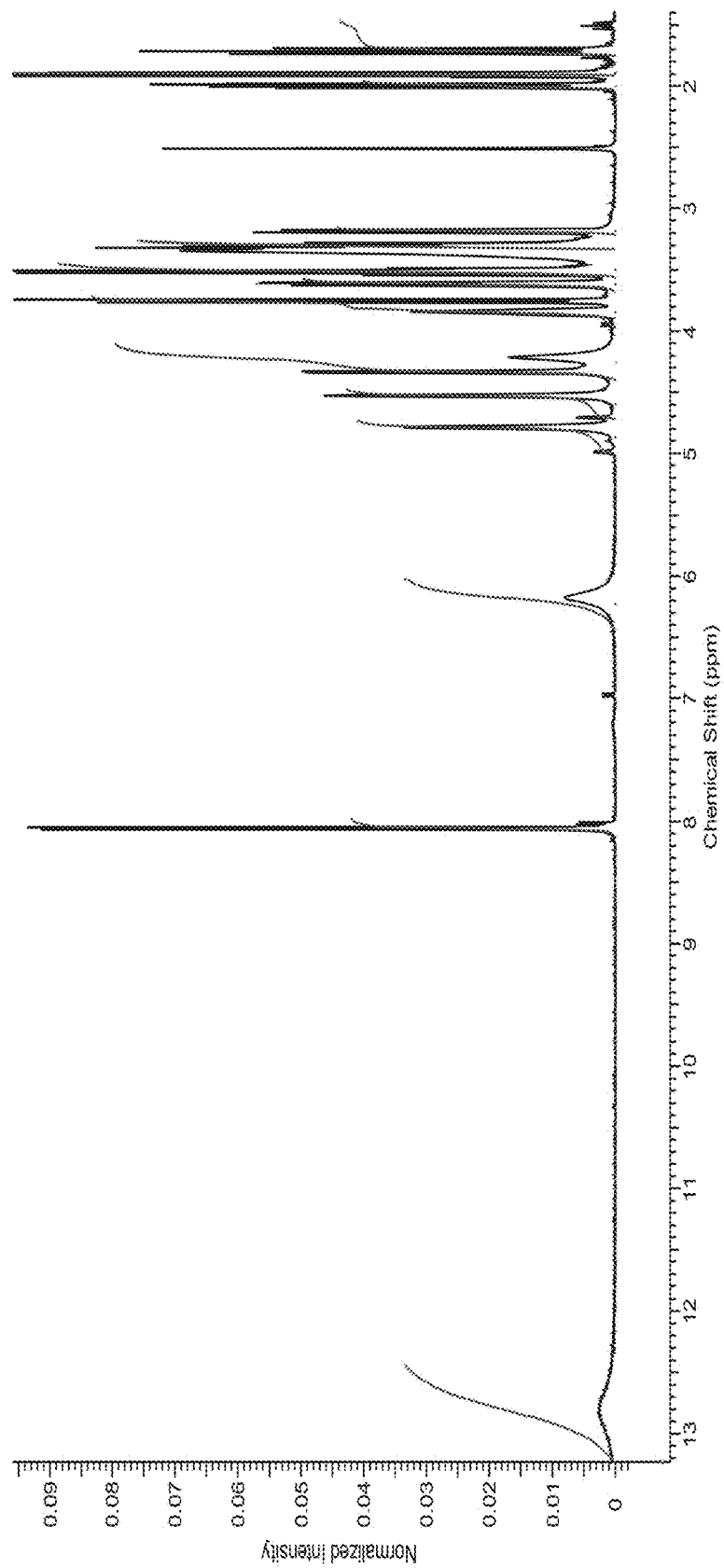
FIG. 41 is a $^1$H-NMR spectrum of polymorphic Form 2.
Figure 42:
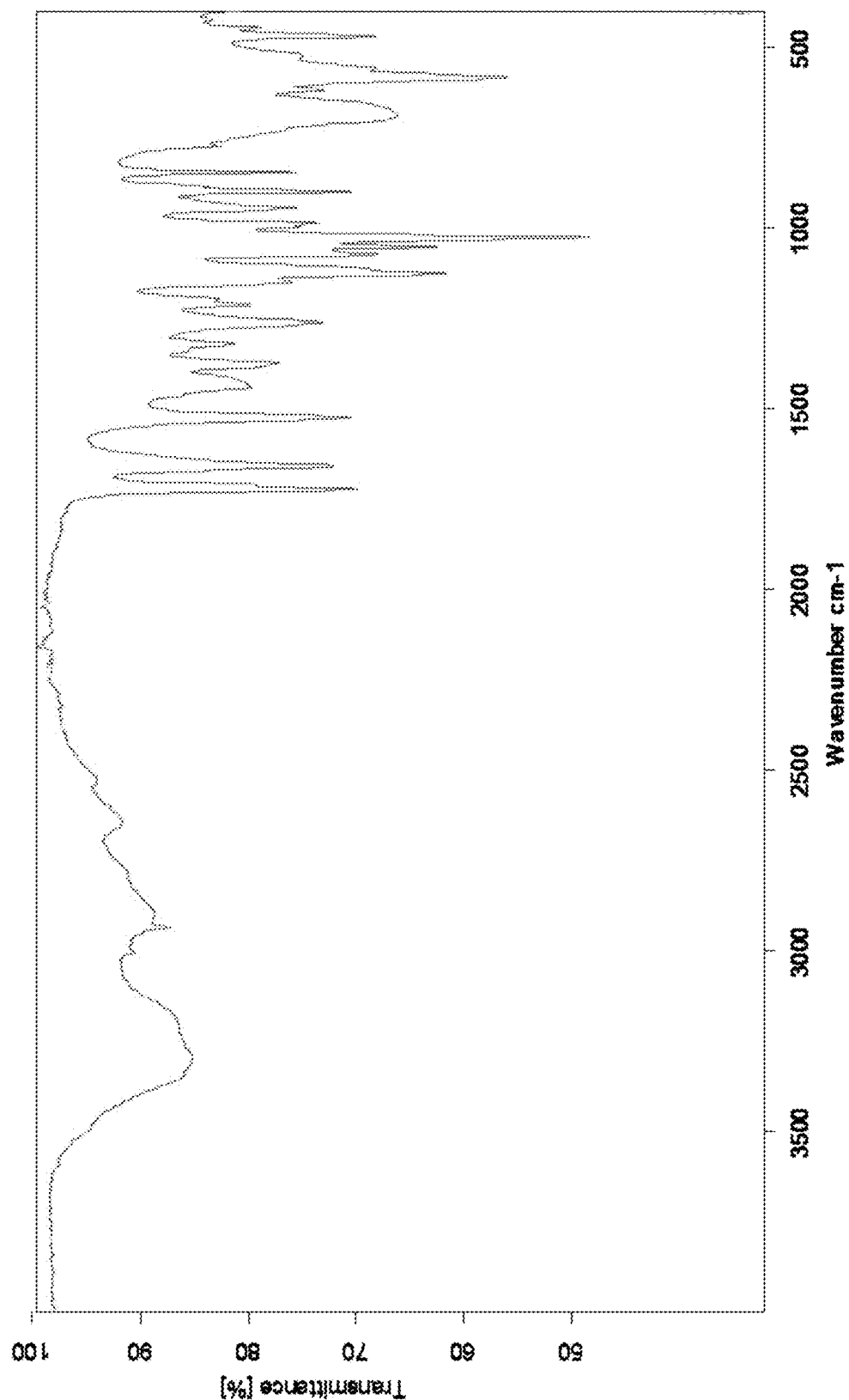
FIG. 42 is an IR spectrum of polymorphic Form 2.
Figure 43:
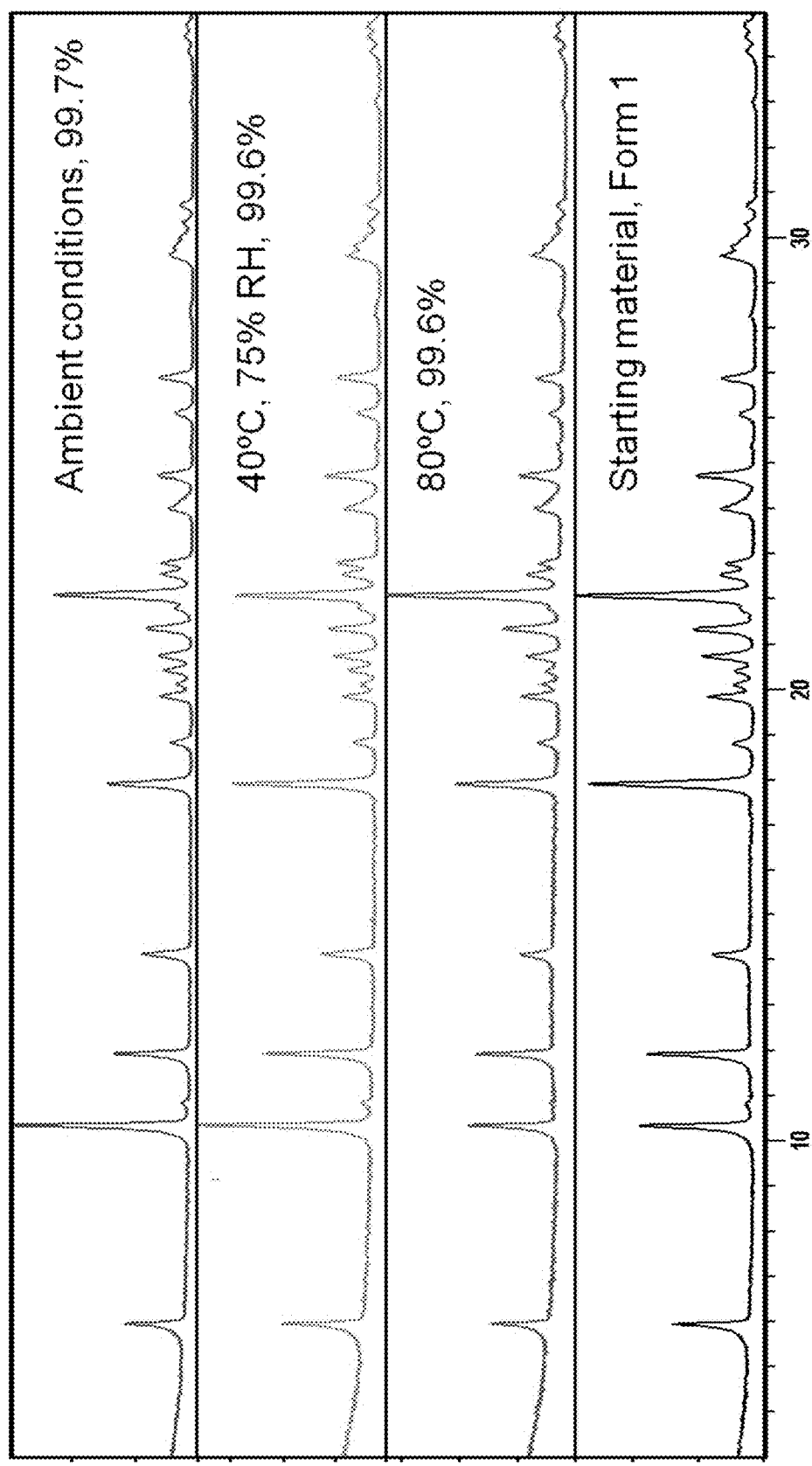
FIG. 43 are stacked diffractograms of polymorphic Form 1 samples after 1 week at ambient conditions (top), 40° C. and 75% relative humidity ($2^{nd}$ from top), 80° C. ($3^{rd}$ from top) and the starting form (bottom). After each condition, the HPLC purity result is detailed.
Figure 44:
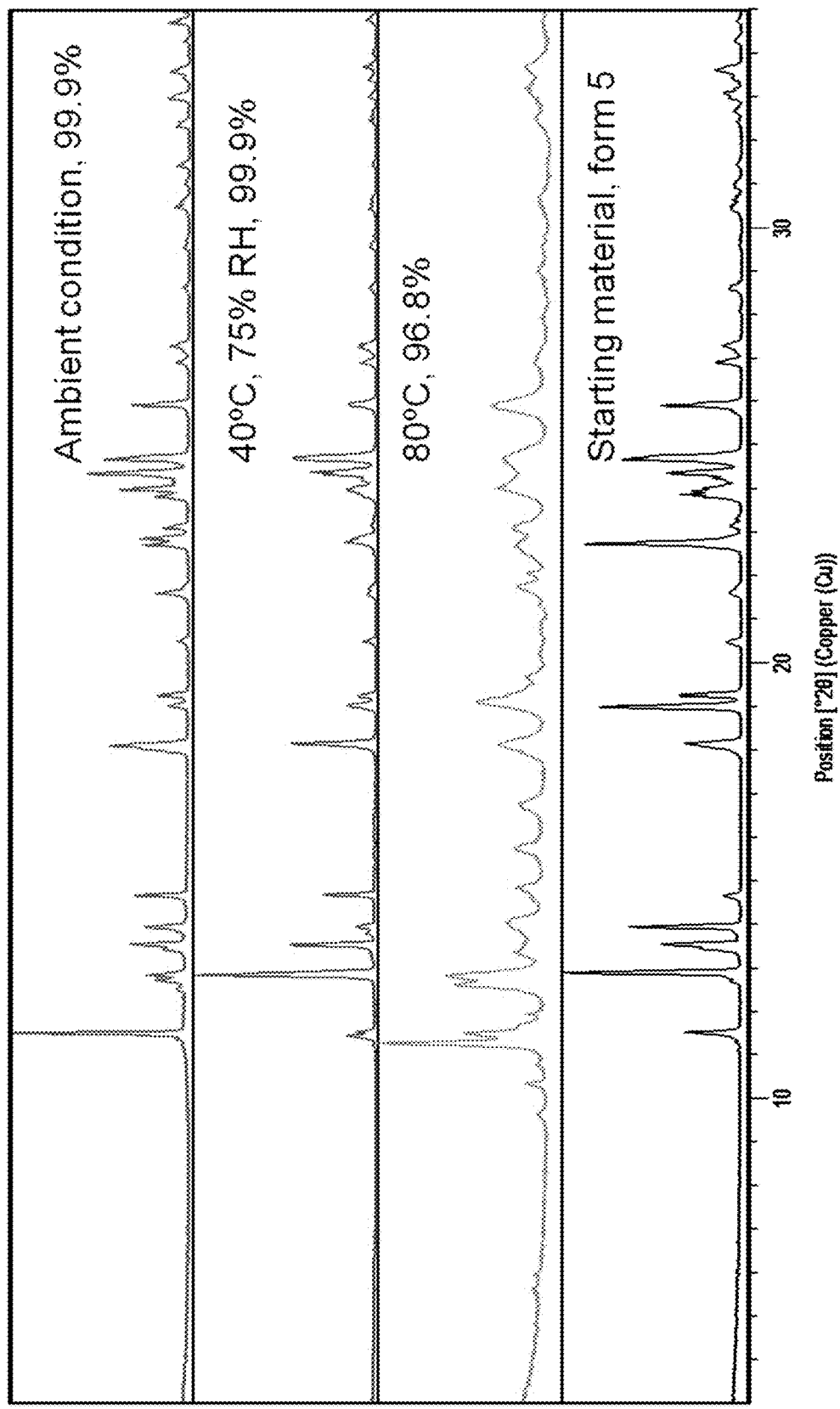
FIG. 44 are stacked diffractograms of polymorphic Form 5 samples after 1 week at ambient conditions (top), 40° C. and 75% relative humidity ($2^{nd}$ from top), 80° C. ($3^{rd}$ from top) and the starting form (bottom). After each condition, the HPLC purity result is detailed.
Figure 45:
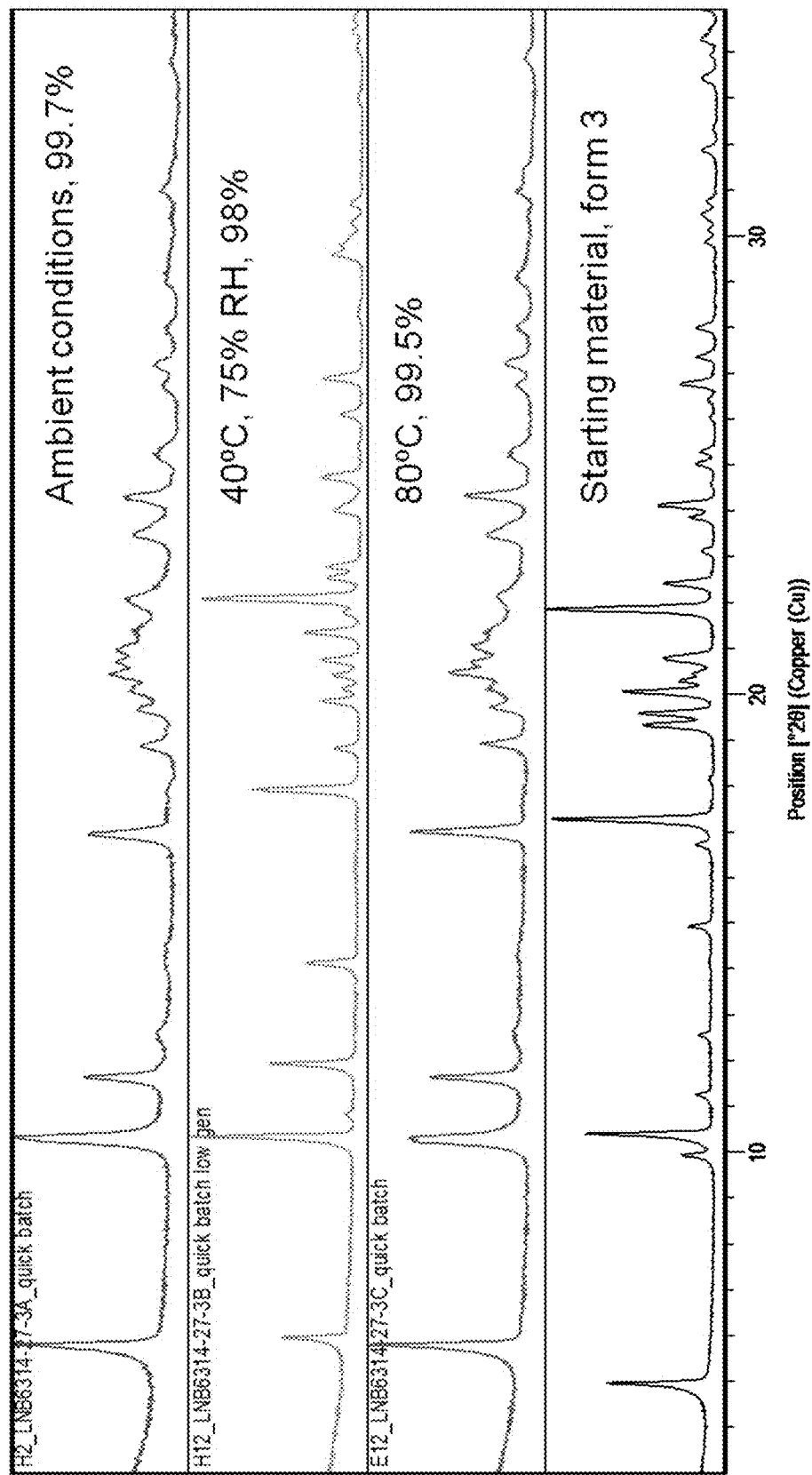
FIG. 45 are stacked diffractograms of polymorphic Form 3 samples after 1 week at ambient conditions (top), 40° C. and 75% relative humidity ($2^{nd}$ from top), 80° C. ($3^{rd}$ from top) and the starting form (bottom). After each condition, the HPLC purity result is detailed.
Figure 46:
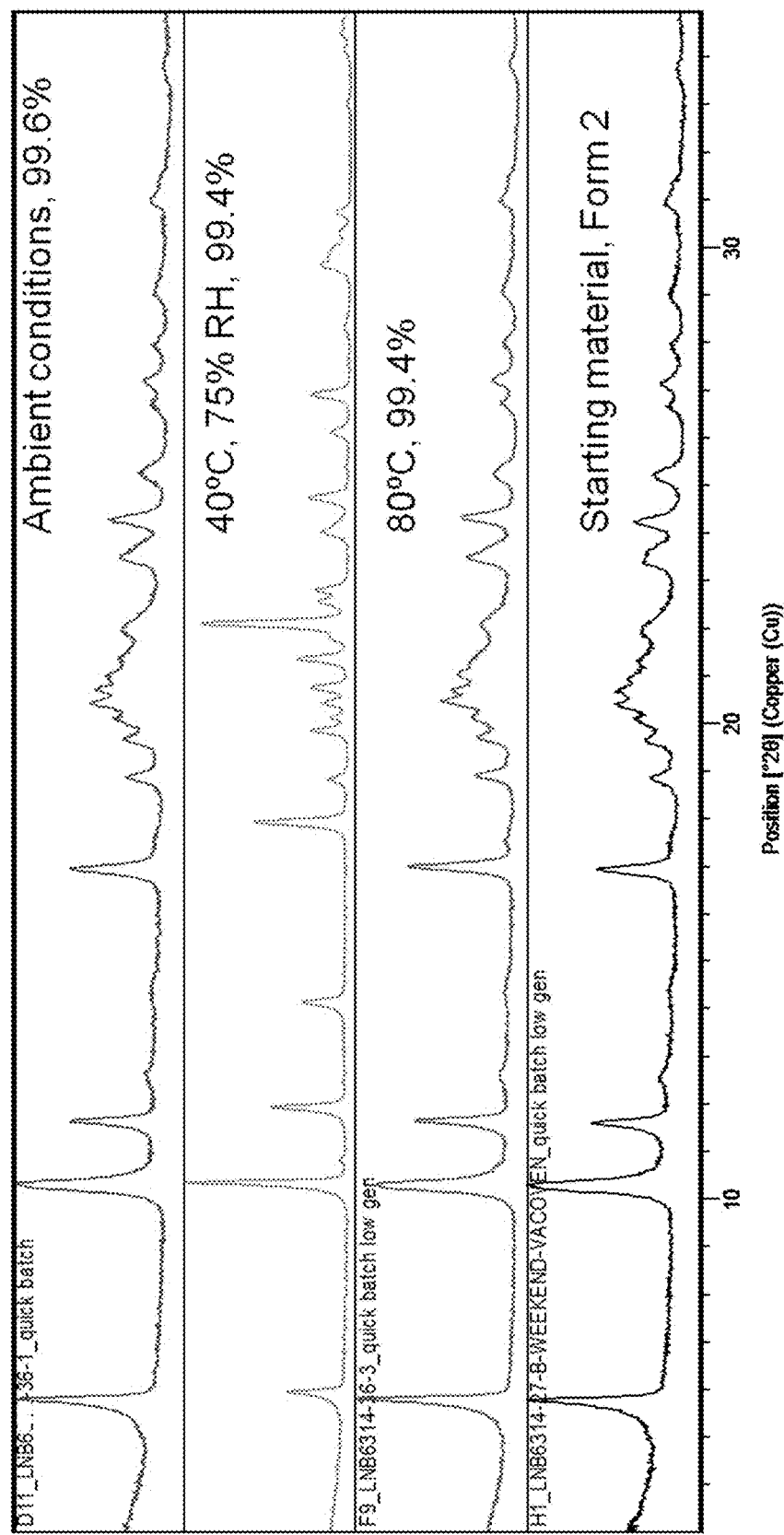
FIG. 46 are stacked diffractograms of polymorphic Form 2 samples after 1 week at ambient conditions (top), 40° C. and 75% relative humidity ($2^{nd}$ from top), 80° C. (3rd from top) and the starting form (bottom). After each condition, the HPLC purity result is detailed.

In one embodiment, the polymorphic Form 2 exhibits a DSC thermogram comprising a single maximum value at about 181.0° C. with the error of margin of about ±2.5; about ±2; about ±1.5; about ±1; about ±0.5; or less. In one specific embodiment, the polymorphic Form 1 exhibits a DSC thermogram that is substantially similar to FIG. 38.

Form 3

In one embodiment, the polymorphic Form 3 exhibits an XRPD comprising peaks at about 4.97; 9.95; 10.42; 14.94; and 17.28 degrees two-theta with the margin of error of about ±0.5; about ±0.4; about ±0.3; about ±0.2; about ±0.1; about ±0.05; or less. In another embodiment, the XRPD of the polymorphic Form 3 further comprises peaks at about 19.58; 20.05; 21.85; 24.12; and 26.76 degrees two-theta with the margin of error of about ±0.5; about ±0.4; about ±0.3; about ±0.2; about ±0.1; about ±0.05; or less. In some embodiments, the XRPD of the polymorphic Form 3 comprises three or more peaks at degree two-theta selected from the group consisting of: 4.97; 9.95; 10.42; 14.94; 17.28; 19.58; 20.05; 21.85; 24.12; and 26.76 with the margin of error of about ±0.5; about ±0.4; about ±0.3; about ±0.2; about ±0.1; about ±0.05; or less. In some embodiments, the XRPD of the polymorphic Form 3 comprises five or more peaks at degree two-theta selected from the group consisting of: 4.97; 9.95; 10.42; 14.94; 17.28; 19.58; 20.05; 21.85; 24.12; and 26.76 with the margin of error of about ±0.5; about ±0.4; about ±0.3; about ±0.2; about ±0.1; about ±0.05; or less. In yet another embodiment, the polymorphic Form 3 exhibits an XRPD comprising peaks shown in the table below:

TABLE 3

XRPD Table of the polymorphic Form 3.

| Pos. [° 2θ] | Height [cts] | d-spacing [Å] | Rel. Int. [%] |
|---|---|---|---|
| 4.9715 | 3682.49 | 17.77549 | 61.45 |
| 9.9459 | 1133.91 | 8.89346 | 18.92 |
| 10.4150 | 4494.15 | 8.49393 | 74.99 |
| 11.2669 | 646.90 | 7.85354 | 10.79 |
| 12.5747 | 525.53 | 7.03959 | 8.77 |
| 14.9391 | 919.37 | 5.93031 | 15.34 |
| 16.7154 | 645.94 | 5.30391 | 10.78 |
| 17.2789 | 5701.74 | 5.13219 | 95.14 |
| 18.1565 | 202.02 | 4.88605 | 3.37 |
| 19.3237 | 2503.57 | 4.59347 | 41.77 |
| 19.5799 | 2694.99 | 4.53394 | 44.97 |
| 20.0498 | 3254.20 | 4.42873 | 54.30 |
| 20.2731 | 1262.30 | 4.38045 | 21.06 |
| 20.4535 | 786.19 | 4.34222 | 13.12 |
| 20.7689 | 1502.48 | 4.27346 | 25.07 |
| 21.8538 | 5993.11 | 4.06707 | 100.00 |
| 22.4202 | 1826.91 | 3.96557 | 30.48 |
| 23.1042 | 449.63 | 3.84970 | 7.50 |
| 23.8591 | 832.41 | 3.72958 | 13.89 |
| 24.1177 | 2004.80 | 3.69017 | 33.45 |
| 24.5727 | 146.36 | 3.62287 | 2.44 |
| 24.9950 | 655.11 | 3.56261 | 10.93 |
| 25.2803 | 523.44 | 3.52304 | 8.73 |
| 26.0257 | 187.35 | 3.42381 | 3.13 |
| 26.4247 | 246.16 | 3.37300 | 4.11 |
| 26.7579 | 1240.63 | 3.33176 | 20.70 |
| 27.3471 | 678.20 | 3.26129 | 11.32 |
| 27.9806 | 696.77 | 3.18889 | 11.63 |
| 28.6076 | 36.32 | 3.11782 | 0.61 |
| 29.1773 | 51.99 | 3.05822 | 0.87 |
| 29.4436 | 95.40 | 3.03368 | 1.59 |
| 29.8618 | 363.32 | 2.99215 | 6.06 |
| 30.1240 | 274.48 | 2.96669 | 4.58 |
| 30.4710 | 532.10 | 2.93370 | 8.88 |
| 30.7498 | 313.38 | 2.90533 | 5.23 |
| 31.8447 | 473.53 | 2.80788 | 7.90 |
| 32.3126 | 122.45 | 2.77058 | 2.04 |
| 33.4448 | 509.35 | 2.67933 | 8.50 |
| 33.9594 | 230.06 | 2.63990 | 3.84 |
| 34.2786 | 543.23 | 2.61605 | 9.06 |
| 34.4976 | 227.58 | 2.59778 | 3.80 |

Figure 3:
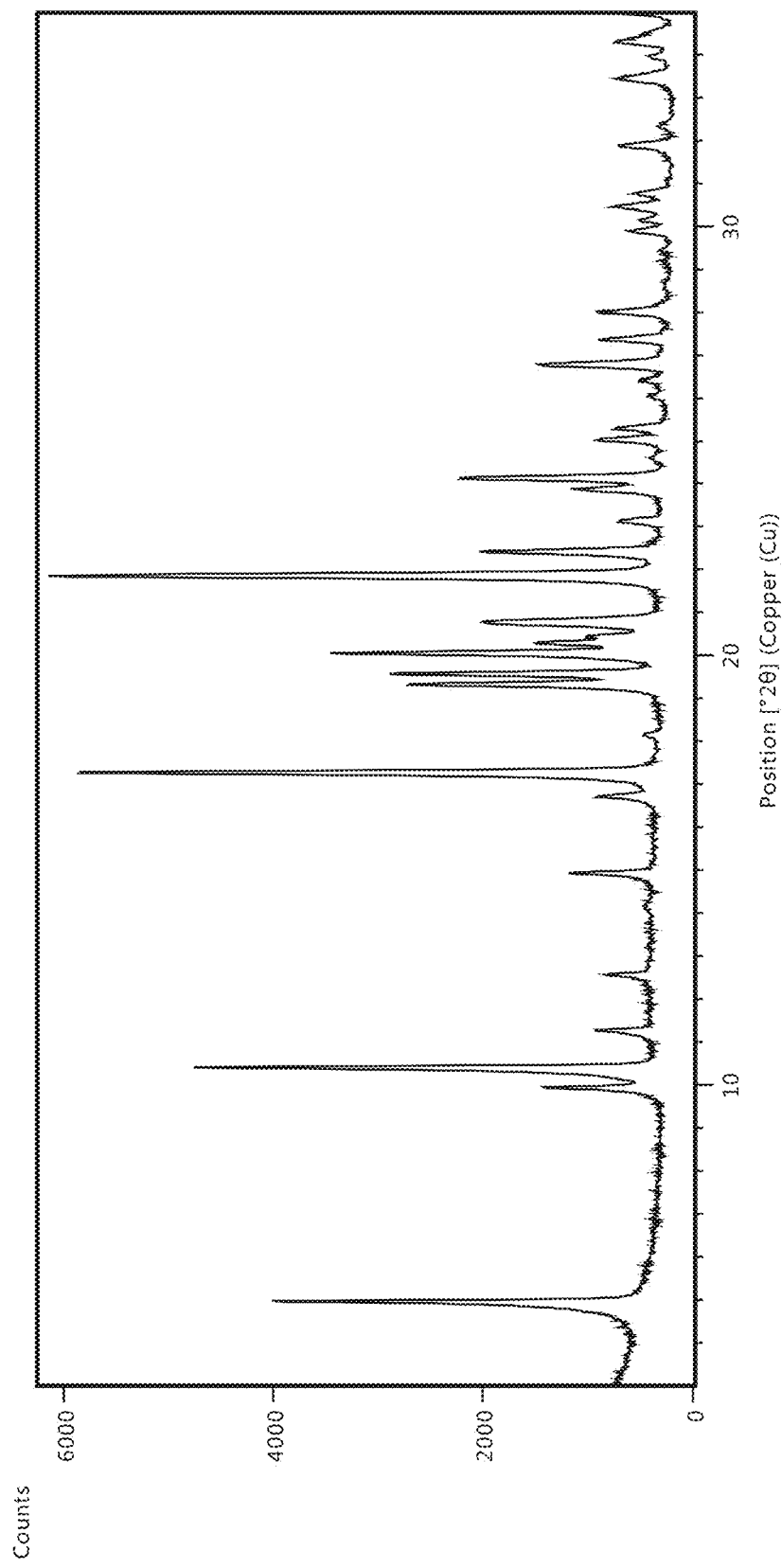
FIG. 3 shows are graphs of a XRPD pattern of polymorphic Form 3.

In one specific embodiment, the polymorphic Form 3 exhibits an XRPD that is substantially similar to FIG. 3.

Figure 30:
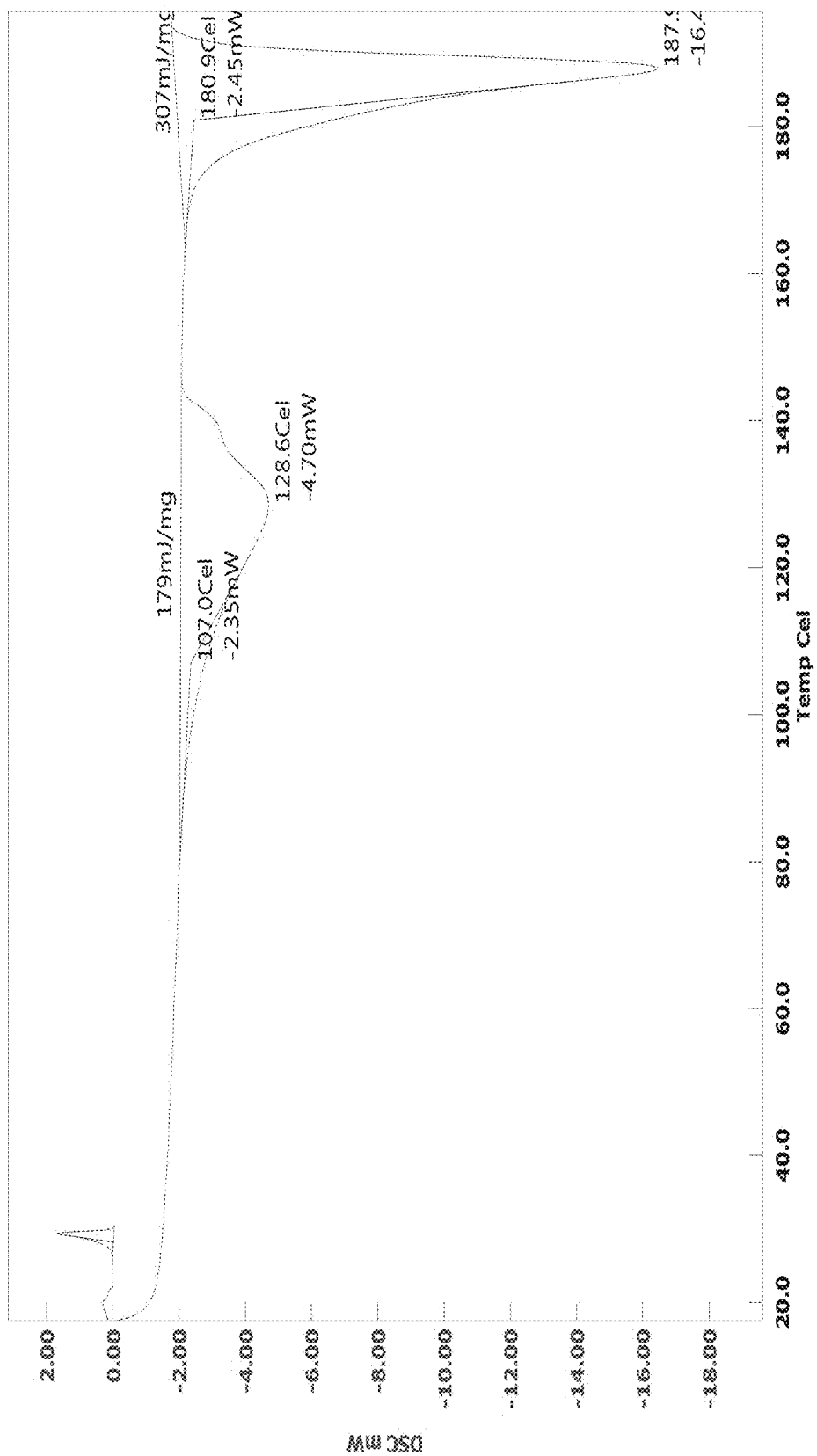
FIG. 30 is a DSC thermogram of polymorphic Form 3.
Figure 31:
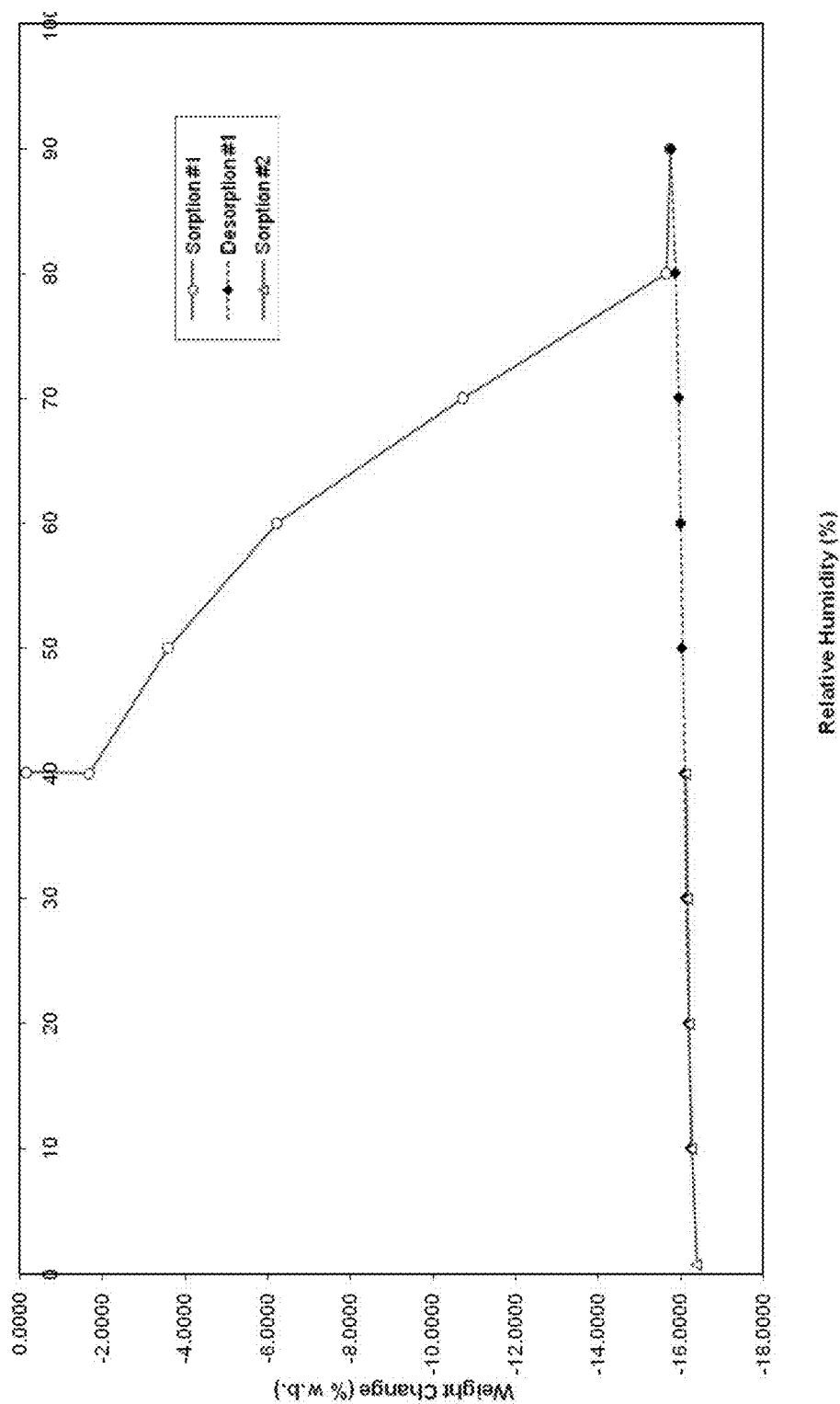
FIG. 31 is an isothermal plot for GVS experiment on polymorphic Form 3.
Figure 32:
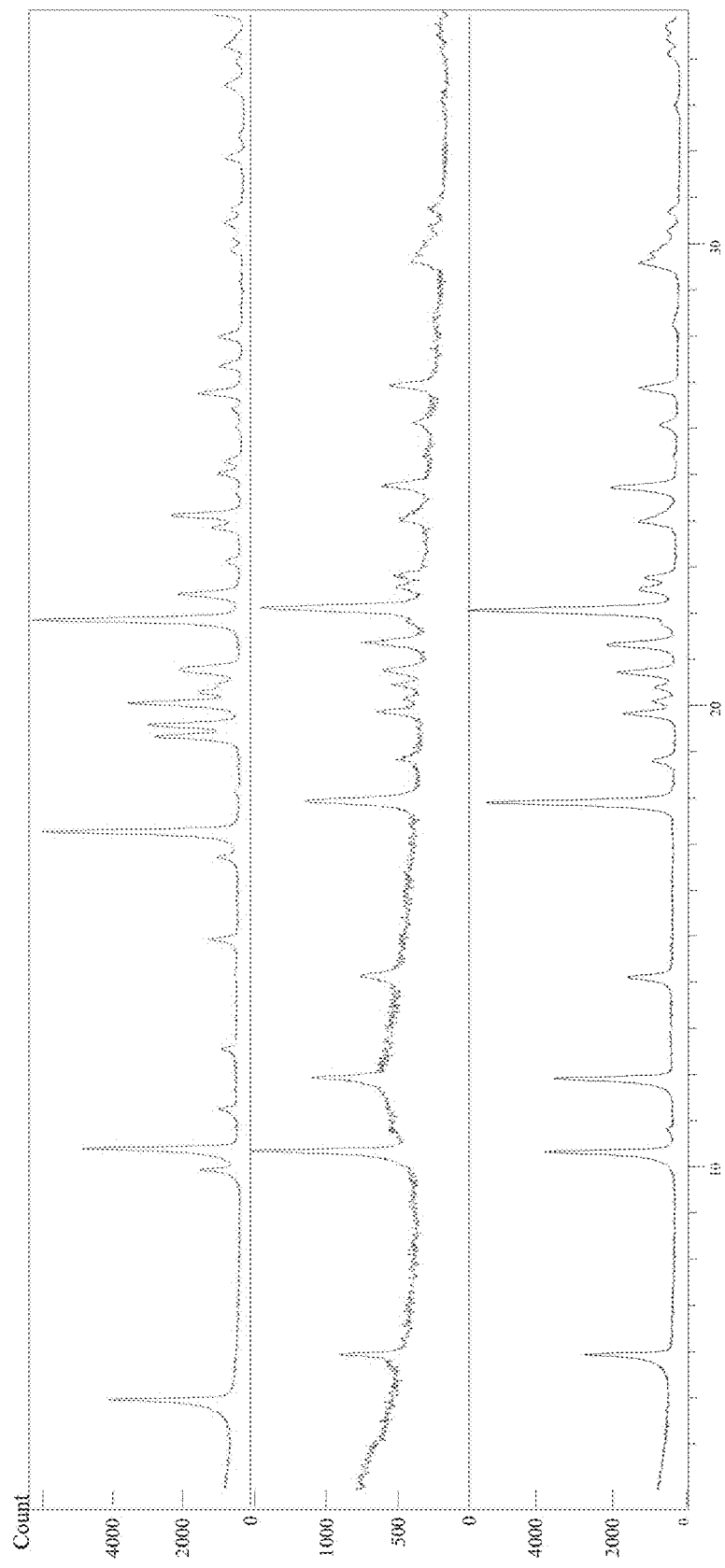
FIG. 32 are stacked XRPD patterns of polymorphic Form 3 before GVS (top), after GVS (middle) and polymorphic Form 1 (bottom).
Figure 33:
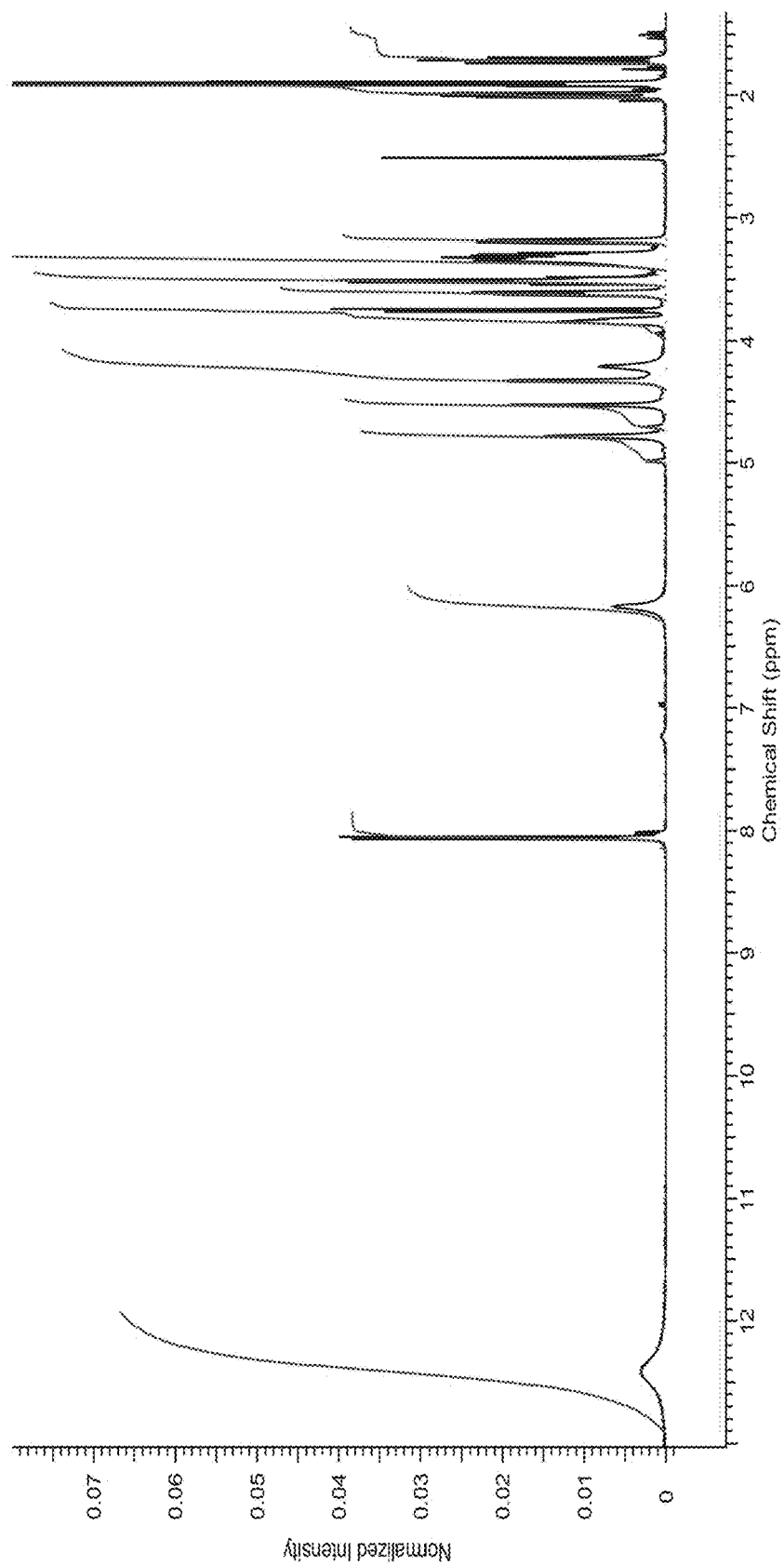
FIG. 33 is a $^1$H-NMR spectrum of polymorphic Form 3 in DMSO.
Figure 34:
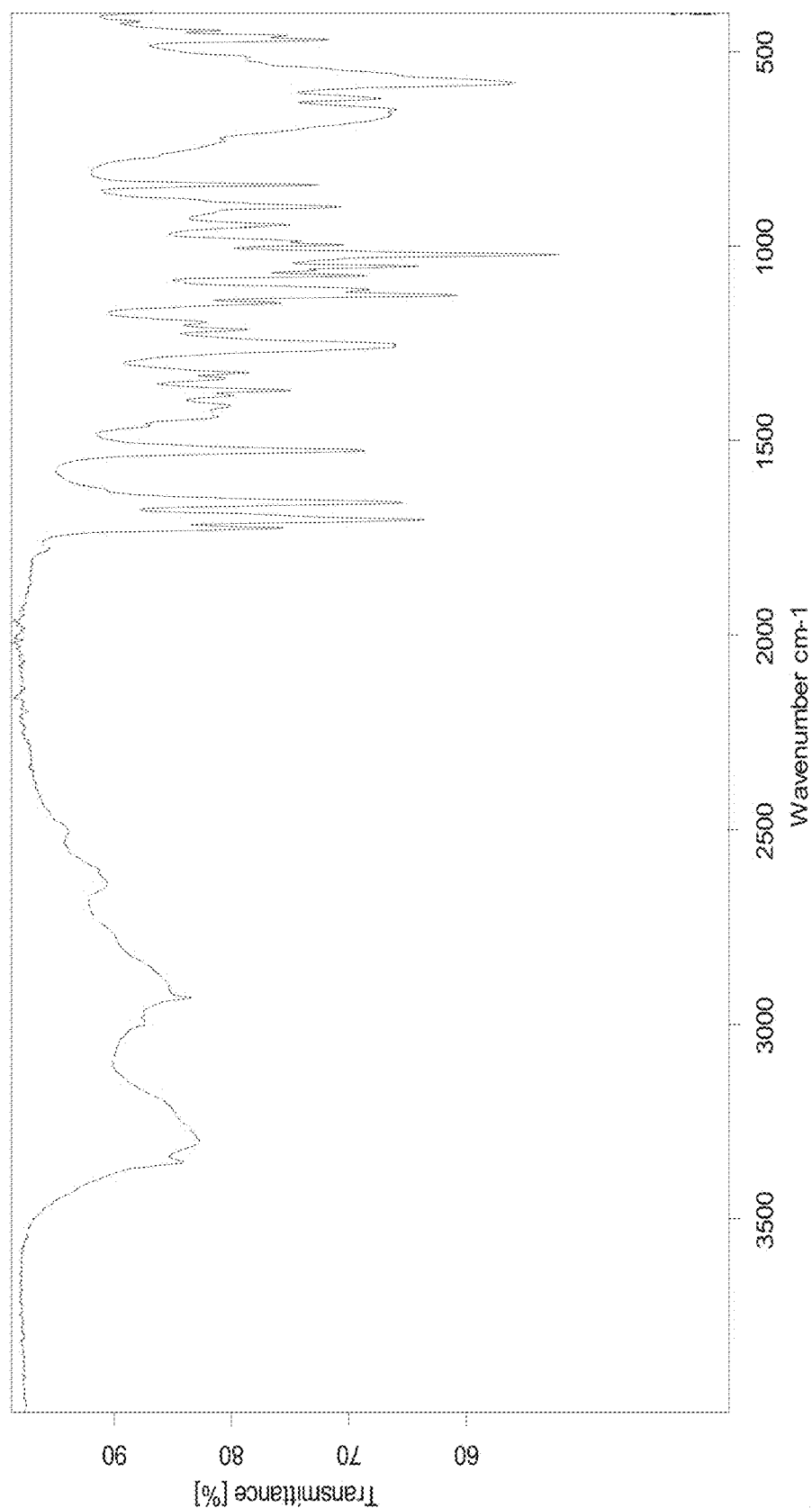
FIG. 34 is an IR spectrum of polymorphic Form 3.
Figure 35:
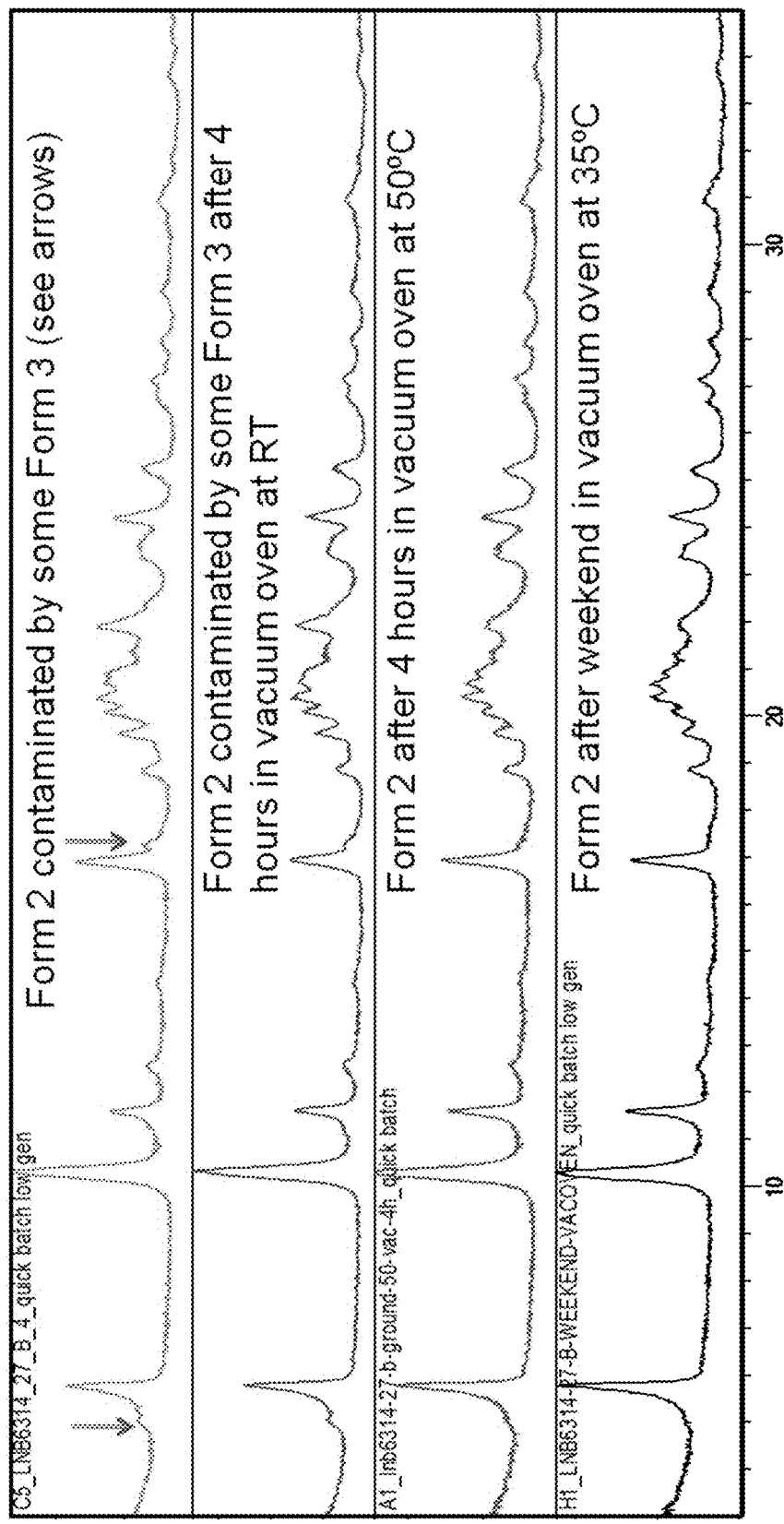
FIG. 35 are stacked patterns showing the formation of polymorphic Form 2 by drying of polymorphic Form 3 under vacuum and heating.
Figure 37:
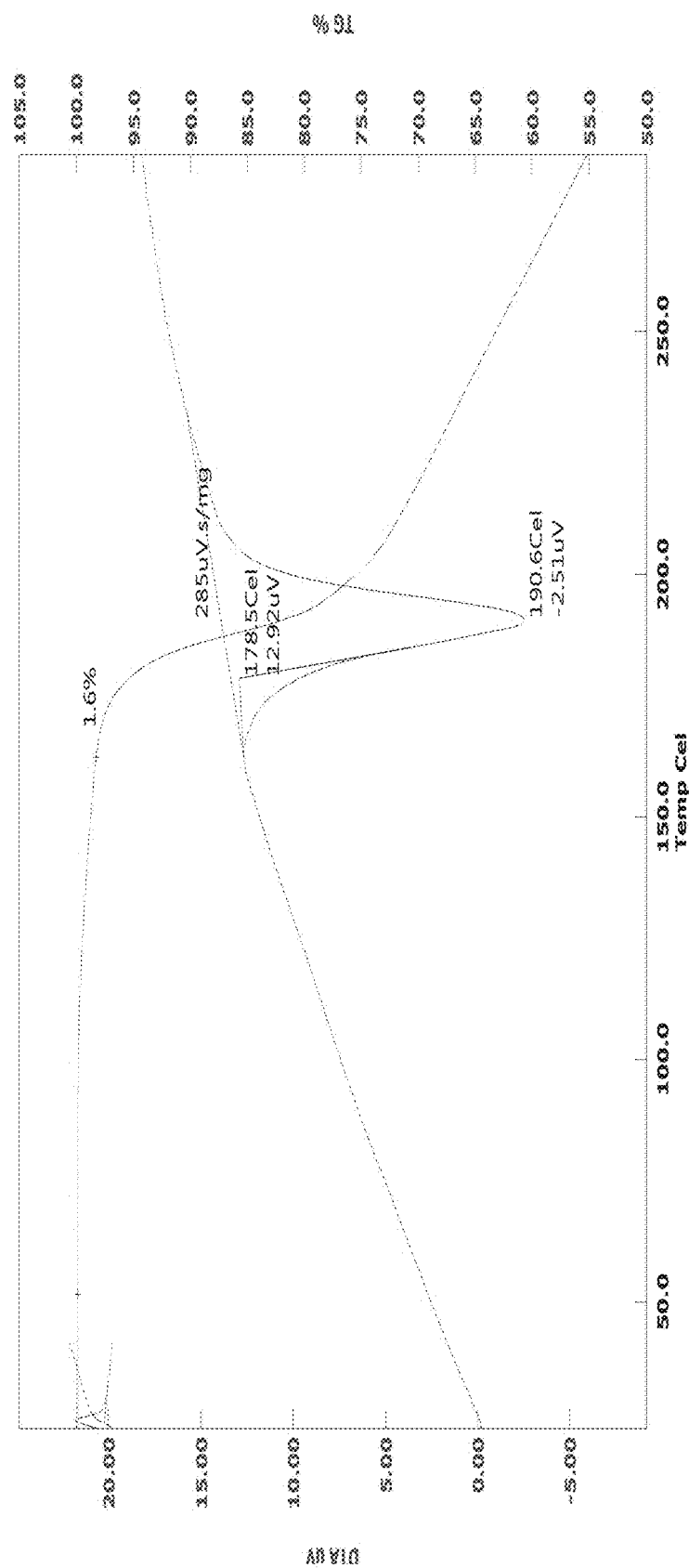
FIG. 37 is an overlay of TG and DTA thermograms of polymorphic Form 2.

In one embodiment, the polymorphic Form 3 exhibits a DSC thermogram comprising a single maximum value at about 180.9° C. with the error of margin of about ±2.5; about ±2; about ±1.5; about ±1; about ±0.5; or less. In one specific embodiment, the polymorphic Form 1 exhibits a DSC thermogram that is substantially similar to FIG. 30.

Form 4

In one embodiment, the polymorphic Form 4 exhibits an XRPD comprising peaks at about 5.20; 7.81; 15.63; 16.73; 18.30, and 18.86 degrees two-theta with the margin of error of about ±0.5; about ±0.4; about ±0.3; about ±0.2; about ±0.1; about ±0.05; or less. In another embodiment, the XRPD of the polymorphic Form 4 further comprises peaks at about 20.94; 22.42; and 24.61 degrees two-theta with the margin of error of about ±0.5; about ±0.4; about ±0.3; about ±0.2; about ±0.1; about ±0.05; or less. In some embodiments, the XRPD of the polymorphic Form 4 comprises three or more peaks at degree two-theta selected from the group consisting of: 5.20; 7.81; 15.63; 16.73; 18.30; 18.86; 20.94; 22.42; and 24.61 with the margin of error of about ±0.5; about ±0.4; about ±0.3; about ±0.2; about ±0.1; about ±0.05; or less. In some embodiments, the XRPD of the polymorphic Form 4 comprises five or more peaks at degree two-theta selected from the group consisting of: 5.20; 7.81; 15.63; 16.73; 18.30; 18.86; 20.94; 22.42; and 24.61 with the margin of error of about ±0.5; about ±0.4; about ±0.3; about ±0.2; about ±0.1; about ±0.05; or less. In yet another embodiment, the polymorphic Form 4 exhibits an XRPD comprising peaks shown in the table below:

TABLE 4

XRPD Table of the polymorphic Form 4.

| Pos. [° 2θ] | Height [cts] | d-spacing [Å] | Rel. Int. [%] |
|---|---|---|---|
| 5.0847 | 224.30 | 17.37988 | 28.70 |
| 5.2046 | 563.28 | 16.97987 | 72.06 |
| 7.6448 | 125.80 | 11.56453 | 16.09 |
| 7.8122 | 781.68 | 11.31715 | 100.00 |
| 10.4221 | 59.99 | 8.48819 | 7.67 |
| 15.6272 | 360.47 | 5.67070 | 46.11 |
| 15.7117 | 297.90 | 5.64041 | 38.11 |
| 16.7258 | 512.15 | 5.30063 | 65.52 |
| 18.2957 | 534.19 | 4.84919 | 68.34 |
| 18.8553 | 469.35 | 4.70652 | 60.04 |
| 19.7999 | 296.51 | 4.48406 | 37.93 |
| 20.9437 | 547.78 | 4.24170 | 70.08 |
| 21.1382 | 244.98 | 4.20309 | 31.34 |
| 21.6241 | 114.34 | 4.10974 | 14.63 |
| 22.2735 | 371.05 | 3.99136 | 47.47 |
| 22.4163 | 495.53 | 3.96626 | 63.39 |
| 22.8619 | 483.94 | 3.88996 | 61.91 |
| 23.6102 | 187.02 | 3.76834 | 23.92 |
| 24.6055 | 405.95 | 3.61811 | 51.93 |
| 25.8832 | 97.17 | 3.44233 | 12.43 |
| 27.3702 | 255.97 | 3.25860 | 32.75 |
| 27.9582 | 60.13 | 3.18875 | 7.69 |
| 28.3220 | 113.02 | 3.15122 | 14.46 |
| 28.9557 | 130.84 | 3.08367 | 16.74 |
| 29.8280 | 42.09 | 2.99545 | 5.39 |
| 30.8125 | 55.33 | 2.90195 | 7.08 |
| 32.1151 | 31.83 | 2.78717 | 4.07 |
| 33.2634 | 133.70 | 2.69130 | 17.10 |
| 33.3964 | 84.91 | 2.68088 | 10.86 |

Figure 4:
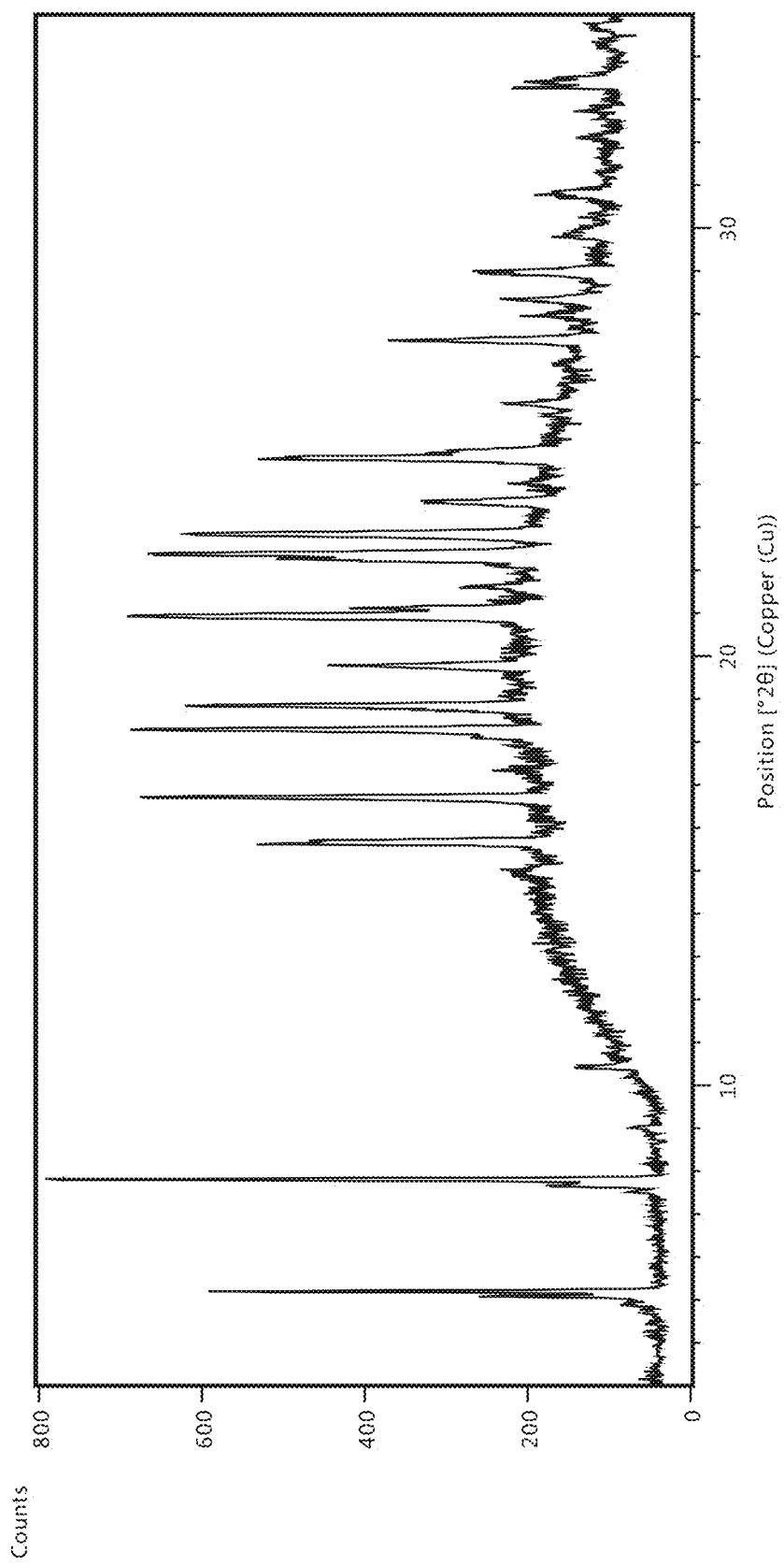
FIG. 4 shows are graphs of a XRPD pattern of polymorphic Form 4.

In one specific embodiment, the polymorphic Form 4 exhibits an XRPD that is substantially similar to FIG. 4.

Form 5

In one embodiment, the polymorphic Form 5 exhibits an XRPD comprising peaks at about 11.51; 12.90; 13.94; 18.13; and 18.99 degrees two-theta with the margin of error of about ±0.5; about ±0.4; about ±0.3; about ±0.2; about ±0.1; about ±0.05; or less. In another embodiment, the XRPD of the polymorphic Form 5 further comprises peaks at about 19.25; 22.73; 23.86; 24.35; 24.75; and 25.90 degrees two-theta with the margin of error of about ±0.5; about ±0.4; about ±0.3; about ±0.2; about ±0.1; about ±0.05; or less. In some embodiments, the XRPD of the polymorphic Form 5 comprises three or more peaks at degree two-theta selected from the group consisting of: 11.51; 12.90; 13.94; 18.13; 18.99; 19.25; 22.73; 23.86; 24.35; 24.67; 24.75, and 25.90 with the margin of error of about ±0.5; about ±0.4; about ±0.3; about ±0.2; about ±0.1; about ±0.05; or less. In some embodiments, the XRPD of the polymorphic Form 4 comprises five or more peaks at degree two-theta selected from the group consisting of: 11.51; 12.90; 13.94; 18.13; 18.99; 19.25, 22.73, 23.86, 24.35, 24.67; 24.75, and 25.90 with the margin of error of about ±0.5; about ±0.4; about ±0.3; about ±0.2; about ±0.1; about ±0.05; or less. In yet another embodiment, the polymorphic Form 5 exhibits an XRPD comprising peaks shown in the table below:

TABLE 5

XRPD Table of the polymorphic Form 5.

| Pos. [° 2θ] | Height [cts] | d-spacing [Å] | Rel. Int. [%] |
|---|---|---|---|
| 11.1154 | 141.06 | 7.96024 | 1.42 |
| 11.2815 | 166.06 | 7.83695 | 1.67 |
| 11.5126 | 2132.26 | 7.68013 | 21.43 |
| 12.6900 | 555.55 | 6.97588 | 5.58 |
| 12.9001 | 9948.38 | 6.86271 | 100.00 |
| 13.4430 | 2176.75 | 6.58674 | 21.88 |
| 13.5563 | 4409.92 | 6.53194 | 44.33 |
| 13.9387 | 6205.15 | 6.35362 | 62.37 |
| 14.6548 | 923.32 | 6.04471 | 9.28 |
| 18.1323 | 2408.31 | 4.88846 | 24.21 |
| 18.9902 | 7686.38 | 4.67338 | 77.26 |
| 19.2472 | 3453.36 | 4.61155 | 34.71 |
| 20.4813 | 820.79 | 4.33639 | 8.25 |
| 21.6299 | 658.98 | 4.10864 | 6.62 |
| 22.7291 | 8792.90 | 3.91238 | 88.39 |
| 23.1458 | 660.62 | 3.84288 | 6.64 |
| 23.3134 | 325.73 | 3.81562 | 3.27 |
| 23.8592 | 2757.33 | 3.72647 | 27.72 |
| 23.9363 | 2190.48 | 3.71465 | 22.02 |
| 24.0063 | 1761.62 | 3.70397 | 17.71 |
| 24.2374 | 1293.07 | 3.66917 | 13.00 |
| 24.3540 | 4162.41 | 3.65188 | 41.84 |
| 24.6741 | 6586.32 | 3.60522 | 66.20 |
| 24.7496 | 4798.25 | 3.60332 | 48.23 |
| 25.8958 | 4377.64 | 3.43784 | 44.00 |
| 25.9739 | 2238.63 | 3.43619 | 22.50 |
| 26.8964 | 1481.57 | 3.31217 | 14.89 |
| 27.2840 | 1055.91 | 3.26600 | 10.61 |
| 28.0716 | 95.86 | 3.17612 | 0.96 |
| 28.5791 | 729.62 | 3.12086 | 7.33 |
| 28.6669 | 590.80 | 3.11151 | 5.94 |
| 29.6084 | 69.48 | 3.01467 | 0.70 |
| 30.4507 | 523.30 | 2.93318 | 5.26 |
| 30.6213 | 445.63 | 2.91722 | 4.48 |
| 30.9059 | 357.19 | 2.89100 | 3.59 |
| 30.9760 | 407.33 | 2.88462 | 4.09 |
| 31.4466 | 292.32 | 2.84251 | 2.94 |
| 31.5153 | 113.39 | 2.83647 | 1.14 |
| 32.4331 | 204.52 | 2.75827 | 2.06 |
| 32.6687 | 393.23 | 2.73891 | 3.95 |
| 32.9581 | 725.33 | 2.71553 | 7.29 |
| 33.0940 | 982.52 | 2.70468 | 9.88 |
| 33.1777 | 376.16 | 2.69805 | 3.78 |
| 33.4151 | 487.76 | 2.67943 | 4.90 |
| 33.6044 | 1439.94 | 2.66476 | 14.47 |
| 33.7037 | 752.60 | 2.66374 | 7.57 |
| 34.2563 | 335.94 | 2.61553 | 3.38 |
| 34.7297 | 257.30 | 2.58095 | 2.59 |

Figure 5:
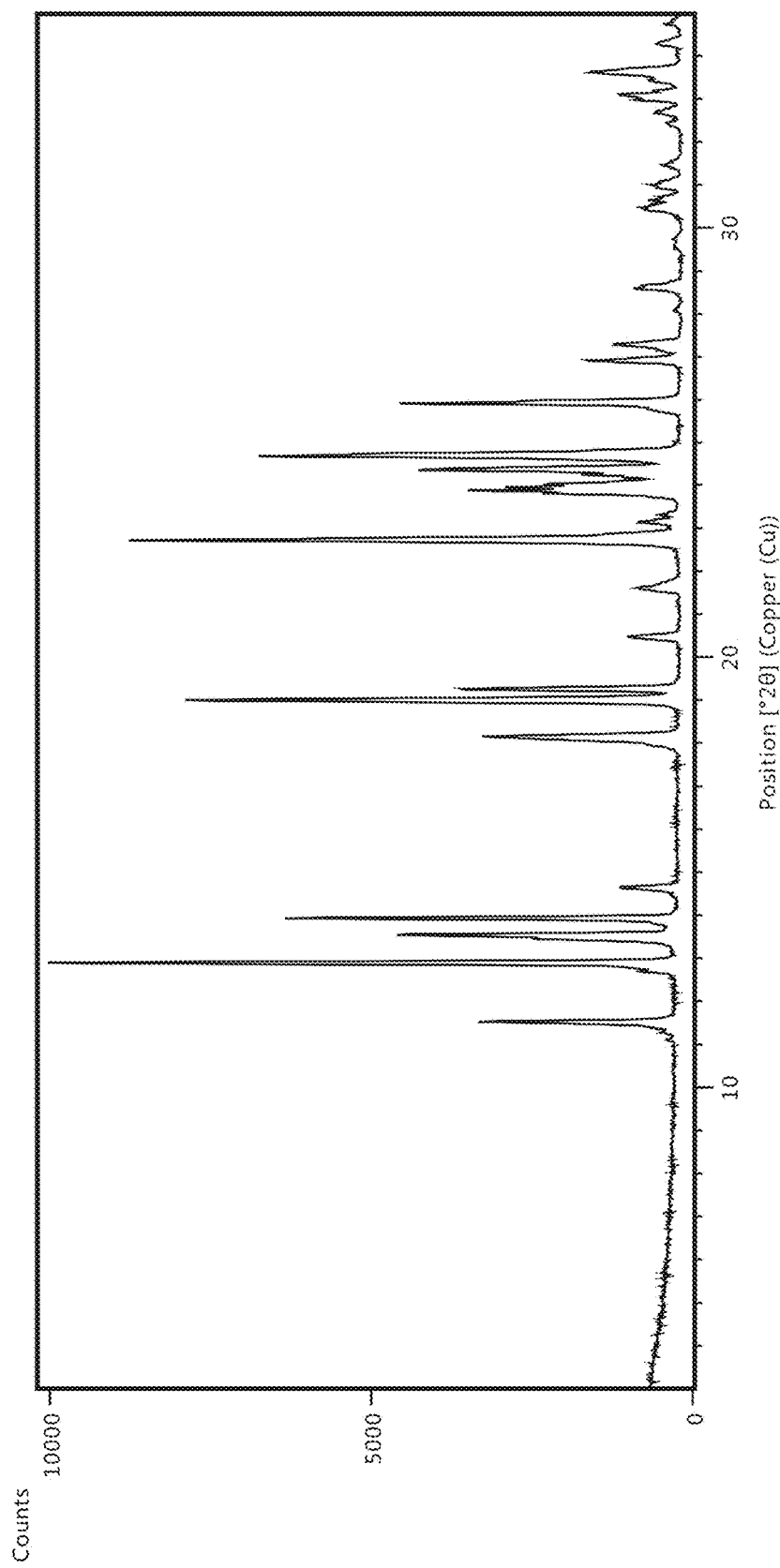
FIG. 5 shows are graphs of a XRPD pattern of polymorphic Form 5.
Figure 6:
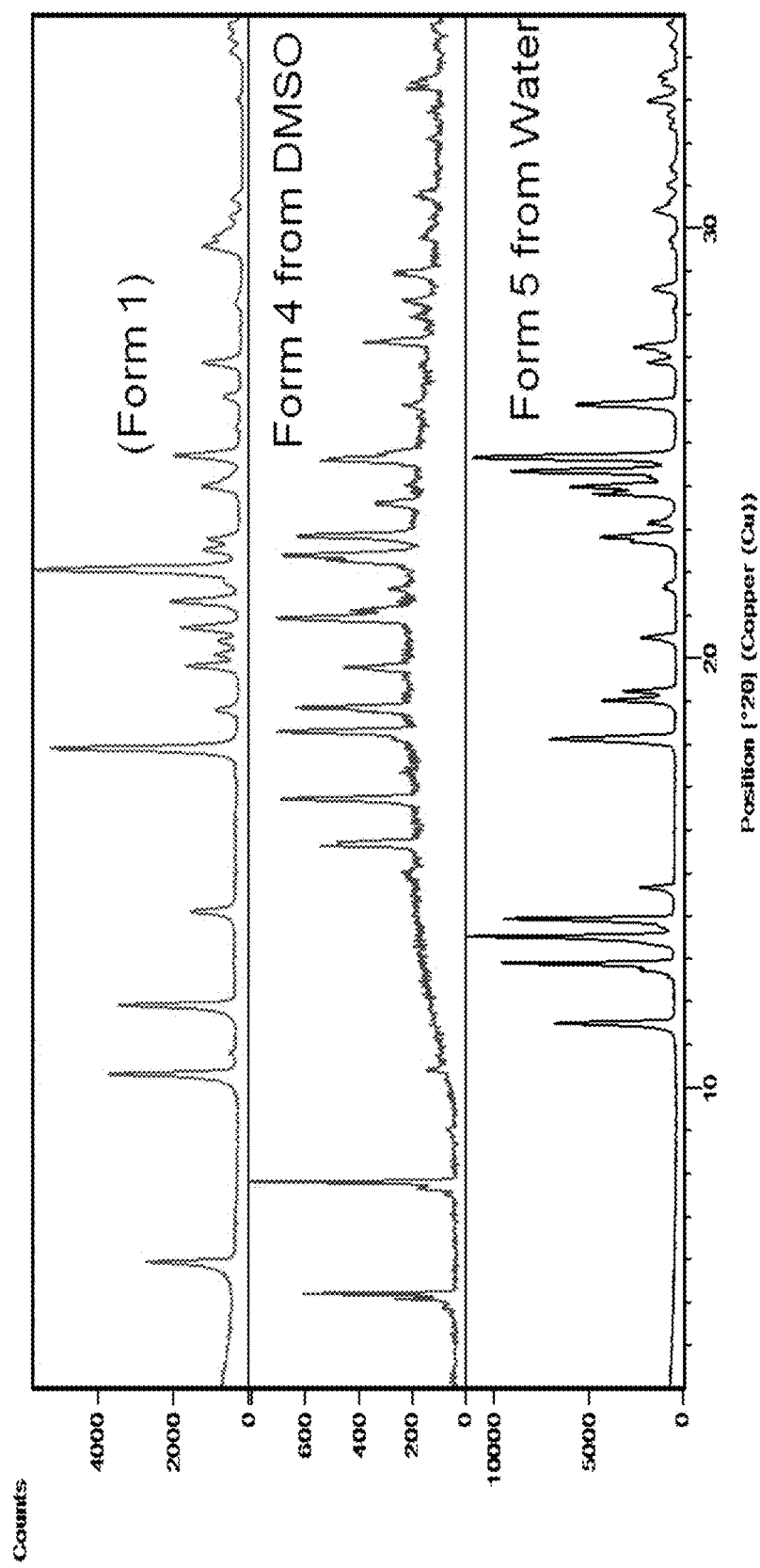
FIG. 6 are stacked diffractograms of the different forms observed in the polymorph screen.

In one specific embodiment, the polymorphic Form 5 exhibits an XRPD that is substantially similar to FIG. 5.

Figure 22:
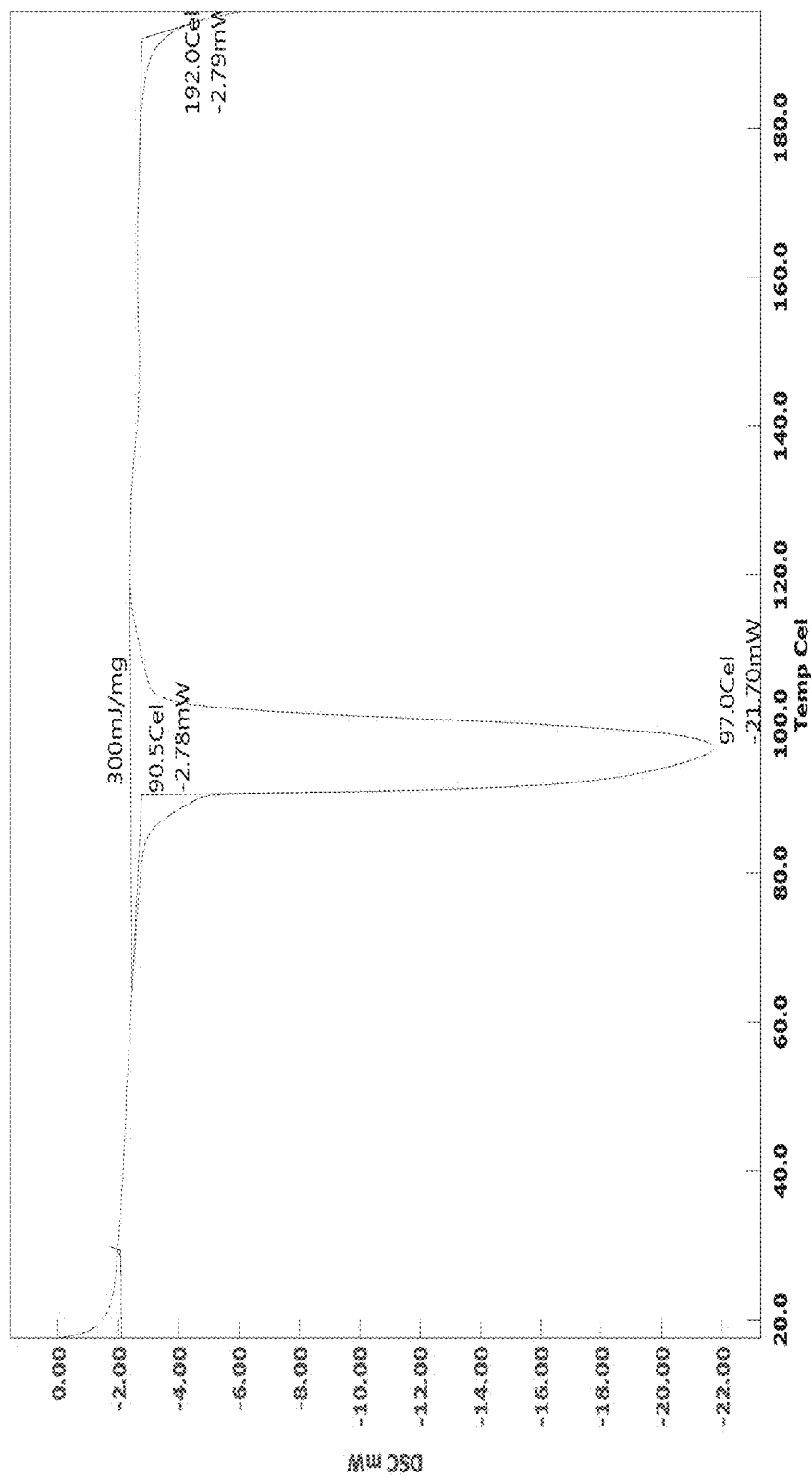
FIG. 22 is a DSC thermogram of polymorphic Form 5.

In one embodiment, the polymorphic Form 5 exhibits a DSC thermogram comprising a single maximum value at about 192.0° C. with the error of margin of about ±2.5; about ±2; about ±1.5; about ±1; about ±0.5; or less. In one specific embodiment, the polymorphic Form 1 exhibits a DSC thermogram that is substantially similar to FIG. 22.

Pharmaceutical Compositions

In another embodiment, the present invention provides a pharmaceutical composition comprising a therapeutically effective amount of one or more crystalline forms as described in the present disclosure, combined with a pharmaceutically acceptable excipient or carrier. The excipients are added to the formulation for a variety of purposes.

Diluents may be added to the formulations of the present invention. Diluents increase the bulk of a solid pharmaceutical composition, and may make a pharmaceutical dosage form containing the composition easier for the patient and care giver to handle. Diluents for solid compositions include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT), potassium chloride, powdered cellulose, sodium chloride, sorbitol, and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g., carbopol), carboxymethylcellulose sodium, dextrin, ethyl cellulose, gelatin, guar gum, hydrogenated vegetable oil, hydroxyethyl cellulose, hydroxypropyl cellulose (e.g., KLUCEL), hydroxypropyl methyl cellulose (e.g., METHOCEL), liquid glucose, magnesium aluminum silicate, maltodextrin, methylcellulose, polymethacrylates, povidone (e.g., KOLLIDON, PLASDONE), pregelatinized starch, sodium alginate, and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g., AC-DI-SOL and PRIMELLOSE), colloidal silicon dioxide, croscarmellose sodium, crospovidone (e.g., KOLLIDON and POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB), and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions prepared using the crystalline forms of the present invention, one or more crystalline forms as described and any other solid excipients are dissolved or suspended in a liquid carrier such as water, vegetable oil, alcohol, polyethylene glycol, propylene glycol, or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition may also contain a buffer such as guconic acid, lactic acid, citric acid or acetic acid, sodium guconate, sodium lactate, sodium citrate, or sodium acetate. Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and lozenges, as well as liquid syrups, suspensions and elixirs.

The oral dosage form of the present invention is preferably in the form of an oral capsule or tablet having a dosage of about 15 mg to about 1500 mg in total weight including the active ingredient and other excipients. In some embodiments, the oral dosage form contains about 100 mg to about 1000 mg of sialic acid in each unit dosage. In some embodiments, the oral dosage form contains about 325 or about 500 mg of sialic acid in each unit dosage.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The active ingredient and excipients may be formulated into compositions and dosage forms according to methods known in the art.

In some embodiments, an extended release formulation as described in WO 2012/009474 and WO 2013/109906 comprising the crystalline forms of the present invention is particularly useful. For example, such an extended release formulation can contain a drug load of about 35-50% (e.g., one or more crystalline forms of sialic acid and crystalline forms of the salts and/or solvates of sialic acid), about 20-30% w/w of at least one water-swellable, pH independent polymer or a hydrogel, about 20-25% w/w of at least one anionic, pH-dependent, gel-forming copolymer, and about 1-5% w/w of at least one hydrocolloid polymer.

Therapeutic Use

As used herein, administering of the presently disclosed crystalline forms can be effected or performed using any of the various methods known to those skilled in the art. The crystalline form can be administered, for example, subcutaneously, intravenously, parenterally, intraperitoneally, intradermally, intramuscularly, topically, enteral (e.g., orally), rectally, nasally, buccally, sublingually, vaginally, by inhalation spray, by drug pump or via an implanted reservoir in dosage formulations containing conventional non-toxic, physiologically acceptable carriers or vehicles.

Further, the presently disclosed crystalline forms can be administered to a localized area in need of treatment. This can be achieved by, for example, and not by way of limitation, local infusion during surgery, topical application, transdermal patches, by injection, by catheter, by suppository, or by implant (the implant can optionally be of a porous, non-porous, or gelatinous material), including membranes, such as sialastic membranes or fibers.

Additionally, administration can comprise administering to the subject a plurality of dosages over a suitable period of time. Such administration regimens can be determined according to routine methods, upon a review of the instant disclosure.

The crystalline forms of the present application can be employed as the sole active agent in a pharmaceutical or can be used in combination (e.g., administered proximate in time to each other or even in the same formulation) with other active ingredients, e.g., neurotrophins, or other factors or drugs.

Provided herein are also methods of treating and/or preventing sialic acid deficiencies in an individual in need thereof by administering an effective amount of one or more crystalline forms of sialic acid and crystalline forms of the salts and/or solvates of sialic acid in any pharmaceutical composition described herein. The methods may comprise administration of an effective amount of any of the compositions, including any of the extended release formulations as described above.

In some embodiments, the methods of treating and/or preventing sialic acid deficiencies increase sialic acid production. In some embodiments, the methods of treating and/or preventing sialic acid deficiencies increase sialylation of effected tissue.

Sialic acid is important for proper development and functioning of many organs and tissues, and a deficiency of sialic acid can give rise to many different types of diseases and conditions. Other types of muscle diseases have also shown that glycosylation is important for muscle function. Nishino and Ozawa, Curr. Opin. Neurol. 15:539-544 (2002). In some embodiments, the sialic acid deficiency is a myopathy, muscular atrophy and/or muscular dystrophy. Myopathies that can be treated with the present compositions and methods also include distal myopathy with rimmed vacuoles (Nonaka myopathy) and the muscular dystrophy hereditary inclusion body myopathy (HIBM). In some embodiments, the methods of treating and/or preventing increase sialylation of muscle tissue. The methods of treating and/or preventing can improve muscle function and reduce muscle injury from physical activity, as measures by creatine kinase plasma levels after exercise. In some embodiments, the methods of treating or preventing muscle dysfunction will improve independent ambulation, stair climbing, foot drop, getting up from a chair and walking, hand grip and manipulation and pulmonary function. In some embodiments, the method further comprises identifying an individual in need thereof by determining genotype or expression levels of the gene GNE.

In some embodiments, the sialic acid deficiency is a kidney condition and diseases (e.g., those involving proteinuria and hematuria). Proteinuria involves leakage of protein from the blood into the urine. If the amount of protein in the urine is very high, this condition is often called nephrotic syndrome. Several types of diseases exhibit the symptoms of proteinuria, including high blood pressure, infections, reflux nephropathy, diabetes, and various types of glomerulonephritis, including minimal change nephrosis. Hematuria simply means blood in the urine (e.g., gross hematuria or microscopic hematuria). In some embodiments, the methods of treating and/or preventing increase sialylation of kidney tissue.

In embodiments of any of the methods, a therapeutically effective amount of one or more crystalline forms of sialic acid and crystalline forms of the salts and/or solvates of sialic acid is provided over a period of greater than about any of 1, 2, 3, 4, 5, 6, 7, 8, 9, 10, 11, 12, 13, 14, 15, 16, 17, 18, 19, 20, 21, 22, 23, or 24 hours. In some embodiments, a therapeutically effective amount of one or more crystalline forms of sialic acid and crystalline forms of the salts and/or solvates of sialic acid is provided over a period of greater than about 12 hours or greater than about 24 hours. In embodiments of any of the methods, a therapeutically effective amount of one or more crystalline forms of sialic acid and crystalline forms of the salts and/or solvates of sialic acid is provided over a period of between about any of 1-24 hours, 4-24 hours, 6-24 hours, 8-24 hours, or 12-24 hours. In embodiments of any of the methods, a therapeutically effective amount of one or more crystalline forms of sialic acid and crystalline forms of the salts and/or solvates of sialic acid is provided over a period of about any of 1, 2, 3, 4, 5, 6, 7, 8, 9, 10, 11, 12, 13, 14, 15, 16, 17, 18, 19, 20, 21, 22, 23, or 24 hours. In some embodiments, a therapeutically effective amount of one or more crystalline forms of sialic acid and crystalline forms of the salts and/or solvates of sialic acid is provided over a period of about 12 hours or about 24 hours.

In some embodiments, the therapeutically effective amount is provided to the bloodstream of the individual. In some embodiments, the therapeutically effective amount is provided to muscle tissue of the individual.

In embodiments of any of the methods, one or more crystalline forms of sialic acid and crystalline forms of the salts and/or solvates of sialic acid are administered to an individual in need thereof between about any of 0.1-50 g/day, 0.5-25 g/day, 1-15 g/day, 1-10 g/day, 2-5 g/day, 0.2-25 g/day, 0.3-12 g/day, 0.4-10 g/day, 0.5-8 g/day, and 0.7-6 g/day. In some embodiments, one or more crystalline forms of sialic acid and crystalline forms of the salts and/or solvates of sialic acid are administered between about 2 g/day and 5 g/day.

In one embodiment, one or more crystalline forms of sialic acid and crystalline forms of the salts and/or solvates of sialic acid are administered about 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1 g, 1.5 g, 2 g, 2.5 g, 3 g, 3.5 g, 4 g, 4.5 g, 5 g, 5.5 g, 6 g, 6.5 g, 7 g, 7.5 g, 8 g, 8.5 g, 9 g, 9.5 g, 10 g, 10.5 g, 11 g, 11.5 g, 12 g, 12.5 g, 13 g, 13.5 g, 14 g, or 14.5 g per day. In one embodiment, one or more crystalline forms of sialic acid and crystalline forms of the salts and/or solvates of sialic acid are administered about 3 g, 4 g, 5 g, 6 g, 7 g, 8 g, 9 g, 10 g, 11 g, or 12 g per day.

In embodiments of any of the methods, one or more crystalline forms of sialic acid and crystalline forms of the salts and/or solvates of sialic acid are administered to an individual in need thereof between about any of 0.01-750 mg/kg, 0.5-500 mg/kg, 1-250 mg/kg, 2.5-100 mg/kg, or 5-50 mg/kg. In some embodiments, one or more crystalline forms of sialic acid and crystalline forms of the salts and/or solvates of sialic acid are administered to an individual in need thereof between about 5 mg/kg and 50 mg/kg.

In some embodiments, the effective amount of one or more crystalline forms of sialic acid and crystalline forms of the salts and/or solvates of sialic acid in a pharmaceutical composition described herein is administered once a day, twice a day, three times a day, or four times a day. In addition, each time an effective amount of one or more crystalline forms of sialic acid and crystalline forms of the salts and/or solvates of sialic acid in a pharmaceutical composition described herein is administered; multiple dosage forms may be administered at a time. That is, a subject prescribed to take 1 g of one or more crystalline forms of sialic acid and crystalline forms of the salts and/or solvates of sialic acid, three times a day for a total daily dose of 3 g may be prescribed to take two unit doses each containing 500 mg of sialic acid.

In one embodiment, a pharmaceutical composition comprising one or more crystalline forms of sialic acid and crystalline forms of the salts and/or solvates of sialic acid is in an extended release form. In another embodiment, the extended release composition such as those disclosed in WO 2012/009474 and WO 2013/109906 may be useful, the disclosures of which are hereby incorporated by reference in their entireties for all purposes.

In one embodiment, an extended release formulation comprising one or more crystalline forms of sialic acid and/or crystalline forms of the salts and/or solvates of sialic acid is present in about 20% w/w to about 80% w/w; about 20% w/w to about 60% w/w; about 20% w/w to about 50% w/w; about 20% w/w to about 40% w/w; about 20% w/w to about 30% w/w; about 15% w/w to about 60% w/w; about 15% w/w to about 50% w/w; about 15% w/w to about 40% w/w; about 25% w/w to about 60% w/w; about 25% w/w to about 50% w/w; 25% w/w to about 40% w/w; about 25% w/w to about 30% w/w; about 30% w/w to about 60% w/w; about 30% w/w to about 50% w/w; about 30% w/w to about 45% w/w; about 30% w/w to about 40% w/w; about 35% w/w to about 60% w/w; about 35% w/w to about 50% w/w; about 35% w/w to about 45% w/w; or about 40% w/w to about 45% w/w of the formulation. In another embodiment, an extended release formulation comprising one or more crystalline forms of sialic acid and/or crystalline forms of the salts and/or solvates of sialic acid is present in about any of 35% w/w, 36% w/w, 37% w/w, 38% w/w, 39% w/w, 40% w/w, 41% w/w, 42% w/w, 43% w/w, 44% w/w, 45% w/w, 46% w/w, 47% w/w, 48% w/w, 49% w/w and 50% w/w of the formulation. In one embodiment, an extended release formulation comprising one or more crystalline forms of sialic acid and/or crystalline forms of the salts and/or solvates of sialic acid is present in about 40% to about 45% w/w of the formulation.

In one embodiment of the extended release formulations disclosed herein, the crystalline form of sialic acid is a crystalline form of NeuAc. In another embodiment, the crystalline form of sialic acid is polymorphic Form 1 of NeuAc. In another embodiment, the crystalline form of sialic acid is polymorphic Form 2 of NeuAc. In another embodiment, the crystalline form of sialic acid is polymorphic Form 3 of NeuAc. In another embodiment, the crystalline form of sialic acid is polymorphic Form 4 of NeuAc. In another embodiment, the crystalline form of sialic acid is polymorphic Form 5 of NeuAc.

In one embodiment, extended release formulations comprising one or more crystalline forms of sialic acid and/or crystalline forms of the salts and/or solvates of sialic acid as described herein may include one or more polymers. The polymer may be a natural polymer (e.g., polysaccharide or protein), modified natural polymer, and/or synthetic polymer. The polymer may be, for example, a hydrophobic polymer, hydrophilic polymer, hydrogel, soluble polymer, biodegradable polymer, nonbiodegradable polymer, and/or mucoadhesive polymer.

In some embodiments, the polymer is a hydrophobic polymer. Examples of hydrophobic polymers include polyethylene, polyvinyl chloride, ethyl cellulose or acrylate polymers and their copolymers.

In some embodiments, the polymer is a hydrophilic polymer. Examples of hydrophilic polymers include a) cellulose derivatives such as methylcellulose (MC), hydroxyethyl-cellulose, hydroxypropylmethyl-cellulose (HPMC), or sodium carboxymethylcellulose, b) noncellulose natural or semisynthetic polymers such as agar-agar, carob gum, alginates, molasses, polysaccharides of mannose and galactose, or chitosan and modified starches and c) polymers of acrylic acid such as carbopol polymers.

In some embodiments, the polymer is a hydrogel. Examples of hydrogels include, but are not limited to, polyhydroxyethyle methylacrylate (PHEMA), polyvinyl alcohol (PVA), polyvinyl pyrrolidone (PVP), polyethylene oxide (PEO), or polyacrylamide (PA). In some embodiments, the hydrogel is polyethylene oxide (e.g., Polyox™ water soluble resin, Dow Chemical Company, Mich., USA). In one embodiment, an extended release formulation may comprise hydrogel or hydrogeol-forming polymer in about 20% w/w to about 50% w/w; about 20% w/w to about 40% w/w, about 20% w/w to about 30% w/w; about 20% w/w to about 25% w/w; about 25% w/w to about 30% w/w; about 22% w/w to about 27% w/w; or about any of 20% w/w, 21% w/w, 22% w/w, 23% w/w, 24% w/w, 25% w/w, 26% w/w, 27% w/w, 28% w/w, 29% w/w and 30% w/w of the formulation.

In some embodiments, the polymer is a soluble polymer. Examples of soluble polymers include, but are not limited to, polyethylene glycol (PEG), PVA, PVP, or HPMC.

In some embodiments, the polymer is a biodegradable polymer. Examples of biodegradable polymers include, but are not limited to, polylactic acid (PLA), polyglycolic acid (PGA), poly(lactic/glycolic acid) (PLGA), polycaprolactone (PCL), polyanhydrides, or polyorthoesters.

In some embodiments, the polymer is a nonbiodegradable polymer. Examples of nonbiodegradable polymers include, but are not limited to, polyethylene vinyl acetate, polydimethyl siloxane (PDS), polyether urethane (PEU), polyvinyl chloride (PVC), cellulose acetate (CA), or ethyl cellulose (EC).

In some embodiments, the polymer is a mucoadhesive polymer. Examples of mucoadhesive polymers include, but are not limited to, polycarbophil, sodium carboxymethyl cellulose, polyacrylic acid, tragacanth, methyl cellulose, pectin, natural gums, xanthan gum, guar gum, or karaya gum.

In some embodiments, the extended release pharmaceutical formulation includes two polymers. In some embodiments, the polymer is not polylactide. In some embodiments, the polymer is not a polylactide copolymer such as PLGA.

In some embodiments, the extended release formulation comprises one or more polymers selected from the group consisting of a) a water-swellable, pH independent polymer, b) an anionic, pH-dependent, gel-forming copolymer, c) a cationic polymer, and d) a hydrocolloid polymer. In one embodiment, the extended release formulation comprises: (i) a hydrocolloid polymer; (ii) an anionic, pH-dependent, gel forming co-polymer, and (iii) either a water-swellable, pH independent polymer or a hydrogel.

Examples of a water-swellable, pH independent polymer include, but are not limited to, carbohydrate-based polymers such as, for example, hypromellose (formerly known as the family of hydroxypropyl methylcellulose), hydroxypropyl ethyl celluloses, hydroxypropyl cellulose, hydroxyethyl cellulose, methyl cellulose or other constituents Grades of these hypromellose copolymers typically used with the present invention include the E and K series such as for example, Dow Chemical Company's (Midland, Mich. USA) or Aqualon's (with a North American presence in Wilmington, Del.) E4M, E10M, K100LV, K4M, K15M, K25M, K100M, K200M and mixtures of various molecular weights and grades. Grades of hydroxyethyl cellulose include, for example, Aqualon's Natrasol polymers HHX (mol. Wt. 1,300,000), HX (mol. wt. 1,000,000), H (mol. wt. 1,000,000), M (mol. wt. 720,000 and G (mol. wt. 1,150,000), and mixtures thereof. Grades of hydroxypropyl cellulose include, for example, Aqualon's HPC polymers MF and MXF (mol. wt. 580,000) and KF and HXF (mol. wt. 1,150,000), and mixtures thereof. Grades and ethyl cellulose include, for example, Dow Chemical Company's Ethocel polymers 7FP, 10FP and 100FP and Aqualon's polymers T10EC, N7, N10, N17, N22, N50, N100 and N200, and mixtures thereof. In some embodiments, the water-swellable, pH independent polymer is hypromellose (e.g., hypromellose Type 2208). In some embodiments, the water-swellable, pH independent polymer is Methocel® (e.g., Methocel® K100MPremium CR, Colorcon). In one embodiment, an extended release formulation may comprise water-swellable, pH independent polymer in about 20% w/w to about 50% w/w; about 20% w/w to about 40% w/w, about 20% w/w to about 30% w/w; about 20% w/w to about 25% w/w; about 25% w/w to about 30% w/w; about 22% w/w to about 27% w/w; or about any of 20% w/w, 21% w/w, 22% w/w, 23% w/w, 24% w/w, 25% w/w, 26% w/w, 27% w/w, 28% w/w, 29% w/w and 30% w/w of the formulation. In one embodiment, about 20% to about 30% w/w water-swellable, pH independent polymer is present in an enxtended release formulation.

Examples of anionic, pH-dependent, gel-forming copolymer include, but are not limited to, mono-valent alginate salt such as sodium, potassium or ammonium alginate salts, or combinations thereof, and sodium carboxymethyl cellulose and the like, or mixtures of one or more alginate salt and carboxymethyl cellulose and the like. In some embodiments, the anionic, pH-dependent, gel-forming copolymer is sodium alginate (e.g., Protanal®, FMC BioPolymer). In one embodiment, an extended release formulation may comprise an anionic, pH-dependent, gel forming polymer in about 15% w/w to about 30% w/w; about 15% w/w to about 25% w/w; about 15% w/w to about 20% w/w; about 20% w/w to about 30% w/w; about 20% w/w to about 25% w/w; about 20% w/w to about 23% w/w; or about any of 15% w/w, 16% w/w, 17% w/w, 18% w/w, 19% w/w, 20% w/w, 21% w/w, 22% w/w, 23% w/w, 24% w/w and 25% w/w of the formulation. In one embodiment, about 20% to about 25% w/w of one or more anionic, pH-dependent, gel-forming copolymer is present in an extended release formulation of the present disclosure.

Examples of a cationic polymer include, for example, chitosan or a derivative thereof including, for example, trimethylchitosan and quartermised chitosan, and chitosan-derived materials including, for example, those taught in U.S. Pat. No. 5,747,475. Either high or low molecular weight chitosan products can be used in the pharmaceutical formulations of the present invention and are readily available in pharmaceutical grade from suppliers located worldwide.

The hydrocolloid polymer used in the formulations of the present invention can be carrageenan. Carrageenans are available as iota, kappa and lambda carrageenans, with iota being used most frequently used and lambda being used least frequently. Various salt forms of carrageenans are also available including, for example sodium carrageenan. Typically used grades of iota carrageenan include, without limitation, carrageenan NF AEP brand colloids (Hadley, N.Y. USA) FD433 (1% viscosity; 300-400 cps) and FD384 (1% viscosity; about 100 cps). Viscosity of other carrageenan products ranges from about 50 to about 4000 cps. In some embodiments, the carrageenan is lambda carrageenan (e.g., Viscarin GP-209, FMC BioPolymer). In some embodiments, the carrageenan has a viscosity of about 1500-2000 cPs. In some embodiments, the carrageenan has a viscosity of about 1600 cPs. In one embodiment, hydrocolloid polymer may be present in the extended release formulation in about 1% w/w to about 10% w/w; about 1% w/w to about 5% w/w; about 3% w/w to about 8% w/w; about 4% w/w to about 6% w/w; or about any of 1% w/w, 2% w/w, 3% w/w, 4% w/w, 5% w/w, 6% w/w, 7% w/w, 8% w/w, 9% w/w and 10% w/w of the formulation. In one embodiment, about 1% w/w to about 5% w/w of one or more hydrocolloid polymers or one or more cationic polymers are present in the extended release formulation described herein.

The formulation and polymers useful in the extended release formulation are further described in U.S. Patent Application 2010/0160363, published on Jun. 24, 2010, and U.S. Patent Application 2010/0159001, published Jun. 24, 2010, which are incorporated herein by reference in their entireties and specifically with respect to the polymers provided therein.

In one embodiment, the extended release formulation according to the present disclosure further comprises one or more pharmaceutically acceptable carrier or excipients, including a diluent, an antioxidant, a lubricant, a colorant, a binder, a disintegrant, and the like. In a non-limiting example, one or more pharmaceutically acceptable excipients include hypromellose, polyethylene oxide, magnesium stearate, microcrystalline cellulose, colloidal silicon dioxide, and combinations thereof. In one embodiment, one or more excipients may be present in the extended release formulation in about 1% w/w to about 20% w/w; about 1% w/w to about 15% w/w; about 1% w/w to about 10% w/w; about 1% w/w to about 5% w/w; about 5% w/w to about 20% w/w; about 5% w/w to about 15% w/w; about 5% w/w to about 10% w/w; or about any one of 1% w/w, 2% w/w, 3% w/w, 4% w/w, 5% w/w, 6% w/w, 7% w/w, 8% w/w, 9% w/w and 10% w/w of the formulation.

The amount of the extended release formulation according to an embodiment of the invention to be administered to a human body may be appropriately selected in accordance with the absorption rate in the body, rate of inactivation, rate of excretion, the age, gender and condition of the patient, severity of the disease, or the like. Such factors can be readily determined by the clinician employing animal models or other test systems that are available in the art.

Administration of the therapeutic agents in accordance with the present invention may be in a single dose, in multiple doses, multiple unit doses per administration, in a continuous or intermittent manner, depending, for example, upon the recipient's physiological condition, whether the purpose of the administration is therapeutic or prophylactic, and other factors known to skilled practitioners. The administration of one or more crystalline forms of sialic acid and crystalline forms of the salts and/or solvates of sialic acid may be essentially continuous over a pre-selected period of time or may be in a series of spaced doses. Both local and systemic administration is contemplated.

The following examples further illustrate the present invention but should not be construed as in any way limiting its scope.

EXAMPLES

Methods of Analysis
X-ray Powder Diffraction (XRPD)
XRPD analysis was carried out on a Panalytical X'pert Pro, scanning the samples between 3 and 35° 2θ. The material was gently ground and loaded onto a multi well plate with Kapton or mylar polymer film to support the sample. The multi well plate was then loaded into a Panalytical diffractometer running in transmission mode and analysed, using the following experimental conditions.

| Raw Data Origin: | XRD measurement (*.XRDML) |
|---|---|
| Scan Axis: | Gonio |
| Start Position [° 2θ]: | 3.0066 |
| End Position [° 2θ]: | 34.9866 |
| Step Size [° 2θ]: | 0.0130 |
| Scan Step Time [s]: | 18.8700 |
| Scan Type: | Continuous |
| PSD Mode: | Scanning |
| PSD Length [° 2θ]: | 3.35 |
| Offset [° 2θ]: | 0.0000 |
| Divergence Slit Type: | Fixed |
| Divergence Slit Size [°]: | 1.0000 |
| Measurement Temperature [° C.]: | 25.00 |
| Anode Material: | Cu |
| K-Alpha1 [Å]: | 1.54060 |
| K-Alpha2 [Å]: | 1.54443 |
| K-Beta [Å]: | 1.39225 |
| K-A2/K-A1 Ratio: | 0.50000 |
| Generator Settings: | 40 mA, 40 kV |
| Goniometer Radius [mm]: | 240.00 |
| Dist. Focus-Diverg. Slit [mm]: | 91.00 |
| Incident Beam Monochromator: | No |
| Spinning: | No |

Polarised Light Microscopy (PLM)

The presence of crystallinity (birefringence) was determined using an Olympus BX50 polarising microscope, equipped with a Motic camera and image capture software (Motic Images Plus 2.0). All images were recorded using the 20× objective, unless otherwise stated.

Thermogravimetric/Differential Thermal Analysis (TG/DTA)

Approximately, 10 mg of material was weighed into an open aluminium pan and loaded into a simultaneous thermogravimetric/differential thermal analyser (TG/DTA) and held at room temperature. The sample was then heated at a rate of 10° C./min from 25° C. to 300° C. during which time the change in sample weight was recorded along with any differential thermal events (DTA). Nitrogen was used as the purge gas, at a flow rate of 300 cm$^3$/min.

Differential Scanning Calorimetry (DSC)

Approximately, 5 mg of material was weighed into an aluminium DSC pan and sealed non-hermetically with a pierced aluminium lid. The sample pan was then loaded into a Seiko DSC6200 (equipped with a cooler) cooled and held at 25° C. Once a stable heat-flow response was obtained, the sample and reference were heated to 210° C. at a scan rate of 10° C./min and the resulting heat flow response monitored. Nitrogen was used as the purge gas, at a flow rate of 50 cm$^3$/min.

$^1$H Nuclear Magnetic Resonance Spectroscopy ($^1$H NMR)

$^1$H NMR experiments were performed on a Bruker AV500 spectrometer (Frequency: 500 MHz). Experiments were performed in deuterated DMSO and each sample was prepared to ca. 10 mM concentration.

Gravimetric Vapour Sorption (GVS)

Approximately 10-20 mg of sample was placed into a mesh vapour sorption balance pan and loaded into an IGASorp Moisture Sorption Analyser balance by Hiden Analytical. The sample was subjected to a ramping profile from 40-90% relative humidity (RH) at 10% increments, maintaining the sample at each step until a stable weight had been achieved (98% step completion). After completion of the sorption cycle, the sample was dried using the same procedure to 0% RH, and finally taken back to the starting point of 40% RH. The weight change during the sorption/desorption cycles were plotted, allowing for the hygroscopic nature of the sample to be determined.

High Performance Liquid Chromatography-Ultraviolet Detection (HPLC-UV)

The chemical purity was measured on an Agilent HP1100 HPLC system fitted with an Agilent variable wavelength UV detector. Samples were prepared by dissolving in diluent at a concentration of 1 mg/mL before being analysed under the following HPLC conditions:

| Column: | 2 × Bio-rad Aminex HPx-87H 300 mm × 7.8 mm, 9 µm connected in series |
|---|---|
| Mobile Phase: | 10 mM Sulphuric Acid |
| Flow Rate: | 0.5 mL/min |
| Runtime: | 50 minutes |
| Detector Wavelength: | 205 nm |
| Column Temperature: | 40° C. |
| Injection Volume: | 15 µL (sample may be adjusted as required) |
| Diluent: | Water |

Infrared Spectroscopy (IR)

Infrared spectroscopy was carried out on a Bruker ALPHA P spectrometer. Sufficient material was placed onto the centre of the plate of the spectrometer and the spectra were obtained using the following parameters:

| Resolution: | 4 cm$^{-1}$ |
|---|---|
| Background Scan Time: | 16 scans |
| Sample Scan Time: | 16 scans |
| Data Collection: | 4000 to 400 cm$^{-1}$ |
| Result Spectrum: | Transmittance |
| Software: | OPUS version 6 |

Karl Fischer Coulometric Titration (KF)

10-15 mg of solid material was accurately weighed into a vial. The solid was then manually introduced into the titration cell of a Mettler Toledo C30 Compact Titrator. The vial was back-weighed after the addition of the solid and the weight of the added solid entered on the instrument. Titration was initiated once the sample had fully dissolved in the cell. The water content was calculated automatically by the instrument as a percentage and the data printed.

Experimental

Initial Characterization

Initial physical characterization of sialic acid was carried out using PLM, XRPD analysis, $^1$H NMR and I.R. spectroscopy, DSC, TG/DTA, GVS (with post-GVS XRPD), Karl Fischer titration for water content and HPLC analysis for purity.

Solvent Solubility Screen

Approximately 10 mg of sialic acid was used to check the solubility in 31 different solvents or solvent mixtures.

TABLE 6

Solvents used for solubility screen

| Number | Solvent system | ICH Class |
|---|---|---|
| 1 | Acetic acid | 3 |
| 2 | Acetone | 3 |
| 3 | Acetone:Water (90:10) v/v | 3 |
| 4 | Acetone:Ethyl Acetate (50:50) v/v | 3 |
| 5 | Acetone:Ethanol (50:50) v/v | 3 |
| 6 | Acetonitrile | 2 |
| 7 | 1-Butanol | 3 |
| 8 | Dichloromethane | 2 |
| 9 | Diisopropyl ether | 4 (Not classified) |
| 10 | Dimethylacetamide | 2 |

TABLE 6-continued

Solvents used for solubility screen

| Number | Solvent system | ICH Class |
|---|---|---|
| 11 | Dimethylsulfoxide | 3 |
| 12 | 1,4-Dioxane | 2 |
| 13 | Ethanol | 3 |
| 14 | Ethanol:Water (90:10) v/v | 3 |
| 15 | Ethanol:Acetone:Ethyl acetate(85:12:3 | 3 |
| 16 | 2-Ethoxyethanol | 2 |
| 17 | Ethyl acetate | 3 |
| 18 | n-Heptane | 3 |
| 19 | Isopropyl acetate | 3 |
| 20 | Methanol | 2 |
| 21 | Methylethyl ketone | 3 |
| 22 | Methylisobutyl ketone | 3 |
| 23 | 2-Methyl THF | 4 (Not classified) |
| 24 | Nitromethane | 2 |
| 25 | N-Methyl-2-pyrrolidone | 2 |
| 26 | 2-Propanol | 3 |
| 27 | tert-Butylmethyl ether | 3 |
| 28 | Tetrahydrofuran | 2 |
| 29 | Toluene | 2 |
| 30 | Water | N/A |
| 31 | Water:Acetic Acid (80:20) v/v | 3 |

50 µl aliquots of solvent were added in attempts to dissolve the sialic acid. The volume range used varied between 50 µl and 2 ml. Dissolution was aided by heating to 40° C. and shaking the vial between aliquots.

The mixture of solvents Ethanol:Acetone:Ethyl acetate (85:12:3 wt %) will be referred to as "Ethynol" hereafter.

Primary Polymorph Screen

The polymorph screen was conducted using 24 solvent systems chosen based on the solubility screen results, chemical diversity as well as the solvents used in the manufacturing process of sialic acid (See Table 7).

TABLE 7

Solvents used for primary polymorph screen

| 1 | Acetic acid |
| 2 | Acetone |
| 3 | Acetone:Water (90:10) v/v |
| 4 | Acetone:Ethanol (50:50) v/v |
| 5 | Acetonitrile |
| 6 | Dichloromethane |
| 7 | Diisopropyl ether |
| 8 | Dimethylacetamide |
| 9 | Dimethylsulfoxide |
| 10 | 1,4-Dioxane |
| 11 | Ethanol |
| 12 | Ethanol:Water (90:10) v/v |
| 13 | Ethynol |
| 14 | Ethyl acetate |
| 15 | Methanol |
| 16 | Methylethyl ketone |
| 17 | Methylisobutyl ketone |
| 18 | 2-Methyl THF |
| 19 | N-Methyl-2-pyrrolidone |
| 20 | 2-propanol |
| 21 | Tetrahydrofuran |
| 22 | Toluene |
| 23 | Water |
| 24 | Water:Acetic Acid (80:20) v/v |

General Methodology for Primary Screen

For solvents in which sialic acid showed poor solubility (i.e. 19 solvents), slurries were prepared using 10 ml of each solvent at ambient temperature.

For solvents showing higher solubility of sialic acid (i.e. 5 solvents), slurries using 2 ml of each solvent were prepared at ambient temperature. These solvents were dimethylacetamide, dimethylsulfoxide, N-methyl-2-pyrrolidone, water and water/acetic acid (80:20) v/v.

For the slurry experiments, freeze-dried sialic acid was used. The aim of doing so, was to produce amorphous sialic acid in order for the sialic acid not to have a defined physical form before the slurry experiments. However the freeze-dried sialic acid was not completely amorphous, containing some Form 1.

Slurries were shaken and temperature cycled for 68 hours between ambient temperature and 40° C. in 4 hour cycles. The slurries were then filtered and the saturated solution split up for evaporation, crash cooling and anti-solvent addition. The excess solid was reclaimed in order to analyse the solid form from the slurry.

Crash Cooling Experiments:

2 ml of the saturated solution was used for crystallization by crash cooling in a freezer (ca.<-20° C.) and in a fridge (ca. 2-8° C.), for poor solubilising solvents.

500 µl of the saturated solution was used for crystallization by crash cooling in a freezer (ca.<-20° C.) and in a fridge (ca. 2-8° C.), for good solubilising solvents.

Figure 62:
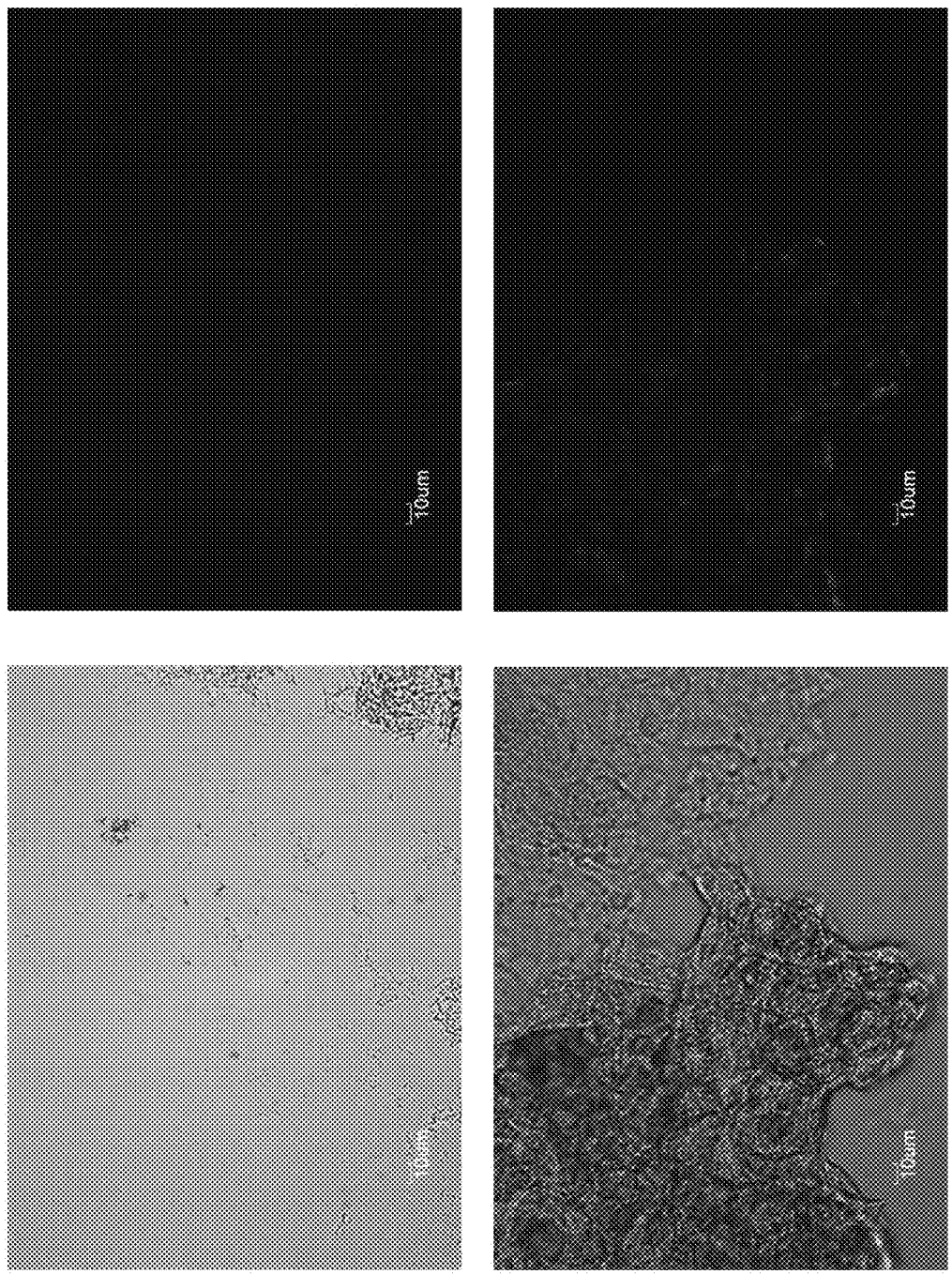
FIG. 62 includes PLM images under a non-polarized lens (left) and a polarized lens (right) from cooling (5 and −20° C.) experiments for solvents: acetone/ethanol 50/50 v/v (−20° C.; top); dimethylacetamide (−20° C.; bottom).
Figure 63:
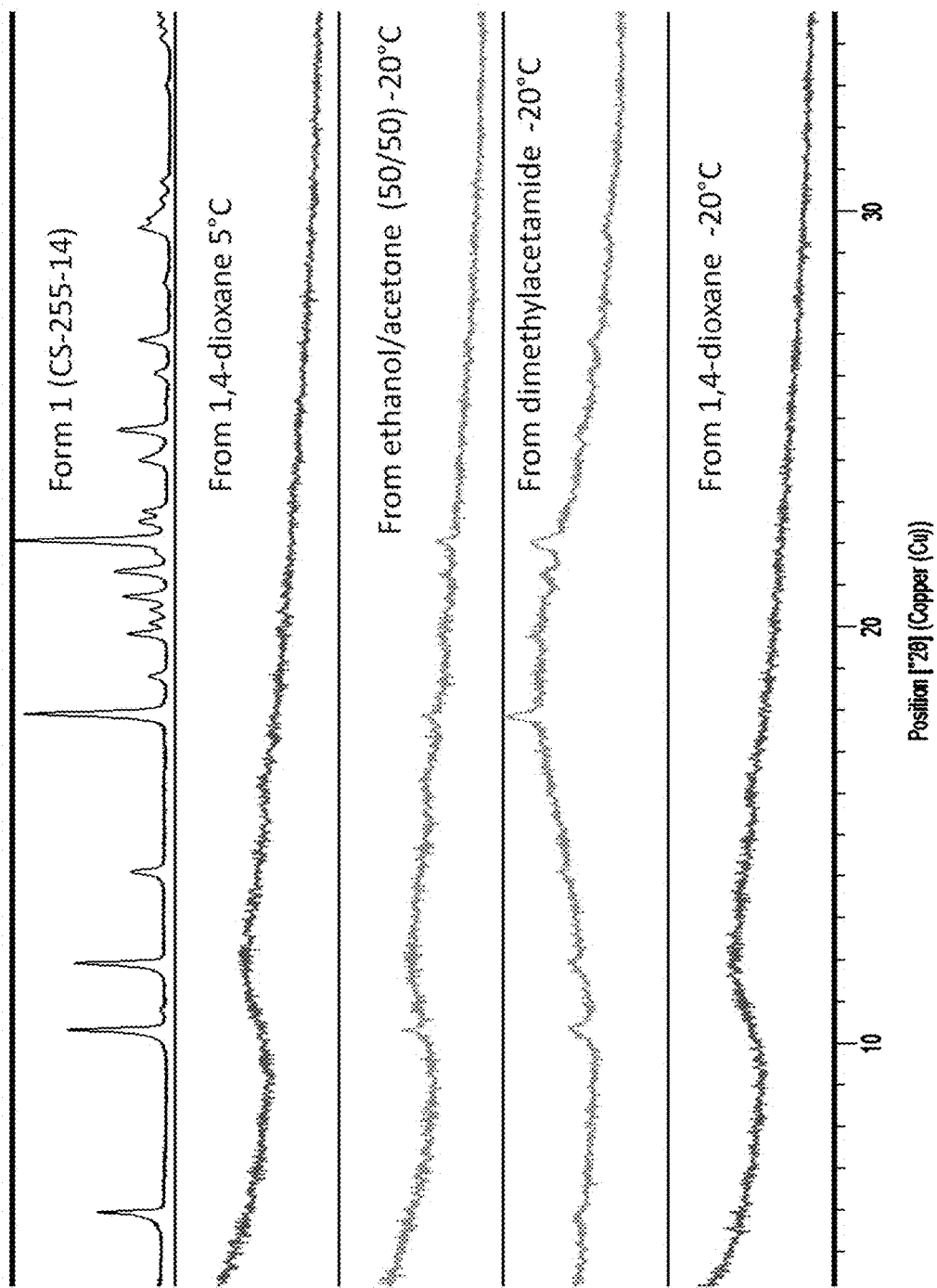
FIG. 63 are XRPD diffractograms from cooling (5 and −20° C.) experiments. When polymorphic Form 1 is identified the pattern is in orange, when polymorphic Form 4 is identified the pattern is in green, when polymorphic Form 5 is identified the pattern is in red and when no form is identified the pattern is in fuchsia.
Figure 64A:
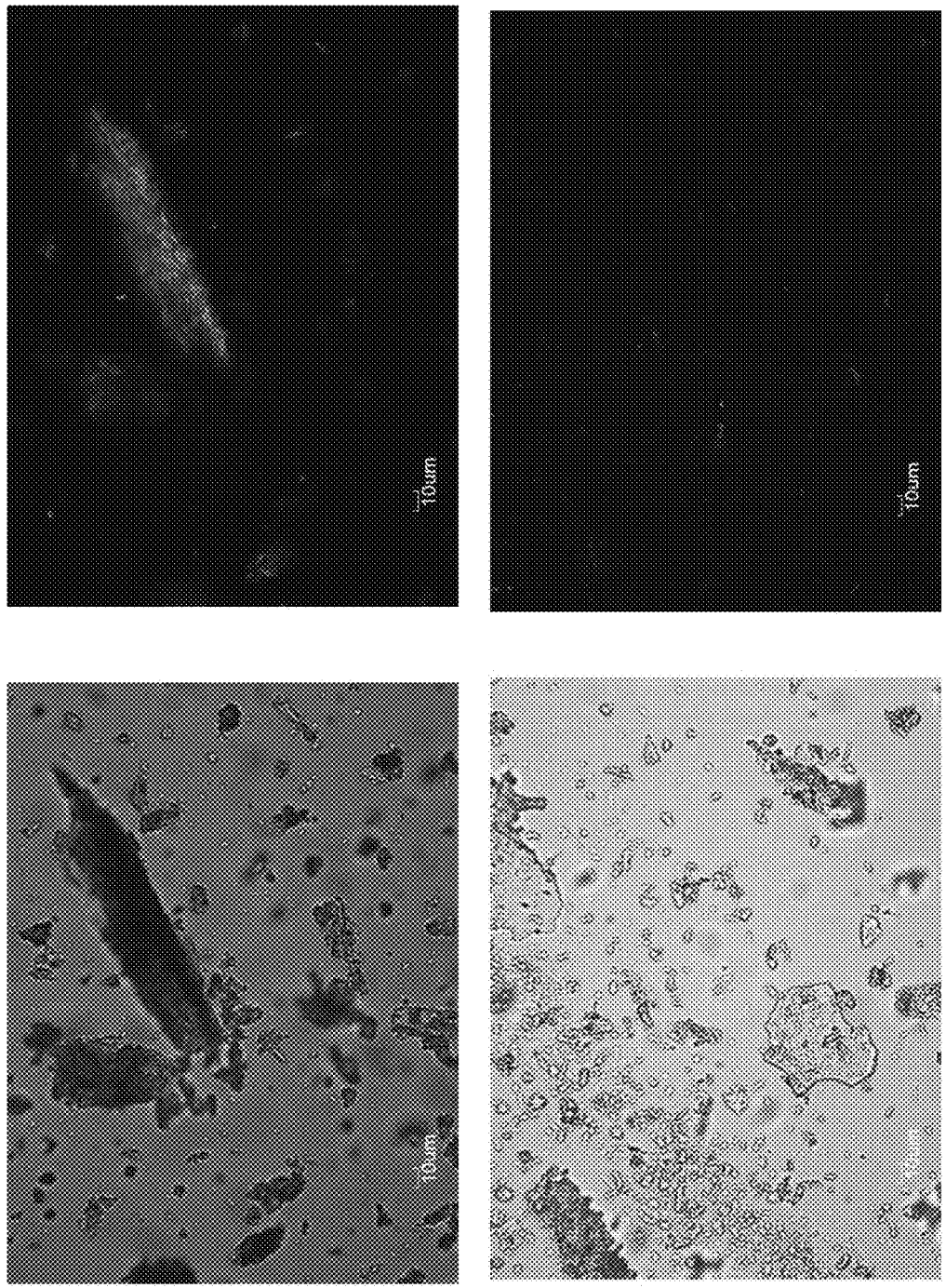
FIG. 64A includes PLM images under a non-polarized lens (left) and a polarized lens (right) from evaporation experiments conducted in different solvent systems: acetone/water 90/10 v/v (top); acetone/ethanol 50/50 v/v (bottom).
Figure 64C:
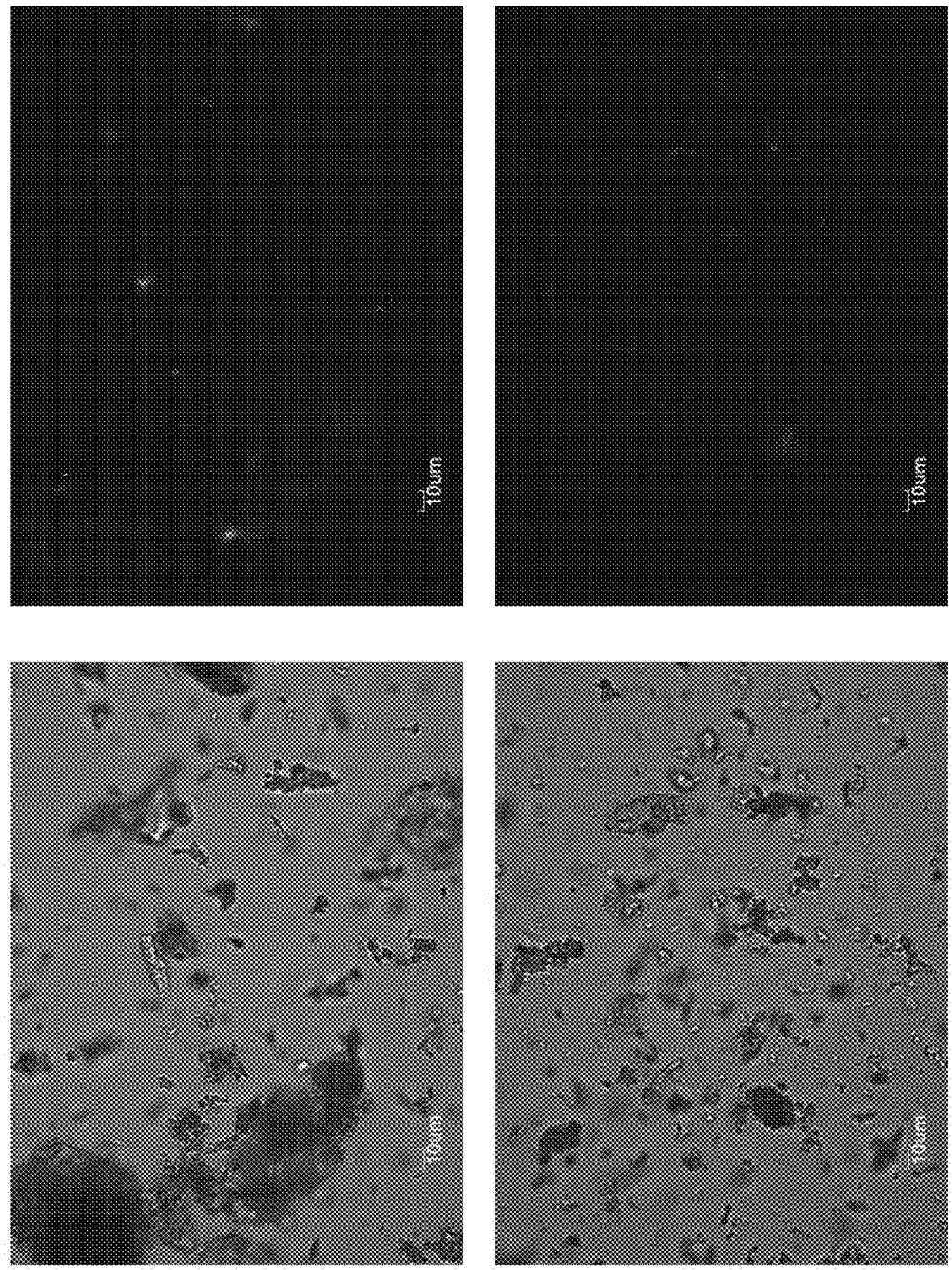
FIG. 64C includes PLM images under a non-polarized lens (left) and a polarized lens (right) from evaporation experiments conducted in different solvent systems: ethanol (top); ethanol/water 90/10 v/v (bottom).
Figure 64D:
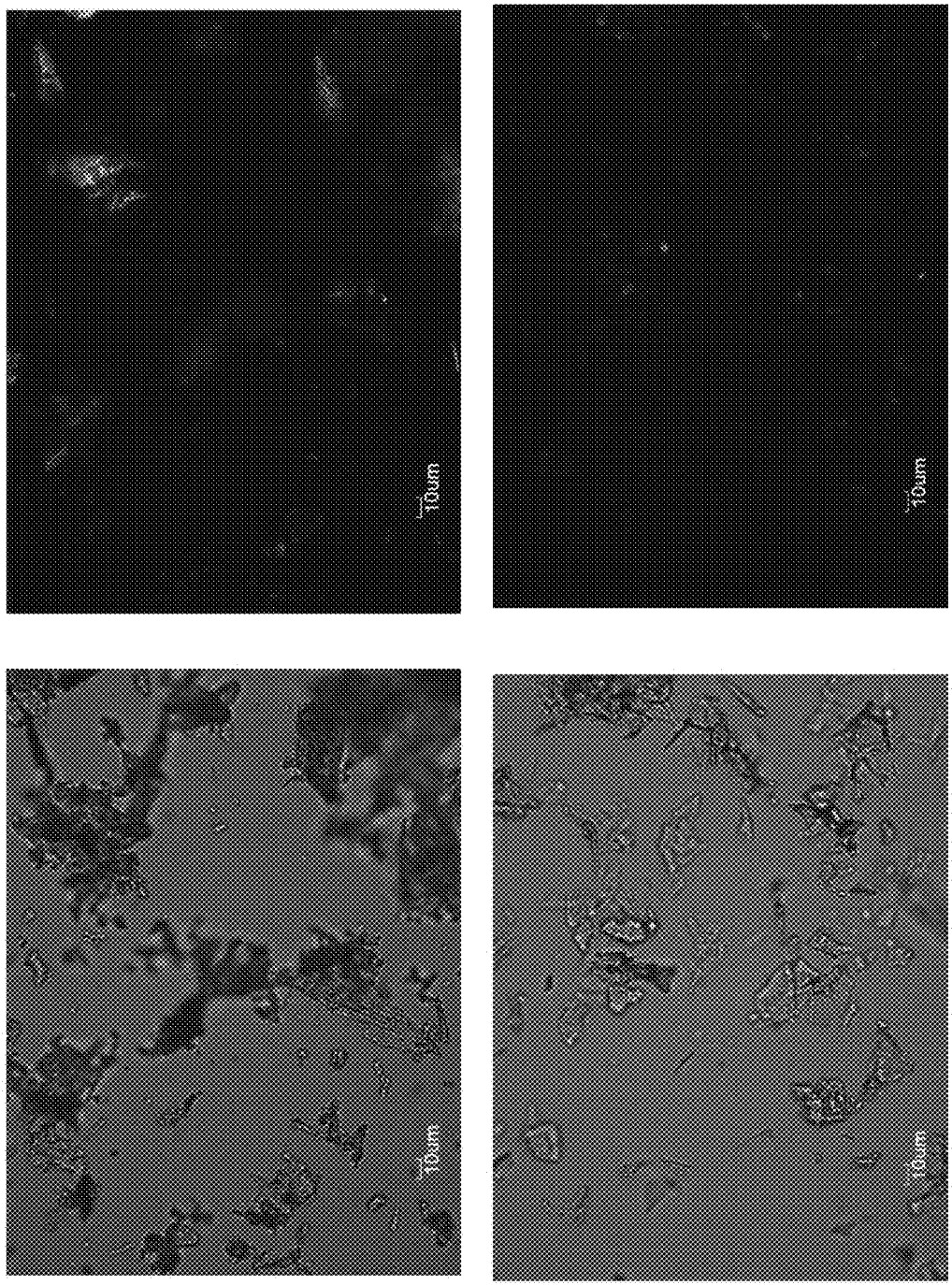
FIG. 64D includes PLM images under a non-polarized lens (left) and a polarized lens (right) from evaporation experiments conducted in different solvent systems: ethynol (top); ethyl acetate (bottom).
Figure 64E:
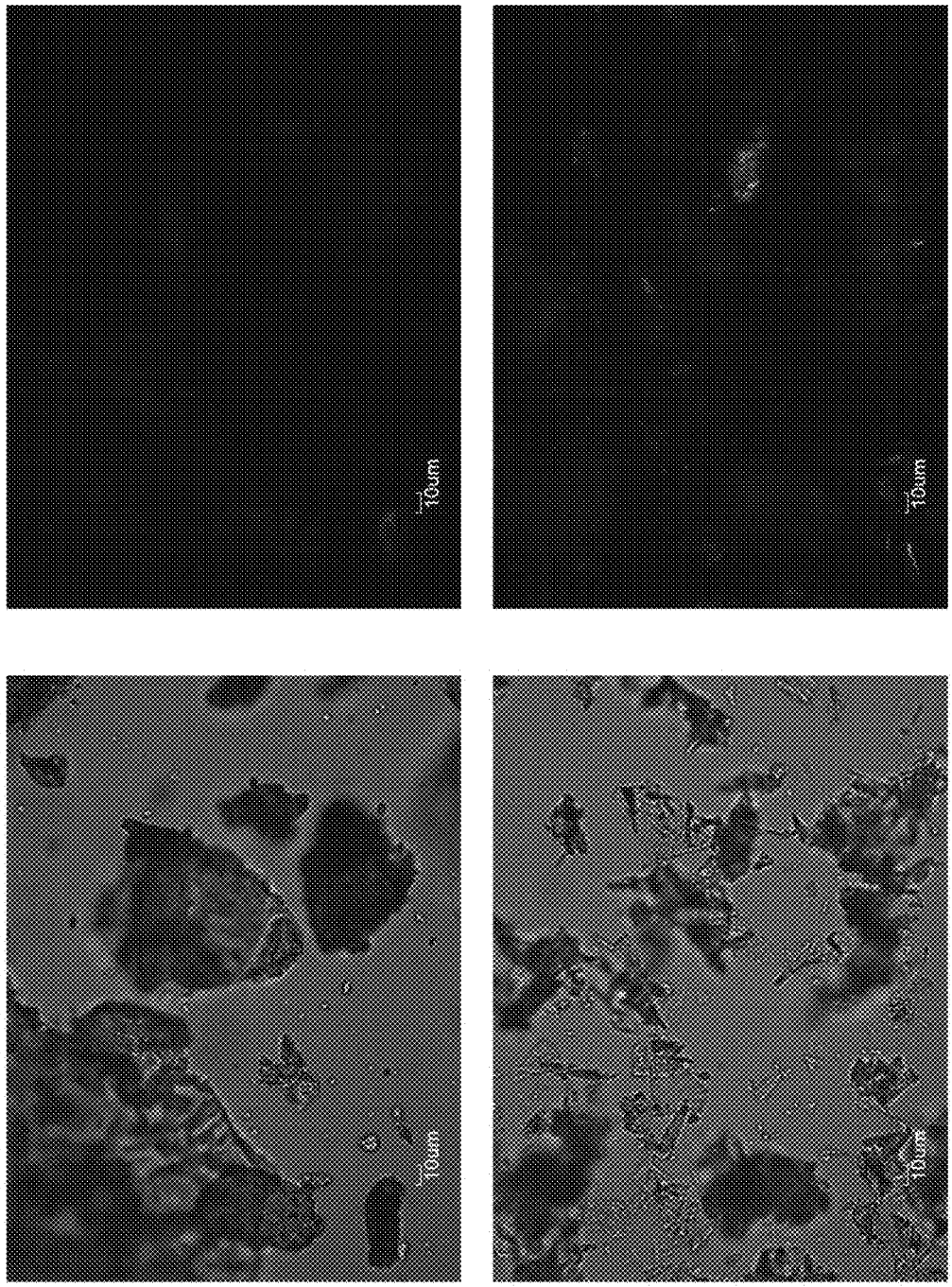
FIG. 64B includes PLM images under a non-polarized lens (left) and a polarized lens (right) from evaporation experiments conducted in different solvent systems: dimethylacetamide (top); dimethylsulfoxide (botom).
FIG. 64F includes PLM images under a non-polarized lens (left) and a polarized lens (right) from evaporation experiments conducted in different solvent systems: water (top); water/acetic acid 80/20 v/v (bottom). Some crystals were crushed while trying to recover solid for running XRPD experiments. The morphology thus observed is altered slightly.

FIG. 62 shows PLM images under a non-polarized lens from crash cooling experiments. In addition, FIG. 63 shows XRPD diffractograms from the cooling experiments.

Anti-Solvent Addition Experiments:

850 µl of the saturated solution was used for crystallization by anti-solvent addition using TBME as anti-solvent, for poor solubilising solvents.

500 µl of the saturated solution was used for crystallization by anti-solvent addition using acetonitrile as anti-solvent for good solubilising solvents.

Figure 67B:
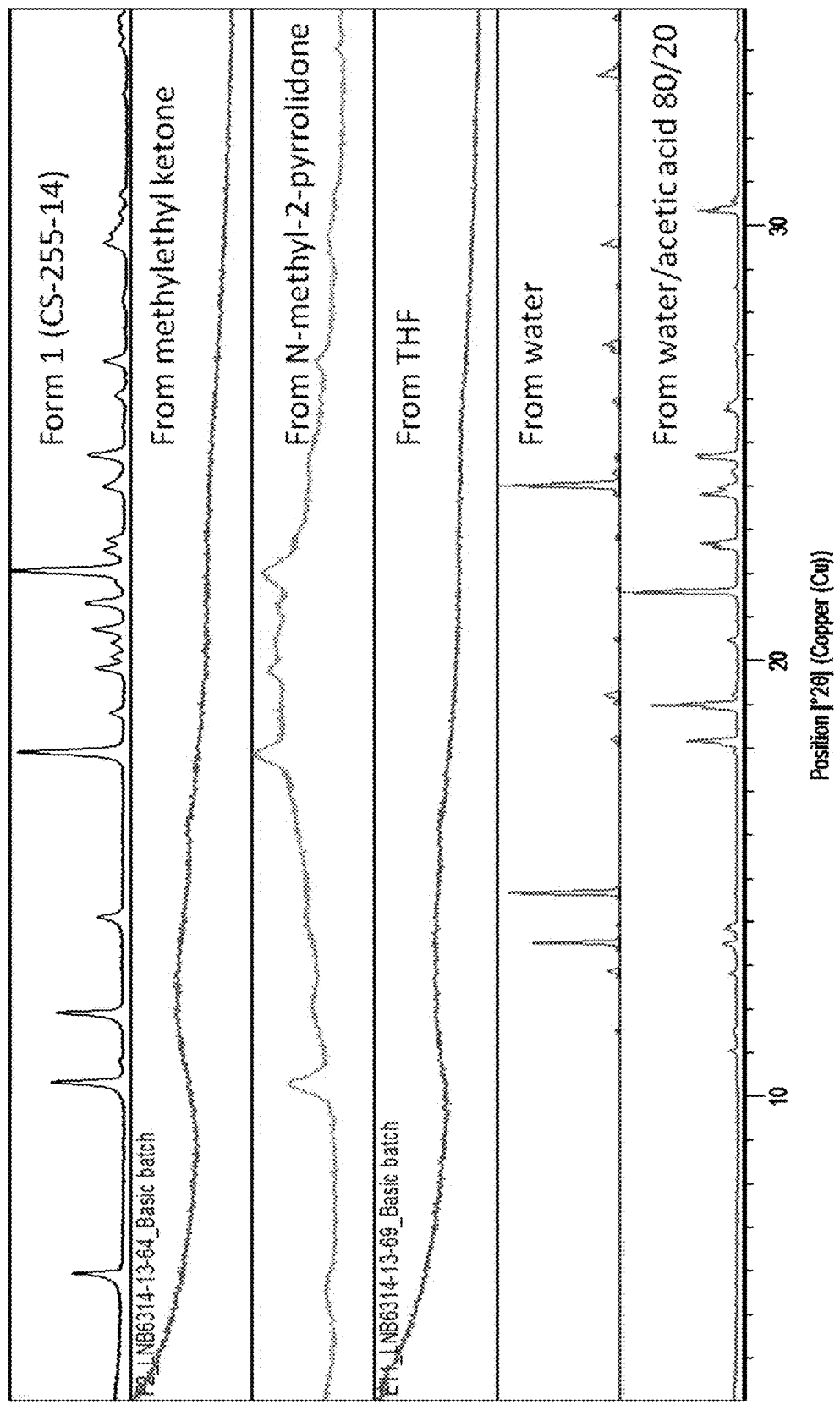

FIGS. 66A-66D show PLM images under a non-polarized lens from anti-solvent addition experiments conducted in different solvent systems. In addition, FIGS. 67A and 67B show XRPD diffractograms from the anti-solvent addition experiments.

Evaporation Experiments:

2 ml of the saturated solution was used for crystallization by evaporation for poor solubilising solvents.

500 µl of the saturated solution was used for crystallization by evaporation for good solubilising solvents.

Figure 65A:
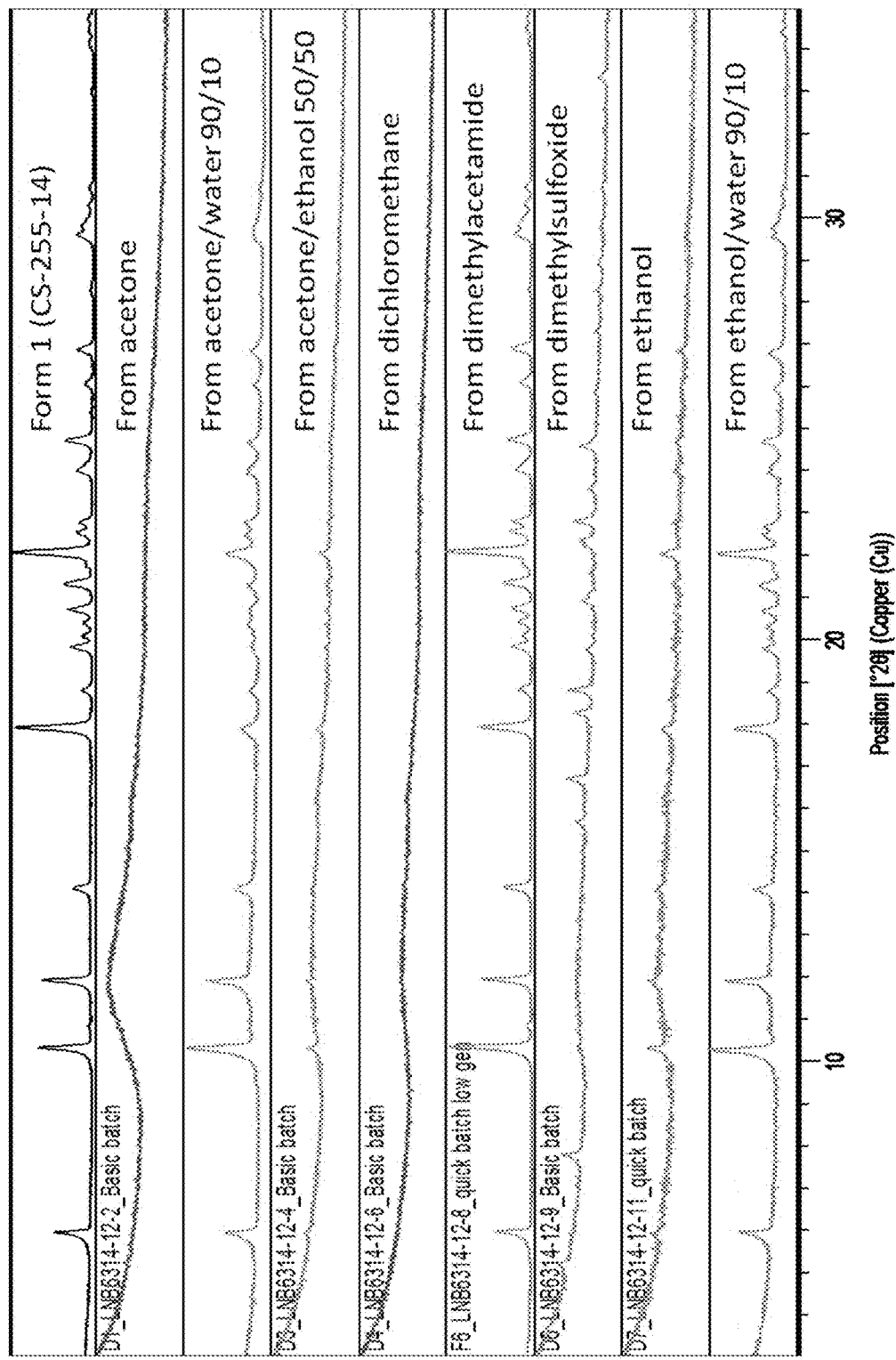
FIGS. 65A and 65B are XRPD from evaporation experiments. When polymorphic Form 1 is identified the pattern is in orange, when polymorphic Form 4 is identified the pattern is in green, when polymorphic Form 5 is identified the pattern is in red and when no form is identified the pattern is in fuchsia.
Figure 65B:
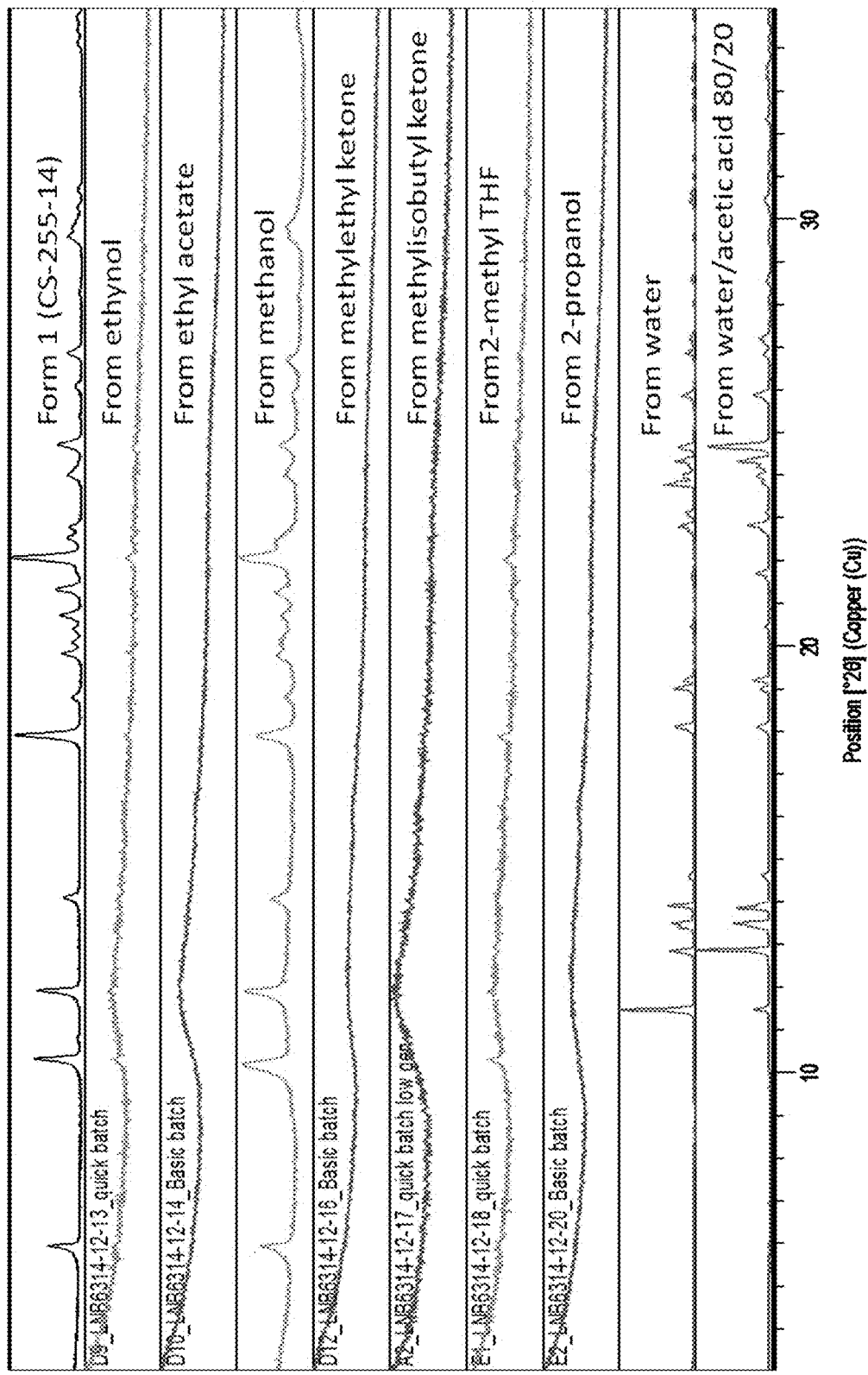
Figure 66A:
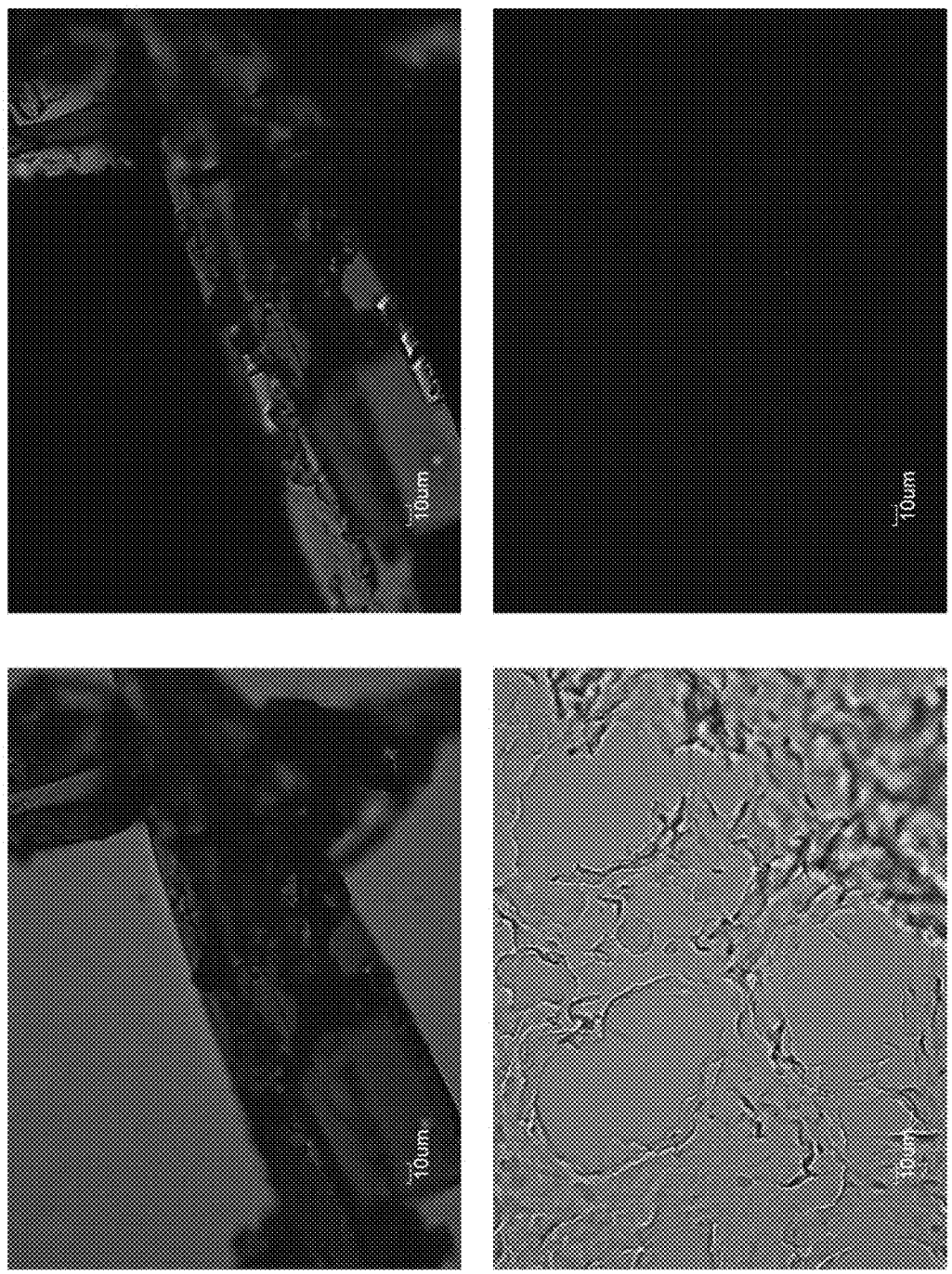
FIG. 66A are PLM images under a non-polarized lens (left) and a polarized lens (right) from anti-solvent additions experiments conducted in different solvent systems: acetone/water 90/10 v/v with TBME as anti-solvent (top); THF with TBME as anti-solvent (bottom).
Figure 66B:
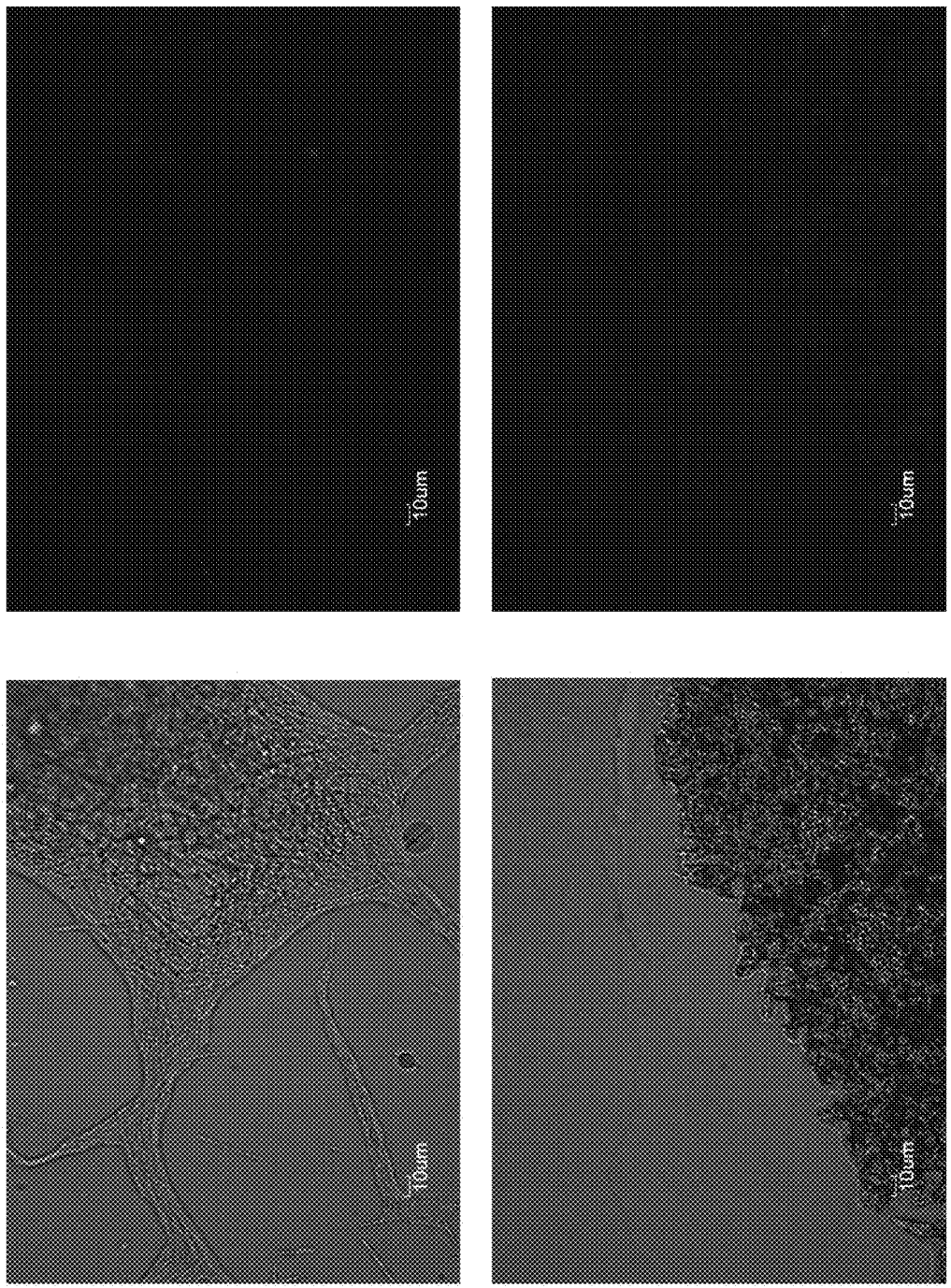
FIG. 66B are PLM images under a non-polarized lens (left) and a polarized lens (right) from anti-solvent additions experiments conducted in different solvent systems: water with acetonitrile as anti-solvent (top); ethanol with TBME as anti-solvent (bottom).
Figure 66D:
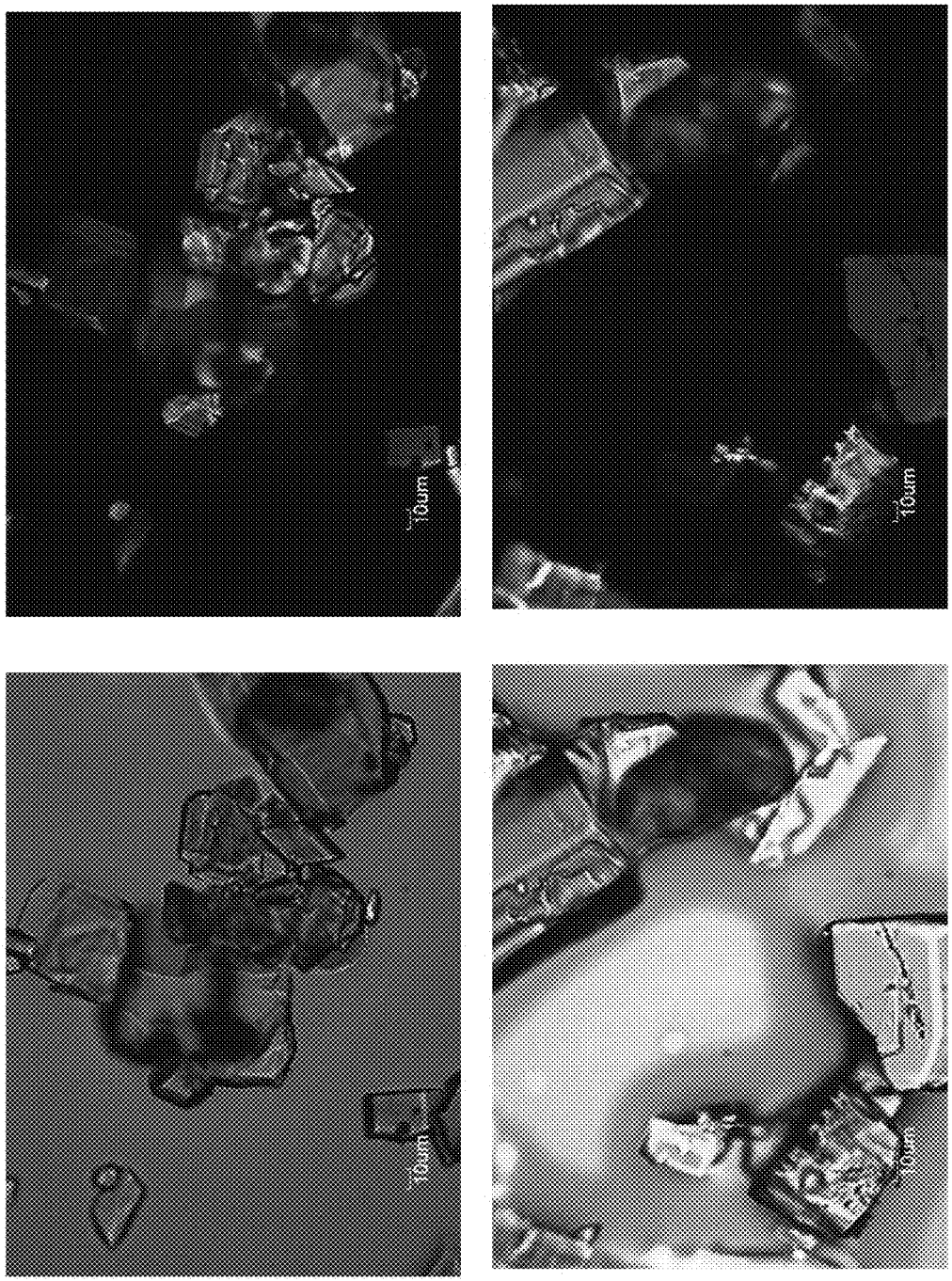
FIG. 66D are PLM images under a non-polarized lens (left) and a polarized lens (right) from anti-solvent additions experiments conducted in different solvent systems: dimethylsulfoxide with acetonitrile as anti-solvent (top); water/acetic acid 80/20 v/v with acetonitrile as anti-solvent (bottom).

FIGS. 64A-64F show PLM images under a non-polarized lens from evaporation experiments conducted in different solvent systems. In addition, FIGS. 65A and 65B show XRPD diffractograms from the cooling experiments.

Temperature Cycling Slurry Experiments:

Excess solid from the slurries was collected in order to analyze the solid forms obtained from temperature cycling.

All isolated solids were then analyzed by XRPD for identification of the physical forms so that the different sialic acid polymorphs could be identified during this polymorph screen.

Figure 61A:
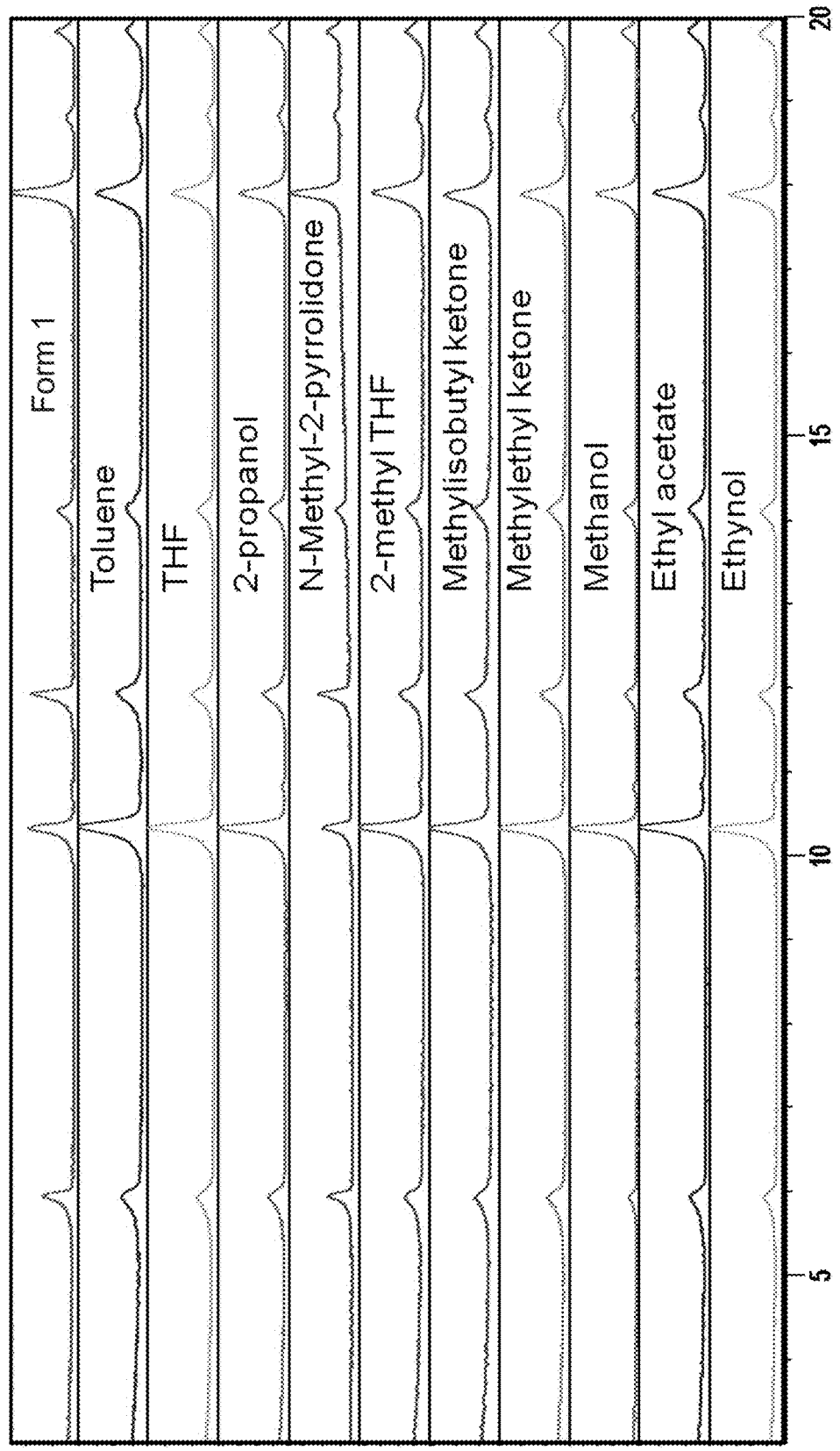
FIGS. 61A and 61B are diffractograms of temperature cycled sialic acid for which the isolated physical form was polymorphic Form 1.
Figure 61B:
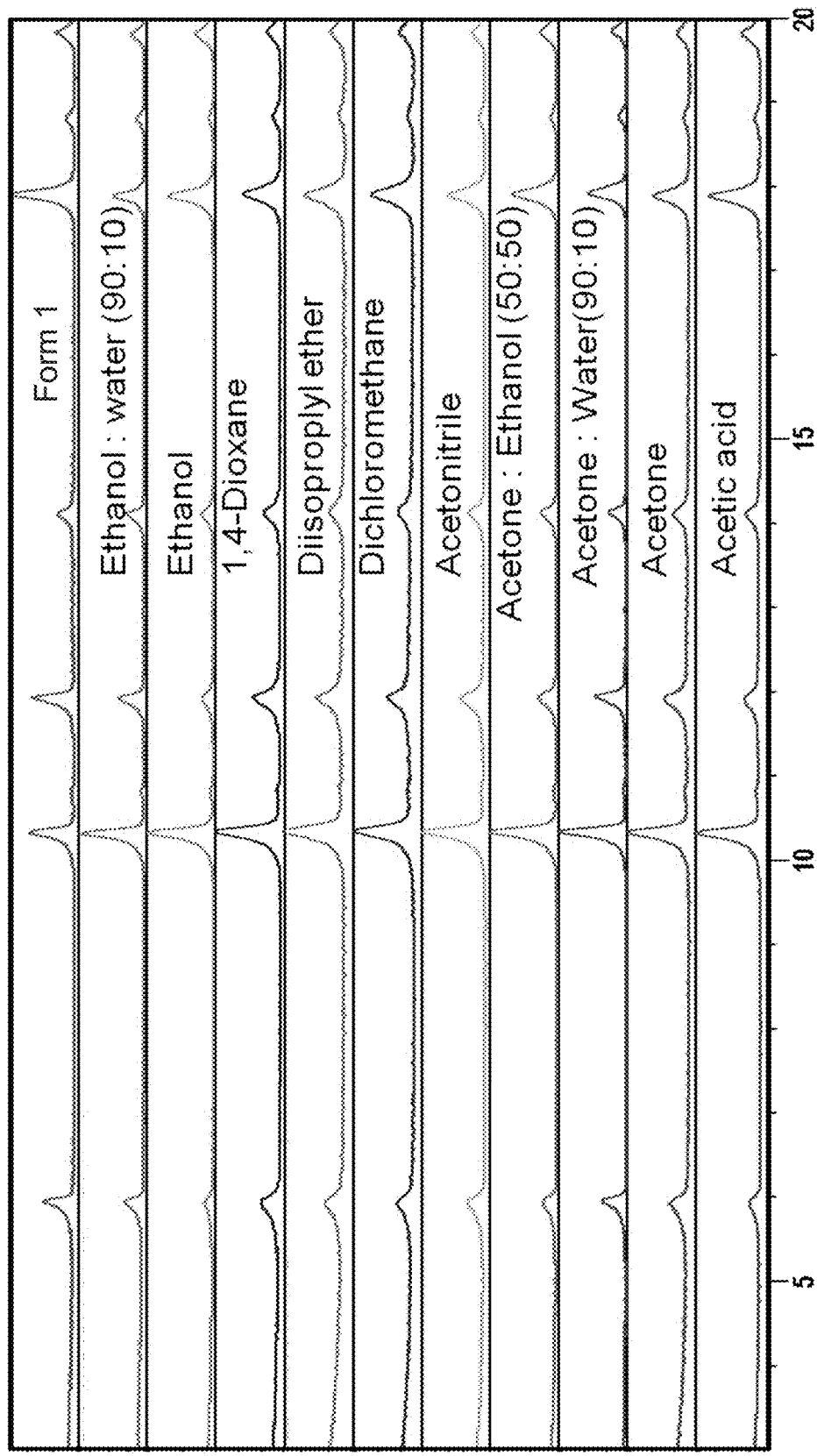

FIGS. 49-60 show PLM images under a non-polarized lens from temperature cycling experiments conducted in different solvent systems. For those solvent systems which yielded an isolated polymorphic Form 1, XRPD diffractograms are shown in FIGS. 61A-61B.

Further Polymorph Screening

Figure 69:
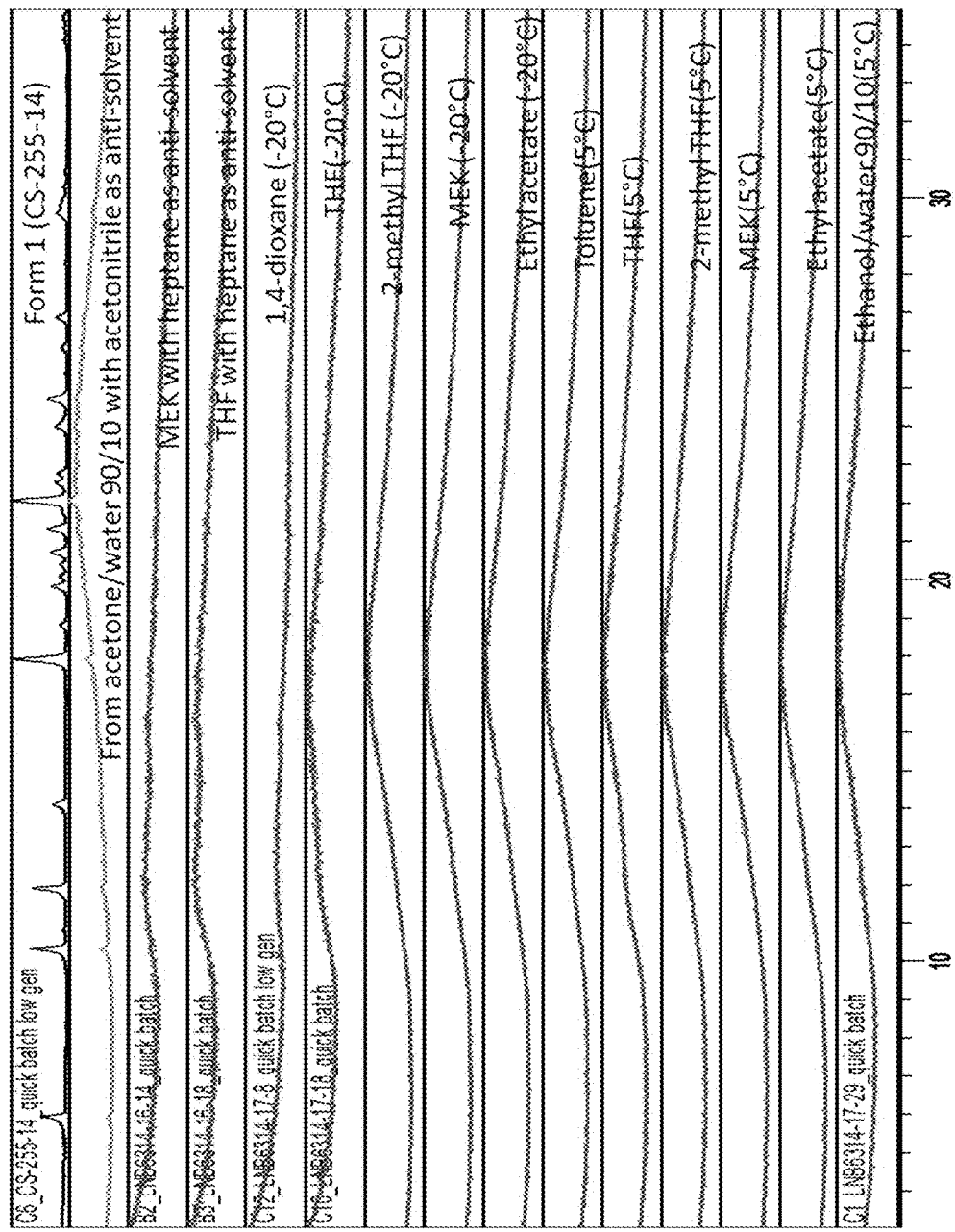
FIG. 69 is XRPD diffractograms collected from experiments described in FIG. 68.

Due to low solubility of sialic acid in 19 of the chosen solvent systems, many crystallization experiments did not yield enough solid for analysis. Therefore, 19 further slurries in these solvents were prepared, introducing 10% NMP as a co-solvent in order to improve solubility and thus to increase the likelihood of isolating solids from the different experiments. Form 1 was observed from adding acetonitrile as anti-solvent to the acetone/water/NMP mixture (FIG. 68). In addition, FIG. 69 shows XRPD diffractograms from the screening conditions where 10% NMP was used as co-solvent.

For these new experiments, only anti-solvent additions and crash cooling experiments were carried out using saturated solutions obtained from the slurries. For these experiments, the anti-solvent used was mostly heptane. Acetonitrile was used for the filtrates from acetic acid, acetone/water 90/10 v/v, ethanol/water 90/10 v/v and methanol. TBME was used for the filtrate from acetonitrile.

Secondary Screen

Form 5

To prepare Form 5, a slurry of 1.925 g of sialic acid in 10 ml of water was stirred for 16 hours at 5° C., then stirred at room temperature (ca. 22° C.) for 1 hour. The solid was isolated by filtration using a Buchner funnel and filter paper and further washed with cold water (3 times 5 ml) and air dried on the Buchner funnel for 30 minutes. The filtrate was split into two vials both containing around 4 ml of saturated aqueous sialic acid solution.

Approximately 300 mg of Form 5, obtained from the residual solid left after slurrying, was reclaimed for the secondary screen analysis.

Form 3

The two vials containing 4 ml of saturated aqueous sialic acid solution were used to produce Form 3 by addition of 16 ml of acetic acid. The samples were stored in a fridge (ca. 2-8° C.). Form 3 precipitated slowly from the solution over 1 day. The solid was then filtered using a Buchner funnel and air dried for 30 min. Around 500 mg of Form 3 was reclaimed from one vial for the secondary screen analysis Form 2

The second batch of Form 3 was used to make Form 2 by drying the Form 3 obtained initially at ambient under vacuum for 4 hours, followed by 50° C. under vacuum for 4 hours and finally at 35° C. under vacuum over a weekend (68 hours). Around 500 mg of Form 2 was isolated and used for the secondary screen analysis.

The selected Forms (5, 3 and 2) were fully characterized by PLM, XRPD, $^1$H NMR and IR spectroscopy, DSC, TG/DTA, GVS (with post-GVS XRPD), Karl Fischer titration for water content and HPLC analysis for purity. All of these forms with the addition of Form 1 were also placed under a stress-stability test, at three different conditions for one week (ambient conditions, 40° C. and 75% relative humidity, 80° C.). In addition to this, an approximate solubility test was conducted on the different solid forms using a solvent addition method.

Polymorph Stability

Competitive slurry experiments were conducted between Forms 1 and 3 and between Forms 1 and 2. A mixture of the two forms (25 mg per form) being investigated was slurried in 1 mL of solvent for one day at 20° C. or 60° C. in five different solvents (acetone, acetic acid, ethanol, ethyl acetate and ethynol).

The reclaimed solid from these experiments was then analyzed to determine which form was the most stable under the conditions studied.

Approximate Solubility

Approximately 50 mg of each form (1, 2, 3 and 5) was weighed into a 2 ml vial. 20 µl aliquots of deionized water was added to each vial until complete dissolution of the solid was observed. The volume was noted down and the approximate water solubility calculated.

Results

Approximate Solubility Screen

Sialic acid was found to be poorly soluble in most of the tested solvents. The results of this assessment are given below in Table 8.

TABLE 8

Solubility of Sialic Acid

| Solvent | Solubility in mg/mL | Visual Observation |
| --- | --- | --- |
| Acetic acid | <5.4 | Partial Solubility |
| Acetone | <5.6 | Low Solubility |
| Acetone:Water (90:10) v/v | <5.1 | Partial Solubility |
| Acetone:Ethyl Acetate (50:50) v/v | <4.8 | Low Solubility |
| Acetone:Ethanol (50:50) v/v | <5.1 | Partial Solubility |
| Acetonitrile | <4.8 | Low Solubility |
| 1-Butanol | <6.1 | Partial Solubility |
| Dichloromethane | <5.1 | Partial Solubility |
| Diisopropyl ether | <4.8 | Low Solubility |
| Dimethylacetamide | >72.6 | Soluble |
| Dimethylsulfoxide | >301.4 | Soluble |
| 1,4-Dioxane | <4.9 | Partial Solubility |
| Ethanol | <5.1 | Partial Solubility |
| Ethanol:Water (90:10) v/v | <5.2 | Partial Solubility |
| Ethynol | <5.3 | Partial Solubility |
| 2-Ethoxy ethanol | <6.8 | Partial Solubility |
| Ethyl acetate | <5.8 | Extremely low solubility |
| n-Heptane | <5.3 | Extremely low solubility |
| Isopropyl acetate | <6.5 | Extremely low solubility |
| Methanol | <5.2 | Partial Solubility |
| Methylethyl ketone | <5.7 | Partial Solubility |
| Methylisobutyl ketone | <6.3 | Low Solubility |
| 2-Methyl THF | <5.2 | Partial Solubility |
| Nitromethane | <6 | Low Solubility |
| N-Methyl-2-pyrrolidone | >72.1 | Soluble |
| 2-propanol | <5 | Partial Solubility |
| tert-Butylmethyl ether | <4.6 | Extremely low solubility |
| Tetrahydrofuran | <5.3 | Low Solubility |
| Toluene | <5.9 | Partial Solubility |
| Water | >211.8 | Soluble |
| Water:Acetic Acid (80:20) v/v | >212.6 | Soluble |

As can be seen from

Table 8, sialic acid was poorly soluble in the majority of solvents tested. Only five solvents showed good solubility, including dimethylacetamide, dimethylsulfoxide, N-methyl-2-pyrrolidone, water and water/acetic acid (80:20 v/v). Due to the technique used, it is difficult to estimate exactly how much material went into solution for the "low solubility" and moreover the "extremely low solubility" experiments, however, by visual observation, very little material dissolved in these cases.

Primary Polymorph Screen

Slurries of sialic acid were prepared in the 24 solvents chosen from the 31 on which the solubility screen was conducted. The filtrates of the sialic acid temperature cycling slurries were utilised further for anti-solvent addition, crash cooling (ca. −20 and 5° C.) and evaporation experiments.

All of the solids obtained from these experiments were analyzed by XRPD and PLM. The results are summarized in Table 9.

TABLE 9

Primary Polymorph Screen

| Solvent | Slurry | Evaporation | Cooling 5° C. | Cooling −20° C. | Anti-solvent |
|---|---|---|---|---|---|
| Acetic acid | Form 1 | — | NS | N/A | NS |
| Acetone | Form 1 | — | NS | NS | NS |
| Acetone:Water (90:10) | Form 1 | Form 1 | NS | NS | Form 5 |
| Acetone:Ethanol (50:50) | Form 1 | Form 1 | NS | Form 1 | NS |
| Acetonitrile | Form 1 | NS | NS | NS | NS |
| Dichloromethane | Form 1 | — | NS | NS | — |
| Diisopropyl ether | Form 1 | NS | NS | NS | NS |
| Dimethylacetamide | Form 1 | Form 1 | NS | Form 1 | Form 1 |
| Dimethylsulfoxide | Form 4 | Form 4 | N/A | N/A | Form 4 |
| 1,4-Dioxane | Form 1 | NS | — | — | — |
| Ethanol | Form 1 | Form 1 | NS | NS | Form 1 |
| Ethanol:Water (90:10) | Form 1 | Form 1 | NS | NS | NS |
| Ethynol | Form 1 | Form 1 | NS | NS | NS |
| Ethyl acetate | Form 1 | — | NS | NS | NS |
| Methanol | Form 1 | Form 1 | NS | NS | NS |
| Methylethyl ketone | Form 1 | — | NS | NS | — |
| Methylisobutyl ketone | Form 1 | — | NS | NS | NS |
| 2-Methyl THF | Form 1 | Form 1 | NS | NS | NS |
| N-Methyl-2-pyrrolidone | Form 1 | NS | NS | NS | Form 1 |
| 2-propanol | Form 1 | — | NS | NS | NS |
| Tetrahydrofuran | Form 1 | NS | NS | NS | — |
| Toluene | Form 1 | NS | NS | NS | NS |
| Water | Form 5 * | Form 5 * | NS | N/A | Form 5 PO |
| Water:Acetic Acid (80:20) | Form 5 * | Form 5 * | NS | N/A | Form 5 PO |

NS = no solid;
— indicates not enough solid (poor diffraction);
* indicates disclouration;
PO = preferred orientation;
N/A = not applicable It can be seen that many experiments did not give enough solid or any solid for analysis, these are left in white as no form could be attributed. For the samples obtained from water and water acetic mixture, the star is indicative of a discoloration (the liquid changed to a brown color). Preferred orientation describes a sample for which the form has been ascertained but in which the relative intensities of the diffraction peaks are different due to particle size.

A second attempt, of the polymorph screen was carried out using 10% NMP to try to dissolve more sialic acid and thus obtain more solid from the cooling and anti-solvent addition crystallizations.

Due to the discolouration of samples during slurry experiments in water and water/acetic acid mixtures, slurries of sialic acid (Form 1) were made at 5° C. in water, water/acetic acid (80/20 v/v) mixture, ethyl acetate and acetic acid and stirred for 24 hours. Diffractograms of the slurried solids were recorded after 10 minutes, 4 hours, 20 hours and 28 hours. Form 5 was obtained in slurries containing water at all time points. Form 1 was obtained for acetic acid and ethyl acetate for all time points. No discolouration was seen in these low temperature slurries. Form 1 to Form 5 conversion is rapid in the presence of water, as the diffractogram after 10 minutes of slurrying already showed Form 5.

In general, it is clear to see that, from the experiments conducted during the polymorph screen, Form 1 is the most recovered form, Form 4 is associated with DMSO being present and Form 5 is associated with the presence of water.

As seen by the stacked diffractograms, these three forms are clearly distinct forms.

Sialic acid Form 1 is an anhydrous sialic acid form.

Form 4 only formed with DMSO being present and is likely to be a DMSO solvate.

Form 5 is only formed with water being present and is likely to be a hydrate.

Characterization of Form 1

Form 1 of sialic acid was characterized by the techniques described above.

Figure 7:
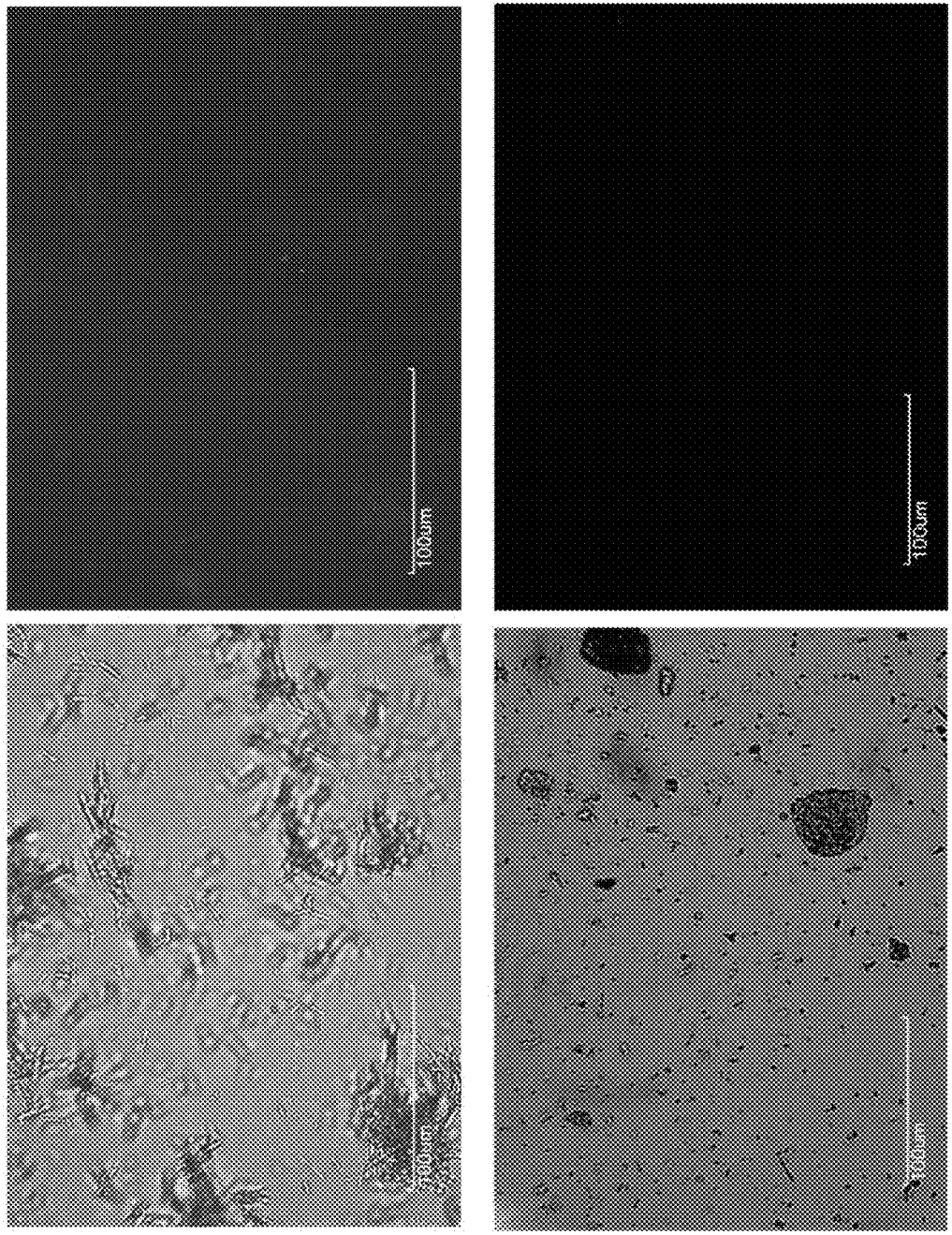
FIG. 7 are Polarized Light Microscopy (PLM) images under a non-polarized lens (left top and left bottom) and polarized lens (right top and right bottom) of polymorphic Form 1. These images represent different batches of Form 1 (top vs bottom).
Figure 8:
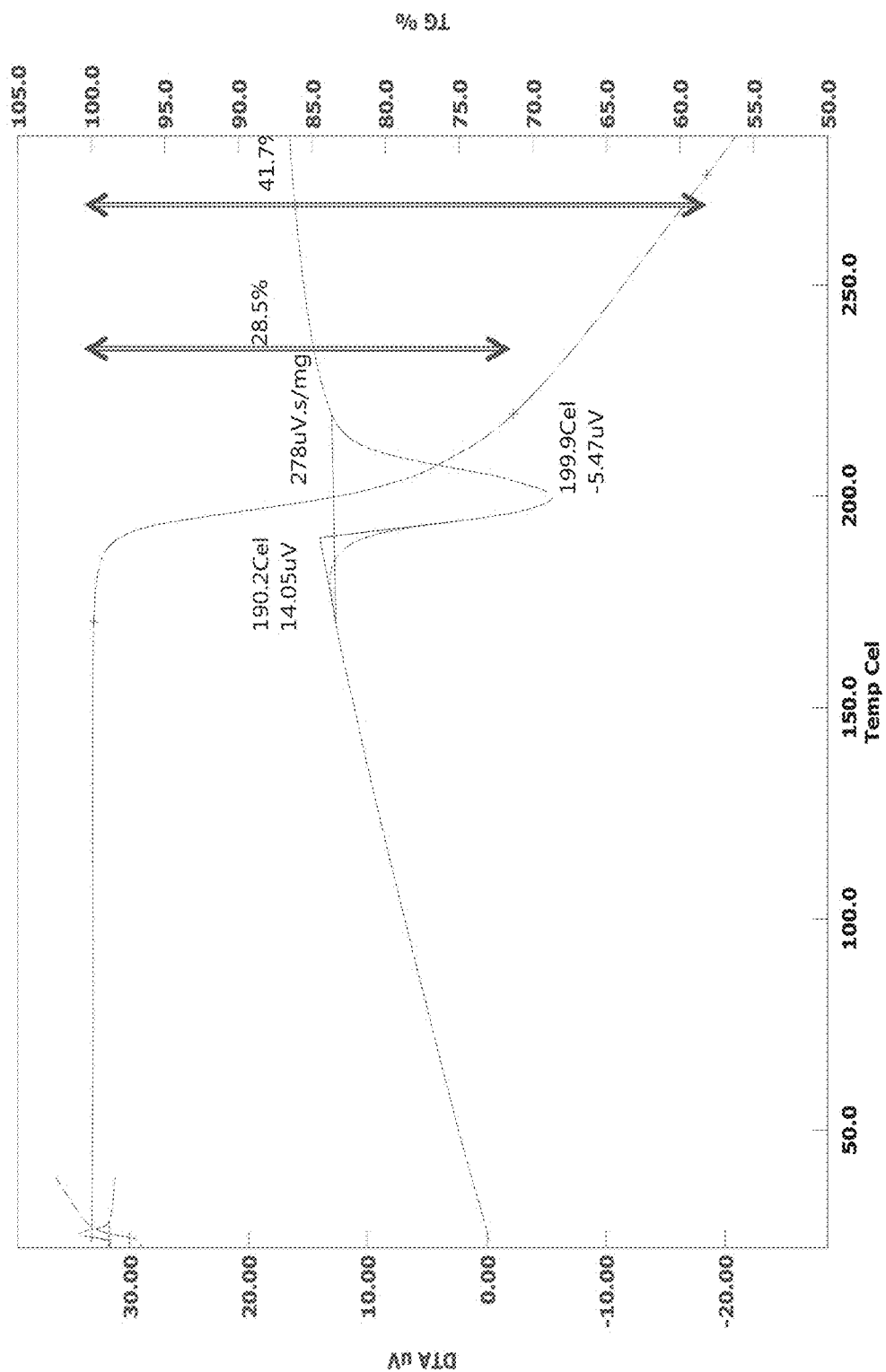
FIG. 8 is an overlay of Thermogravimetric (TG) and Differential Thermal Analyser (DTA) thermograms of polymorphic Form 1.

Referring to PLM images (FIG. 7), Form 1 particles appear as non-birefringent small needles (length <10 µm), or small non-birefringence particles. Birefringence is weak due to the particle size. As shown in FIG. 7, the morphology of the particles under PLM is not necessarily a determining factor in determining polymorphic forms, by its data alone. XRPD pattern exhibits five major peaks before 20° 2θ. From the TG trace, no significant weight losses are observed prior to decomposition. One single endothermic event is seen which corresponds with decomposition at 190.2° C. (onset of the endotherm on the DTA trace). This correlates well with the KF water content analysis showing the material to have 0.29% water content. The DSC analysis of Form 1 is consistent with the TG/DTA trace. Only one endotherm, corresponding with the decomposition, can be seen with onset at 188.6° C. From this GVS experiment, it is observed that Form 1 is very slightly hygroscopic as only 1.4% mass difference is seen between 0-90% relative humidity. The observed behaviour, with mass increasing while the relative humidity is increased and decreasing with decreasing humidity, is indicative that no phase change occurred during the GVS run. This is further confirmed by the XRPD analysis of the material recovered from the GVS. The material reclaimed after the GVS experiment is of the same polymorphic form (Form 1). Form 1 is therefore stable when exposed to different humidity levels. The $^1$H NMR spectrum is consistent with the structure of sialic acid, 19 protons have been integrated as expected. Small extra peaks are likely to be due to annomerism in solution and no significant solvent peaks can be seen. The IR spectrum is consistent with the material, 2 ν C=O (1722 and 1664 cm$^{-1}$) being seen. Hydrogen bonds can be seen in the spectrum as a large absorption band with defined peaks present at wave numbers above 3000 cm$^{-1}$. The chromatogram of Form 1 is consistent with sialic acid Form 1 being highly pure (99.50% by averaging the two injections of the same sample). Only one known impurity could be detected in this chromatogram. It is N-acetyl-D-glucosamine, with a percentage area of 0.078. KF water content analysis showed the material to have 0.29% water content, which is consistent with the material being anhydrous.

HPLC results of polymorphic Form 1 are shown below (with the purity in % area and retention time).

| RT (min) | PeakName | Area (mAU*s) | Area % | Peak Type |
|---|---|---|---|---|
| 14.01 | | 56.131 | 0.322 | BB |
| 15.61 | | 9.903 | 0.057 | VV |
| 18.75 | Sialic acid | 1.735e4 | 99.498 | VV R |

Further Investigations of Form 4

A weight loss of 33.1% is observed, prior to decomposition, which coincides with an onset in the DTA profile at ca. 108.8° C. (onset of the endotherm). The second endothermic event corresponds with decomposition at ca. 186.3° C.

(onset of the endotherm). The 33.1% of loss of weight corresponds to 1.96 molecules of DMSO for 1 molecule of sialic acid. It is thus very likely that Form 4 is a stoichiometric bis-solvate (2:1). The $^1$H NMR spectrum is consistent with sialic acid. The only noticeable difference between the spectra of Form 1 and Form 4 is the relative size of the resonance at ca. 2.5 ppm. This is due to DMSO, which further supports that Form 4 is a DMSO solvate. Form 4 (green) converted to Form 1 (pink and red) after 15 min at 100° C. under vacuum.

Further Investigations of Form 5

As expected for a dihydrate, Form 5 loses weight (10.3%) prior to decomposition. More detailed analysis is reported for this form in the secondary screen. The $^1$H NMR spectrum of Form 5 is consistent with the sialic acid being a hydrate. A broad resonance at ca. 3.5 ppm can be seen, which is attributed to water being part of the material.

Primary Screen and Production of Forms 2 and 3

A polymorph screen was carried out on sialic acid using 24 solvents and 5 different crystallization techniques. From this screen, 3 potential crystalline forms were found. Form 1, the received material, was observed to be an anhydrous form, Form 4, a DMSO solvate which desolvates to Form 1 and Form 5, a hydrate that was observed in different experiments when water was present.

A polymorph screen on sialic acid was carried out as different forms were produced during the manufacturing process. However, these forms (Forms 2 and 3) were not seen during this screen.

It was thus decided to follow more closely the conditions that gave these forms during the process. Therefore, acetic acid was added to a saturated aqueous solution of sialic acid. After 2 hours at ca. 2-8° C., a precipitate was obtained. The XRPD analysis of this solid was consistent to the Form 3. Form 3 was allowed to dry under ambient conditions. After 19 hrs, the XRPD of the solid was consistent with the Form 2.

Characterization of Form 5

Form 5 of sialic acid was characterized by the techniques described above.

Figure 23:
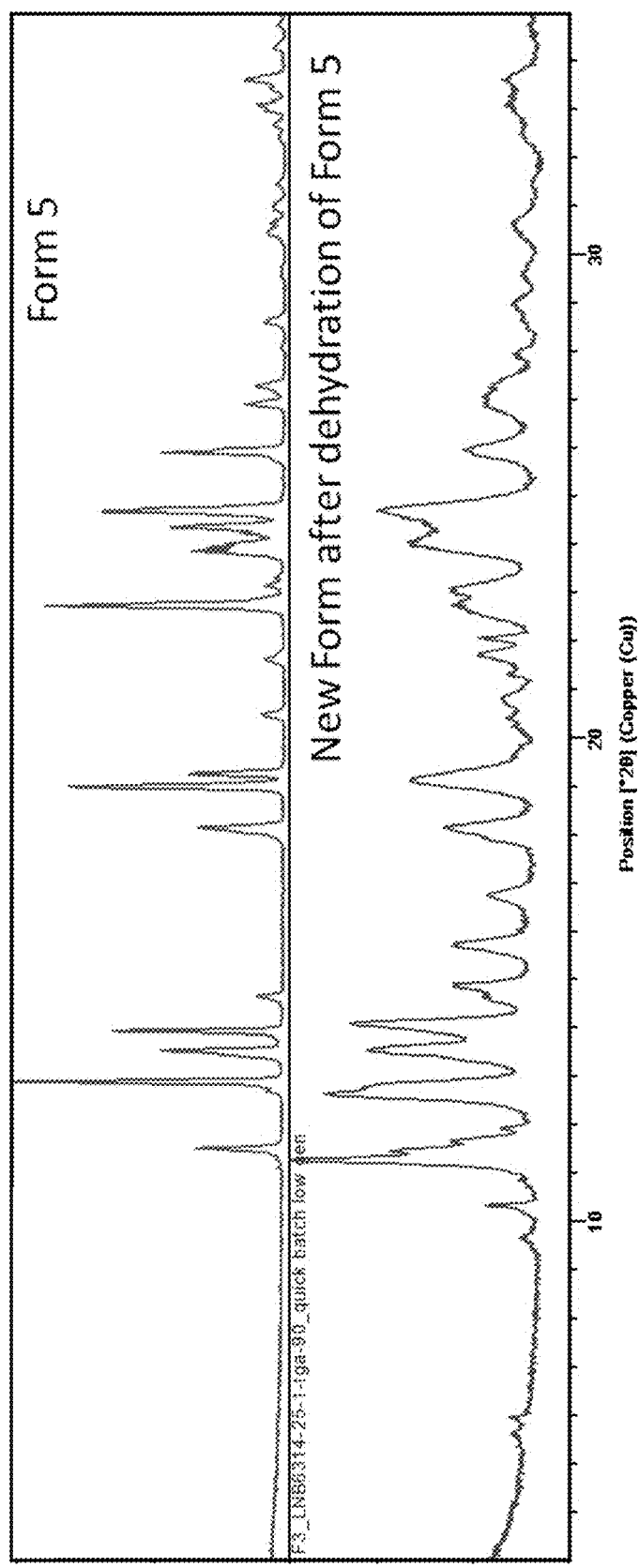
FIG. 23 are stacked diffractograms of Form 5 (top) and the dehydrated material (bottom).
Figure 24:
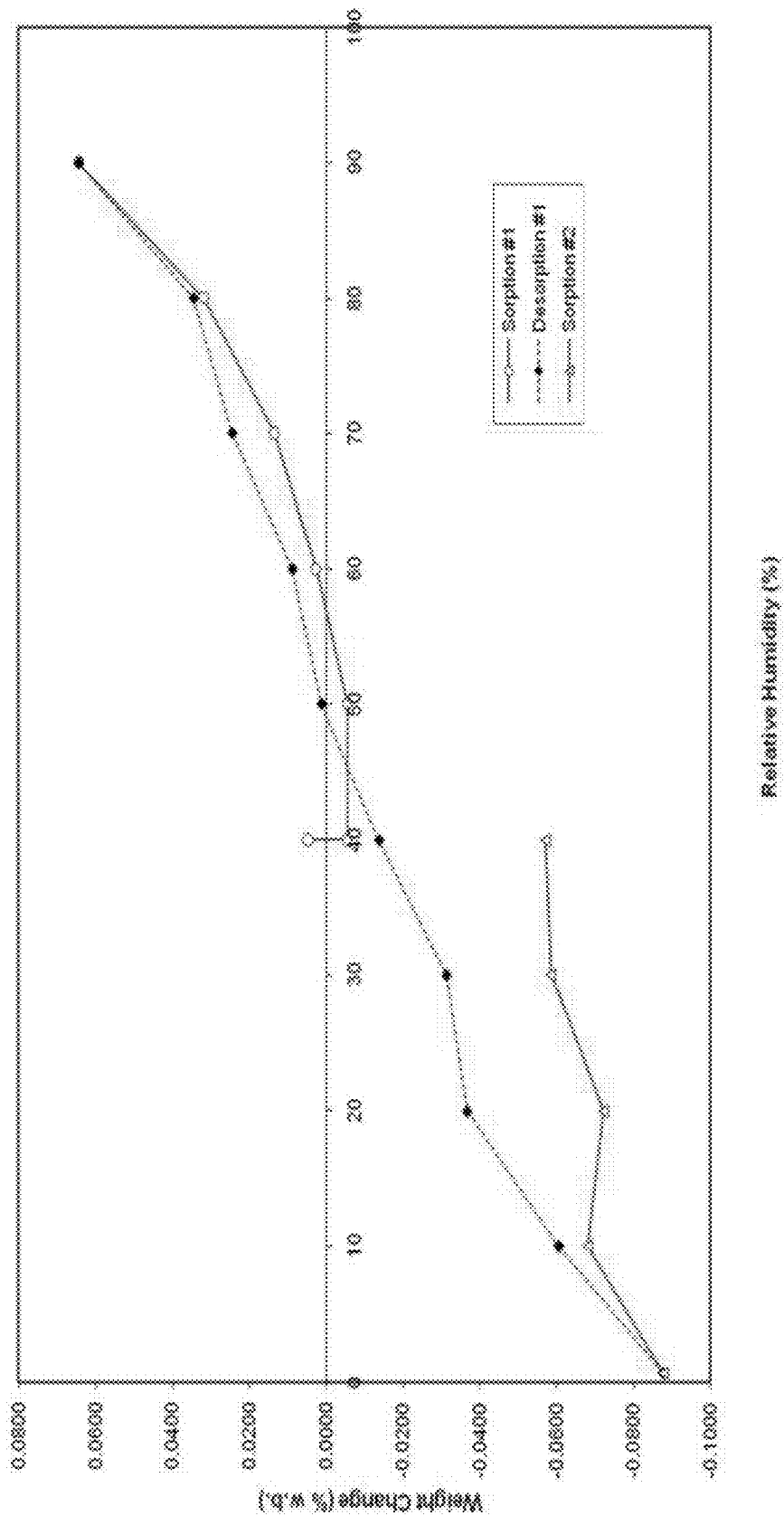
FIG. 24 is a GVS isothermal plot polymorphic Form 5.
Figure 25:
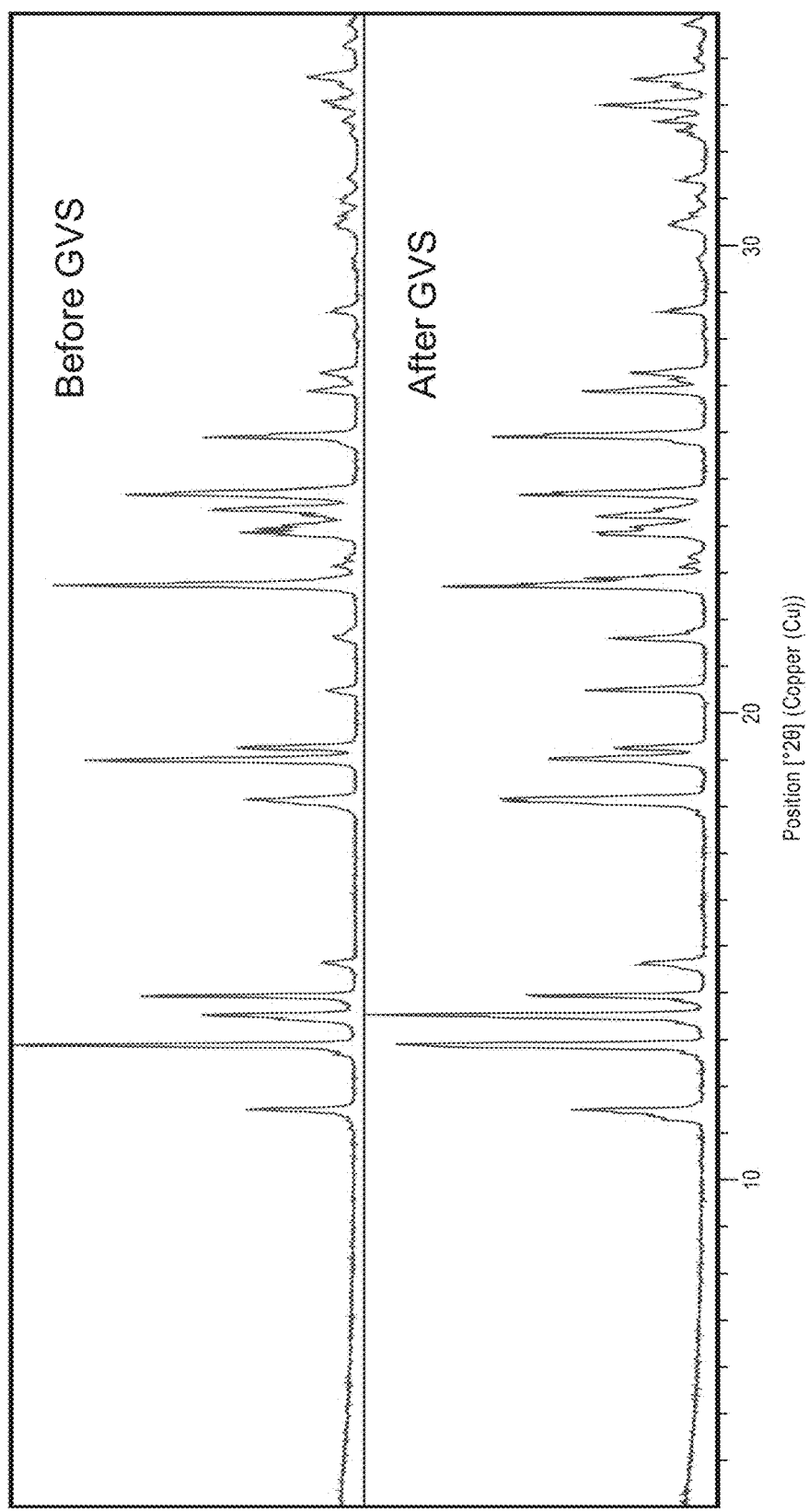
FIG. 25 are graphs of a XRPD pattern of polymorphic Form 5 before (top) and after the GVS run (bottom).
Figure 26:
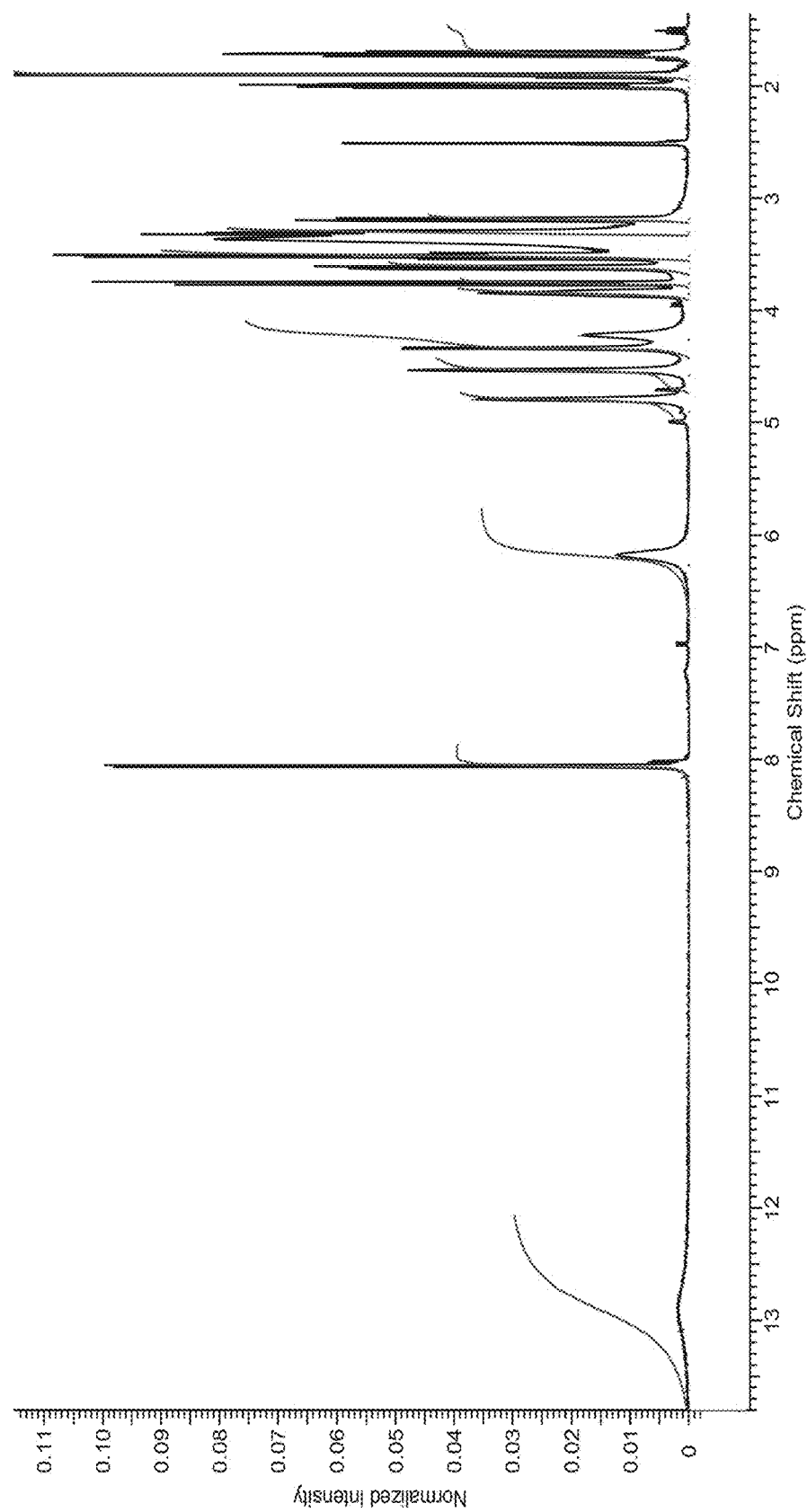
FIG. 26 is a $^1$H-NMR spectrum of polymorphic Form 5.
Figure 27:
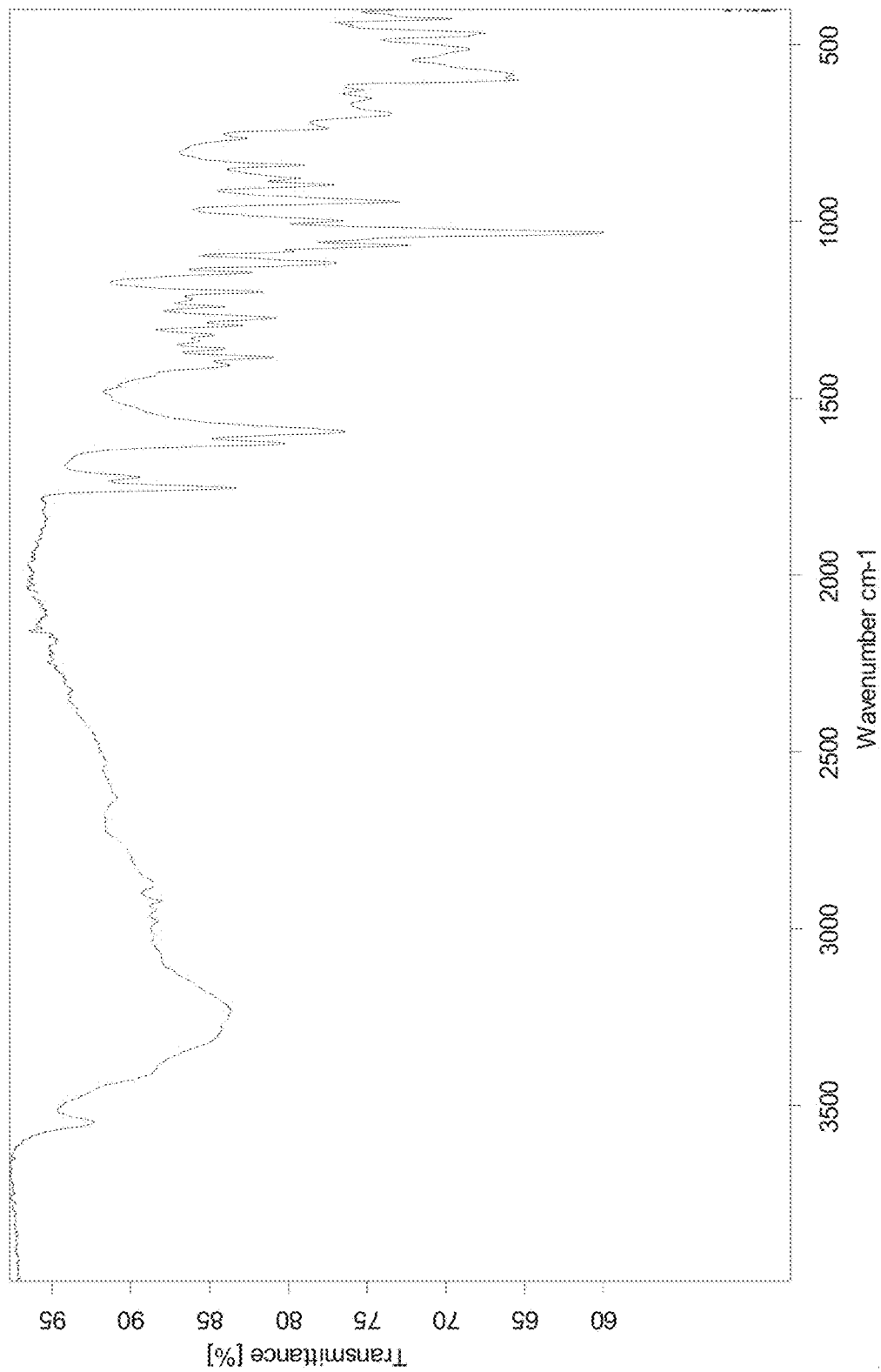
FIG. 27 is an IR spectrum of polymorphic Form 5.
Figure 29:
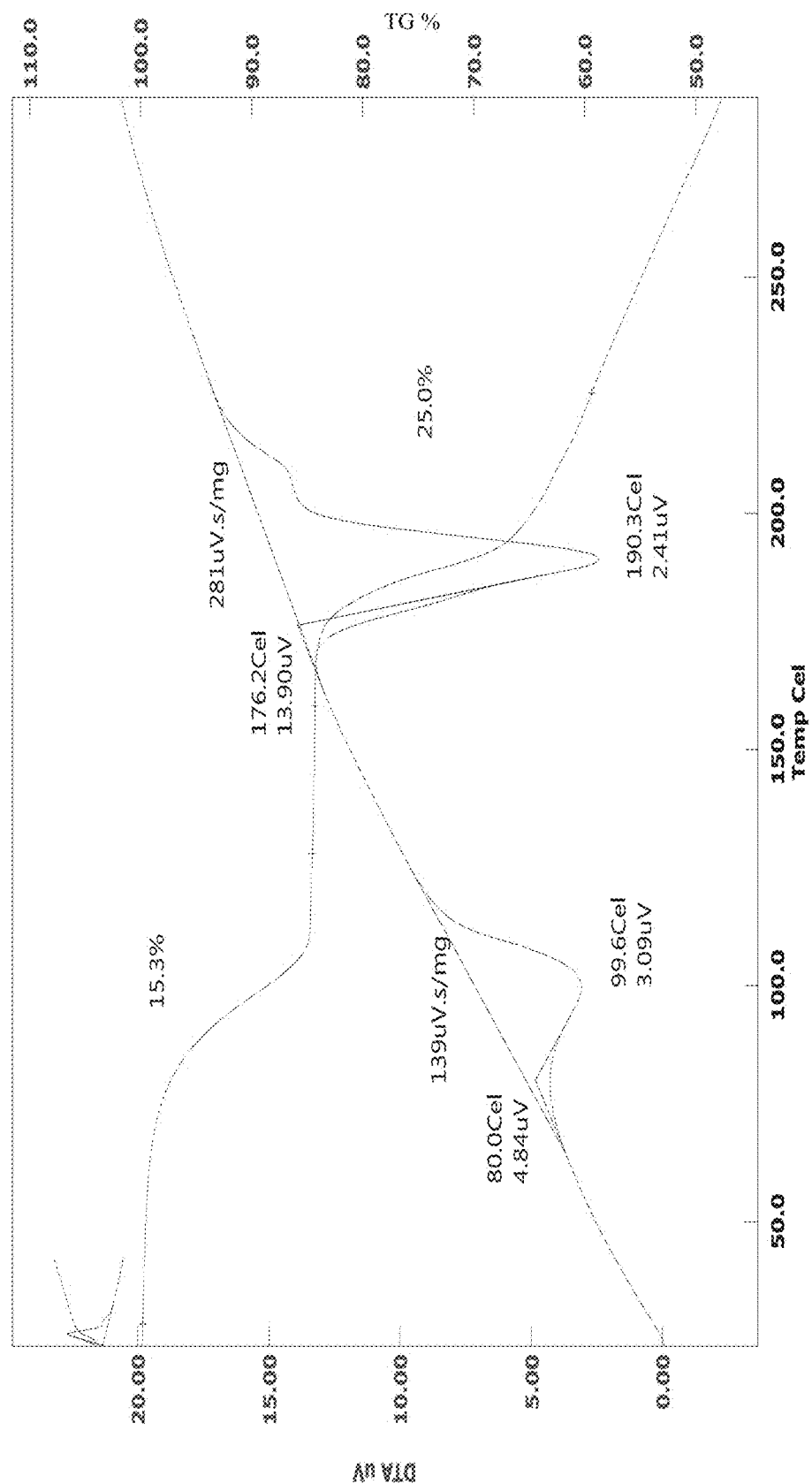
FIG. 29 is an overlay of TG and DTA thermograms of polymorphic Form 3.

Referring to PLM images (FIG. 20), the habit of Form 5 is block-like with a length around 100 µm. Strong birefringence is observed. Form 5 is crystalline; XRPD pattern exhibits five major peaks below 20° 2θ. As it can be seen from the TG trace, an initial weight loss of 10.5% is observed (onset ca. 88.4° C. for the endotherm in the DTA trace). Further weight losses are present, which may be due to decomposition. The loss of weight of 10.5% correlates very well with the KF Titration (10.34%). It is very likely Form 5 is a dihydrate (expected loss of weight for a dihydrate is 10.44%). The DSC for sialic acid Form 5 shows one endotherm corresponding with the dehydration (onset at ca. 90.5° C.) and the start of a second endotherm at the start of the decomposition (onset at ca. 192° C.). This possibly indicates the formation of a new anhydrous form by desolvation of Form 5 (onset seen for Form 1 is ca. 188.9° C.). The difference between the TG/DTA and the DSC traces is likely to be due to the difference in pan (open pan for TG/DTA and pierced closed pan for DSC). As it can be seen from FIG. 23, the dehydrated material obtained from Form 5 is an unknown form. Form 5 was dehydrated in the TG/DTA apparatus by holding the temperature at 90° C. for 35 min. When the material had lost 10.44% of its weight (dehydration), the material was taken out and the XRPD pattern was collected. From this GVS experiment, it can be concluded that Form 5 is very slightly hygroscopic, only 1.45% mass difference is seen between 0-90% relative humidity. This behaviour, with mass increasing while relative humidity is increased and decreasing when the humidity is decreased, is indicative that no phase change occurred during the GVS run. This is further supported by the XRPD analysis of the material recovered from the GVS. Material reclaimed after the GVS experiment is of the same polymorphic form (Form 5). Form 5 is stable when exposed to different humidity levels. Form 5 is consistent with the previous $^1$H NMR spectra obtained for sialic acid. A broad resonance at ca. 3.5 ppm is attributed to the water present, as this form is hydrated. The IR spectrum is consistent with the material, 2 ν C=O (1753-1723 (convoluted) and 1626 cm-1, due to very different environments for the carbonyl groups in this hydrate. As expected, a broad hydrogen bond absorption band is found at wave numbers >3000 cm$^{-1}$. Form 5 was found to have high purity by HPLC analysis, with the percentage area obtained for sialic acid being 99.87%. No known impurities were detected. By KF titration, the water content of Form 5 was found to be 10.34%, which is consistent with Form 5 being a dihydrate.

HPLC results of polymorphic Form 5 are shown below (with the purity in % area and retention time).

| RT (min) | PeakName | Area (mAU*s) | Area % | Peak Type |
|---|---|---|---|---|
| 14.00 | | 16.154 | 0.107 | MM |
| 17.52 | | 7.069 | 0.047 | BV |
| 18.75 | Sialic acid | 1.503e4 | 99.846 | VV R |
| 0.00 | Sodium Pyruvate | 0.000 | 0.000 | |
| 14.00 | | 15.752 | 0.105 | MM |
| 18.75 | Sialic acid | 1.502e4 | 99.895 | VV R |
| 0.00 | Sodium Pyruvate | 0.000 | 0.000 | |
| 0.00 | N-acetyl-D-mannosamine | 0.000 | 0.000 | |
| 0.00 | N-acetyl-D-glucosamine | 0.000 | 0.000 | |

Characterization of Form 3

Form 3 of sialic acid was characterized by the techniques described above.

Referring to PLM images (FIG. 28), crystallization produced fine needle-like crystals (20-30 µm length) that were prone to mild agglomeration. Very slight birefringence was observed due to particle size. Form 3 is crystalline material. The five major peaks below 20° 2θ occur at: 4.92°, 9.93°, 10.38°, 14.92° and 17.25° 2θ. The TGA trace shows a weight loss of 15.3% up to ca. 120° C. (DTA onset at ca. 80° C.). A second weight loss of 25.0% was observed around 175° C., most likely associated with the onset of degradation (DTA onset at ca. 176.2° C.). The loss of weight of 15.3% is likely due to the desolvation of acetic acid (16.26% for a 1:1 acetic acid:sialic acid). The DSC trace of sialic acid Form 3 is consistent with the TG/DTA. One endotherm corresponding with the desolvation (onset at ca. 107° C.) can be seen, the other endotherm seen is due to the decomposition (onset at ca. 180.9° C.). This also corresponds well with the formation of Form 2 by desolvation of Form 3 (onset seen for Form 2 is 181° C.). On increase of humidity, the sample appears to desolvate, losing 16% of its weight, and reverting to an anhydrous form. 16% is close to the expected value (16.26% for a 1:1 solvate) for the desolvation of a mono acetic acid solvate. XRPD analysis indicates that Form 3 converts to Form 1 during the GVS analysis. This conversion occurs during the increase of relative humidity. The $^1$H NMR spectrum for Form 3 is consistent with the previous $^1$H NMR spectra seen of sialic acid. The higher integration value for resonances at 1.25 and 1.95 ppm are due to the acetic acid present in this form. The values obtained match well with a mono acetic acid solvate. The IR spectrum of Form 3 is consistent with the material, 3 v C=O (1724, 1702, 1668 cm$^{-1}$) can be seen, as expected (one extra due to acetic acid) and a large hydrogen bond absorption band at wave numbers >3000 cm$^{-1}$. Form 3 was found to have a high purity by HPLC analsyis. Percentage area obtained for sialic acid was 99.8%. The water content for Form 3 was found to be 0.48% by Karl Fischer titration.

HPLC results of polymorphic Form 3 are shown below (with the purity in % area and retention time).

| RT (min) | PeakName | Area (mAU*s) | Area % | Peak Type |
|---|---|---|---|---|
| 18.75 | Sialic acid | 1.505e4 | 99.756 | FM R |
| 0.00 | Sodium Pyruvate | 0.000 | 0.000 | |
| 0.00 | N-acetyl-D-mannosamine | 0.000 | 0.000 | |
| 0.00 | N-acetyl-D-glucosamine | 0.000 | 0.000 | |
| 0.00 | Acetic acid | 0.000 | 0.000 | |
| 18.74 | Sialic acid | 1.503e4 | 99.749 | FM R |
| 0.00 | Sodium Pyruvate | 0.000 | 0.000 | |
| 0.00 | N-acetyl-D-mannosamine | 0.000 | 0.000 | |
| 0.00 | N-acetyl-D-glucosamine | 0.000 | 0.000 | |
| 0.00 | Acetic acid | 0.000 | 0.000 | |

Characterization of Form 2

Form 2 of sialic acid was characterized by the techniques described above.

Figure 47:
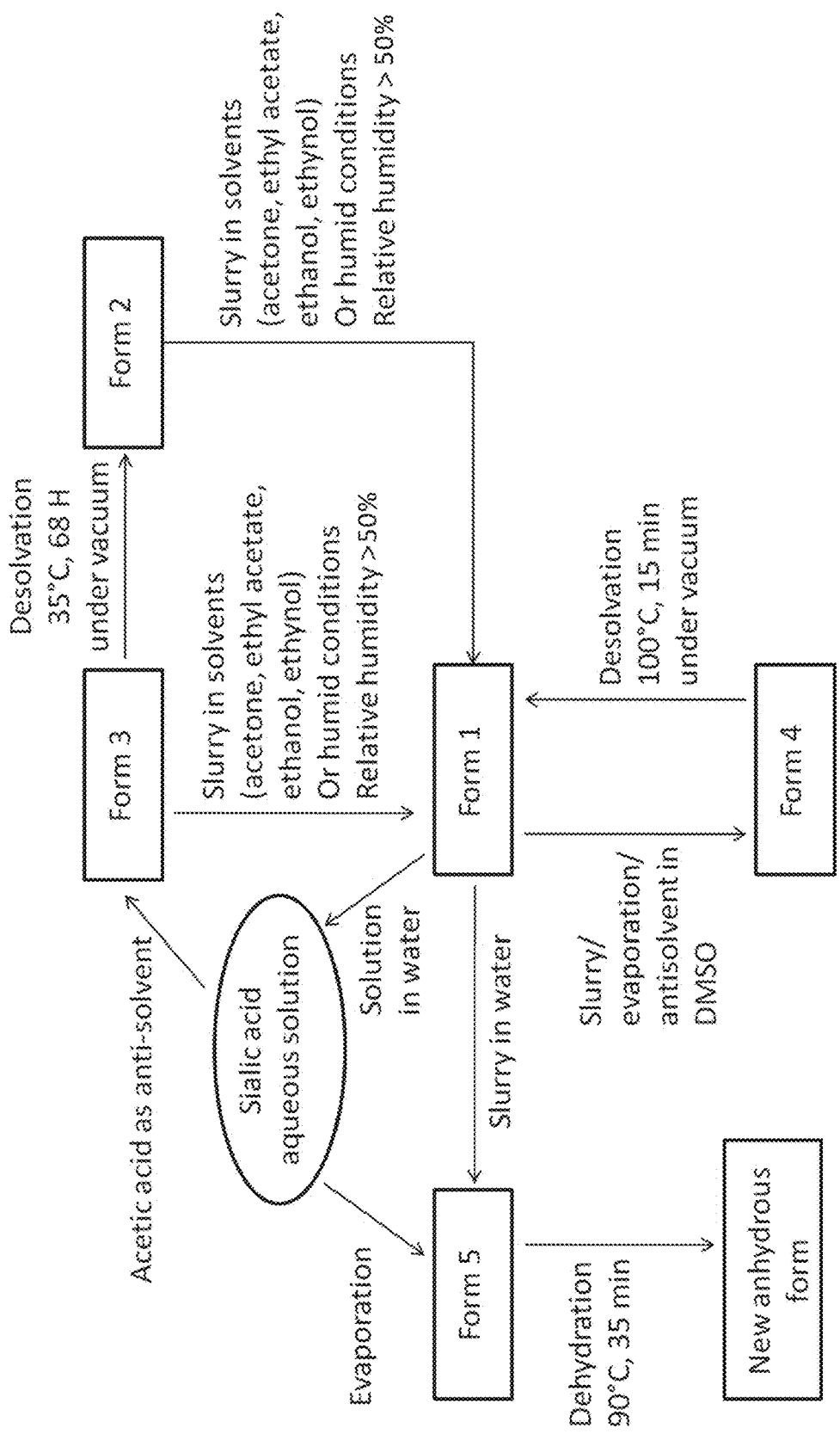
FIG. 47 is phase diagram of the different forms of sialic acid observed during the study.
Figure 48:
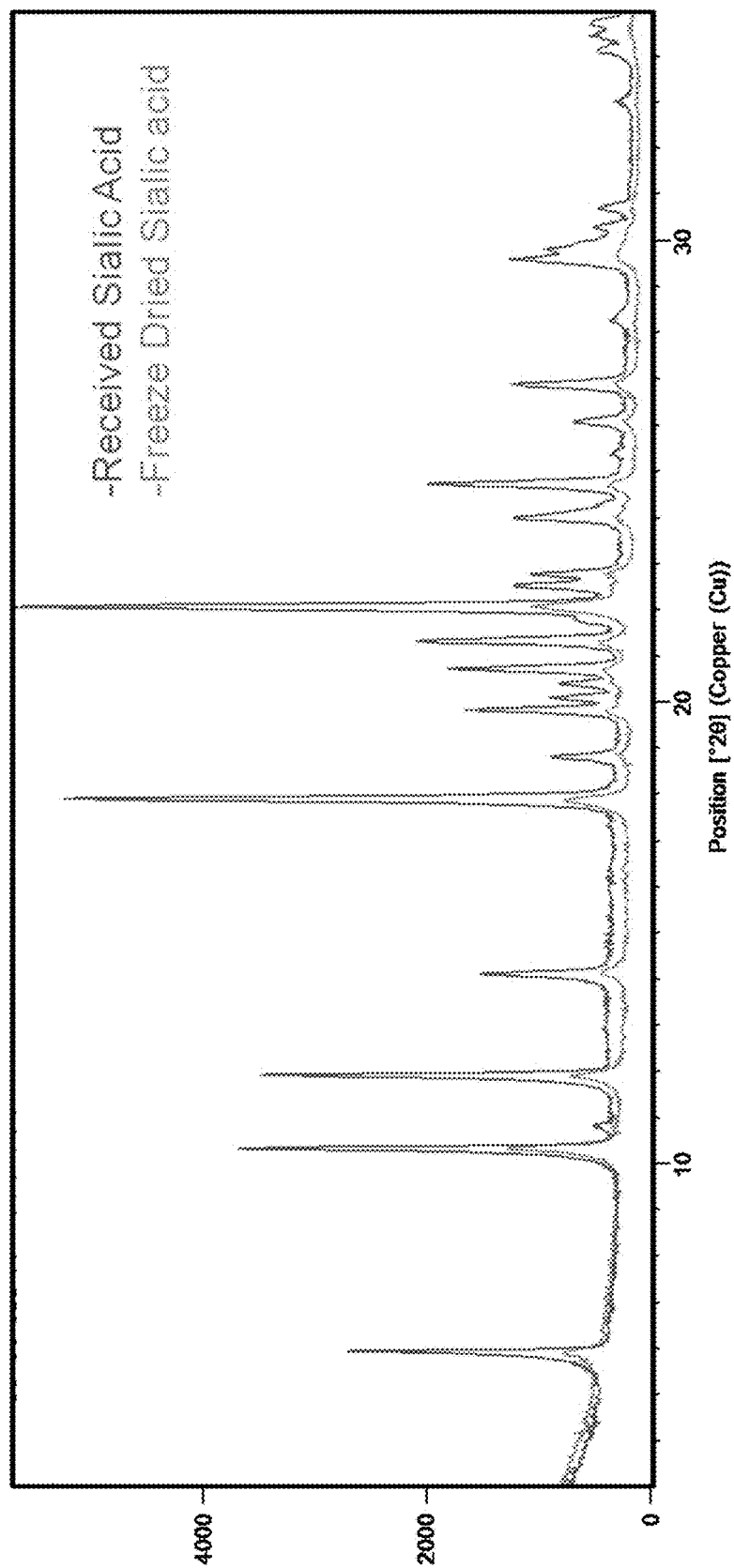
FIG. 48 are diffractograms of polymorphic Form 1 (top, more intense peaks) and the freeze-dried material (bottom, polymorphic Form 1+ amorphous).
Figure 50:
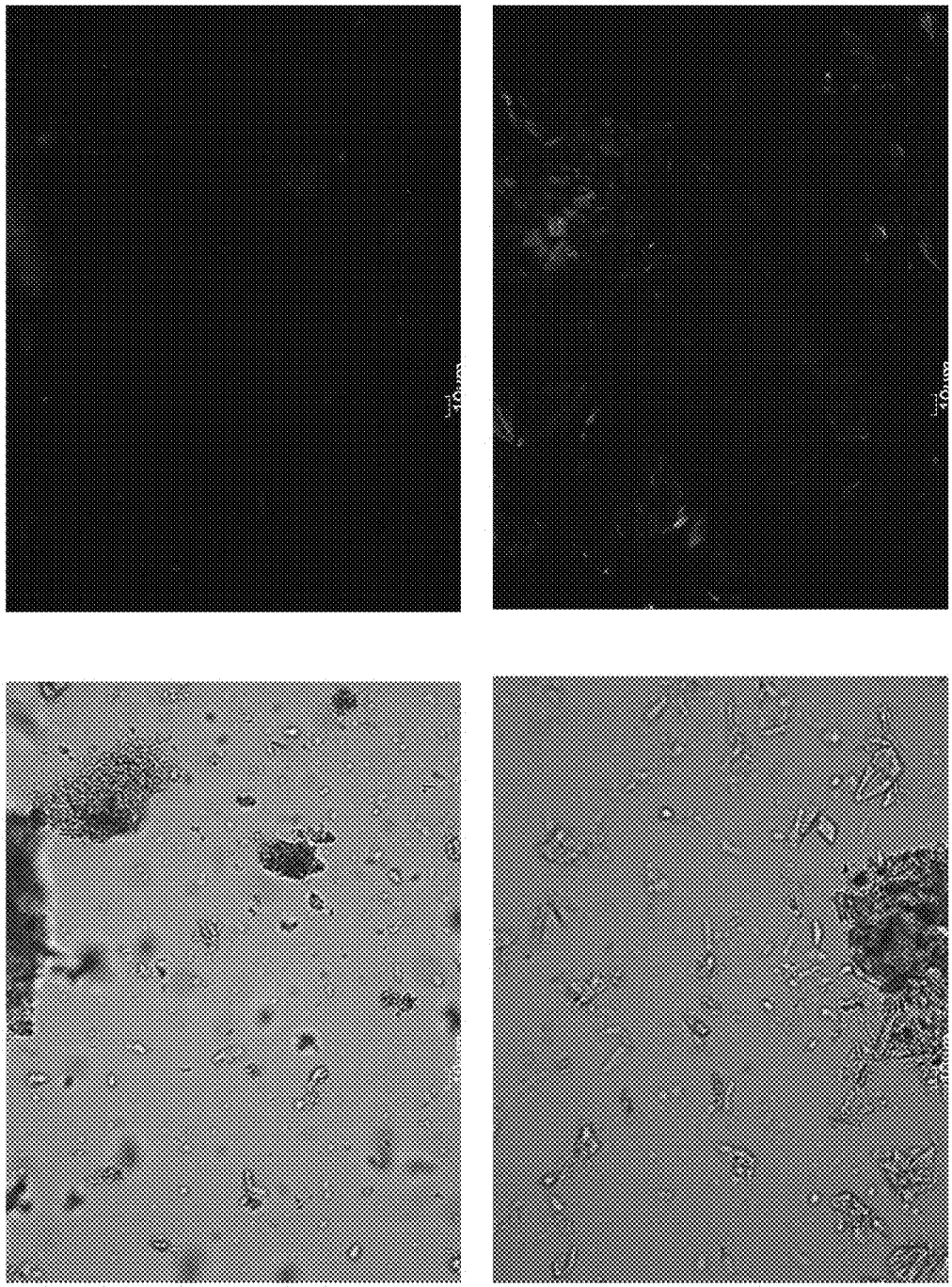
FIG. 50 includes PLM images under a non-polarized lens (left) and under a polarized lens (right) from temperature cycling experiments conducted in different solvent systems: acetone/water 90/10 v/v (top) and acetone/ethanol 50/50 v/v (bottom).
Figure 51:
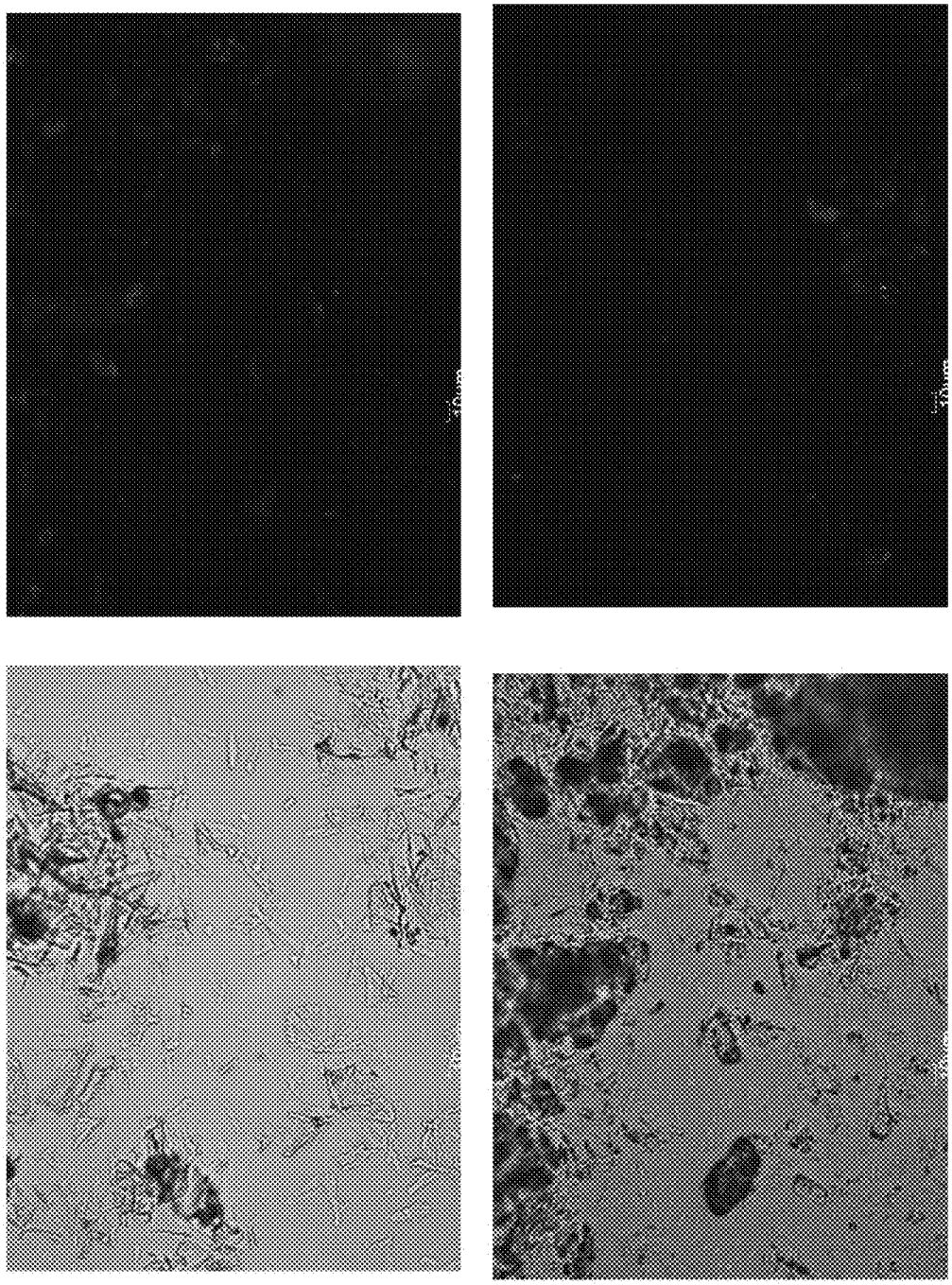
FIG. 51 includes PLM images under a non-polarized lens (left) and under a polarized lens (right) from temperature cycling experiments conducted in different solvent systems: acetonitrile (top) and dichloromethane (bottom)
Figure 52:
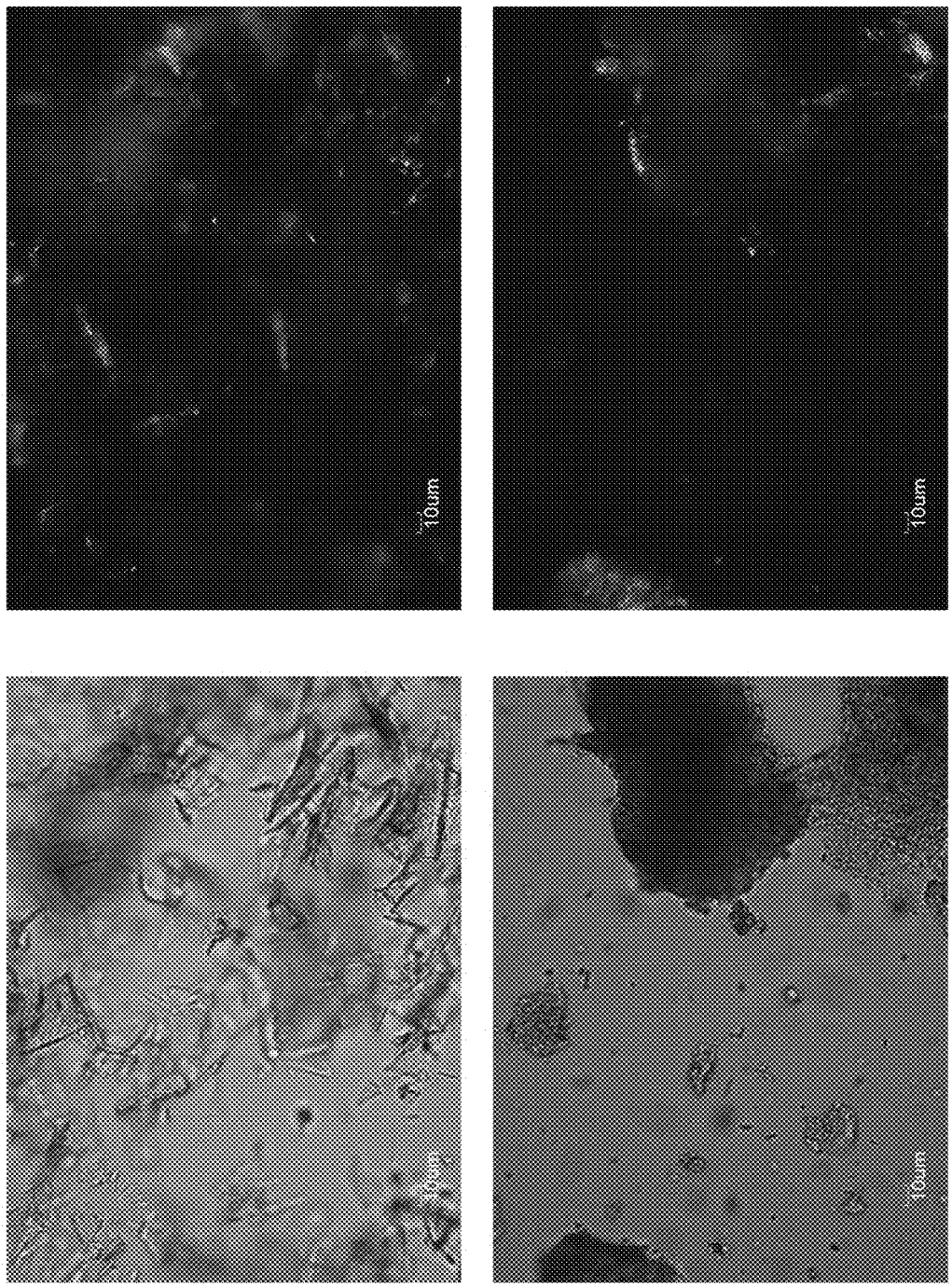
FIG. 52 includes PLM images under a non-polarized lens (left) and under a polarized lens (right) from temperature cycling experiments conducted in different solvent systems: diiospropyl ether (top); dimethylacetamide (bottom).
Figure 53:
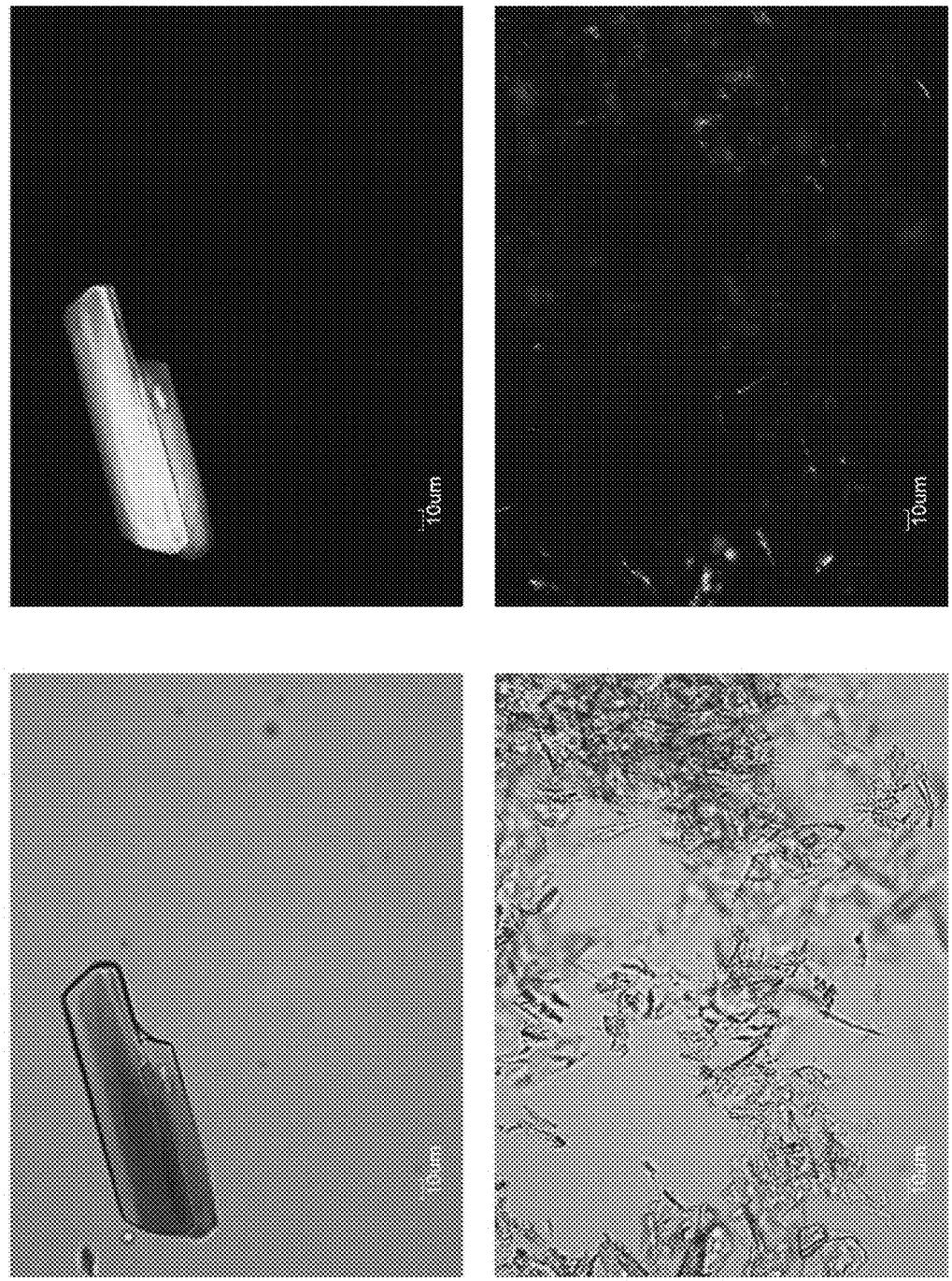
FIG. 53 includes PLM images under a non-polarized lens (left) and under a polarized lens (right) from temperature cycling experiments conducted in different solvent systems: dimethylsulfoxide (top); 1,4-dioxane (bottom).
Figure 55:
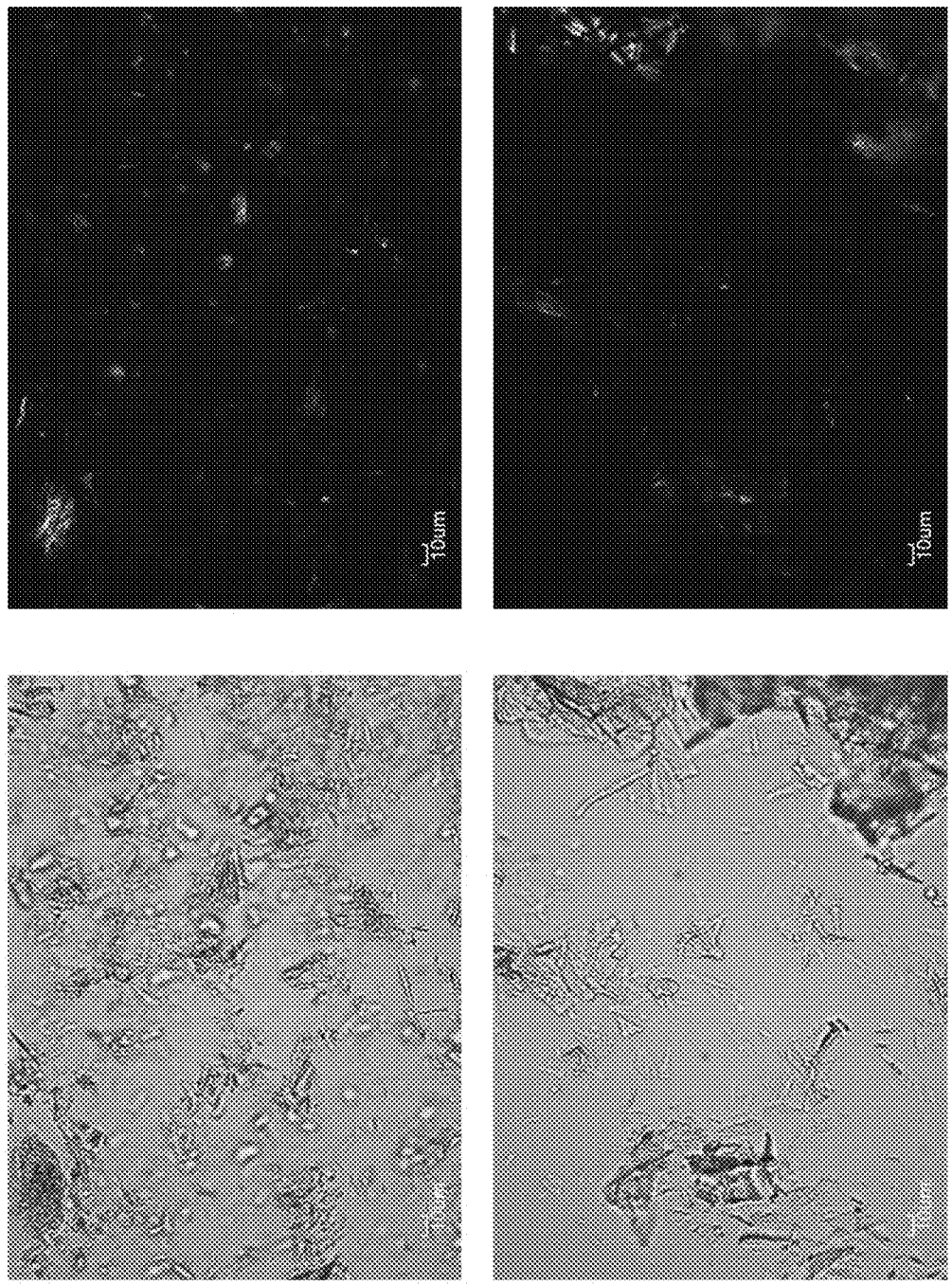
FIG. 55 includes PLM images under a non-polarized lens (left) and under a polarized lens (right) from temperature cycling experiments conducted in different solvent systems: ethynol (top); ethyl acetate (bottom).
Figure 56:
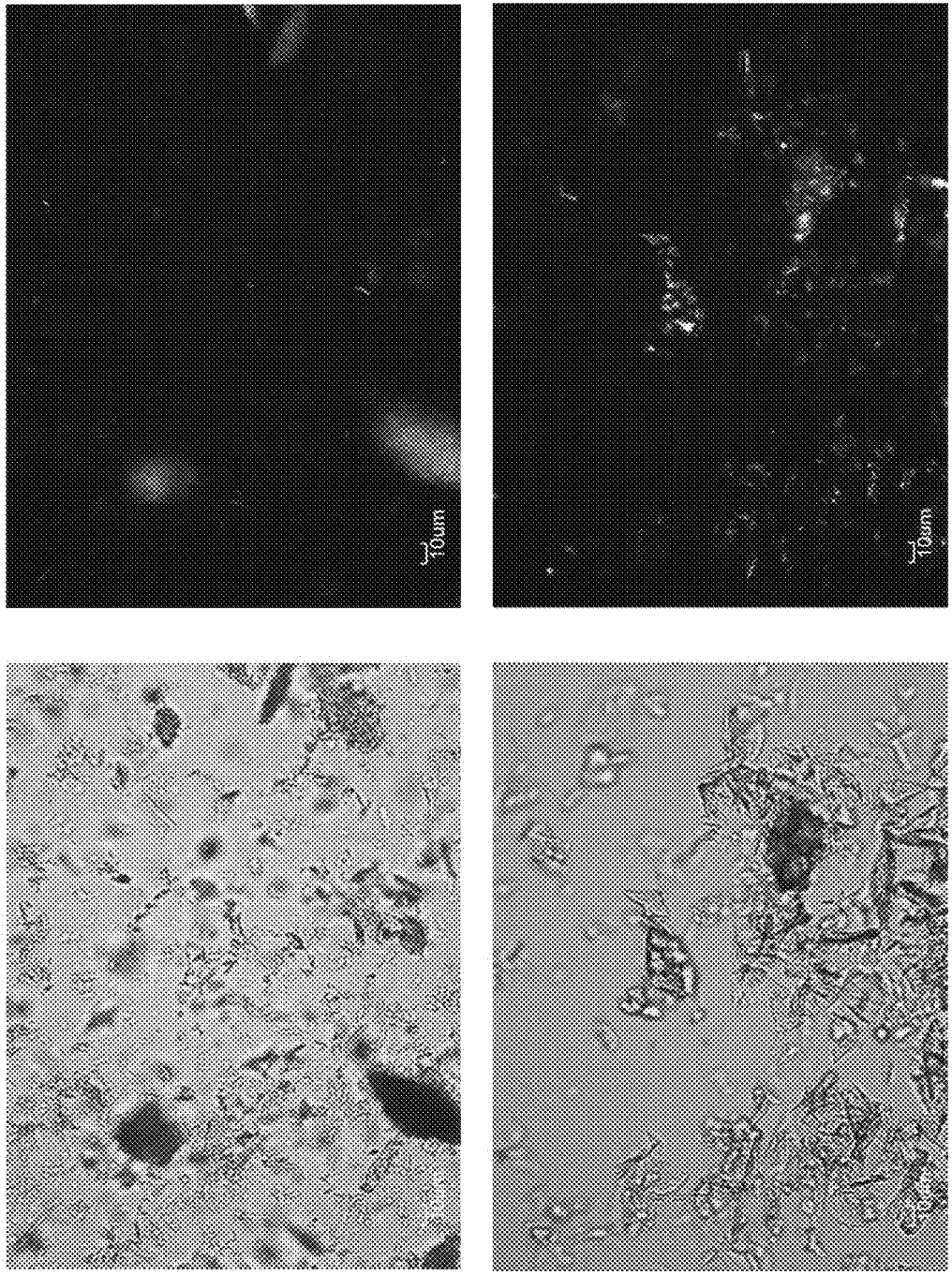
FIG. 56 includes PLM images under a non-polarized lens (left) and under a polarized lens (right) from temperature cycling experiments conducted in different solvent systems: methanol (top); methylethyl ketone (bottom).
Figure 57:
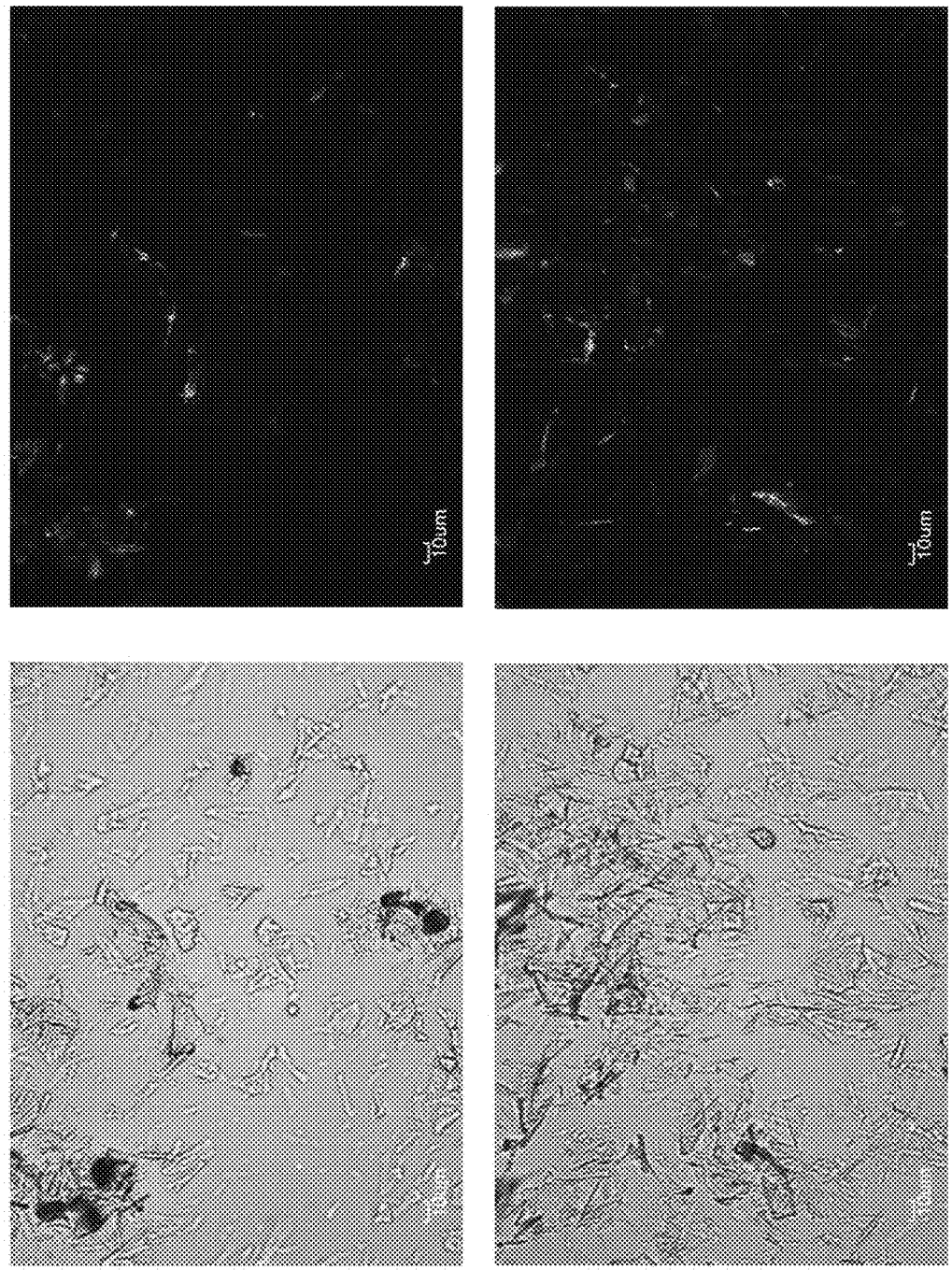
FIG. 57 includes PLM images under a non-polarized lens (left) and under a polarized lens (right) from temperature cycling experiments conducted in different solvent systems: methylisobutyl ketone (top); 2-methyl THF (bottom).
Figure 58:
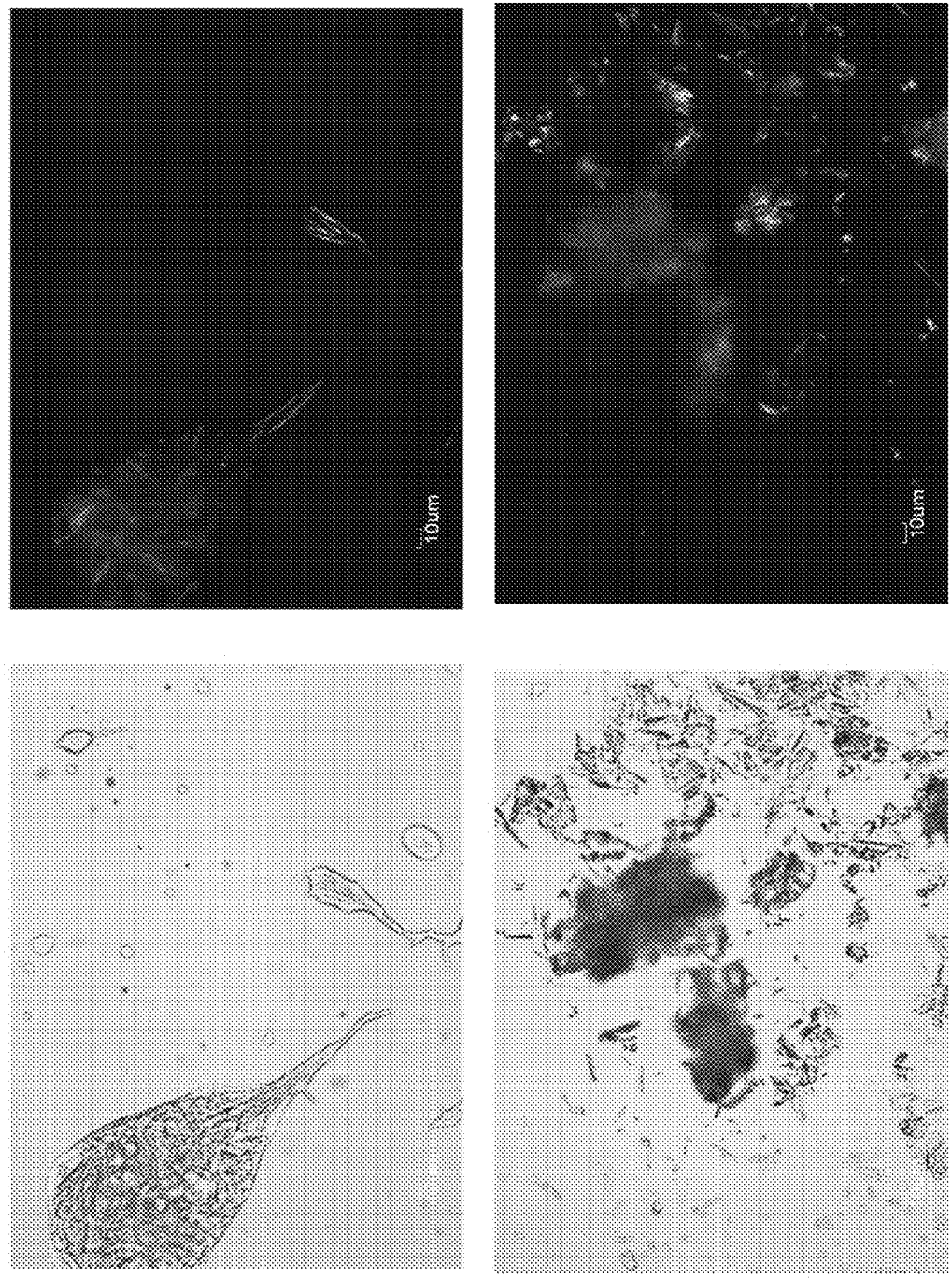
FIG. 58 includes PLM images under a non-polarized lens (left) and under a polarized lens (right) from temperature cycling experiments conducted in different solvent systems: N-methyl-2-pyrrolidone (top); 2-propanol (bottom).
Figure 59:
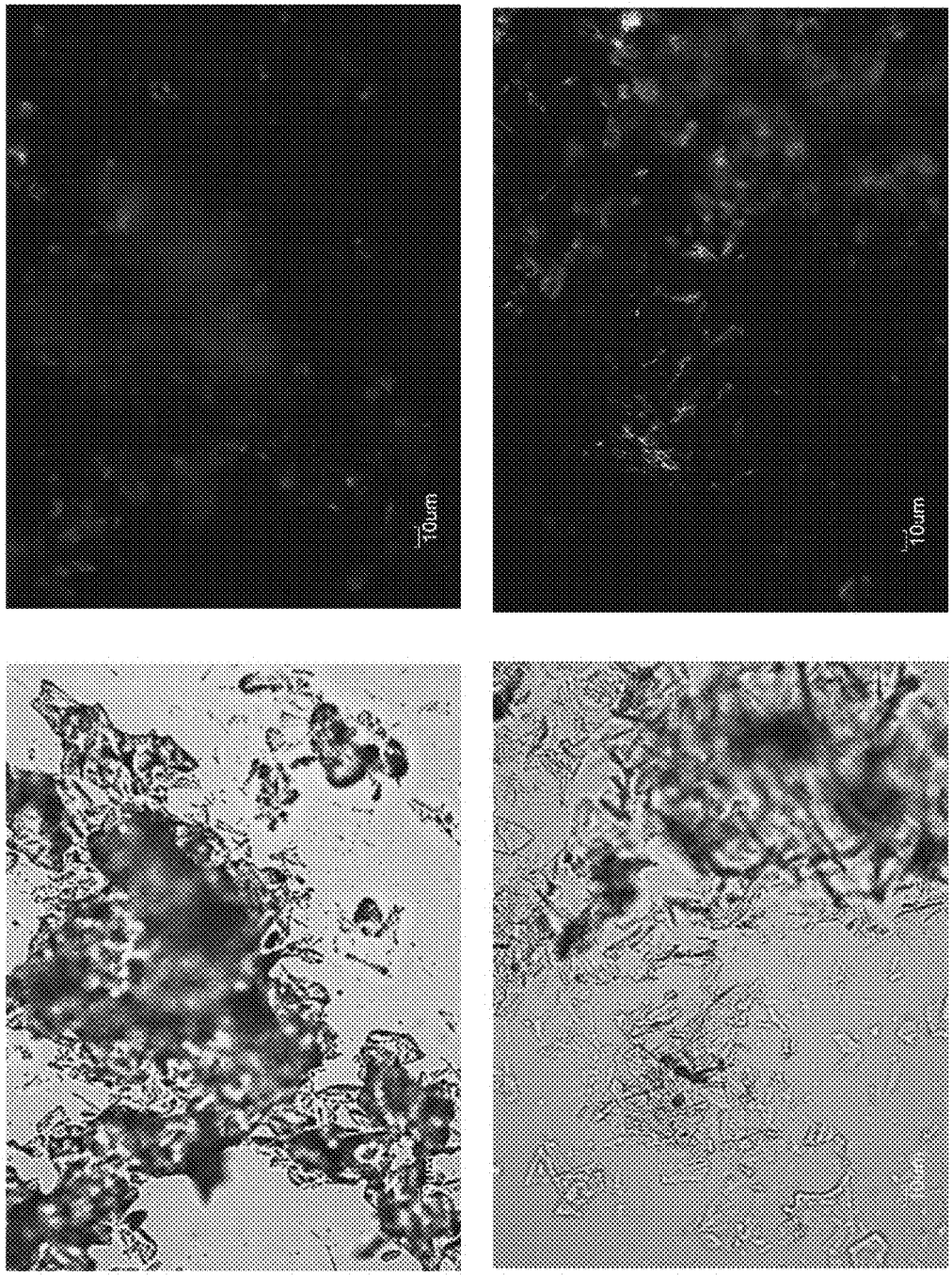
FIG. 59 includes PLM images under a non-polarized lens (left) and under a polarized lens (right) from temperature cycling experiments conducted in different solvent systems: THF (top); toluene (bottom).
Figure 60:
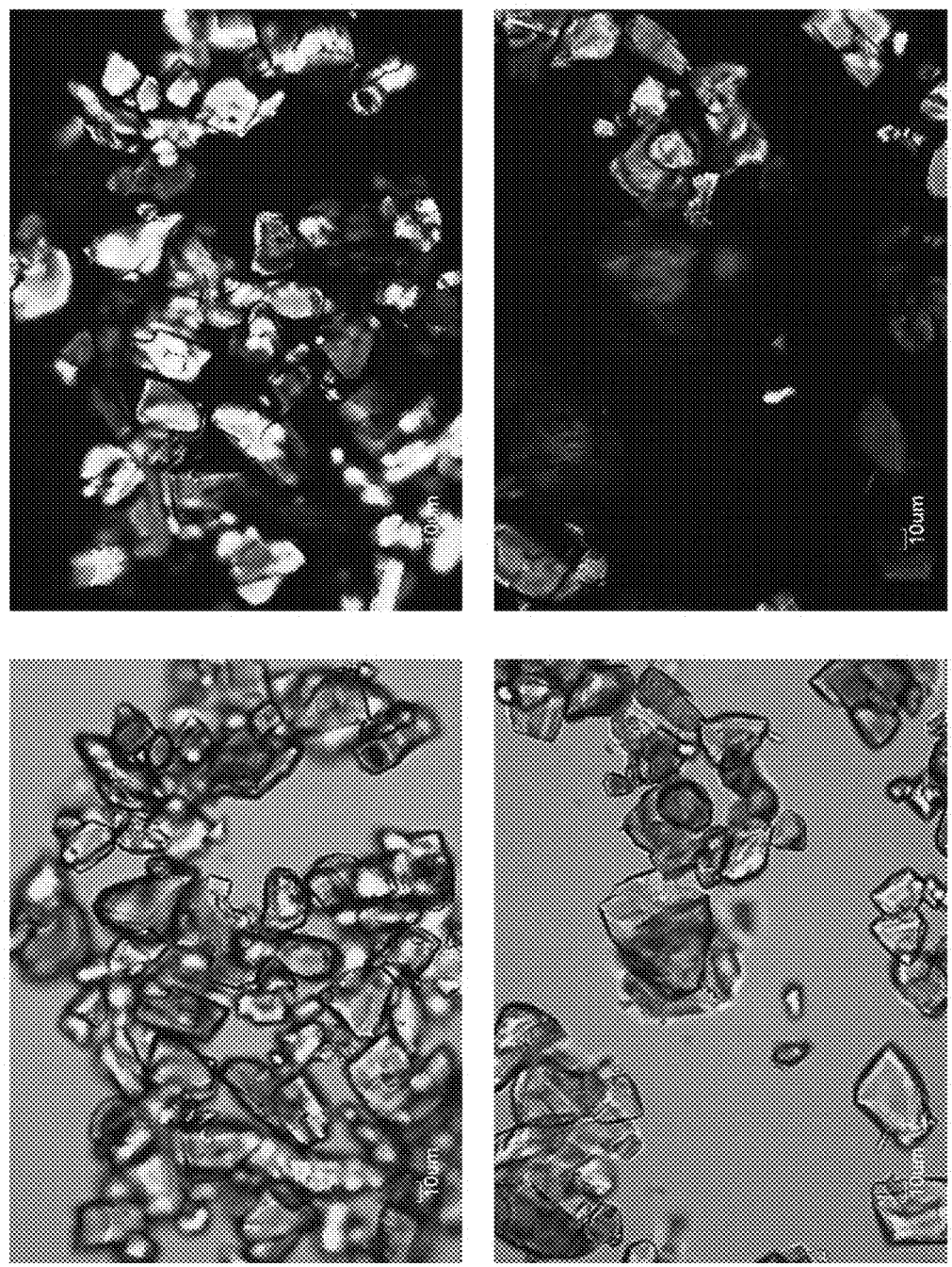
FIG. 60 includes PLM images under a non-polarized lens (left) and under a polarized lens (right) from temperature cycling experiments conducted in different solvent systems: water (top); water/acetic acid 80/20 v/v (bottom).
Figure 76:
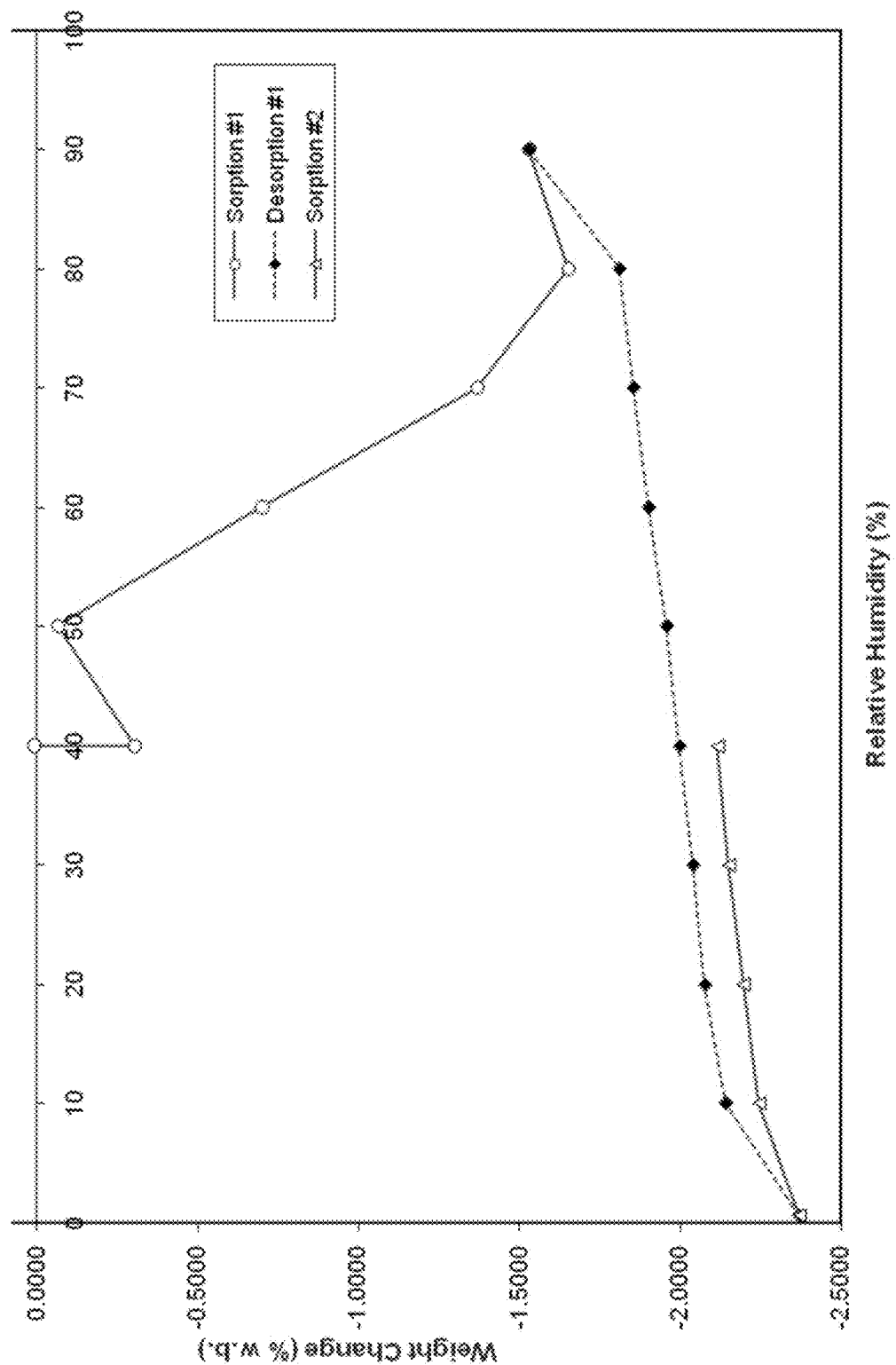
FIG. 76 is GVS of an embodiment of Form 2. It loses weight (on sorption) for RH>50% (ca. 1.5% weight loss). Desorption and further sorption shows behavior characteristic of a slightly hygroscopic material. The behavior is very similar to the prepared Form 2. As expected, Form 2 transformed to Form 1 during the GVS run.
Figure 77:
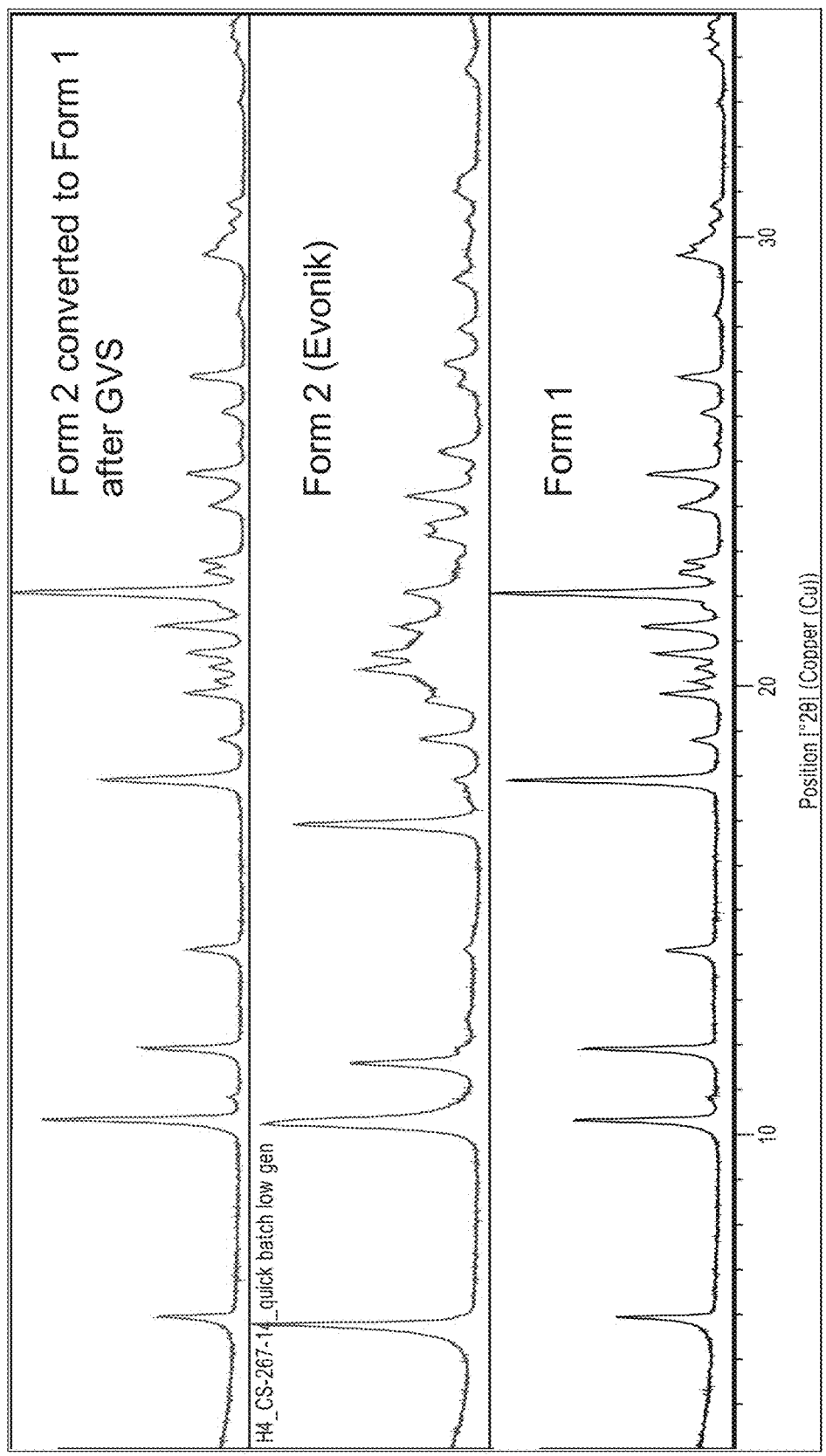
FIG. 77 is XRPD post GVS (red) of an embodiment of Form 2 (blue) and Form 1 (black).
Figure 78:
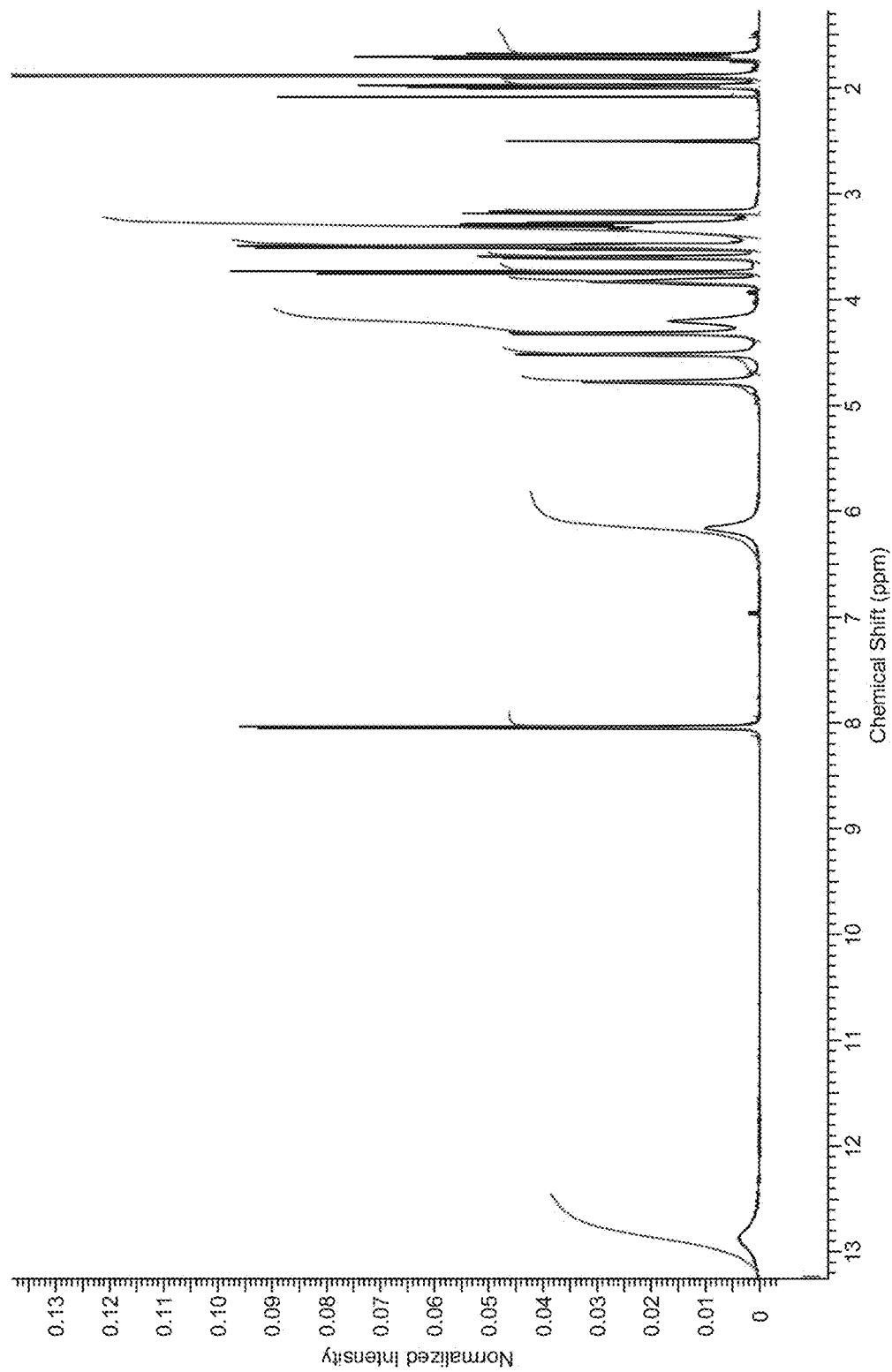
FIG. 78 is $^1$H NMR spectrum of an embodiment of Form 2 in DMSO.
Figure 79:
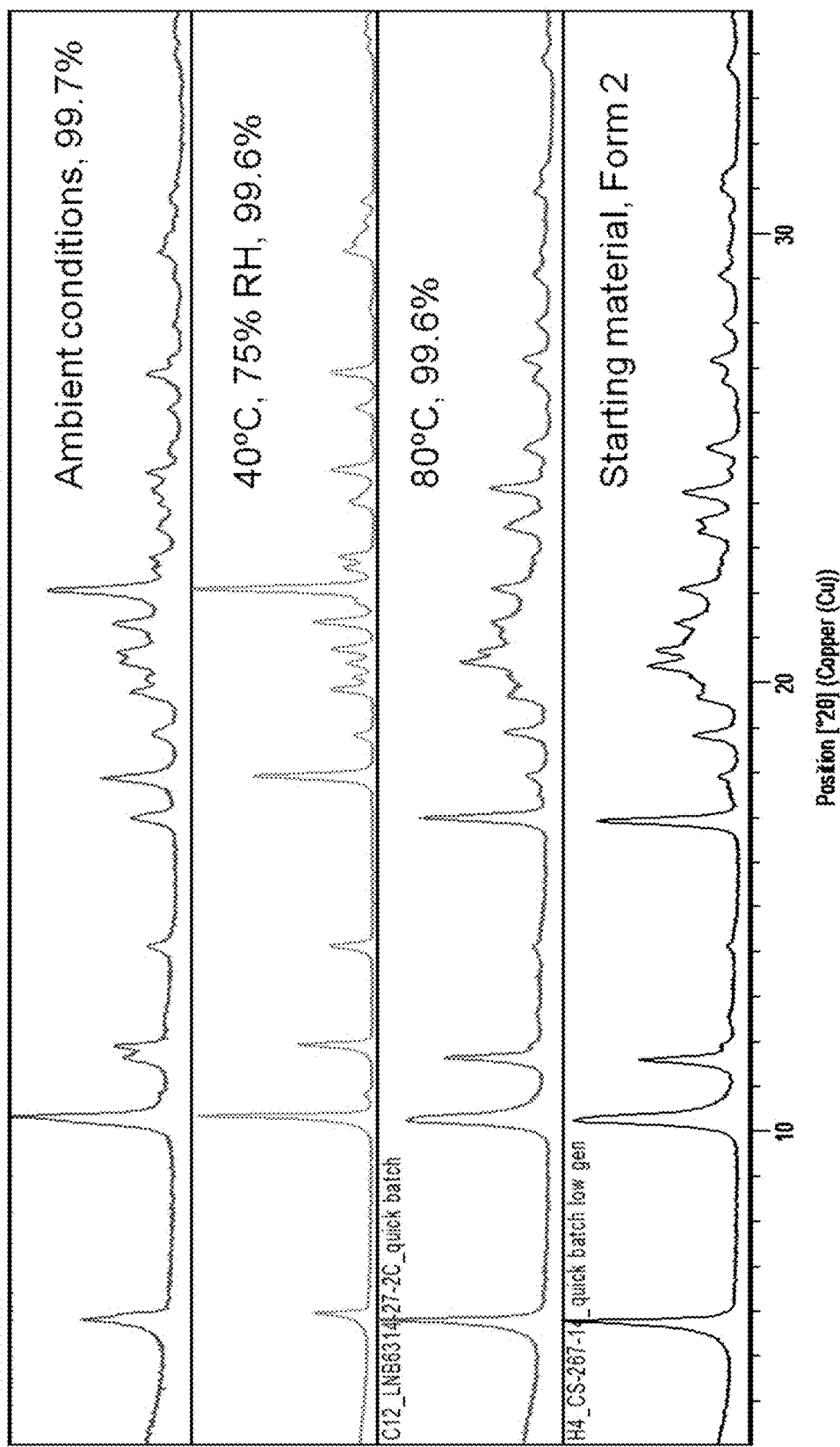
FIG. 79 is stacked diffractograms of an embodiment of Form 2 samples after 1 week at ambient conditions (blue), 40° C. and 75% relative humidity (green), 80° C. (red) and the starting form (black). After each condition, the HPLC purity result is detailed. An embodiment of Form 2 is stable as a physical form (XRPD) at 80° C. but converts to Form 1 at 40° C., 75% RH and more slowly under ambient conditions (mixture of Forms 1 and 2). The chemical stability is good under the conditions studied.

The drying of Form 3 to obtain pure Form 2 was a relatively long process, as illustrated by the following diffractograms. Referring to PLM images (FIG. 36), the particles are very small needles (length 30 µm or smaller), birefringence is weak due to the particle size. Form 2 is less crystalline than Forms 1, 3 or 5. The five major peaks below 20° 2θ occur at: 5.72°, 10.28°, 11.58°, 16.91° and 18.78° 2θ. Form 2 shows a small weight loss (1.6%) prior to its decomposition (onset at ca. 178.5° C.). This loss of weight is likely to be some acetic acid either bound or at the surface of the crystals (Acetic acid is observed in the $^1$H NMR spectrum). The Form 2 DSC trace is consistent with the TG/DTA. Only one endotherm, corresponding with the decomposition, can be seen with an onset at ca. 181° C. Form 2 loses weight (on sorption) for RH>50% (ca. 2.5% weight loss—ca. 1.5% weight loss), which is not an expected behaviour and thus it is likely indicative of a phase change (FIGS. 47 and 76 showing GVS of two different lots of Form 2). Desorption and further sorption show behaviour of a slightly hygroscopic material. The phase change is illustrated by the diffractogram difference between the reclaimed material after the GVS experiment and diffractogram prior to the GVS run (FIGS. 48 and 77 showing results from two different lots of Form 2). As it can be seen from the stacked diffractograms, Form 2 (SFS) has converted to Form 1 at high relative humidity. The $^1$H NMR spectrum of Form 2 is consistent with the previous $^1$H NMR spectra of sialic acid (FIGS. 49 and 79 showing $^1$H NMR spectra of two different lots of Form 2). Resonance at 1.92 ppm is due to some acetic acid (integration 0.42 of δ at 1.92 ppm). The IR spectrum of Form 2 is consistent with the material, 2 v C=O (1721, 1657 cm$^{-1}$) can be seen and hydrogen bonds result in a large absorption band at wave numbers above 3000 cm$^{-1}$. Form 2 was found to have a high purity by HPLC analysis. The percentage area obtained for sialic acid was 99.8%. The water content of Form 2 was found to be 0.034% by Karl Fischer titration.

HPLC results of polymorphic Form 2 are shown below (with the purity in % area and retention time).

| RT (min) | PeakName | Area (mAU*s) | Area % | Peak Type |
|---|---|---|---|---|
| 18.76 | Sialic acid | 1.693e4 | 99.743 | VV R |
| 0.00 | Sodium Pyruvate | 0.000 | 0.000 | |
| 0.00 | N-acetyl-D-mannosamine | 0.000 | 0.000 | |
| 0.00 | N-acetyl-D-glucosamine | 0.000 | 0.000 | |
| 0.00 | Acetic acid | 0.000 | 0.000 | |
| 18.76 | Sialic acid | 1.685e4 | 99.766 | VV R |
| 0.00 | Sodium Pyruvate | 0.000 | 0.000 | |
| 0.00 | N-acetyl-D-mannosamine | 0.000 | 0.000 | |
| 0.00 | N-acetyl-D-glucosamine | 0.000 | 0.000 | |
| 0.00 | Acetic acid | 0.000 | 0.000 | |

Stress Stability Studies and Related Purities

All four Forms (1, 2, 3 and 5) were placed under 7 day stress stability testing. This was carried out by placing the four forms under three different conditions for one week. Their physical stability was then analyzed by comparing the diffractograms and the chemical stability was checked by HPLC.

For each form, stacked diffractograms of the material reclaimed after one week under a chosen condition is presented, associated with the measured purity.

HPLC results of polymorphic Form 1 are shown below: stability under ambient conditions

| RT (min) | PeakName | Area (mAU*s) | Area % | Peak Type |
|---|---|---|---|---|
| 13.99 | | 15.449 | 0.098 | MM |
| 15.61 | | 10.981 | 0.070 | FM |
| 18.75 | Sialic acid | 1.571e4 | 99.705 | VV R |
| 13.99 | | 15.875 | 0.101 | MM |
| 15.60 | | 10.063 | 0.064 | FM |
| 18.75 | Sialic acid | 1.569e4 | 99.711 | VV R | stability under 40° C., 75% RH

| RT (min) | PeakName | Area (mAU*s) | Area % | Peak Type |
|---|---|---|---|---|
| 17.49 | | 18.620 | 0.110 | VV |
| 18.76 | Sialic acid | 1.687e4 | 99.590 | VV R |
| 20.38 | | 7.403 | 0.044 | VB T |
| 0.00 | Sodium Pyruvate | 0.000 | 0.000 | |
| 0.00 | N-acetyl-D-mannosamine | 0.000 | 0.000 | |
| 26.43 | N-acetyl-D-glucosamine | 13.800 | 0.081 | BB |
| 0.00 | Acetic acid | 0.000 | 0.000 | |
| 17.50 | | 19.512 | 0.116 | VV |
| 18.76 | Sialic acid | 1.682e4 | 99.580 | VV R |
| 20.35 | | 7.604 | 0.045 | VV T |
| 0.00 | Sodium Pryuvate | 0.000 | 0.000 | |
| 0.00 | N-acetyl-D-mannosamine | 0.000 | 0.000 | |
| 26.48 | N-acetyl-D-glucosamine | 13.396 | 0.079 | BV |
| 0.00 | Acetic acid | 0.000 | 0.000 | | stability under 80° C.

| RT (min) | PeakName | Area (mAU*s) | Area % | Peak Type |
|---|---|---|---|---|
| 17.50 | | 23.333 | 0.135 | VV |
| 18.76 | Sialic acid | 1.727e4 | 99.613 | VV R |
| 20.41 | | 7.009 | 0.040 | VB T |
| 0.00 | Sodium Pyruvate | 0.000 | 0.000 | |
| 0.00 | N-acetyl-D-mannosamine | 0.000 | 0.000 | |
| 26.47 | N-acetyl-D-glucosamine | 10.817 | 0.062 | VV R |
| 0.00 | Acetic acid | 0.000 | 0.000 | |
| 18.76 | Sialic acid | 1.724e4 | 99.673 | VV R |

-continued

| RT (min) | PeakName | Area (mAU*s) | Area % | Peak Type |
|---|---|---|---|---|
| 0.00 | Sodium Pyruvate | 0.000 | 0.000 | |
| 0.00 | N-acetyl-D-mannosamine | 0.000 | 0.000 | |
| 26.46 | N-acetyl-D-glucosamine | 10.667 | 0.062 | BB |
| 0.00 | Acetic acid | 0.000 | 0.000 | |

HPLC results of polymorphic Form 2 are shown below: stability under ambient conditions

| RT (min) | PeakName | Area (mAU*s) | Area % | Peak Type |
|---|---|---|---|---|
| 13.98 | | 29.957 | 0.176 | BV R |
| 15.60 | | 20.651 | 0.122 | VB |
| 18.71 | Sialic acid | 1.692e4 | 99.561 | FM R |
| 0.00 | Sodium Pyruvate | 0.000 | 0.000 | |
| 13.99 | | 26.223 | 0.154 | BB |
| 15.62 | | 17.080 | 0.101 | VB |
| 18.72 | Sialic acid | 1.692e4 | 99.605 | FM R |
| 0.00 | Sodium Pyruvate | 0.000 | 0.000 | | stability under 40° C., 75% RH

| RT (min) | PeakName | Area (mAU*s) | Area % | Peak Type |
|---|---|---|---|---|
| 15.61 | | 19.367 | 0.107 | FM |
| 17.47 | | 14.873 | 0.082 | FM |
| 18.71 | Sialic acid | 1.804e4 | 99.360 | FM R |
| 0.00 | Sodium Pyruvate | 0.000 | 0.000 | |
| 0.00 | N-acetyl-D-mannosamine | 0.000 | 0.000 | |
| 0.00 | N-acetyl-D-glucosamine | 0.000 | 0.000 | |
| 0.00 | Acetic acid | 0.000 | 0.000 | |
| 18.71 | Sialic acid | 1.801e4 | 99.405 | FM R |
| 0.00 | Sodium Pyruvate | 0.000 | 0.000 | |
| 0.00 | N-acetyl-D-mannosamine | 0.000 | 0.000 | |
| 0.00 | N-acetyl-D-glucosamine | 0.000 | 0.000 | |
| 0.00 | Acetic acid | 0.000 | 0.000 | | stability under 80° C.

| RT (min) | PeakName | Area (mAU*s) | Area % | Peak Type |
|---|---|---|---|---|
| 13.98 | | 20.119 | 0.120 | BB |
| 15.19 | | 10.806 | 0.065 | MF |
| 15.60 | | 21.653 | 0.129 | FM |
| 17.49 | | 7.058 | 0.042 | BV |
| 18.72 | Sialic acid | 1.663e4 | 99.372 | VV R |
| 20.55 | | 12.268 | 0.073 | VB T |
| 22.07 | | 7.825 | 0.047 | VB |
| 23.14 | Sodium Pyruvate | 12.791 | 0.076 | BB |
| 0.00 | N-acetyl-D-mannosamine | 0.000 | 0.000 | |
| 0.00 | N-acetyl-D-glucosamine | 0.000 | 0.000 | |
| 35.28 | Acetic acid | 12.531 | 0.075 | BV R |
| 13.98 | | 18.996 | 0.113 | MM |
| 15.21 | | 13.383 | 0.080 | FM |
| 15.60 | | 21.523 | 0.128 | FM |
| 17.48 | | 10.475 | 0.063 | VV |
| 18.71 | Sialic acid | 1.664e4 | 99.348 | VV R |
| 20.55 | | 12.018 | 0.072 | VB T |
| 22.08 | | 7.754 | 0.046 | VB |
| 23.13 | Sodium Pyruvate | 12.896 | 0.077 | BB |
| 0.00 | N-acetyl-D-mannosamine | 0.000 | 0.000 | |
| 0.00 | N-acetyl-D-glucosamine | 0.000 | 0.000 | |
| 35.28 | Acetic acid | 12.132 | 0.072 | BB |

HPLC results of polymorphic Form 3 are shown below: stability under ambient conditions

| RT (min) | PeakName | Area (mAU*s) | Area % | Peak Type |
|---|---|---|---|---|
| 18.76 | Sialic acid | 1.843e4 | 99.684 | VV R |
| 0.00 | Sodium Pyruvate | 0.000 | 0.000 | |
| 0.00 | N-acetyl-D-mannosamine | 0.000 | 0.000 | |
| 0.00 | N-acetyl-D-glucosamine | 0.000 | 0.000 | |
| 0.00 | Acetic acid | 0.000 | 0.000 | |
| 18.77 | Sialic acid | 1.843e4 | 99.715 | VV R |
| 0.00 | Sodium Pyruvate | 0.000 | 0.000 | |
| 0.00 | N-acetyl-D-mannosamine | 0.000 | 0.000 | |
| 0.00 | N-acetyl-D-glucosamine | 0.000 | 0.000 | |
| 0.00 | Acetic acid | 0.000 | 0.000 | | stability under 40° C., 75% RH

| RT (min) | PeakName | Area (mAU*s) | Area % | Peak Type |
|---|---|---|---|---|
| 15.65 | | 23.519 | 0.176 | FM |
| 17.49 | | 58.466 | 0.439 | VV |
| 18.75 | Sialic acid | 1.306e4 | 98.031 | VB |
| 0.00 | Sodium Pyruvate | 0.000 | 0.000 | |
| 0.00 | N-acetyl-D-mannosamine | 0.000 | 0.000 | |
| 0.00 | N-acetyl-D-glucosamine | 0.000 | 0.000 | |
| 0.00 | Acetic acid | 0.000 | 0.000 | |
| 15.64 | | 23.879 | 0.180 | FM |
| 17.50 | | 62.150 | 0.467 | BV |
| 18.75 | Sialic acid | 1.303e4 | 98.011 | VV R |
| 0.00 | Sodium Pyruvate | 0.000 | 0.000 | |
| 0.00 | N-acetyl-D-mannosamine | 0.000 | 0.000 | |
| 0.00 | N-acetyl-D-glucosamine | 0.000 | 0.000 | |
| 0.00 | Acetic acid | 0.000 | 0.000 | | stability under 80° C.

| RT (min) | PeakName | Area (mAU*s) | Area % | Peak Type |
|---|---|---|---|---|
| 18.76 | Sialic acid | 1.716e4 | 99.526 | VV R |
| 0.00 | Sodium Pyruvate | 0.000 | 0.000 | |
| 0.00 | N-acetyl-D-mannosamine | 0.000 | 0.000 | |
| 0.00 | N-acetyl-D-glucosamine | 0.000 | 0.000 | |
| 0.00 | Acetic acid | 0.000 | 0.000 | |
| 18.76 | Sialic acid | 1.713e4 | 99.523 | VV R |
| 0.00 | Sodium Pyruvate | 0.000 | 0.000 | |
| 0.00 | N-acetyl-D-mannosamine | 0.000 | 0.000 | |
| 0.00 | N-acetyl-D-glucosamine | 0.000 | 0.000 | |
| 0.00 | Acetic acid | 0.000 | 0.000 | |

HPLC results of polymorphic Form 5 are shown below: stability under ambient conditions

| RT (min) | PeakName | Area (mAU*s) | Area % | Peak Type |
|---|---|---|---|---|
| 13.98 | | 13.557 | 0.091 | MM |
| 17.52 | | 9.948 | 0.067 | VV |
| 18.73 | Sialic acid | 1.489e4 | 99.842 | VB |
| 0.00 | Sodium Pyruvate | 0.000 | 0.000 | |
| 13.98 | | 14.096 | 0.095 | MM |
| 18.73 | Sialic acid | 1.485e4 | 99.905 | VB |
| 0.00 | Sodium Pyruvate | 0.000 | 0.000 | |

47

-continued

| RT (min) | PeakName | Area (mAU*s) | Area % | Peak Type |
|---|---|---|---|---|
| 0.00 | N-acetyl-D-mannosamine | 0.000 | 0.000 | |
| 0.00 | N-acetyl-D-glucosamine | 0.000 | 0.000 | | stability under 40° C., 75% RH

| RT (min) | PeakName | Area (mAU*s) | Area % | Peak Type |
|---|---|---|---|---|
| 13.98 | | 15.940 | 0.101 | MM |
| 18.73 | Sialic acid | 1.576e4 | 99.899 | FM |
| 0.00 | Sodium Pyruvate | 0.000 | 0.000 | |
| 0.00 | N-acetyl-D-mannosamine | 0.000 | 0.000 | |
| 0.00 | N-acetyl-D-glucosamine | 0.000 | 0.000 | |
| 13.98 | | 12.685 | 0.081 | MM |
| 18.73 | Sialic acid | 1.574e4 | 99.919 | FM |
| 0.00 | Sodium Pyruvate | 0.000 | 0.000 | |
| 0.00 | N-acetyl-D-mannosamine | 0.000 | 0.000 | |
| 0.00 | N-acetyl-D-glucosamine | 0.000 | 0.000 | | stability under 80° C.

| RT (min) | PeakName | Area (mAU*s) | Area % | Peak Type |
|---|---|---|---|---|
| 13.99 | | 14.175 | 0.077 | MF |
| 14.45 | | 29.382 | 0.160 | MF |
| 15.22 | | 62.173 | 0.448 | MF |
| 15.61 | | 81.601 | 0.445 | MF |
| 16.17 | | 22.473 | 0.123 | FM |
| 17.49 | | 38.667 | 0.211 | FM |
| 18.74 | Sialic acid | 1.774e4 | 96.784 | MF |
| 19.50 | | 74.611 | 0.407 | FM |
| 20.61 | | 59.331 | 0.324 | MF |
| 22.10 | | 85.134 | 0.465 | MF |
| 23.14 | Sodium Pyruvate | 101.679 | 0.555 | FM |
| 0.00 | N-acetyl-D-mannosamine | 0.000 | 0.000 | |
| 0.00 | N-acetyl-D-glucosamine | 0.000 | 0.000 | |
| 0.00 | Acetic acid | 0.000 | 0.000 | |
| 13.99 | | 13.845 | 0.076 | MF |
| 14.44 | | 30.373 | 0.166 | FM |
| 15.22 | | 79.206 | 0.433 | FM |
| 15.61 | | 80.855 | 0.442 | FM |
| 16.17 | | 21.834 | 0.119 | FM |
| 17.49 | | 40.697 | 0.222 | FM |
| 18.74 | Sialic acid | 1.772e4 | 96.777 | FM |
| 19.50 | | 75.291 | 0.411 | FM |
| 20.61 | | 60.808 | 0.332 | FM |
| 21.80 | | 27.937 | 0.153 | FM |
| 22.10 | | 56.936 | 0.311 | FM |
| 23.13 | Sodium Pyruvate | 102.424 | 0.559 | FM |
| 0.00 | N-acetyl-D-mannosamine | 0.000 | 0.000 | |
| 0.00 | N-acetyl-D-glucosamine | 0.000 | 0.000 | |
| 0.00 | Acetic acid | 0.000 | 0.000 | |

In addition, HPLC results of An embodiment of Form 2 are shown below:

| RT (min) | PeakName | Area (mAU*s) | Area % | Peak Type |
|---|---|---|---|---|
| 14.01 | | 23.932 | 0.129 | MM |
| 15.64 | | 13.838 | 0.075 | FM |
| 18.75 | Sialic acid | 1.847e4 | 99.659 | VV R |
| 14.00 | | 24.121 | 0.130 | MM |

48

-continued

| RT (min) | PeakName | Area (mAU*s) | Area % | Peak Type |
|---|---|---|---|---|
| 15.62 | | 11.532 | 0.062 | FM |
| 18.75 | Sialic acid | 1.844e4 | 99.672 | VV R | stability under ambient conditions

| RT (min) | PeakName | Area (mAU*s) | Area % | Peak Type |
|---|---|---|---|---|
| 15.63 | | 13.404 | 0.074 | FM |
| 18.74 | Sialic acid | 1.806e4 | 99.660 | VV R |
| 20.34 | | 25.333 | 0.140 | VB T |
| 0.00 | Sodium Pyruvate | 0.000 | 0.000 | |
| 0.00 | N-acetyl-D-mannosamine | 0.000 | 0.000 | |
| 0.00 | N-acetyl-D-glucosamine | 0.000 | 0.000 | |
| 0.00 | Acetic acid | 0.000 | 0.000 | |
| 13.98 | | 15.651 | 0.088 | MM |
| 15.62 | | 12.311 | 0.068 | FM |
| 18.75 | Sialic acid | 1.804e4 | 99.705 | VV R | stability under 40° C., 75% RH

| RT (min) | PeakName | Area (mAU*s) | Area % | Peak Type |
|---|---|---|---|---|
| 13.99 | | 16.361 | 0.092 | MM |
| 15.20 | | 10.120 | 0.057 | MF |
| 15.62 | | 12.665 | 0.071 | FM |
| 17.50 | | 14.331 | 0.081 | BV |
| 18.75 | Sialic acid | 1.767e4 | 99.573 | VV R |
| 20.35 | | 22.260 | 0.125 | VB T |
| 0.00 | Sodium Pyruvate | 0.000 | 0.000 | |
| 0.00 | N-acetyl-D-mannosamine | 0.000 | 0.000 | |
| 0.00 | N-acetyl-D-glucosamine | 0.000 | 0.000 | |
| 0.00 | Acetic acid | 0.000 | 0.000 | |
| 13.99 | | 17.056 | 0.096 | MM |
| 15.20 | | 8.833 | 0.050 | MF |
| 15.62 | | 12.835 | 0.072 | FM |
| 17.49 | | 14.459 | 0.082 | BV |
| 18.75 | Sialic acid | 1.765e4 | 99.576 | VV R |
| 20.37 | | 22.057 | 0.124 | VV T |
| 0.00 | Sodium Pyruvate | 0.000 | 0.000 | |
| 0.00 | N-acetyl-D-mannosamine | 0.000 | 0.000 | |
| 0.00 | N-acetyl-D-glucosamine | 0.000 | 0.000 | |
| 0.00 | Acetic acid | 0.000 | 0.000 | | stability under 80° C.

| RT (min) | PeakName | Area (mAU*s) | Area % | Peak Type |
|---|---|---|---|---|
| 17.50 | | 13.719 | 0.082 | BV |
| 18.75 | Sialic acid | 1.676e4 | 99.566 | VV R |
| 20.42 | | 22.218 | 0.132 | VB T |
| 23.13 | Sodium Pyruvate | 7.329 | 0.044 | BB |
| 0.00 | N-acetyl-D-mannosamine | 0.000 | 0.000 | |
| 0.00 | N-acetyl-D-glucosamine | 0.000 | 0.000 | |
| 0.00 | Acetic acid | 0.000 | 0.000 | |
| 17.50 | | 14.076 | 0.084 | BV |
| 18.76 | Sialic acid | 1.675e4 | 99.601 | VV R |
| 20.41 | | 22.253 | 0.132 | VB T |
| 0.00 | Sodium Pyruvate | 0.000 | 0.000 | |
| 0.00 | N-acetyl-D-mannosamine | 0.000 | 0.000 | |

-continued

| RT (min) | PeakName | Area (mAU*s) | Area % | Peak Type |
|---|---|---|---|---|
| 0.00 | N-acetyl-D-glucosamine | 0.000 | 0.000 | |
| 0.00 | Acetic acid | 0.000 | 0.000 | |

HPLC results of An embodiment of Form 5 are shown below:

| RT (min) | PeakName | Area (mAU*s) | Area % | Peak Type |
|---|---|---|---|---|
| 13.99 | | 12.785 | 0.088 | MM |
| 18.75 | Sialic acid | 1.445e4 | 99.832 | VV R |
| 20.32 | | 11.543 | 0.080 | VB T |
| 0.00 | Sodium Pyruvate | 0.000 | 0.000 | |
| 14.00 | | 13.401 | 0.093 | MM |
| 18.75 | Sialic acid | 1.443e4 | 99.828 | VV R |
| 20.36 | | 11.468 | 0.079 | VV T |
| 0.00 | Sodium Pyruvate | 0.000 | 0.000 | |

Form 1 is stable as a physical form (XRPD) and also chemically. All purities are higher than 99.5%. N-acetyl-D-glucosamide was found as a known impurity for the sample under ambient conditions (0.076%). Form 5 is stable as a physical form (XRPD) under ambient conditions and 40° C./75% RH, but converts to an unknown form (same form as observed when dehydrating Form 5) at 80° C. Sodium pyruvate was found as a known impurity for the sample under 80° C. (0.559%). The 80° C. sample shows a drop in purity (96.8%) compared with both ambient and 40° C./75% RH samples, which have purities higher than 99.9%. Form 3 is not stable as a physical form (XRPD). Form 3 converts to Form 2 under ambient conditions, to Form 1 under 40° C./75% RH and to Form 2 at 80° C. For all recovered samples, purities are higher than 98%, this showing moderate chemical stability. Form 2 is not stable as a physical form (XRPD) under 40° C./75% RH as it converts to Form 1. Form 2 is stable under ambient conditions and at 80° C. over 1 week. For all recovered samples, purities are higher than 99.4%, thus showing good chemical stability.

Approximate Aqueous Solubility

As expected, Form 5 is the stable Form in water and thus the less soluble.

TABLE 10

Aqueous Solubility

| Sialic acid | Form 1 | Form 2 | Form 3 | Form 5 |
|---|---|---|---|---|
| Solubility in g/L | 98.5 | 105 | 188.2 | 96.6 |

Competitive Slurry Experiment

Competitive slurries were performed to compare the relative stability between two forms at a given temperature in a given solvent. Slurries that did not show a single form after 24 hours, were slurried for a further 24 hours to see if full conversion could be obtained.

TABLE 11

Competitive slurries between Forms 1 and 2

| Solvent | Temperature | Component 1 | Component 2 | Composition after 24 H slurry | Composition after 48 H slurry |
|---|---|---|---|---|---|
| Acetone | 20° C. | Form 1 | Form 2 | Form 1 | N/A |
| Acetic Acid | 20° C. | Form 1 | Form 2 | Form 1 + Form 3 | Form 1 + Form 3 |
| Ethanol | 20° C. | Form 1 | Form 2 | Form 1 | N/A |
| Ethyl Acetate | 20° C. | Form 1 | Form 2 | Form 1 | N/A |
| Ethynol | 20° C. | Form 1 | Form 2 | Form 1 | N/A |
| Acetone | 60° C. | Form 1 | Form 2 | Form 1 | N/A |
| Acetic Acid | 60° C. | Form 1 | Form 2 | Form 1 + Form 3 | Form 1 + Form 3 |
| Ethanol | 60° C. | Form 1 | Form 2 | Form 1 | N/A |
| Ethyl Acetate | 60° C. | Form 1 | Form 2 | Form 1 | N/A |
| Ethynol | 60° C. | Form 1 | Form 2 | Form 1 | N/A |

Figure 72A:
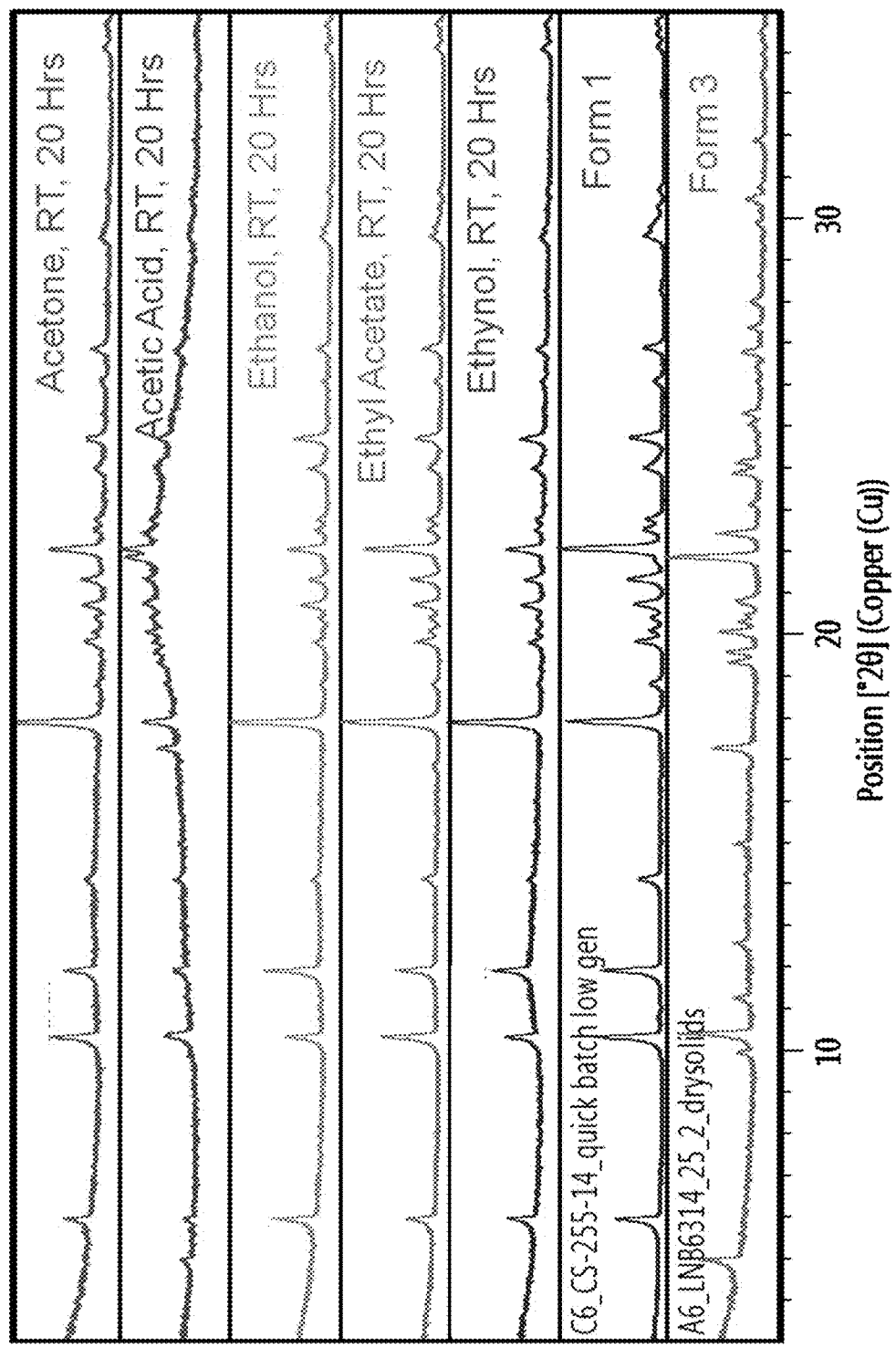
FIGS. 72A and 72B are XRPD Diffractograms from Competitive Slurries between polymorphic Forms 1 and 2.
Figure 72B:
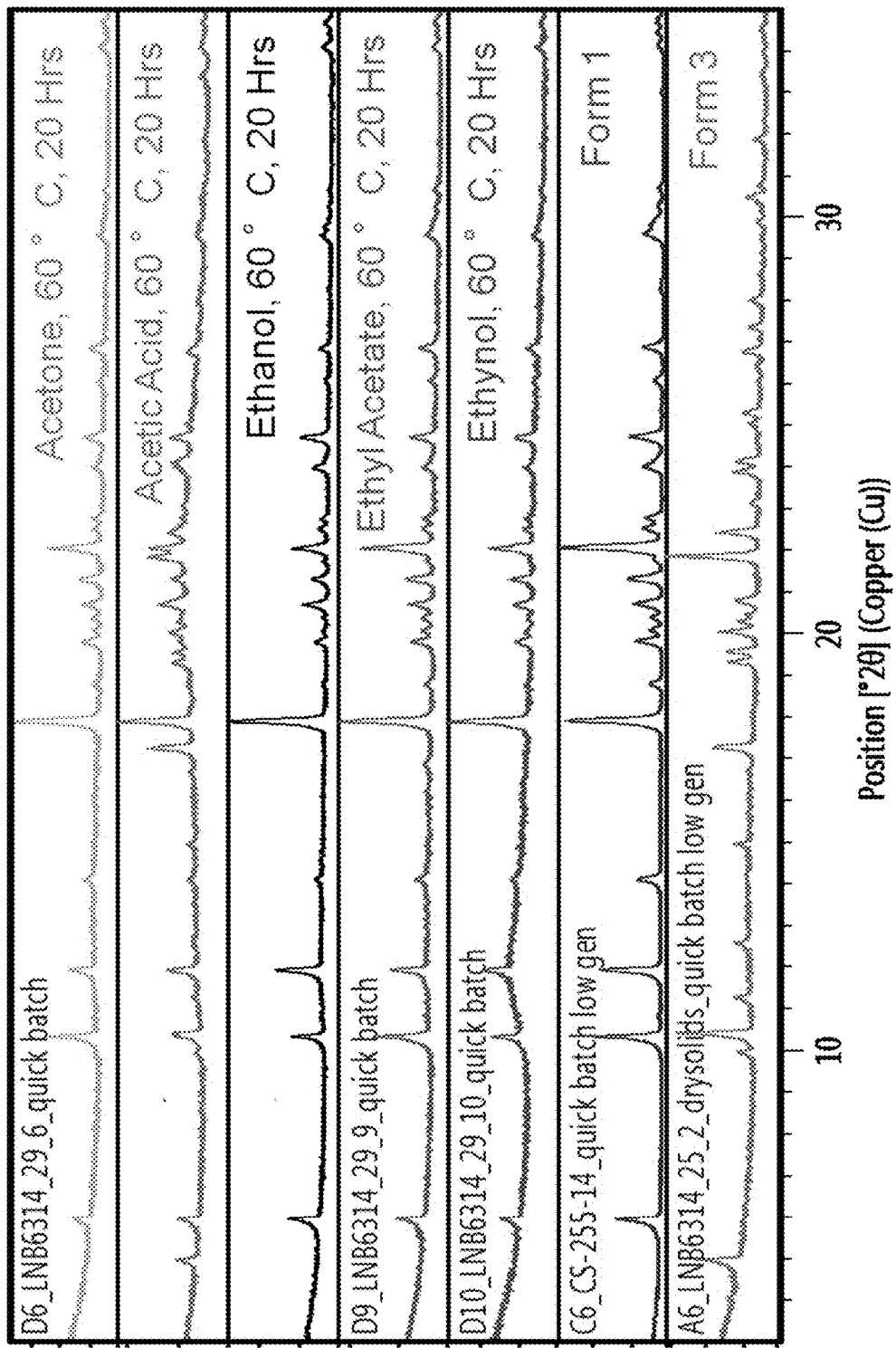

As it can be seen from the competitive slurry results (Table 11 and FIGS. 72A-72B), Form 1 is recovered in most cases (acetone, ethanol, ethyl acetate, ethynol). A pure phase is not obtained in acetic acid (mixture of Forms 1 and 3) and further time slurrying does not allow the mixture to transform fully to Form 1 or 3. Form 1 is therefore more stable than Form 2 for all studied conditions.

TABLE 12

Competitive slurries between Forms 1 and 3

| Solvent | Temperature | Component 1 | Component 2 | Composition after 24 H slurry | Composition after 48 H slurry |
|---|---|---|---|---|---|
| Acetone | 20° C. | Form 1 | Form 3 | Form 1 | N/A |
| Acetic Acid | 20° C. | Form 1 | Form 3 | Form 1 + Form 3 | Form 1 + Form 3 |
| Ethanol | 20° C. | Form 1 | Form 3 | Form 1 | N/A |
| Ethyl Acetate | 20° C. | Form 1 | Form 3 | Form 1 | N/A |
| Ethynol | 20° C. | Form 1 | Form 3 | Form 1 | N/A |
| Acetone | 60° C. | Form 1 | Form 3 | Form 1 | N/A |
| Acetic Acid | 60° C. | Form 1 | Form 3 | Form 1 + Form 3 | Form 1 + Form 3 |
| Ethanol | 60° C. | Form 1 | Form 3 | Form 1 | N/A |
| Ethyl Acetate | 60° C. | Form 1 | Form 3 | Form 1 | N/A |
| Ethynol | 60° C. | Form 1 | Form 3 | Form 1 | N/A |

Figure 73:
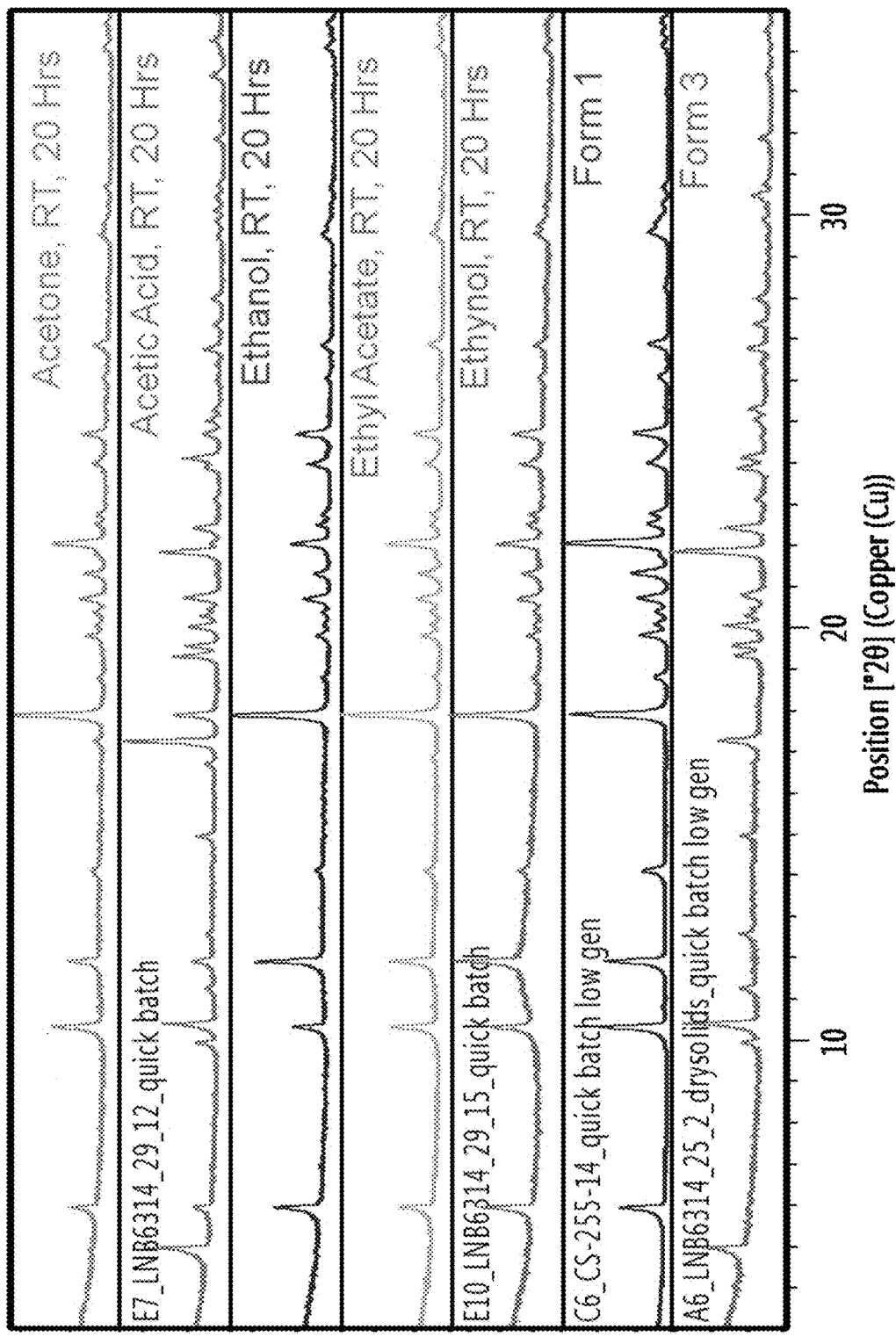
FIGS. 73 and 74 are XRPD Diffractograms from Competitive Slurries between polymorphic Forms 1 and 3.
Figure 74:
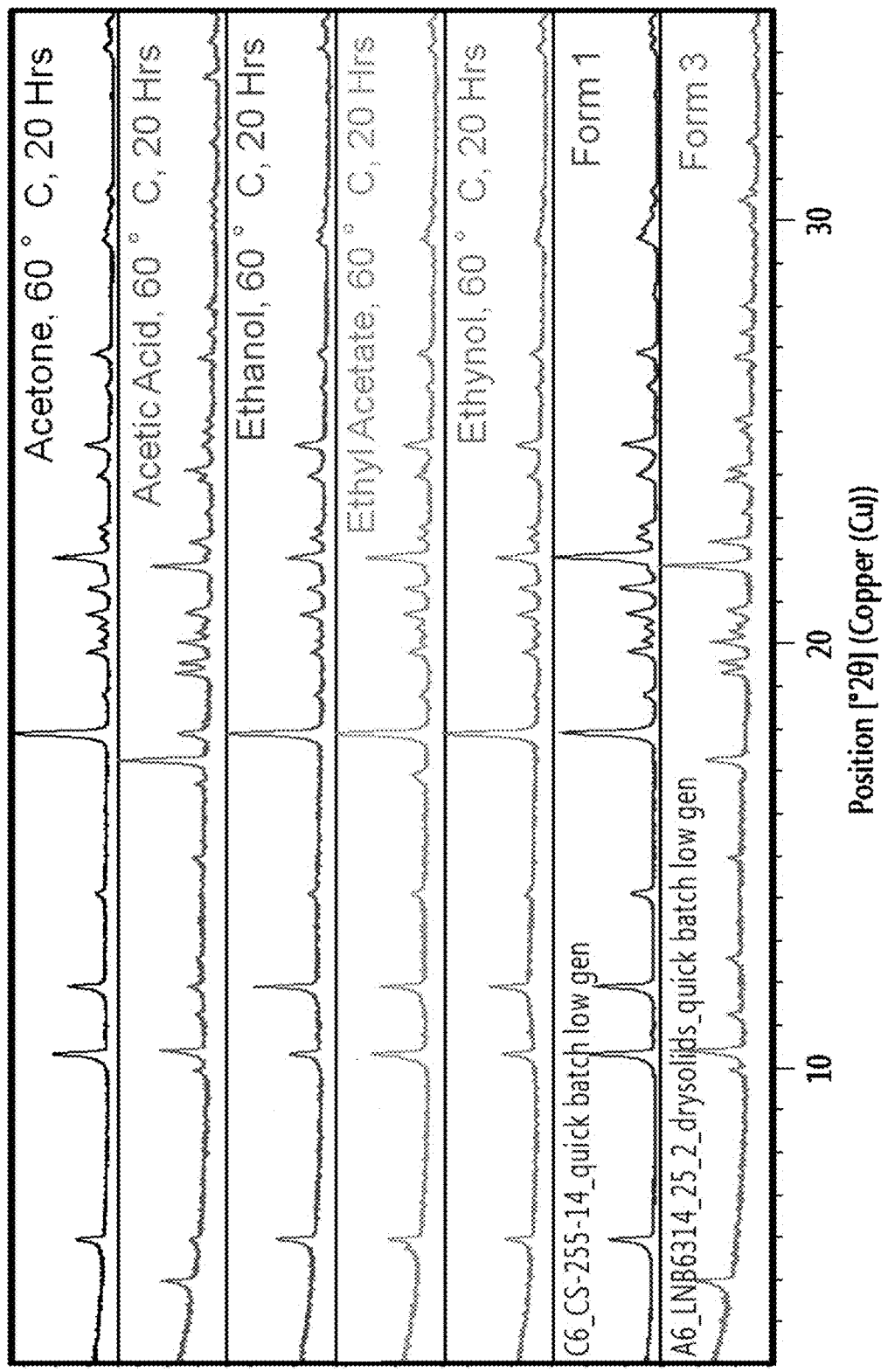

As it can be seen from the competitive slurry results (Table 12 and FIGS. 73-74), Form 1 is recovered in most cases (acetone, ethanol, ethyl acetate, ethynol). A pure phase is not obtained in acetic acid (mixture of Form 1 and 3) and further time does not allow the mixture to transform fully to Form 1 or 3. Form 1 is more stable than Form 3 for all studied conditions except in acetic acid.

TABLE 13

Summary of the characterization results of the study on sialic acid

| Analysis | Form 1 | Form 2 | Form 3 | Form 5 |
|---|---|---|---|---|
| XRPD (crystallinity) | Crystalline | Less Crystalline | Crystalline | Crystalline |
| HPLC (purity) | 99.5% | 99.70% 99.80% | 99.8% | 99.80% 99.90% |
| NMR (stoichiometry) | Clean | Solvent traces | Mono acetic acid | Water Present |

TABLE 13-continued

Summary of the characterization results of the study on sialic acid

| Analysis | Form 1 | Form 2 | Form 3 | Form 5 |
|---|---|---|---|---|
| PLM (morphology) | Small needles <10 μm | Small needles <30 μm | Small needles <30 μm | Blocks <100 μm |
| TGA (weight loss) | Decomposition at 190.2° C. | Decomposition at 178.5° C. | 15.3% (80° C.) Decomposition 176.2° C. | 10.5% (88.4° C.) Decomposition undefined |
| DSC (thermal events) | Endotherm 188.6° C. | Endotherm 181.0° C. | Endotherms 107° C. 181.0° C. | Endotherms 90.5° C. 192° C. |
| DVS (hygroscopicity) | Stable and slightly hygroscopic | Goes to form 1 RH >50% | Goes to form 1 RH >50% | Stable and slightly hygroscopic |
| XRPD post DVS | no change | change | change | no change |
| Stability - XRPD post Stability | no change | Form 1 + 2 at RT Form 1 at 40° C./75% RH Form 2 at 80° C. | Form 2 at RT Form 1 at 40° C./75% RH Form 2 at 80° C. | Form 5 at RT Form 5 at 40° C./75% RH New form 80° C. |
| Approximate solubility | | 98.5 g/L | 105.0 g/L | 188.2 g/L | 96.6 g/L |

Figure 70:
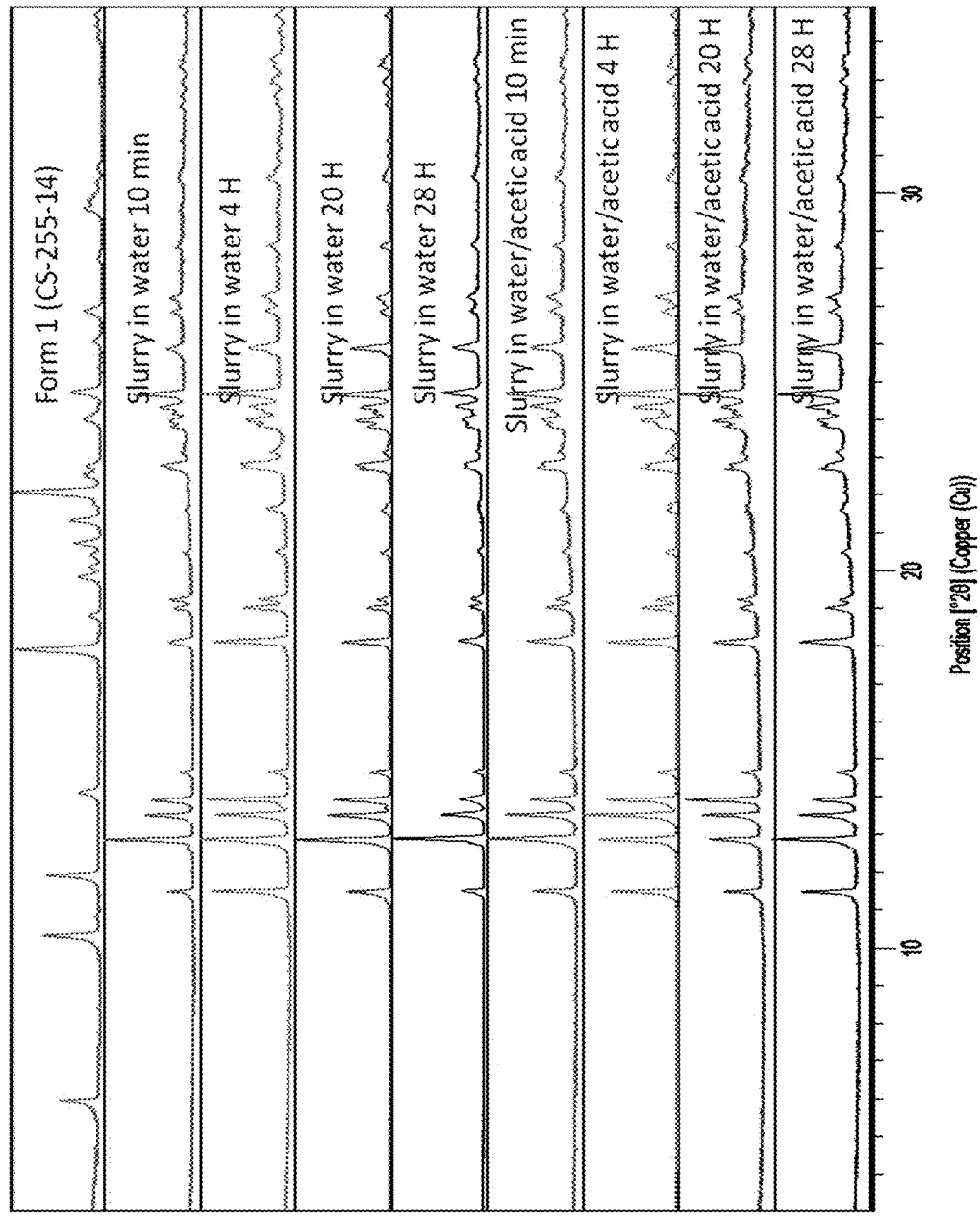
FIG. 70 is diffractograms of slurried sialic acid at 5° C. in water (top four diffractograms) and water/acetic acid (80:20 v/v) (bottom four diffractograms) over time. These diffractograms show that after 10 min, polymorphic Form 1 had already fully converted to polymorphic Form 5 in both solvents.
Figure 71:
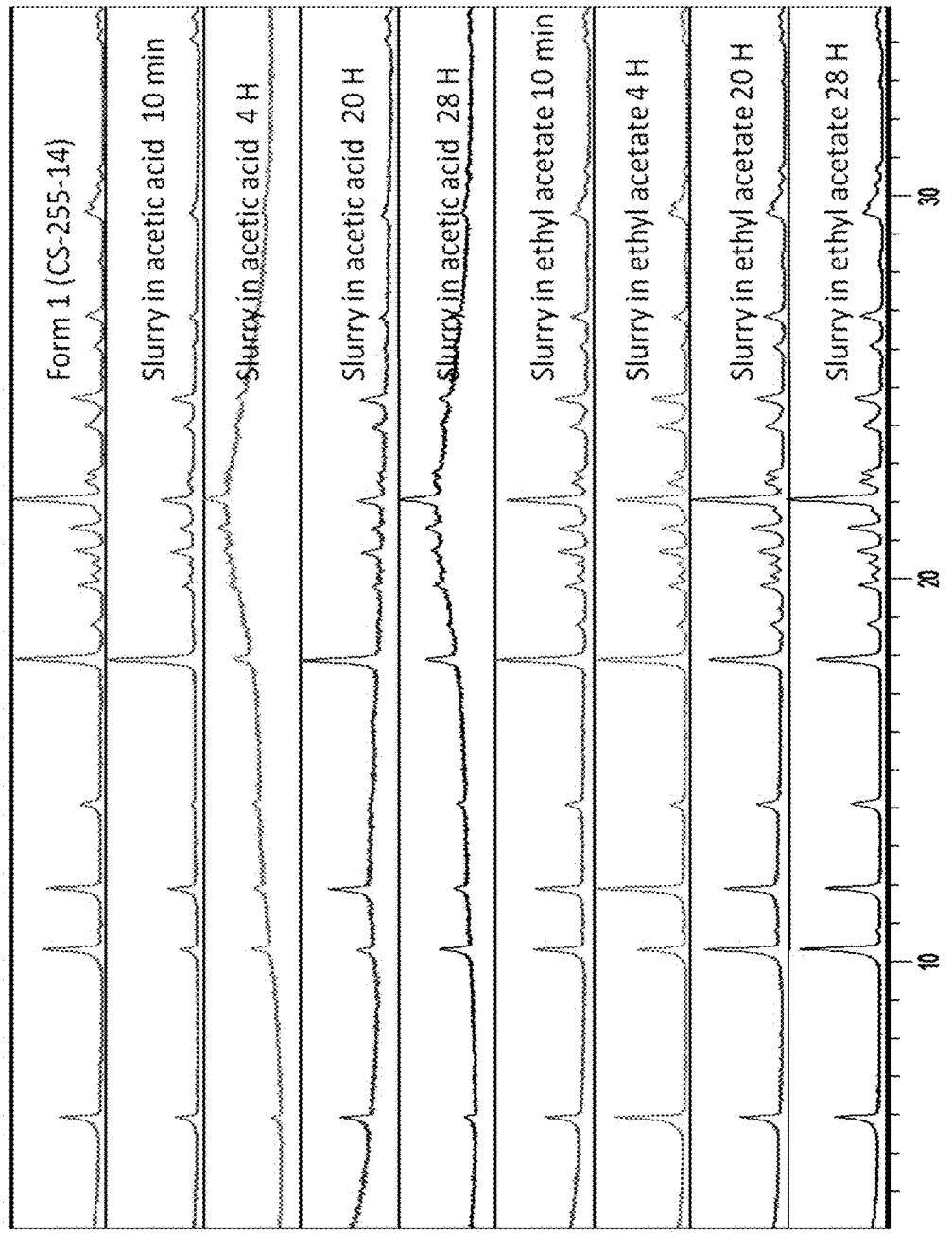
FIG. 71 is diffractograms of slurried sialic acid at 5° C. in acetic acid (top four diffractograms) and ethyl acetate (bottom four diffractograms) over time. These diffractograms show that polymorphic Form 1 did not change in these slurry conditions.

From the competitive slurries, Form 1 is the most stable form in most of the studied conditions. From previous slurries in water and water/acetic acid, it is known that Form 1 converts to Form 5, if the amount of water is sufficient (FIG. 70); however, in the absence of water, Form 1 does not change in slurry conditions of acetic acid or ethyl acetate (FIG. 71).

Forms 2 and 3 can be converted to Form 1 by either exposure to a humid environment (>60% relative humidity) or by being slurried in an appropriate solvent.

No conversion from Form 5 to Form 1 has been observed this far, during the study (although competitive slurries in a low water content solvent may be suitable). The dehydration of Form 5 gives a new form, of which the relative stability is unknown.

Density and Particle Size Characterizations

Different lots of Form 1 was analyzed for density, particle size distribution, and also observed under polarized light microscope (PLM) as shown in Table 14 below.

TABLE 14

PLM analysis, particle size distribution and density of Form 1

| Lot ID | PLM Analysis | $D_{10}$ (μm) | $D_{50}$ (μm) | $D_{90}$ (μm) | Bulk Density (g/ml) | Tapped Density (g/ml) |
|---|---|---|---|---|---|---|
| A | Non-birefringent needles | 1.7 | 6.6 | 28.1 | 0.25 | 0.30 |
| B | Non-birefringent needles | 1.5 | 5.9 | 21.2 | 0.19 | 0.23 |
| C | Non-birefringent needles | 1.1 | 6.1 | 36.4 | 0.39 | 0.43 |
| D | Non-birefringent needles | 1.3 | 5 | 24.1 | 0.25 | 0.30 |
| E | Small non-birefringent particles | 1.2 | 4.3 | 27.8 | 0.43 | 0.50 |
| F | Non-birefringent needles | 1 | 3 | 10 | 0.40 | 0.43 |
| G | Small non-birefringent particles | 1.1 | 3.9 | 19.1 | 0.28 | 0.35 |

In some embodiments, Form 1 has a median particle diameter ($D_{50}$) of about 3 μm to about 10 μm. In some embodiments, Form 1 has a median particle diameter ($D_{50}$) of about 3 μm to about 7 μm.

In some embodiments, Form 1 has a bulk density of about 0.1 g/ml to about 0.5 g/ml. In some embodiments, Form 1 has a bulk density of about 0.19 g/ml to about 0.43 g/ml. In one embodiment, Form 1 has a bulk density of about 0.1 g/ml to about 0.5 g/ml.

In some embodiments, Form 1 has a tapped density of about 0.1 g/ml to about 0.6 g/ml. In some embodiments, Form 1 has a tapped density of about 0.2 g/ml to about 0.5 g/ml.

Summary of Experimental Study

This experiment entailed a polymorph screening study in order to identify polymorphic forms of sialic acid, investigate the nature of these forms and ascertain their relative stability.

Approximate solvent solubility tests indicated low solubility of sialic acid in the majority of the solvent systems assessed, with just 5 of the 31 solvents showing good solubility.

During the primary polymorph screen, 3 polymorphic forms were identified, Form 1, Form 4 and Form 5. Two further polymorphic forms, Form 3 and Form 2, were produced employing solvents/conditions similar to those used during the large scale sialic acid manufacturing process.

Form 1 was observed to be anhydrous and the thermodynamically most stable form. It was also observed to be chemically and physically stable under the one week stress testing conditions assessed. Forms 2 and 3, were further characterized, with Form 3 being identified as a mono acetic acid solvate and Form 2 an anhydrous form which is obtained through the desolvation of Form 3. Form 5 was found to be a dihydrate which was regularly obtained in the presence of water, with Form 4 observed to be a likely DMSO solvate, which desolvates to Form 1.

The screen further identified conditions under which Forms 3 and 2 could be converted to Form 1. These included either exposure to high humidity conditions or extended slurrying in solvents such as acetone, ethanol or ethyl acetate.

As Form 3 is the polymorph which is initially crystallized out of solution, possible further work may include slurry conversion studies in order to assess the conversion from Forms 3 and 2 to Form 1 and the process conditions which allow for the fastest rate of conversion.

The patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A crystalline form of N-acetylneuraminic acid (NeuAc), wherein the crystalline form is polymorphic Form 1 which exhibits an X-ray powder diffraction pattern comprising peaks at about 10.34±0.3; 17.91±0.3; and 22.06±0.3 degrees two-theta.

2. The crystalline form of claim 1, which exhibits an X-ray powder diffraction pattern further comprising peaks at about 5.95±0.3 and 11.93±0.3.

3. The crystalline form of claim 1, which exhibits an X-ray powder diffraction pattern further comprising one or more peaks at degree two-theta selected from the group consisting of: 5.95±0.3; 11.93±0.3; 14.12±0.3; 19.84±0.3; 20.72±0.3; 21.31±0.3; 24.73±0.3; and 29.60±0.3.

4. The crystalline form of claim 1, which exhibits a Differential Scanning calorimetry (DSC) thermogram having an endotherm with an onset of about 188.6° C.

5. The crystalline form of claim 1, which is anhydrous.

6. A dosage form comprising the crystalline form of claim 1.

7. The dosage form of claim 6, which is an oral unit dosage form.

8. The dosage form of claim 7, wherein the oral dosage form contains the crystalline form in an amount equivalent to about 100 mg to about 1000 mg of NeuAc.

9. The dosage form of claim 8, wherein the oral dosage form contains the crystalline form in an amount equivalent to about 325 mg or 500 mg of NeuAc.

10. A pharmaceutical composition comprising the crystalline form of claim 1 and a pharmaceutically acceptable carrier.

11. The pharmaceutical composition of claim 10, wherein the crystalline form has a chemical purity of about 98.5% or higher.

12. The pharmaceutical composition of claim 10, wherein the crystalline form has a polymorphic purity of about 50% or higher.

13. The pharmaceutical composition of claim 10, wherein the crystalline form has a polymorphic purity of 95% or higher.

14. The pharmaceutical composition of claim 10, wherein the crystalline form contains:
    ethanol in an amount of about 1.0% or less; or
    acetic acid in an amount of about 1.0% or less; and/or
    N-acetyl-D-glucosamine in an amount of about 0.5% or less.

15. The pharmaceutical composition of claim 10, wherein the crystalline form contains;
    polymorphic Form 2 of NeuAc in an amount of about 0.5% or less; or
    polymorphic Form 3 of NeuAc in an amount of about 0.5% or less; and/or
    polymorphic Form 4 of NeuAc in an amount of about 0.5% or less.

16. A method for treating a sialic acid deficiency comprising administering to a patient in need of such treatment a therapeutically effective amount of the crystalline form of claim 1.

* * * * *